United States Patent
Chappie et al.

(10) Patent No.: US 12,049,465 B2
(45) Date of Patent: *Jul. 30, 2024

(54) TRICYCLIC COMPOUNDS AND THEIR USE AS PHOSPHODIESTERASE INHIBITORS

(71) Applicant: PFIZER INC., New York, NY (US)

(72) Inventors: Thomas Allen Chappie, Carlisle, MA (US); Nandini Chaturbhai Patel, Waban, MA (US); Patrick Robert Verhoest, Newton, MA (US); Christopher John Helal, Mystic, CT (US); Simone Sciabola, Cambridge, MA (US); Erik Alphie LaChapelle, Uncasville, CT (US); Travis T. Wager, Brookline, MA (US); Ramalakshmi Yegna Chandrasekaran, Gales Ferry, CT (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/886,807

(22) Filed: Aug. 12, 2022

(65) Prior Publication Data

US 2023/0002386 A1    Jan. 5, 2023

Related U.S. Application Data

(63) Continuation of application No. 15/736,942, filed as application No. PCT/IB2016/053398 on Jun. 9, 2016, now Pat. No. 11,472,805.

(60) Provisional application No. 62/180,815, filed on Jun. 17, 2015.

(51) Int. Cl.
| | |
|---|---|
| *C07D 471/14* | (2006.01) |
| *C07D 471/22* | (2006.01) |
| *C07D 487/04* | (2006.01) |
| *C07D 487/14* | (2006.01) |
| *C07D 491/147* | (2006.01) |
| *C07D 491/22* | (2006.01) |
| *C07D 498/22* | (2006.01) |
| *C07D 513/14* | (2006.01) |
| *C07D 519/00* | (2006.01) |

(52) U.S. Cl.
CPC ......... *C07D 471/14* (2013.01); *C07D 471/22* (2013.01); *C07D 487/04* (2013.01); *C07D 487/14* (2013.01); *C07D 491/147* (2013.01); *C07D 491/22* (2013.01); *C07D 498/22* (2013.01); *C07D 513/14* (2013.01); *C07D 519/00* (2013.01)

(58) Field of Classification Search
CPC .................................................. C07D 471/14
See application file for complete search history.

(56) References Cited

U.S. PATENT DOCUMENTS

| | | | |
|---|---|---|---|
| 3,702,321 A | 11/1972 | Yamamoto | |
| 4,022,778 A | 5/1977 | Freed | |
| 7,253,281 B2 | 8/2007 | Bentley | |
| 9,745,316 B2 | 8/2017 | Tavares | |
| 9,815,832 B2 * | 11/2017 | Chappie | ........... A61P 43/00 |
| 10,738,063 B2 * | 8/2020 | Chappie | ........... A61P 25/00 |
| 11,472,805 B2 * | 10/2022 | Chappie | ........... A61P 25/16 |
| 2003/0187257 A1 | 10/2003 | Gaudilliere | |
| 2007/0191337 A1 | 8/2007 | Ivashchenko | |
| 2010/0137320 A1 | 6/2010 | Huang | |

FOREIGN PATENT DOCUMENTS

| | | |
|---|---|---|
| CH | 560201 | 3/1969 |
| DE | 2017857 | 1/1972 |
| DE | 2144272 | 9/1972 |
| EP | 1285922 | 2/2003 |

(Continued)

OTHER PUBLICATIONS

Bandini, et al., "Enantioselectiver Phase-Transfer-Catalyzed Intramolecular Aza-Michael Reaction: Effective Route to Pyrazion-Indole Compounds," Angewandte Chemie, International Edition 47(17):3238-3241 (2008).
Bandini, et al., Versatile Base-Catalyzed Route to Polycyclic Heteroaromatic Compounds by ntramolecular Aza-Michael Addition, European Journal of Organic Chemistry, 2007(18):2917-2920 (2007).
Cannon, "Analog Design," J.G. Cannon, Chapter 19 in Burger's Medicinal Chemistry and Drug Discovery, Fifth Edition, vol. 1: Principles and Practice, Wiley-Intersciences, pp. 783-802 (1995) (20 pages).
Cheng, et al., "Carbamate-Catalyzed Enantioselective Bromolactamization," Angewandte Chemie, International Edition, 54:12102-12106, vol. 54 (2015).

(Continued)

*Primary Examiner* — Nizal S Chandrakumar
(74) *Attorney, Agent, or Firm* — Haley Guiliano LLP; James F. Haley, Jr.; Jacob E. Dander

(57) ABSTRACT

The present invention is directed to compounds of Formula I: or a pharmaceutically acceptable salt thereof, wherein the substituents A, $R^1$, $R^2$, $R^{3a}$, $R^{3b}$, $R^{4a}$, $R^{4b}$ and n are as defined herein. The inventions also directed to pharmaceutical compositions comprising the compounds, methods of treatment using the compounds and methods of preparing the compounds.

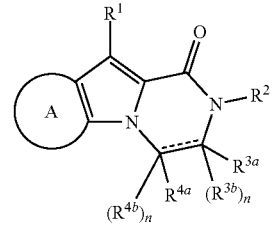

Formula I

10 Claims, No Drawings

(56) References Cited

FOREIGN PATENT DOCUMENTS

| EP | 1200439 | 6/2003 |
|---|---|---|
| EP | 1466996 | 10/2004 |
| GB | 1286701 | 8/1972 |
| JP | 49004237 | 1/1974 |
| WO | WO2002100350 | 12/2002 |
| WO | WO2003045951 | 6/2003 |
| WO | WO2005105213 | 11/2005 |
| WO | WO2006072608 | 7/2006 |
| WO | WO2007048847 | 5/2007 |
| WO | WO2007048848 | 5/2007 |
| WO | WO2009094528 | 7/2009 |
| WO | WO2013163239 | 10/2013 |
| WO | WO2014128585 | 8/2014 |
| WO | WO2014144847 | 9/2014 |

OTHER PUBLICATIONS

Dorwald, "Side Reactions in Organic Synthesis," A Guide to Successful Synthesis Design, Wiley: BCH, Weinheim, pp. 1-15 (37 pages) (2005).

Gatta, et al., "Pyrazine-1,2-a-and 1,4-diazepino-1-2-1-indoles. I. Synthesis of 10-phenyl-1,2,3,4-tetrahydropyrazino-1,2-a-indoles and of 11-phenyl-2,3,4,5-tetrahydro-1H-1, 4-diazepino-1,2-a-indoles," Farmaco Edizione Scientifica, (29):5:386-397 (1974).

Ilyn, et al., "An efficient synthesis of novel heterocycle-fused derivatives of 1-oxo-1,2,3,4-tetrahydropyrazine using Ugi condensation," Tetrahedron Letters, 46:881-884 (2005).

Inaba, et al., "Benzodiazepines, IV. A New Synthesis of 1-Diethylaminoethyl-substituted 1,4-Benzodiazepin-2-ones," Chemical and Pharmaceutical Bulletin, 19(2):263-272 (1971).

Inaba, et al., "Benzodiazepines, VII. Pyrazino[1,2-a]indol-1-ones and their Conversion to 2,3-Dihydro-1H-1,4-benzodiazepines," Chemical and Pharmaceutical Bulletin, 20(8):1628-1636 (1972).

PCT International Search Report and Written Opinion for International Patent Application No. PCT162016053398, dated Sep. 27, 2016 (19 pages).

RN 1185004-21-0 Registry, Database Registry [Online], retrieved from STN, Sep. 16, 2009, searched on: Mar. 26, 2020.

RN 1189642-57-6 Registry, Database Registry [Online], retrieved from STN, Oct. 23, 2009, searched on: Mar. 26, 2020.

Venkatesh et al., "Role of the development scientist in compound lead selection and optimization," Journal of Pharmaceutical Sciences, 89(2):145-154 (2000).

* cited by examiner

TRICYCLIC COMPOUNDS AND THEIR USE AS PHOSPHODIESTERASE INHIBITORS

CROSS-REFERENCE TO RELATED APPLICATIONS

This application is a continuation of U.S. patent application Ser. No. 15/736,942, filed Dec. 15, 2017, which is a national stage application under 35 U.S.C. 371 of PCT/IB2016/053398, filed Jun. 9, 2016, which claims priority from and the benefit of U.S. Provisional Patent Application 62/180,815, filed Jun. 17, 2015, the disclosures of which are hereby incorporated by reference in their entireties.

FIELD OF THE INVENTION

The present invention relates to tricyclic compounds of Formula I, which are inhibitors of PDE4 isozymes, especially with a binding affinity for the PDE4A, PDE4B and PDE4C isoforms, and to the use of such compounds in methods for treating central nervous system (CNS), metabolic, autoimmune and inflammatory diseases or disorders.

BACKGROUND OF THE INVENTION

Phosphodiesterases (PDEs) are a class of intracellular enzymes that cleave the phosphodiester bond in second messenger molecules adenosine 3',5'-cyclic monophosphate (cAMP) and guanosine 3',5'-cyclic monophosphate (cGMP). The cyclic nucleotides cAMP and cGMP serve as secondary messengers in various cellular pathways.

cAMP functions as a second messenger regulating many intracellular processes within the body. One example is in the neurons of the central nervous system, where the activation of cAMP-dependent kinases and the subsequent phosphorylation of proteins are involved in acute regulation of synaptic transmission as well as neuronal differentiation and survival. The complexity of cyclic nucleotide signaling is indicated by the molecular diversity of the enzymes involved in the synthesis and degradation of CAMP. There are at least ten families of adenylyl cyclases, and eleven families of phosphodiesterases. Furthermore, different types of neurons are known to express multiple isozymes of each of these classes, and there is good evidence for compartmentalization and specificity of function for different isozymes within a given neuron.

A principal mechanism for regulating cyclic nucleotide signaling is via phosphodiesterase-catalyzed cyclic nucleotide catabolismthe eleven known families of PDEs are encoded by 21 different genes; each gene typically yields multiple splice variants that further contribute to the isozyme diversity. The PDE families are distinguished functionally based on cyclic nucleotide substrate specificity, mechanism(s) of regulation, and sensitivity to inhibitors. Furthermore, PDEs are differentially expressed throughout the organism, including in the central nervous system. As a result of these distinct enzymatic activities and localization, different PDEs' isozymes can serve distinct physiological functions. Furthermore, compounds that can selectively inhibit distinct PDE isozymes may offer particular therapeutic effects, fewer side effects, or both (Deninno, M., Future Directions in Phosphodiesterase Drug Discovery. *Bioorganic and Medicinal Chemistry Letters* 2012, 22, 6794-6800).

The present invention relates to compounds having a binding affinity for the fourth family of PDEs (i.e., PDE4A, PDE4B, PDE4C, and PDE4D), and, in particular, a binding affinity for the PDE4A, PDE4B and PDE4C isoforms.

The PDE4 isozymes carry out selective, high-affinity hydrolytic degradation of the second messenger adenosine 3',5'-cyclic monophosphate (CAMP mediated beneficial pharmacological effects resulting from that inhibition have been shown in a variety of disease models. A number of other PDE4 inhibitors have been discovered in recent years. For example, Roflumilast (Daliresp®), marketed by Forest Pharmaceuticals, Inc., is approved for severe chronic obstructive pulmonary disease (COPD) to decrease the number of flare-ups or prevent exacerbations of COPD symptoms. Apremilast (Otezla®) has been approved by the U.S. Food and Drug Administration for the treatment of adults with active psoriatic arthritis.

While beneficial pharmacological activity of PDE4 inhibitors has been shown, a common side effect of these treatments has been the induction of gastrointestinal symptoms such as nausea, emesis, and diarrhea, which are hypothesized to be associated with inhibition of the PDE4D isoform. Attempts have been made to develop compounds with an affinity for the PDE4B isoform over the PDE4D isoform (See: Donnell, A. F. et al., Identification of pyridazino[4,5-b]indolizines as selective PDE4B inhibitors. *Bioorganic & Medicinal Chemistry Letters* 2010, 20, 2163-7; and Naganuma, K. et al., Discovery of selective PDE4B inhibitors. *Bioorganic and Medicinal Chemistry Letters* 2009, 19, 3174-6). However, there remains a need to develop selective PDE4 inhibitors, especially those having an affinity for the PDE4A, PDE4B, and PDE4C isoforms. In particular, compounds with enhanced binding affinity for the PDE4A, and PDE4B isoforms over the PDE4D isoform are anticipated to be useful in the treatment of various diseases and disorders of the central nervous system (CNS). The discovery of selected compounds of the present invention addresses this continued need, and provides additional therapies for the treatment of various diseases and disorders of the central nervous system (CNS), as well as metabolic, autoimmune and inflammatory diseases or disorders.

Treatment with the PDE4 inhibitors of the present invention may also lead to a decrease in gastrointestinal side effects (e.g., nausea, emesis and diarrhea) believed to be associated with inhibition of the PDE4D isoform (Robichaud, A. et al., Deletion of Phosphodiesterase 4D in Mice Shortens α2-Adrenoreceptor-Mediated Anesthesia, A Behavioral Correlate of Emesis. *Journal of Clinical Investigation* 2002, 110, 1045-1052).

SUMMARY OF THE INVENTION

The present invention is directed to compounds of Formula I:

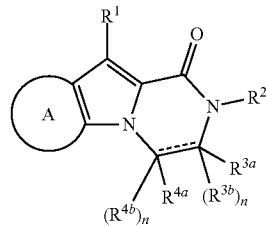

Formula I or a pharmaceutically acceptable salt thereof, wherein:

Ring A is a fused (4- to 8-membered)oxygen-containing heterocycloalkyl ring, a fused phenyl ring, or a fused (5- to 8-membered)nitrogen-containing heteroaryl ring, and, where chemically permissible, the fused (4- to 8-membered)oxygen-containing heterocycloalkyl ring, the fused phenyl ring and the fused (5- to 8-membered) nitrogen-containing heteroaryl ring are optionally substituted with one to six $R^8$;

$R^1$ is selected from the group consisting of $(C_3-C_8)$ cycloalkyl, (4- to 10-membered)-heterocycloalkyl, $(C_6-C_{10})$aryl and (5- to 14-membered)heteroaryl, and, where chemically permissible, the $(C_3-C_8)$cycloalkyl, (4- to 10-membered)heterocycloalkyl, $(C_6-C_{10})$aryl and (5- to 14-membered)heteroaryl moieties are optionally substituted with one to six $R^9$;

$R^2$ is selected from the group consisting of hydrogen, $(C_1-C_6)$alkyl, $(C_2-C_6)$alkenyl, $(C_2-C_6)$alkynyl, $(C_1-C_{15})$alkyl-$OR^5$, —C(=O)—$R^5$, —C(=O)—$OR^5$, —C(=O)—$N(R^5)(R^6)$, —$(SO_2)R^5$, $(C_3-C_8)$cycloalkyl, (4- to 10-membered)heterocycloalkyl, $(C_6-C_{10})$aryl and (5- to 14-membered)heteroaryl, and where chemically permissible, the $(C_1-C_6)$alkyl, $(C_2-C_6)$alkenyl, $(C_2-C_6)$alkynyl, $(C_3-C_8)$cycloalkyl, (4- to 10-membered)heterocycloalkyl, $(C_6-C_{10})$aryl and (5- to 14-membered)heteroaryl are optionally substituted with one to six $R^8$;

$R^{3a}$, where chemically permissible, is selected from the group consisting of hydrogen, halogen, oxo, cyano, hydroxy, —$SF_5$, nitro, —$N(R^5)(R^6)$, optionally substituted $(C_1-C_6)$alkylthio, optionally substituted $(C_1-C_6)$alkyl, optionally substituted $(C_1-C_6)$alkoxy and optionally substituted $(C_3-C_8)$cycloalkyl; or $R^2$ and $R^{3a}$ taken together with the nitrogen and carbon atoms to which they are attached form a (4- to 6-membered)heterocycloalkyl ring, and where chemically permissible, the (4- to 6-membered)heterocycloalkyl ring is optionally substituted with one to six $R^8$;

when present, $R^{3b}$ is selected from the group consisting of hydrogen, halogen, oxo, cyano, hydroxy, —$SF_5$, nitro, $N(R^5)(R^6)$, optionally substituted $(C_1-C_6)$alkylthio, optionally substituted $(C_1-C_6)$alkyl, optionally substituted $(C_1-C_6)$alkoxy and optionally substituted $(C_3-C_5)$cycloalkyl; or $R^{3a}$ and $R^{3b}$ taken together with the carbon atom to which they are attached form a $(C_3-C_6)$cycloalkyl or (4- to 6-membered)heterocycloalkyl, and where chemically permissible, the $(C_3-C_6)$cycloalkyl or (4- to 6-membered)heterocycloalkyl, where chemically permissible, are optionally substituted with one to six $R^8$.

$R^{4a}$, where chemically permissible, is selected from the group consisting of hydrogen, halogen, oxo, cyano, hydroxy, —$SF_5$, nitro, $N(R^5)(R^6)$, optionally substituted $(C_1-C_6)$alkylthio, optionally substituted $(C_1-C_6)$alkyl and optionally substituted $(C_1-C_6)$alkoxy;

when present, $R^{4b}$ is selected from the group consisting of hydrogen, halogen, oxo, cyano, hydroxy, —$SF_5$, nitro, $N(R^5)(R^6)$, optionally substituted $(C_1-C_6)$alkylthio, optionally substituted $(C_1-C_6)$alkyl and optionally substituted $(C_1-C_6)$alkoxy; or $R^{4a}$ and $R^{4b}$ taken together with the carbon atom to which they are attached form a $(C_3-C_6)$cycloalkyl or (4- to 6-membered)heterocycloalkyl, and where chemically permissible, the $(C_3-C_6)$cycloalkyl or (4- to 6-membered)heterocycloalkyl are optionally substituted with one to six$R^8$;

$R^5$ and $R^6$ at each occurrence are each independently selected from the group consisting of hydrogen and $(C_1-C_6)$alkyl;

$R^7$ is $(C_1-C_6)$alkyl;

when present, $R^8$ at each occurrence is independently selected from the group consisting of halogen, oxo, cyano, hydroxy, —$SF_5$, nitro, $N(R^5)(R^6)$, optionally substituted $(C_1-C_6)$alkylthio, optionally substituted $(C_1-C_6)$alkyl, and optionally substituted $(C_1-C_6)$alkoxy;

when present, $R^9$ at each occurrence is independently selected from the group consisting of halogen, oxo, cyano, hydroxy, —$SF_5$, nitro, optionally substituted $(C_1-C_6)$alkyl, optionally substituted $(C_2-C_6)$alkenyl, optionally substituted $(C_2-C_6)$alkynyl, optionally substituted $(C_1-C_6)$alkylthio, optionally substituted $(C_1-C_6)$alkoxy, —$N(R^5)(R^6)$, $N(R^5)(C(O)R^6)$, —C(=O), —C(=O)—$R^5$, —C(=O)—$OR^5$, —$(SO_2)R^7$, and —$S(=O_2)N(R^5)(R^6)$;

------ is absent (forming a single bond) or a bond (forming a double bond); and n is an integer selected from 0 or 1, provided when ------ is present to form a double bond then n is 0, and when ------ is absent to form a single bond n is 1.

Compounds of the invention include Examples 1-97 or a pharmaceutically acceptable salt thereof as described herein.

The compounds of Formula I are inhibitors of the PDE4A, PDE4B and/or PDE4C isoforms.

The compounds of Formula I are useful for treating or preventing diseases and/or disorders of the central nervous system (CNS), pain, trauma, cardiologic, thrombotic, metabolic, autoimmune and inflammatory diseases or disorders, and disorders associated with enhanced endothelial activity/ impaired endothelial barrier function.

The present invention is also directed to the use of the compounds described herein, or a pharmaceutically acceptable salt thereof, in the preparation of a medicament for the treatment or prevention of a condition amenable to modulation of the PDE4A, PDE4B and PDE4C gene families (i.e., PDE4B enzymes).

The present invention is also directed to pharmaceutically acceptable formulations containing an admixture of a compound(s) of the present invention and at least one excipient formulated into a pharmaceutical dosage form. Examples of such dosage forms include tablets, capsules, suppositories, gels, creams, ointments, lotions, solutions/suspensions for injection (e.g., depot), aerosols for inhalation and solutions/ suspensions for oral ingestion.

DETAILED DESCRIPTION OF THE INVENTION

The headings within this document are only being utilized to expedite its review by the reader. They should not be construed as limiting the invention or claims in any manner.

Definitions and Exemplifications

As used throughout this application, including the claims, the following terms have the meanings defined below, unless specifically indicated otherwise. The plural and singular should be treated as interchangeable, other than the indication of number:

As used herein, the term "n-membered" where n is an integer typically describes the number of ring-forming atoms in a moiety where the number of ring-forming atoms is n. For example, pyridine is an example of a 6-membered heteroaryl ring and thiazole is an example of a 5-membered heteroaryl group.

At various places in the present specification, substituents of compounds of the invention are disclosed in groups or in ranges. It is specifically intended that the invention include each and every individual subcombination of the members of such groups and ranges. For example, the term "$(C_1-C_6)$ alkyl" is specifically intended to include $C_1$ alkyl (methyl), $C_2$ alkyl (ethyl), $C_3$ alkyl, $C_4$ alkyl, $C_5$ alkyl, and $C_6$ alkyl. For another example, the term "a 5- to 14-membered heteroaryl group" is specifically intended to include any 5-, 6-, 7-, 8-, 9-, 10-, 11-, 12-, 13- and 14-membered heteroaryl group.

The term "$(C_1-C_6)$alkyl" as used herein, refers to a saturated, branched- or straight-chain alkyl group containing from 1 to 6 carbon atoms, such as, but not limited to, methyl, ethyl, n-propyl, isopropyl, n-butyl, sec-butyl, isobutyl, tert-butyl, n-pentyl, isopentyl, neopentyl, and n-hexyl.

The term "optionally substituted $(C_1-C_6)$alkyl", as used herein, refers to a $(C_1-C_6)$alkyl as defined above, in which one or more hydrogen atoms are replaced by a substituent selected from the group consisting of halogen, oxo, cyano, hydroxy, —$SF_5$, $(C_1-C_6)$alkylthio, nitro, —C(=O)—$R^5$ and —N($R^5$)($R^6$), in which $R^5$ and $R^6$ are each independently hydrogen or $(C_1-C_6)$alkyl. For example, a $(C_1-C_6)$alkyl moiety can be substituted with one or more halogen atoms to form a "halo$(C_1-C_6)$alkyl". Representative examples of a halo$(C_1-C_6)$alkyl include, but are not limited to, fluoromethyl, difluoromethyl, 2-fluoroethyl, trifluoromethyl, pentafluoroethyl, and 2-chloro-3-fluoropentyl.

The term "$(C_2-C_6)$alkenyl" refers to an aliphatic hydrocarbon having from 2 to 6 carbon atoms and having at least one carbon-carbon double bond, including straight chain or branched chain groups having at least one carbon-carbon double bond. Representative examples include, but are not limited to, ethenyl, 1-propenyl, 2-propenyl (allyl), isopropenyl, 2-methyl-1-propenyl, 1-butenyl, 2-butenyl, and the like. When the compounds of the invention contain a $C_2-C_6$alkenyl group, the compound may exist as the pure E (entgegen) form, the pure Z (zusammen) form, or any mixture thereof.

The term "optionally substituted $(C_2-C_6)$alkenyl" refers to a $(C_2-C_6)$alkenyl as defined above, in which one or more hydrogen atoms are replaced by a substituent selected from the group consisting of halogen, oxo, cyano, hydroxy, —$SF_5$, —$(C_1-C_6)$alkylthio, nitro, —C(=O)—$R^5$, and —N($R^5$)($R^6$), in which $R^5$ and $R^6$ are each independently hydrogen or $(C_1-C_6)$alkyl.

The term "$(C_2-C_6)$alkynyl" refers to an aliphatic hydrocarbon having two to six carbon atoms and at least one carbon-carbon triple bond, including straight chains and branched chains having at least one carbon-carbon triple bond. Representative examples include, but are not limited to, ethynyl, propynyl, butynyl, pentynyl, and hexynyl.

The term "optionally substituted $(C_2-C_6)$alkynyl" refers to a $(C_2-C_6)$alkynyl as defined above, in which one or more hydrogen atoms are replaced by a substituent selected from the group consisting of halogen, oxo, cyano, hydroxy, —$SF_5$, $(C_1-C_6)$alkylthio, nitro, —C(=O)—$R^5$, and —N($R^5$)($R^6$), in which $R^5$ and $R^6$ are each independently hydrogen or $(C_1-C_6)$alkyl.

The term "$(C_1-C_6)$alkoxy" as used herein, refers to a $(C_1-C_6)$alkyl group, as defined above, attached to the parent molecular moiety through an oxygen atom. Representative examples of a $(C_1-C_6)$alkoxy include, but are not limited to, methoxy, ethoxy, propoxy, 2-propoxy, butoxy, tert-butoxy, pentyloxy, and hexyloxy.

The term "optionally substituted $(C_1-C_6)$alkoxy" as used herein, refers to a $(C_1-C_6)$alkoxy group, as defined above, in which one or more hydrogen atoms are replaced by a substituent selected from the group consisting of halogen, oxo, cyano, hydroxy, —$SF_5$, $(C_1-C_6)$alkylthio, nitro, —C(=O)—$R^5$, and —N($R^5$)($R^6$), in which $R^5$ and $R^6$ are each independently hydrogen or $(C_1-C_6)$alkyl. For example, a "$(C_1-C_6)$alkoxy can be substituted with one or more halogen atoms to form a "halo$(C_1-C_6)$alkoxy". Representative examples of a halo$(C_1-C_6)$alkoxy include, but are not limited to, fluoromethoxy, difluoromethoxy, 2-fluoroethoxy, trifluoromethoxy, and pentafluoroethoxy.

The term "$(C_1-C_6)$alkylthio" as used herein, refers to a $(C_1-C_6)$alkyl group, as defined above, attached to the parent molecular moiety through sulfur atom. Representative examples of a $(C_1-C_6)$alkylthio include, but are not limited to, thiomethyl, thioethyl, thiopropyl, and the like.

The term "optionally substituted $(C_1-C_6)$alkylthio" as used herein, refers to a $(C_1-C_6)$alkylthio group, as defined above, in which one or more hydrogen atoms are replaced by a substituent selected from the group consisting of halogen, oxo, cyano, hydroxy, —$SF_5$, $(C_1-C_6)$alkylthio, nitro, —C(=O)—$R^5$, and —N($R^5$)($R^6$), in which $R^5$ and $R^6$ are each independently hydrogen or $(C_1-C_6)$alkyl.

As used herein, the term "$(C_3-C_8)$cycloalkyl" refers to a carbocyclic substituent obtained by removing hydrogen from a saturated carbocyclic molecule wherein the cyclic framework has 3 to 8 carbons. A "$(C_3-C_6)$cycloalkyl" refers to a carbocyclic substituent obtained by removing hydrogen from a saturated carbocyclic molecule having from 3 to 6 carbon atoms. A "cycloalkyl' may be a monocyclic ring, examples of which include cyclopropyl, cyclobutyl, cyclopentyl, cyclohexyl, cycloheptyl, and cyclooctyl. Also included in the definition of cycloalkyl are unsaturated non-aromatic cycloalkyls such as, but not limited to, cyclohexenyl, cyclohexadienyl, cyclopentenyl, cycloheptenyl, and cyclooctenyl. Alternatively, a cycloalkyl may contain more than one ring such as a "$(C_4-C_8)$bicycloalkyl". The term "$(C_4-C_8)$bicycloalkyl" refers to a bicyclic ring system containing from 4 to 8 carbon atoms. The bicycloalkyl may be fused, such as bicyclo[1.1.0]butanyl, bicyclo[2.1.0]pentanyl, bicyclo[2.2.0]hexanyl, bicyclo[3.1.0]hexanyl, bicyclo [3.2.0]heptanyl, and bicyclo[3.3.0]-octanyl. The term "bicycloalkyl" also includes bridged bicycloalkyl systems such as, but not limited to, bicyclo[2.2.1]heptanyl and bicyclo [1.1.1]pentanyl.

The term "optionally substituted "$(C_3-C_8)$cycloalkyl" refers to a $(C_3-C_8)$cycloalkyl, as defined above, in which one or more hydrogen atoms are replaced by a substituent selected from the group consisting of halogen, oxo, cyano, hydroxy, —$SF_5$, nitro, —C(=O)—$R^5$, and —N($R^5$)($R^6$), in which $R^5$ and $R^6$ are each independently hydrogen or $(C_1-C_6)$alkyl.

A "heterocycloalkyl," as used herein, refers to a cycloalkyl as defined above, wherein at least one of the ring carbon atoms is replaced with a heteroatom selected from nitrogen, oxygen or sulfur. The term "(4- to 6-membered)heterocycloalkyl" means the heterocycloalkyl substituent contains a total of 4 to 6 ring atoms, at least one of which is a heteroatom. The term "(4- to 8-membered)heterocycloalkyl" means the heterocycloalkyl substituent contains a total of 4 to 8 ring atoms, at least one of which is a heteroatom. A "(4- to 10-membered)heterocycloalkyl" means the heterocycloalkyl substituent contains a total of 4 to 10 ring atoms. A "(6-membered)heterocycloalkyl" means the heterocycloalkyl substituent contains a total of 6 ring atoms, at least one of which is a heteroatom. A "(4- to 8-membered)oxygen-containing heterocycloalkyl" means the heterocycloalkyl substituent contains a total of 4 to 8 ring atoms at least one of which is an oxygen atom. A "(4- to 6-membered)oxygen-containing heterocycloalkyl" means the heterocycloalkyl substituent contains a total of 4 to 6 ring atoms at least one of which is an oxygen atom. A "(5-membered)heterocycloalkyl" means the heterocycloalkyl substituent contains a total of 5 ring atoms at least one of which is a heteroatom. A heterocycloalkyl may be a single ring with up to 10 total members. Alternatively, a heterocycloalkyl as defined above may comprise 2 or 3 rings fused together, wherein at least one such ring contains a heteroatom as a ring atom (i.e., nitrogen, oxygen, or sulfur). The heterocycloalkyl substituent may be attached to the core of the compounds of the present invention via a nitrogen atom having the appropriate valence, or via any ring carbon atom. The heterocycloalkyl moiety may be optionally substituted with one or more substituents at a nitrogen atom having the appropriate valence, or at any available carbon atom.

Also included in the definition of "heterocycloalkyl" are heterocycloalkyls that are fused to a phenyl or naphthyl ring or to a heteroaryl ring such as, but not limited to, a pyridinyl ring or a pyrimidinyl ring.

Examples of heterocycloalkyl rings include, but are not limited to, azetidinyl, dihydrofuranyl, dihydrothiophenyl, tetrahydrothiophenyl, tetrahydrofuranyl, tetrahydrotriazinyl, tetrahydropyrazolyl, tetrahydrooxazinyl, tetrahydropyrimidinyl, octahydrobenzofuranyl, octahydrobenzimidazolyl, octahydrobenzothiazolyl, imidazolidinyl, pyrrolidinyl, piperidinyl, piperazinyl, oxazolidinyl, thiazolidinyl, pyrazolidinyl, thiomorpholinyl, tetrahydropyranyl, tetrahydrothiazinyl, tetrahydrothiadiazinyl, tetrahydro-oxazolyl, morpholinyl, oxetanyl, dioxetanyl, dioxolanyl, dioxanyl, oxapanyl, dioxapanyl, oxacanyl, dioxacanyl, tetrahydrodiazinyl, oxazinyl, oxathiazinyl, quinuclidinyl, chromanyl, isochromanyl, dihydrobenzodioxinyl, benzodioxolyl, benzoxazinyl, indolinyl, dihydrobenzofuranyl, tetrahydroquinolyl, isochromyl, dihydro-1H-isoindolyl, 2-azabicyclo[2.2.1]heptanonyl, 3-azabicyclo[3.1.0]hexanyl, 3-azabicyclo[4.1.0]heptanyl and the like. Further examples of heterocycloalkyl rings include tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, 1,3-oxazolidin-3-yl, 1,4-oxazepan-1-yl, isothiazolidinyl, 1,3-thiazolidin-3-yl, 1,2-pyrazolidin-2-yl, 1,2-tetrahydrothiazin-2-yl, 1,3-thiazinan-3-yl, 1,2-tetrahydrodiazin-2-yl, 1,3-tetrahydrodiazin-1-yl, 1,4-oxazin-4-yl, oxazolidinonyl, 2-oxo-piperidinyl (e.g., 2-oxo-piperidin-1-yl), and the like.

The term "optionally substituted heterocycloalkyl" [e.g., optionally substituted (4- to 10-membered)heterocycloalkyl] refers to a heterocycloalkyl, as defined above, in which one or more hydrogen atoms are replaced by a substituent selected from the group consisting of halogen, oxo, cyano, hydroxy, $—SF_5$, $(C_1-C_6)$alkylthio, nitro, $—C(=O)—R^5$, and $N(R^5)(R^6)$, in which $R^5$ and $R^6$ are each independently hydrogen or $(C_1-C_6)$alkyl.

"$(C_6-C_{10})$aryl" refers to an all-carbon monocyclic or fused-ring polycyclic aromatic group having a conjugated pi-electron system containing from 6 to 10 carbon atoms, such as phenyl, or naphthyl.

The term "optionally substituted $(C_6-C_{10})$aryl" refers to a $(C_6-C_{10})$aryl, as defined above, in which one or more hydrogen atoms are replaced by a substituent selected from the group consisting of halogen, oxo, cyano, hydroxy, $—SF_5$, $(C_1-C_6)$alkylthio, nitro, $—C(=O)—R^5$, and $—N(R^5)(R^6)$, in which $R^5$ and $R^6$ are each independently hydrogen or $(C_1-C_6)$alkyl.

As used herein, the term "heteroaryl" refers to monocyclic or fused-ring polycyclic aromatic heterocyclic groups with one or more heteroatom ring members (ring-forming atoms) each independently selected from oxygen (O), sulfur (S) and nitrogen (N) in at least one ring. A "(5- to 14-membered) heteroaryl" ring refers to a heteroaryl ring having from 5 to 14 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. A "(5- to 10-membered)heteroaryl" ring refers to a heteroaryl ring having from 5 to 10 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. A "(5- to 8-membered)heteroaryl" ring refers to a heteroaryl ring having from 5 to 8 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. A "(5- to 8-membered) nitrogen-containing heteroaryl" ring refers to a heteroaryl ring having from 5 to 8 ring atoms in which at least one of the ring atoms is nitrogen, with the remaining ring atoms being independently selected from the group consisting of carbon, oxygen, sulfur and nitrogen. A "(5- to 6-membered) heteroaryl" refers to a heteroaryl ring having from 5 to 6 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. A "(5- to 6-membered)nitrogen-containing heteroaryl" refers to a heteroaryl ring having from 5 to 6 ring atoms in which at least one of the ring atoms is nitrogen, with the remaining ring atoms being independently selected from the group consisting of carbon, oxygen, sulfur and nitrogen. A "(6-membered) nitrogen-containing heteroaryl" refers to a heteroaryl ring having 6 ring atoms in which at least one of the ring atoms is nitrogen, with the remaining ring atoms being independently selected from the group consisting of carbon, oxygen, sulfur and nitrogen A "(5-membered)nitrogen-containing heteroaryl" refers to a heteroaryl ring having 5 ring atoms in which at least one of the ring atoms is nitrogen, with the remaining ring atoms being independently selected from the group consisting of carbon, oxygen, sulfur and nitrogen A heteroaryl may be a single ring or 2 or 3 fused rings. Examples of heteroaryls include, but are not limited to, 6-membered ring substituents such as pyridinyl, pyrazinyl, pyrimidinyl and pyridazinyl; 5-membered heteroaryls such as triazolyl, imidazolyl, furanyl, isoxazolyl, isothiazolyl, 1,2,3-, 1,2,4, 1,2,5-, or 1,3,4-oxadiazolyl, oxazolyl, thiophenyl, thiazolyl, isothiazolyl, and pyrazolyl; 6/5-membered fused ring substituents such as indolyl, indazolyl, benzofuranyl, benzimidazolyl, benzothienyl, benzoxadiazolyl, benzothiazolyl, isobenzothiofuranyl, benzothiofuranyl, benzisoxazolyl, benzoxazolyl, benzodioxolyl, furanopyridinyl, purinyl, imidazopyridinyl, imidazopyrimidinyl, pyrrolopyridinyl, pyrazolopyridinyl, pyrazolopyrimidinyl, thienopyridinyl, triazolopyrimidinyl, triazolopyridinyl (e.g., 5,6,7,8-tetrahydro[1,2,4]triazolo[1,5-a]pyridin-2-yl), and anthranilyl; and 6/6-membered fused ring substituents such as quinolinyl, isoquinolinyl, cinnolinyl, quinazolinyl, oxochromanyl, and 1,4-benzoxazinyl.

Nitrogen-containing heteroaryls include, but are not limited to, triazolyl, imidazolyl, isoxazolyl, isothiazolyl, 1,2,3-, 1,2,4, 1,2,5-, or 1,3,4-oxadiazolyl, oxazolyl, thiazolyl, isothiazolyl, pyrazolyl, pyridinyl, pyrazinyl, pyrimidinyl, pyridazinyl, indolyl, indazolyl, benzimidazolyl, benzoxadiazolyl, benzothiazolyl, benzisoxazolyl, benzoxazolyl, furanopyridinyl, purinyl, imidazopyridinyl, imidazopyrimidinyl, pyrrolopyridinyl, pyrazolopyridinyl, pyrazolopyrimidinyl, thienopyridinyl, triazolopyrimidinyl, triazolopyridinyl quinolinyl, isoquinolinyl, cinnolinyl, and quinazolinyl. 5-membered nitrogen-containing heteroaryls include, but are not limited to, triazolyl, imidazolyl, isoxazolyl, isothiazolyl, 1,2,3-, 1,2,4, 1,2,5-, or 1,3,4-oxadiazolyl, oxazolyl, thiazolyl, isothiazolyl, and pyrazolyl. 6-membered nitrogen-containing heteroaryls, include, but are not limited to, pyridinyl, pyrazinyl, pyrimidinyl and pyridazinyl.

It is to be understood that the heteroaryl may be optionally fused to a cycloalkyl group, or to a heterocycloalkyl group, as defined herein.

The heteroaryl substituent may be attached to the core of the compounds of the present invention via a nitrogen atom having the appropriate valence, or via any ring carbon atom or to the nitrogen of the amide moiety on the core. The heteroaryl moiety may be optionally substituted with one or more substituents at a nitrogen atom having the appropriate valence, or at any available carbon atom.

The terms "optionally substituted (5- to 14-membered) heteroaryl", "optionally substituted (5- to 8-membered)heteroaryl" "optionally substituted (5- to 6-membered)heteroaryl" and "optionally substituted (5- to 6-membered) nitrogen-containing heteroaryl" refer to a (5- to 14-membered)heteroaryl, a (5- to 8-membered)heteroaryl, a (5- to 6-membered)heteroaryl, and a (5- to 6-membered) nitrogen-containing heteroaryl, as defined above, in which one or more hydrogen atoms are replaced, where chemically permissible, by a substituent selected from the group consisting of halogen, oxo, cyano, hydroxy, —$SF_5$, ($C_1$-$C_6$) alkylthio, nitro, —C(=O)—$R^5$, and —N($R^5$)($R^6$), in which $R^5$ and $R^6$ are each independently hydrogen or optionally substituted ($C_1$-$C_6$)alkyl. The substituent can be attached to the heteroaryl moiety at any available carbon atom or to a heteroatom when the heteroatom is nitrogen having the appropriate valence.

"halo" or "halogen" as used herein, refers to a chlorine, fluorine, bromine, or iodine atom.

"hydroxy" or "hydroxyl" as used herein, means an —OH group.

"cyano" as used herein, means a —CN group, which also may be depicted:

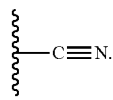

"nitro" as used herein, means an —$NO_2$ group.

"oxo" as used herein, means a =O moiety. When an oxo is substituted on a carbon atom, they together form a carbonyl moiety [—C(=O)—]. When an oxo is substituted on a sulfur atom, they together form a sulfonyl moiety [—S(=O)—]; when two oxo groups are substituted on a sulfur atom, they together form a sulfonyl moiety [—S(=O)2-].

"optionally substituted" as used herein, means that substitution is optional and therefore includes both unsubstituted and substituted atoms and moieties. A "substituted" atom or moiety indicates that any hydrogen on the designated atom or moiety can be replaced with a selection from the indicated substituent group (up to and including that every hydrogen atom on the designated atom or moiety is replaced with a selection from the indicated substituent group), provided that the normal valency of the designated atom or moiety is not exceeded, and that the substitution results in a stable compound. For example, if a methyl group (i.e., —$CH_3$) is optionally substituted, then up to 3 hydrogen atoms on the carbon atom can be replaced with substituent groups.

As used herein, unless specified, the point of attachment of a substituent can be from any suitable position of the substituent. For example, pyridinyl (or pyridyl) can be 2-pyridinyl (or pyridin-2-yl), 3-pyridinyl (or pyridin-3-yl), or 4-pyridinyl (or pyridin-4-yl).

"Therapeutically effective amount" refers to that amount of the compound being administered which will relieve to some extent one or more of the symptoms of the disorder being treated.

"Patient" refers to warm blooded animals such as, for example, pigs, cows, chickens, horses, guinea pigs, mice, rats, gerbils, cats, rabbits, dogs, monkeys, chimpanzees, and humans.

"Treating" or "treat", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

"Pharmaceutically acceptable" indicates that the substance or composition must be compatible, chemically and/or toxicologically, with the other ingredients comprising a formulation, and/or the mammal being treated therewith.

"Isoform" means any of several different forms of the same protein.

"Isozyme" or "isoenzyme" means a closely related variant of an enzyme that differs in amino acid sequence but catalyzes the same chemical reaction.

"Isomer" means "stereoisomer" and "geometric isomer" as defined below.

"Stereoisomer" refers to compounds that possess one or more chiral centers, which may each exist in the R or S configuration. Stereoisomers include all diastereomeric, enantiomeric and epimeric forms as well as racemates and mixtures thereof.

"Geometric isomer" refers to compounds that may exist in cis, trans, anti, entgegen (E), and zusammen (Z) forms as well as mixtures thereof.

This specification uses the terms "substituent," "radical," and "group" interchangeably.

If substituents are described as being "independently selected" from a group, each instance of a substituent is selected independent of the other. Each substituent therefore may be identical to or different from the other substituent(s).

As used herein the term "Formula I" may be hereinafter referred to as a "compound(s) of the invention." Such terms are also defined to include all forms of the compound of the invention including hydrates, solvates, isomers, crystalline and non-crystalline forms, isomorphs, polymorphs, and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist as clathrates or other complexes. Included within the scope of the invention are complexes such as clathrates, drug-host inclusion complexes wherein the drug and host are present in stoichiometric or non-stoichiometric amounts. Also included are complexes of the compounds of the invention containing two or more organic and/or inorganic components, which may be in stoichiometric or non-stoichiometric amounts. The resulting complexes may be ionized, partially ionized, or non-ionized. For a review of such complexes, see J. Pharm. Sci., 64 (8), 1269-1288 by Haleblian (August 1975).

The compounds of the invention have asymmetric carbon atoms. The carbon-carbon bonds of the compounds of the invention may be depicted herein using a solid line (———), a solid wedge (◢▬▬▬) or a dotted wedge (⋯⋯⋯ııı). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that the stereoisomer shown is present. When present in racemic compounds, solid and dotted wedges are used to define relative stereochemistry, rather than absolute stereochemistry. Racemic compounds possessing such indicated relative stereochemistry may be marked with (+/−). For example, unless stated otherwise, it is intended that the compounds of the invention can exist as stereoisomers, which include cis and trans isomers, optical isomers such as R and S enantiomers, diastereomers, geometric isomers, rotational isomers, conformational isomers, atropoisomers, and mixtures thereof (such as racemates and diastereomeric pairs). The compounds of the invention may exhibit more than one type of isomerism. Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of the present invention with an acid whose anion, or a base whose cation, is generally considered suitable for human consumption. Pharmaceutically acceptable salts are particularly useful as products of the methods of the present invention because of their greater aqueous solubility relative to the parent compound.

Suitable pharmaceutically acceptable acid addition salts of the compounds of the present invention when possible include those derived from inorganic acids, such as, but not limited to, hydrochloric, hydrobromic, hydrofluoric, boric, fluoroboric, phosphoric, meta-phosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include but are not limited to aliphatic, cycloaliphatic, aromatic, araliphatic, heterocyclic, carboxylic, and sulfonic classes of organic acids.

Specific examples of suitable organic acids include but are not limited to acetate, trifluoroacetate, formate, propionate, succinate, glycolate, gluconate, digluconate, lactate, malate, tartrate, citrate, ascorbate, glucuronate, maleate, fumarate, pyruvate, aspartate, glutamate, benzoate, anthranilate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylamino-ulfonate, algenic acid, ß-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalene-sulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanol-amine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

In one embodiment, hemisalts of acids and bases may also be formed, for example, hemisulphate and hemicalcium salts.

Certain compounds of the invention may exist as geometric isomers. The compounds of the invention may possess one or more asymmetric centers, thus existing as two, or more, stereoisomeric forms. The present invention includes all the individual stereoisomers and geometric isomers of the compounds of the invention and mixtures thereof. Individual enantiomers can be obtained by chiral separation or using the relevant enantiomer in the synthesis.

In addition, the compounds of the present invention can exist in unsolvated as well as solvated forms with pharmaceutically acceptable solvents such as water, ethanol and the like. In general, the solvated forms are considered equivalent to the unsolvated forms for the purposes of the present invention. The compounds may also exist in one or more crystalline states, i.e., polymorphs, or they may exist as amorphous solids. All such forms are encompassed by the claims.

Also within the scope of the present invention are so-called "prodrugs" of the compound of the invention. Thus, certain derivatives of the compound of the invention that may have little or no pharmacological activity themselves can, when administered into or onto the body, be converted into the compound of the invention having the desired activity, for example, by hydrolytic cleavage. Such derivatives are referred to as "prodrugs." Further information on the use of prodrugs may be found in "Pro-drugs as Novel Delivery Systems, Vol. 14, ACS Symposium Series (T. Higuchi and W. Stella) and "Bioreversible Carriers in Drug Design," Pergamon Press, 1987 (ed. E. B. Roche, American Pharmaceutical Association). Prodrugs in accordance with the invention can, for example, be produced by replacing appropriate functionalities present in the compounds of the present invention with certain moieties known to those skilled in the art as "pro-moieties" as described, for example, in "Design of Prodrugs" by H. Bundgaard (Elsevier, 1985).

This invention also encompasses compounds of the invention containing protective groups. One skilled in the art will also appreciate that compounds of the invention can also be prepared with certain protecting groups that are useful for purification or storage and can be removed before administration to a patient. The protection and deprotection of functional groups is described in "Protective Groups in Organic Chemistry", edited by J. W. F. McOmie, Plenum Press (1973) and "Protective Groups in Organic Synthesis", 3rd edition, T. W. Greene and P. G. M. Wuts, Wiley-Interscience (1999).

The present invention also includes all pharmaceutically acceptable isotopically-labeled compounds, which are identical to those recited herein, wherein one or more atoms are replaced by an atom having the same atomic number, but an atomic mass or mass number different from the atomic mass or mass number which predominates in nature. Examples of isotopes suitable for inclusion in the compounds of the present invention include, but are not limited to, isotopes of hydrogen, such as $^2$H, $^3$H; carbon, such as $^{11}$C, $^{13}$C, and $^{14}$C; chlorine, such as $^{36}$Cl; fluorine, such as $^{18}$F; iodine, such as $^{123}$I and $^{125}$I; nitrogen, such as $^{13}$N and $^{15}$N; oxygen, such as $^{15}$O, $^{17}$O, and $^{18}$O; phosphorus, such as $^{32}$P; and sulfur, such as $^{35}$S. Certain isotopically-labeled compounds of the present invention, for example, those incorporating a radioactive isotope, are useful in drug and/or substrate tissue distribution studies (e.g., assays). The radioactive isotopes tritium, i.e., $^3$H, and carbon-14, i.e., $^{14}$C, are particularly useful for this purpose in view of their ease of incorporation and ready means of detection. Substitution with heavier isotopes such as deuterium, i.e., $^2$H, may afford certain therapeutic advantages resulting from greater metabolic stability, for example, increased in vivo half-life or reduced dosage requirements and, hence, may be preferred in some circumstances. Substitution with positron emitting isotopes, such as $^{11}$C, $^{15}$F, $^{18}$F, $^{15}$O and $^{13}$N, can be useful in positron emission tomography (PET) studies for examining substrate receptor occupancy. Isotopically-labeled compounds of the present invention can generally be prepared by conventional techniques known to those skilled in the art or by processes analogous to those described in the accompanying Schemes and/or in the Examples and Preparations using an appropriate isotopically-labeled reagent in place of the non-labeled reagent previously employed. Pharmaceutically acceptable solvates in accordance with the invention include those wherein the solvent of crystallization may be isotopically substituted, e.g., D$_2$O, acetone-d$_6$, or DMSO-d$_6$. Compounds of the invention which includes compounds exemplified in Examples 1-97 described below, include isotopically-labeled versions of these compounds, such as, but not limited to, the deuterated and tritiated isotopes and all other isotopes discussed above.

In certain embodiments, the present invention is directed to novel, selective, radiolabelled PDE4 ligands which are useful for imaging and quantifying the PDE4B receptor in tissues (e.g., brain), using positron-emission tomography (PET).

In certain embodiments, the present invention is directed to 4-(8-Cyclopropyl-9-oxo-6,7,8,9-tetrahydropyrido[2',3':4,5]pyrrolo[1,2-a]pyrazin-10-yl)-2-[$^{18}$F]fluorobenzonitrile, or a pharmaceutically acceptable salt thereof and its use for imaging a tissue, cells or host, in vitro or in vivo.

Compounds

The compounds of Formula I, as described above, have a pyrrolo[1,2-a]pyrazinone core fused to a ring moiety represented by A. As described above, A along with the carbon atoms to which it is attached can form a fused (4- to 8-membered)oxygen-containing heterocycloalkyl ring, a fused phenyl ring, or a fused (5- to 8-membered)nitrogen-containing heteroaryl ring (i.e., the 4- to 8-membered) oxygen-containing heterocycloalkyl, phenyl or heteroaryl of ring A is fused to the pyrrole ring of the pyrrolo[1,2-a] pyrazinone core and thus is referred to as fused (4- to 8-membered)oxygen-containing heterocycloalkyl, a fused phenyl and fused heteroaryl).

In certain embodiments, in Formula I, A is selected from the group consisting of an optionally substituted fused (4- to 8-membered)oxygen-containing heterocycloalkyl ring, an optionally substituted fused phenyl ring, or an optionally substituted fused (5- to 6-membered) nitrogen-containing heteroaryl ring.

In certain embodiments, when A is a fused (4- to 8-membered)oxygen-containing heterocycloalkyl ring, the heterocycloalkyl ring is selected from the group consisting of oxetanyl, dihydrofuranyl, tetrahydrofuranyl, tetrahydropyranyl, oxepanyl, and oxocanyl.

In certain embodiments, A is a fused (4- to 6-membered) oxygen-containing heterocycloalkyl ring selected from the group consisting of oxetanyl, dihydrofuranyl, tetrahydrofuranyl, and tetrahydropyranyl. In certain embodiments, the fused (4- to 6-membered)oxygen-containing heterocycloalkyl ring is tetrahydropyranyl.

In certain other embodiments, A is a fused phenyl ring.

In certain other embodiments, when A is a fused (5- to 6-membered)nitrogen-containing heteroaryl ring the heteroaryl ring is selected from the group consisting of pyridinyl, pyrazinyl, pyrimidinyl pyridazinyl, triazolyl, imidazolyl, isoxazolyl, isothiazolyl, 1,2,3-, 1,2,4, 1,2,5-, or 1,3, 4-oxadiazolyl, oxazolyl, thiazolyl, isothiazolyl, and pyrazolyl.

In certain embodiments, A is a fused (5-membered)nitrogen-containing heteroaryl ring selected from the group consisting of triazolyl, imidazolyl, isoxazolyl, isothiazolyl, 1,2, 3-, 1,2,4, 1,2,5-, or 1,3,4-oxadiazolyl, oxazolyl, thiazolyl, isothiazolyl, and pyrazolyl. In certain embodiments the fused (5-membered)nitrogen-containing heteroaryl ring is thiazolyl.

In certain embodiments, A is a fused (6-membered)nitrogen-containing heteroaryl ring selected from the group consisting of pyridinyl, pyrazinyl, pyrimidinyl and pyridazinyl. In certain embodiments, A is a fused pyridinyl ring. In certain embodiments, A is a fused pyrimidinyl ring. In certain embodiments, A is a fused pyrazinyl ring. In certain embodiments, A is a fused pyridazinyl ring.

In any of the preceding embodiments, where chemically permissible, A is optionally substituted with one to three $R^8$, wherein each $R^8$ is independently selected from the group consisting of halogen, oxo, cyano, hydroxy, —$SF_5$, nitro, $N(R^5)(R^6)$, optionally substituted $(C_1-C_6)$alkylthio, optionally substituted $(C_1-C_6)$alkyl, and optionally substituted $(C_1-C_6)$alkoxy. In certain embodiments, when $R^8$ is a halogen, the halogen is selected from fluoro and chloro.

In certain other embodiments, when $R^8$ is an optionally substituted $(C_1-C_6)$alkyl, the alkyl is selected from methyl, ethyl or propyl, and the methyl, ethyl and propyl are optionally substituted with one to three fluorine atoms. For example, an optionally substituted alkyl includes, but is not limited to, fluoromethyl, difluoromethyl, trifluoromethyl, fluoroethyl, difluoroethyl, trifluoroethyl, and the like.

In yet another embodiment, when $R^8$ is an optionally substituted $(C_1-C_6)$alkoxy, the alkoxy is selected from methoxy, ethoxy or propoxy and the methoxy, ethoxy and propoxy are optionally substituted with one to three fluorine atoms. For example, an optionally substituted alkoxy includes, but is not limited to, fluoromethoxy, difluoromethoxy, trifluoromethoxy, fluoroethoxy, difluoroethoxy, trifluoroethoxy, and the like.

In certain embodiments A is unsubstituted.

It is to be understood that any of the above-mentioned subgenuses of A can be combined together with any of the embodiments for $R^1$, $R^2$, $R^{3a}$, $R^{3b}$, $R^{4a}$, $R^{4b}$ and n as described above and hereinafter.

In another embodiment, in Formula I as described above, $R^1$ is selected from the group consisting of an optionally substituted $(C_3-C_6)$cycloalkyl, an optionally substituted (4- to 10-membered)heterocycloalkyl, an optionally substituted $(C_6-C_{10})$aryl, and an optionally substituted (5- to 14-membered)heteroaryl.

In certain embodiments, when $R^1$ is an optionally substituted $(C_3-C_6)$cycloalkyl the cycloalkyl is selected from the group consisting of cyclopropyl, cyclobutyl, cyclopentyl, cyclohexyl, cyclohexenyl, cyclohexadienyl, and cyclopentenyl. In certain embodiments, $(C_3-C_6)$cycloalkyl is cyclopentyl.

In another embodiment, when $R^1$ is an optionally substituted (4- to 10-membered)heterocycloalkyl the heterocycloalkyl is selected from the group consisting of azetidinyl, dihydrofuranyl, dihydrothiophenyl, tetrahydrothiophenyl, tetrahydrofuranyl, tetrahydrotriazinyl, tetrahydropyrazolyl, tetrahydrooxazinyl, tetrahydropyrimidinyl, octahydrobenzofuranyl, octahydrobenzimidazolyl, octahydrobenzothiazolyl, imidazolidinyl, pyrrolidinyl, piperidinyl, piperazinyl, oxazolidinyl, thiazolidinyl, pyrazolidinyl, thiomorpholinyl, tetrahydropyranyl, tetrahydrothiazinyl, tetrahydrothiadiazinyl, tetrahydrooxazolyl, morpholinyl, oxetanyl, tetrahydrodiazinyl, oxazinyl, oxathiazinyl, quinuclidinyl, chromanyl, isochromanyl, dihydrobenzodioxinyl, benzodioxolyl, benzoxazinyl, indolinyl, dihydrobenzofuranyl, tetrahydroquinolyl, isochromyl, dihydro-1H-isoindolyl, 2-azabicyclo[2.2.1]heptanonyl, 3-azabicyclo[3.1.0]hexanyl, 3-azabicyclo[4.1.0]heptanyl and the like. Further examples of heterocycloalkyl rings include tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, 1,3-oxazolidin-3-yl, 1,4-oxazepan-1-yl, isothiazolidinyl, 1,3-thiazolidin-3-yl, 1,2-pyrazolidin-2-yl, 1,2-tetrahydrothiazin-2-yl, 1,3-thiazinan-3-yl, 1,2-tetrahydrodiazin-2-yl, 1,3-tetrahydrodiazin-1-yl, 1,4-oxazin-4-yl, oxazolidinonyl, 2-oxo-piperidinyl. In certain embodiments, the (4- to 10-membered)heterocycloalkyl is dihydrobenzofuranyl.

In certain other embodiments, $R^1$ is an optionally substituted (4- to 6-membered)heterocycloalkyl selected from the group consisting of azetidinyl, dihydrofuranyl, dihydrothiophenyl, tetrahydrothiophenyl, tetrahydrofuranyl, tetrahydrotriazinyl, tetrahydropyrazolyl, tetrahydrooxazinyl, tetrahydropyrimidinyl, imidazolidinyl, pyrrolidinyl, piperidinyl, piperazinyl, oxazolidinyl, thiazolidinyl, pyrazolidinyl, thiomorpholinyl, tetrahydropyranyl, tetrahydrothiazinyl, tetrahydrothiadiazinyl, tetrahydrooxazolyl, morpholinyl, oxetanyl, oxazinyl, and oxathiazinyl.

In certain other embodiments, when $R^1$ is an optionally substituted $(C_6-C_{10})$aryl the aryl is selected from phenyl or naphthyl. In certain embodiments, the $(C_6-C_{10})$aryl is phenyl.

In certain embodiments, when $R^1$ is an optionally substituted (5- to 10-membered)heteroaryl the heteroaryl is selected from the group consisting of pyridinyl, pyrazinyl, pyrimidinyl, pyridazinyl, triazolyl, imidazolyl, furanyl, isoxazolyl, isothiazolyl, 1,2,3-, 1,2,4, 1,2,5-, 1,3,4-oxadiazolyl, oxazolyl, thiophenyl, thiazolyl, isothiazolyl, pyrazolyl, indolyl, indazolyl, benzofuranyl, benzimidazolyl, benzothienyl, benzoxadiazolyl, benzothiazolyl, isobenzothiofuranyl, benzothiofuranyl, benzisoxazolyl, benzoxazolyl, benzodioxolyl, furanopyridinyl, purinyl, imidazopyridinyl, imidazopyrimidinyl, pyrrolopyridinyl, pyrazolopyridinyl, pyrazolopyrimidinyl, thienopyridinyl, triazolopyrimidinyl, triazolopyridinyl, anthranilyl, quinolinyl, cinnolinyl, quinazolinyl, oxochromanyl, and 1,4-benzoxazinyl. In certain embodiments, the (5- to 10-membered)heteroaryl is triazolopyridinyl or furopyridinyl.

In certain other embodiments, $R^1$ is an optionally substituted (5- to 6-membered)heteroaryl selected from the group consisting of oxazolyl, pyrazolyl, thiophenyl, thiazolyl, triazolyl, pyridinyl, and pyrimidinyl.

In certain embodiments, $R^1$ is an optionally substituted (5-membered)nitrogen-containing heteroaryl selected from pyrazolyl or triazolyl.

In certain other embodiments, $R^1$ is an optionally substituted (6-membered)nitrogen-containing heteroaryl selected from pyridinyl or pyrimidinyl.

In any of the preceding embodiments, where chemically permissible, $R^1$ is optionally substituted with one to three $R^9$, wherein each $R^9$ is independently selected from the group consisting of halogen, oxo, cyano, hydroxy, —$SF_5$, nitro, optionally substituted $(C_1-C_6)$alkylthio, optionally substituted $(C_1-C_6)$alkyl, optionally substituted $(C_1-C_6)$alkoxy, —$N(R^5)(R^6)$, —$(SO_2)R^7$, and —$S(=O_2)N(R^5)(R^6)$, wherein $R^5$ and $R^6$ at each occurrence are each independently selected from the group consisting of hydrogen and $(C_1-C_6)$alkyl, and $R^7$ is a $(C_1-C_6)$alkyl.

In certain embodiments, when $R^9$ is a halogen, the halogen is selected from fluoro and chloro.

In certain other embodiments, when $R^9$ is an optionally substituted $(C_1-C_6)$alkyl, the alkyl is selected from methyl, ethyl or propyl, and the methyl, ethyl and propyl are optionally substituted with one to three fluorine atoms. For example, an optionally substituted alkyl includes, but is not limited to, fluoromethyl, difluoromethyl, trifluoromethyl, fluoroethyl, difluoroethyl, trifluoroethyl, and the like.

In yet another embodiment, when $R^9$ is an optionally substituted $(C_1-C_6)$alkoxy, the alkoxy is selected from methoxy, ethoxy or propoxy and the methoxy, ethoxy and propoxy are optionally substituted with one to three fluorine atoms. For example, an optionally substituted alkoxy includes, but is not limited to, fluoromethoxy, difluoromethoxy, trifluoromethoxy, fluoroethoxy, difluoroethoxy, trifluoroethoxy, and the like.

It is to be understood that any of the above-mentioned subgenuses of $R^1$ can be combined together with any of the embodiments for A, $R^2$, $R^{3a}$, $R^{3b}$, $R^{4a}$, $R^{4b}$ and n as described above and hereinafter.

In another embodiment, in Formula I as described above, $R^2$ is selected from the group consisting of hydrogen, optionally substituted $(C_1-C_6)$alkyl, optionally substituted $(C_3-C_8)$cycloalkyl, optionally substituted (4- to 6-membered)heterocycloalkyl and optionally substituted (5- to 6-membered)heteroaryl.

In certain embodiments, $R^2$ is hydrogen.

In certain other embodiments, when $R^2$ is an optionally substituted $(C_1-C_6)$alkyl the alkyl is selected from methyl, ethyl, propyl, butyl, pentyl or hexyl. In certain embodiments the alkyl is methyl. In other embodiments, the alkyl is ethyl. In other embodiments, the alkyl is propyl.

In certain other embodiments, when $R^2$ is an optionally substituted $(C_3-C_8)$cycloalkyl the cycloalkyl is selected from cyclopropyl, cyclobutyl, cyclopentyl, cyclohexyl, cyclopentyl or cyclooctyl. In certain embodiments the cycloalkyl is cyclopropyl.

In certain other embodiments, when $R^2$ is an optionally substituted (4- to 6-membered)heterocycloalkyl the heterocycloalkyl is selected from the group consisting of azetidinyl, dihydrofuranyl, dihydrothiophenyl, tetrahydrothiophenyl, tetrahydrofuranyl, tetrahydrotriazinyl, tetrahydropyrazolyl, tetrahydrooxazinyl, tetrahydropyrimidinyl, imidazolidinyl, pyrrolidinyl, piperidinyl, piperazinyl, oxazolidinyl, thiazolidinyl, pyrazolidinyl, thiomorpholinyl, tetrahydropyranyl, tetrahydrothiazinyl, tetrahydrothiadiazinyl, tetrahydrooxazolyl, morpholinyl, oxetanyl, oxazinyl, and oxathiazinyl.

In certain other embodiments, when $R^2$ is an optionally substituted (5- to 6-membered)heteroaryl the heteroaryl is selected from the group consisting of oxazolyl, pyrazolyl, thiophenyl, thiazolyl, triazolyl, pyridinyl, and pyrimidinyl. In certain embodiments, $R^2$ is oxazolyl. In certain other embodiments, $R^2$ is triazolyl. In certain other embodiments, $R^2$ is pyrimidinyl.

In any of the preceding embodiments, where chemically permissible, $R^2$ is optionally substituted with one to three $R^8$, wherein each $R^8$ is independently selected from the group consisting of halogen, oxo, cyano, hydroxy, —$SF_5$, optionally substituted $(C_1-C_6)$alkylthio, optionally substituted, nitro, optionally substituted $(C_1-C_6)$alkyl, and optionally substituted $(C_1-C_6)$alkoxy.

In certain embodiments, when $R^8$ is a halogen, the halogen is selected from fluoro and chloro.

In certain other embodiments, when $R^8$ is an optionally substituted $(C_1-C_6)$alkyl, the alkyl is selected from methyl, ethyl or propyl, and the methyl, ethyl and propyl are optionally substituted with one to three fluorine atoms. For example, an optionally substituted alkyl includes, but is not limited to, fluoromethyl, difluoromethyl, trifluoromethyl, fluoroethyl, difluoroethyl, trifluoroethyl, and the like.

In yet another embodiment, when $R^8$ is an optionally substituted $(C_1-C_6)$alkoxy, the alkoxy is selected from methoxy, ethoxy or propoxy and the methoxy, ethoxy and propoxy are optionally substituted with one to three fluorine atoms. For example, an optionally substituted alkoxy includes, but is not limited to, fluoromethoxy, difluoromethoxy, trifluoromethoxy, fluoroethoxy, difluoroethoxy, trifluoroethoxy, and the like.

It is to be understood that any of the above-mentioned subgenuses of $R^2$ can be combined together with any of the embodiments for A, $R^1$, $R^{3a}$, $R^{3b}$, $R^{4a}$, $R^{4b}$ and n as described above and hereinafter.

In certain embodiments, in Formula I, $R^{3a}$, where chemically permissible, is selected from the group consisting of hydrogen, halogen, oxo, cyano, hydroxy, —$SF_5$, nitro, $N(R^5)(R^6)$, optionally substituted $(C_1-C_6)$alkylthio, optionally substituted $(C_1-C_6)$alkyl, optionally substituted $(C_1-C_6)$alkoxy, and optionally substituted $(C_3-C_8)$cycloalkyl.

In certain embodiments, $R^{3a}$ is a hydrogen.

In certain embodiments, when $R^{3a}$ is a halogen, the halogen is selected from fluoro and chloro.

In certain other embodiments, when $R^{3a}$ is an optionally substituted $(C_1-C_6)$alkyl, the alkyl is selected from methyl, ethyl or propyl, and the methyl, ethyl and propyl are optionally substituted with one to three fluorine atoms. For example, an optionally substituted alkyl includes, but is not limited to, fluoromethyl, difluoromethyl, trifluoromethyl, fluoroethyl, difluoroethyl, trifluoroethyl, and the like. In certain embodiments, $R^{3a}$ is methyl.

In yet another embodiment, when $R^{3a}$ is an optionally substituted $(C_1-C_6)$alkoxy, the alkoxy is selected from methoxy, ethoxy or propoxy and the methoxy, ethoxy and propoxy are optionally substituted with one to three fluorine atoms. For example, an optionally substituted alkoxy includes, but is not limited to, fluoromethoxy, difluoromethoxy, trifluoromethoxy, fluoroethoxy, difluoroethoxy, trifluoroethoxy, and the like.

It is to be understood that any of the above-mentioned subgenuses of $R^{3a}$ can be combined together with any of the embodiments for A, $R^1$, $R^2$, $R^{3b}$, $R^{4a}$, $R^{4b}$ and n as described above and hereinafter.

In certain embodiments, in Formula I, $R^2$ and $R^{3a}$ taken together with the nitrogen and carbon atoms to which they are attached form an optionally substituted (4- to 6-membered)heterocycloalkyl ring selected from the group consisting of azetidinyl, pyrrolidinyl, and morpholinyl.

In any of the preceding embodiments, when $R^2$ and $R^{3a}$ taken together with the nitrogen and carbon atoms to which they are attached form a (4- to 6-membered)heterocycloalkyl, where chemically permissible, the heterocycloalkyl can be substituted with one to three $R^8$ wherein each $R^8$ is independently selected from the group consisting of halogen, oxo, cyano, hydroxy, —$SF_5$, nitro, optionally substituted $(C_1-C_6)$alkyl, and optionally substituted $(C_1-C_6)$alkoxy.

It is to be understood that any of the above-mentioned subgenuses of $R^2$ and $R^{3a}$ taken together with the nitrogen to which they are attached can be combined together with any of the embodiments for A, $R^1$, $R^{3b}$, $R^{4a}$, $R^{4b}$ and n as described above and hereinafter.

In certain embodiments, in Formula I, when present $R^{3b}$, where chemically permissible, is selected from the group consisting of hydrogen, halogen, oxo, cyano, hydroxy, —$SF_5$, nitro, $N(R^5)(R^6)$, optionally substituted $(C_1-C_6)$alkylthio, optionally substituted $(C_1-C_6)$alkyl, optionally substituted $(C_1-C_6)$alkoxy, and optionally substituted $(C_3-C_8)$cycloalkyl.

In certain embodiments, $R^{3b}$ is a hydrogen.

In certain embodiments, when $R^{3b}$ is a halogen, the halogen is selected from fluoro and chloro.

In certain other embodiments, when $R^{3b}$ is an optionally substituted $(C_1-C_6)$alkyl, the alkyl is selected from methyl, ethyl or propyl, and the methyl, ethyl and propyl are optionally substituted with one to three fluorine atoms. For example, an optionally substituted alkyl includes, but is not limited to, fluoromethyl, difluoromethyl, trifluoromethyl, fluoroethyl, difluoroethyl, trifluoroethyl, and the like. In certain embodiments, $R^{3b}$ is methyl.

In yet another embodiment, when $R^{3b}$ is an optionally substituted $(C_1-C_6)$alkoxy, the alkoxy is selected from methoxy, ethoxy or propoxy and the methoxy, ethoxy and propoxy are optionally substituted with one to three fluorine atoms. For example, an optionally substituted alkoxy includes, but is not limited to, fluoromethoxy, difluoromethoxy, trifluoromethoxy, fluoroethoxy, difluoroethoxy, trifluoroethoxy, and the like.

It is to be understood that any of the above-mentioned subgenuses of $R^{3b}$ can be combined together with any of the embodiments for A, $R^1$, $R^2$, $R^{3a}$, $R^{4a}$, $R^{4b}$ and n as described above and hereinafter.

In certain embodiments, in Formula I, where chemically permissible. $R^{3a}$ and $R^{3b}$ taken together with the carbon atom to which they are attached form an optionally substituted $(C_3-C_6)$cycloalkyl selected from cyclopropyl, cyclobutyl, cyclopentyl or cyclohexyl. In certain embodiments, the cycloalky is cyclopropyl.

It is to be understood that any of the above-mentioned subgenuses of $R^{3a}$ and $R^{3b}$ taken together with the carbon atom to which they are attached can be combined together with any of the embodiments for A, $R^1$, $R^2$, $R^{4a}$, and $R^{4b}$ as described above and hereinafter.

In certain embodiments, in Formula I, where chemically permissible, $R^{4a}$ is selected from the group consisting of hydrogen, halogen, oxo, cyano, hydroxy, —$SF_5$, nitro, —$N(R^5)(R^6)$, optionally substituted $(C_1-C_6)$alkylthio, optionally substituted $(C_1-C_6)$alkyl, optionally substituted $(C_1-C_6)$alkoxy, and optionally substituted $(C_3-C_8)$cycloalkyl.

In certain embodiments, $R^{4a}$ is a hydrogen.

In certain embodiments, when $R^{4a}$ is a halogen, the halogen is selected from fluoro and chloro.

In certain other embodiments, when $R^{4a}$ is an optionally substituted $(C_1-C_6)$alkyl, the alkyl is selected from methyl, ethyl or propyl, and the methyl, ethyl and propyl are optionally substituted with one to three fluorine atoms. For example, an optionally substituted alkyl includes, but is not limited to, fluoromethyl, difluoromethyl, trifluoromethyl, fluoroethyl, difluoroethyl, trifluoroethyl, and the like. In certain embodiments, $R^{4a}$ is methyl.

In yet another embodiment, when $R^{4a}$ is an optionally substituted $(C_1-C_6)$alkoxy, the alkoxy is selected from methoxy, ethoxy or propoxy and the methoxy, ethoxy and propoxy are optionally substituted with one to three fluorine atoms. For example, an optionally substituted alkoxy includes, but is not limited to, fluoromethoxy, difluoromethoxy, trifluoromethoxy, fluoroethoxy, difluoroethoxy, trifluoroethoxy, and the like.

It is to be understood that any of the above-mentioned subgenuses of $R^{4a}$ can be combined together with any of the embodiments for A, $R^1$, $R^2$, $R^{3a}$, $R^{3b}$, $R^{4b}$ and n as described above and hereinafter.

In certain embodiments, in Formula I, when present $R^{4b}$, where chemically permissible, is selected from the group consisting of hydrogen, halogen, oxo, cyano, hydroxy, —$SF_5$, nitro, —$N(R^5)(R^6)$, optionally substituted $(C_1-C_6)$ alkylthio, optionally substituted $(C_1-C_6)$alkyl, optionally substituted $(C_1-C_6)$alkoxy, and optionally substituted $(C_3-C_8)$cycloalkyl.

In certain embodiments, $R^{4b}$ is a hydrogen.

In certain embodiments, when $R^{4b}$ is a halogen, the halogen is selected from fluoro and chloro.

In certain other embodiments, when $R^{4b}$ is an optionally substituted $(C_1-C_6)$alkyl, the alkyl is selected from methyl, ethyl or propyl, and the methyl, ethyl and propyl are optionally substituted with one to three fluorine atoms. For example, an optionally substituted alkyl includes, but is not limited to, fluoromethyl, difluoromethyl, trifluoromethyl, fluoroethyl, difluoroethyl, trifluoroethyl, and the like. In certain embodiments, $R^{4b}$ is methyl.

In yet another embodiment, when $R^{4b}$ is an optionally substituted $(C_1-C_6)$alkoxy, the alkoxy is selected from methoxy, ethoxy or propoxy and the methoxy, ethoxy and propoxy are optionally substituted with one to three fluorine atoms. For example, an optionally substituted alkoxy includes, but is not limited to, fluoromethoxy, difluoromethoxy, trifluoromethoxy, fluoroethoxy, difluoroethoxy, trifluoroethoxy, and the like.

In yet another embodiment, $R^{4a}$ and $R^{4b}$ taken together with the carbon atom to which they are attached form a $(C_3-C_6)$cycloalkyl or (4- to 6-membered)heterocycloalkyl, and where chemically permissible, the $(C_3-C_6)$cycloalkyl or (4- to 6-membered)heterocycloalkyl are optionally substituted with one to three $R^8$;

It is to be understood that any of the above-mentioned subgenuses of $R^{4a}$ and $R^{4b}$ can be combined together with any of the embodiments for A, $R^1$, $R^2$, $R^{3a}$, $R^{3b}$ and n as described above.

In certain embodiments, in Formula I, ------ is absent or a bond. In certain embodiments ------- is a bond and n is 0. In certain embodiments ------ is absent and n is 1.

It is to be understood that any of the above-mentioned subgenuses of ------- can be combined together with any of the embodiments for A, $R^1$, $R^2$, $R^{3a}$, $R^{3b}$, $R^{4a}$ and $R^{4b}$ as described above.

In another embodiment, selected compounds of the present invention may be useful for treating a PDE4A, PDE4B, and/or PDE4C-mediated disorders, comprising administering to a mammal (preferably a human) in need thereof a therapeutically effective amount of a compound of the invention effective in inhibiting PDE4A, PDE4B and/or PDE4C activity; more preferably, administering an amount of a compound of the invention having improved binding affinity for PDE4A, PDE4B and/or PDE4C while at the same time possessing less inhibitory activity toward PDE4D.

In certain other embodiments, selected compounds of the present invention may exhibit a binding affinity for the PDE4B isoform In certain other embodiments, selected compounds of the present invention may exhibit a binding affinity for the PDE4A isoform. In certain other embodiments, selected compounds of the present invention may exhibit a binding affinity for the PDE4C isoform.

In certain embodiments, the compounds of the present invention have an enhanced binding affinity for the PDE4B isoform over the PDE4D isoform such that the compounds display about a 2-fold to about a 325-fold binding affinity for the PDE4B isoform over the PDE4D isoform. In certain other embodiments, the compounds of the present invention display about a 10-fold to about a 50-fold binding affinity for the PDE4B isoform over the PDE4D isoform. In certain other embodiments, the compounds of the present invention display about a 51-fold to about a 100-fold binding affinity for the PDE4B isoform over the PDE4D isoform. In certain other embodiments, the compounds of the present invention display about a 101-fold to about a 200-fold binding affinity for the PDE4B isoform over the PDE4D isoform. In certain embodiments, the compounds of the present invention display at least about a 2-fold binding affinity for the PDE4B isoform over the PDE4D isoform. In certain embodiments, the compounds of the present invention display at least about a 5-fold binding affinity for the PDE4B isoform over the PDE4D isoform. In certain embodiments, the compounds of the present invention display at least about a 10-fold binding affinity for the PDE4B isoform over the PDE4D isoform. In certain embodiments, the compounds of the present invention display at least about a 20-fold binding affinity for the PDE4B isoform over the PDE4D isoform. In certain other embodiments, the compounds of the present invention display at least about a 40-fold binding affinity for the PDE4B isoform over the PDE4D isoform. In certain other embodiments, the compounds of the present invention display at least about a 50-fold binding affinity for the PDE4B isoform over the PDE4D isoform. In certain other embodiments, the compounds of the present invention display at least about a 75-fold binding affinity for the PDE4B isoform over the PDE4D isoform. In certain other embodiments, the compounds of the present invention display at least about a 100-fold binding affinity for the PDE4B isoform over the PDE4D isoform. In certain other embodiments, the compounds of the present invention display at least about a 200-fold binding affinity for the PDE4B isoform over the PDE4D isoform. In certain other embodiments, the compounds of the present invention display at least about a 325-fold binding affinity for the PDE4B isoform over the PDE4D isoform. The binding affinities of the compounds of the present invention for the PDE4B and PDE4D isoforms are shown in Tables 9 and 10 of the Experimental Section below.

In another embodiment, the present invention provides a pharmaceutical composition comprising a compound of the present invention, or a pharmaceutically acceptable salt thereof, in admixture with at least one pharmaceutically acceptable excipient.

In yet another embodiment, administration of the compounds of the present invention to a patient in need thereof may also lead to a decrease in gastrointestinal discomfort such as emesis, diarrhea, and nausea, which is currently believed to be associated with administration of compounds having binding affinity for other PDE4 isoforms, especially the PDE4D isoform, resulting in an increase in patient compliance as well as overall treatment outcome.

In another embodiment, the present invention provides a method of treating central nervous system (CNS), neuroinflammatory, metabolic, autoimmune and inflammatory diseases or disorders comprising administering to the mammal, particularly a human, in need of such treatment a therapeutically effect amount of a compound of the present invention, or a pharmaceutically acceptable salt thereof.

In another embodiment, the present invention provides the use of a compound of the present invention, or a pharmaceutically acceptable salt thereof, in the manufacture of a medicament for treating central nervous system (CNS), neuroinflammatory, autoimmune and inflammatory diseases or disorders.

Pharmacology

Phosphodiesterases (PDEs) of the PDE4 family are characterized by selective, high-affinity hydrolytic degradation of the second messenger cyclic nucleotide, adenosine 3',5'-cyclic monophosphate (cAMP). The PDE4A, PDE4B and PDE4D subtypes are known to be widely expressed throughout the brain, with regional and intracellular distribution for the PDE4A, PDE4B and PDE4D subtypes being distinct, whereas the PDE4C subtype is expressed at lower levels throughout the central nervous system (See; Siuciak, J. A. et al., *Antipsychotic profile of rolipram: efficacy in rats and reduced sensitivity in mice deficient in the phosphodiesterase-4B (PDE4B) enzyme*, Psychopharmacology (2007) 192:415-424). The location of the PDE4 subtypes makes them an interesting target for exploring new treatments for central nervous system diseases and disorders. For example, PDE4B has been identified as a genetic susceptibility factor for schizophrenia (See: Millar, J. K. et al., *Disrupted in schizophrenia 1 and phosphodiesterase 4B: towards an understanding of psychiatric illness*, J. Physiol. 584 (2007) pp. 401-405).

The PDE4 inhibitor rolipram has been shown to be useful in treating or reversing Aβ-induced memory deficits in rats via the attenuation of neuronal inflammation and apoptosis-mediated cAMP/CREB signaling, and is a potential target for treatment of cognitive deficits associated with AD. (See: Wang, C. et al., *The phosphodiesterase-4 inhibitor rolipram reverses Aβ-induced cognitive impairment and neuroinflammatory and apoptotic responses in rats*, International Journal of Neuropsychopharmacology (2012), 15, 749-766).

PDE4 inhibitors have also been shown to possess antidepressant effects by decreasing brain levels of PDE4 in individuals with major depressive disorder (MDD) (See: Fujita, M. et al., *C-(R-)-Rolipram Positron Emission Tomography in Major Depressive Disorder*, Biological Psychiatry, 71, 2012, 548-554).

Furthermore, PDE4 inhibitors have been shown to possess therapeutic activity with implications for the treatment of multiple sclerosis (See: Sun, X. et al., *Rolipram promotes remyelination possibly via MEK-ERK signal pathway in cuprizone-induced demyelination mouse*, Experimental Neurology 2012; 237:304-311).

In view of the above, in certain embodiments, the compounds of the present invention have a wide range of therapeutic applications for the treatment of conditions or diseases of the central nervous system which include neurologic, neurodegenerative and/or psychiatric disorders. Neurologic, neurodegenerative and/or psychiatric disorders, include but are not limited to, (1) mood [affective] disorders; (2) neurotic, stress-related and somatoform disorders including anxiety disorders; (3) disorders comprising the symptom of cognitive deficiency in a mammal, including a human; (4) disorders comprising attention deficits, executive function deficits (working memory deficits), dysfunction of impulse control, extrapyramidal symptoms, disorders that are based on a malfunction of basal ganglia; (5) behavioral and emotional disorders with onset usually occurring in childhood and adolescence; (6) disorders of psychological development; (7) systemic atrophies primarily affecting the central nervous system; (8) extrapyramidal and movement disorders; (9) behavioral syndromes associated with physiological disturbances and physical factors; (10) disorders of adult personality and behavior; (11) schizophrenia and other psychotic disorders; (12) mental and behavioral disorders due to psychoactive substance use; (13) sexual dysfunction comprising excessive sexual drive; (14) mental retardation; (15) factitious disorders, e.g., acute hallucinatory mania; (16) episodic and paroxysmal disorders, epilepsy; (17) narcolepsy; (18) dementia.

Examples of mood [affective] disorders that can be treated according to the present invention include, but are not limited to, bipolar disorder I, hypomania (manic and mixed form), bipolar disorder II; depressive disorders such as single depressive episode or recurrent major depressive disorder, chronic depression, psychotic depression, minor depressive disorder, depressive disorder with postpartum onset, depressive disorders with psychotic symptoms; persistent mood [affective] disorders such as cyclothymia, dysthymia, euthymia; premenstrual syndrome (PMS) and premenstrual dysphoric disorder.

Examples of neurotic, stress-related and somatoform disorders that can be treated according to the present invention include, but are not limited to, anxiety disorders, social anxiety disorder, general anxiety disorder, panic disorder with or without agoraphobia, specific phobia, social phobia, chronic anxiety disorders; obsessive compulsive disorder; reaction to sever stress and adjustment disorders, such as post traumatic stress disorder (PTSD), acute stress disorder; other neurotic disorders such as depersonalization-derealization syndrome.

The phrase "cognitive deficiency" as used here in "disorder comprising as a symptom cognitive deficiency" refers to a subnormal functioning or a suboptimal functioning in one or more cognitive aspects such as memory, intellect, learning and logic ability, or attention and executive function (working memory) in a particular individual comparative to other individuals within the same general age population.

Examples of disorders comprising as a symptom cognitive deficiency that can be treated according to the present invention include, but are not limited to, cognitive deficits primarily but not exclusively related to amnesia, psychosis (schizophrenia), Parkinson's disease, Alzheimer's disease, multi infarct dementia, senile dementia, Lewis body dementia, stroke, frontotemporal dementia, progressive supranuclear palsy, Huntington's disease, HIV disease (HIV-associated dementia), cerebral trauma and drug abuse; mild cognitive disorder ADHD, Asperger's syndrome, and age-associated memory impairment.

Examples of disorders usually first diagnosed in infancy, childhood and adolescence that can be treated according to the present invention include, but are not limited to, hyperkinetic disorders including disturbance of activity and attention, attention deficit/hyperactivity disorder (ADHD), hyperkinetic conduct disorder; attention deficit disorder (ADD); conduct disorders, including but not limited to depressive conduct disorder; tic disorders including transient tic disorder, chronic motor or vocal tic disorder, combined vocal and multiple motor tic disorder (Gilles de la Tourette's syndrome), substance induced tic disorders; autistic disorders; Batten disease, excessive masturbation nail-biting, nose-picking and thumb-sucking.

Examples of disorders of psychological development that can be treated according to the present invention include, but are not limited to pervasive developmental disorders, including but not limited to Asperger's syndrome and Rett syndrome, autistic disorders, childhood autism and overactive disorder associated with mental retardation and stereotyped movements, specific developmental disorder of motor function, specific developmental disorders of scholastic skills.

Examples of systemic atrophies primarily affecting the central nervous system that can be treated according to the present invention include, but are not limited to, multiple sclerosis systemic atrophies primarily affecting the basal ganglia including Huntington's disease, and amyotrophic lateral sclerosis.

Examples of extrapyramidal and movement disorders with malfunction and/or degeneration of basal ganglia that can be treated according to the present invention include, but are not limited to, Parkinson's disease; second Parkinsonism such as postencephalitic Parkinsonism; Parkinsonism comprised in other disorders; Niemann-Pick disease, Lewy body disease; degenerative diseases of the basal ganglia; other extrapyramidal and movement disorders including tremor, essential tremor and drug-induced tremor, myoclonus, chorea and drug-induced chorea, drug-induced tics and tics of organic origin, drug-induced acute dystonia, drug-induced tardive dyskinesia, muscular spasms and disorders associated with muscular spasticity or weakness including tremors; mental deficiency (including spasticity, Down syndrome and fragile X syndrome)L-dopa-induced dyskinesia; restless leg syndrome Stiff-man syndrome.

Further examples of movement disorders with malfunction and/or degeneration of basal ganglia that can be treated according to the present invention include, but are not limited to, dystonia including but not limited to focal dystonia, multiple-focal or segmental dystonia, torsion dystonia, hemispheric, generalized and tardive dystonia (induced by psychopharmacological drugs). Focal dystonia include cervical dystonia (torticolli), blepharospasm (cramp of the eyelid), appendicular dystonia (cramp in the extremities, like the writer's cramp), oromandibular dystonia and spasmodic dysphonia (cramp of the vocal cord); neuroleptic-induced movement disorders including but not limited to neuroleptic malignant syndrome (NMS), neuroleptic induced parkinsonism, neuroleptic-induced early onset or acute dyskinesia, neuroleptic-induced acute dystonia, neuroleptic-induced acute akathisia, neuroleptic-induced tardive dyskinesia, neuroleptic-induced tremor.

Examples of behavioral syndromes associated with physiological disturbances and physical factors according to the present invention include, but are not limited to nonorganic sleep disorders, including but not limited to nonorganic hypersomnia, nonorganic disorder of the sleep-wake schedule (circadian rhythm sleep disorder), insomnia, parasomnia and sleep deprivation; mental and behavioral disorders associated with the puerperium including postnatal and postpartum depression; eating disorders, including but not limited to anorexia nervosa, bulimia nervosa, binge eating disorder, hyperphagia, obesity, compulsive eating disorders and pagophagia.

Examples of disorders of adult personality and behavior that can be treated according to the present invention include, but are not limited to, personality disorders, including but not limited to emotionally unstable, borderline, obsessive-compulsive, anankastic, dependent and passive-aggressive personality disorder; habit and impulse disorders (impulse-control disorder) including intermittent explosive disorder, pathological gambling, pathological fire-setting (pyromania), pathological stealing (kleptomania), trichotillomania; Munchausen syndrome.

Examples of schizophrenia and other psychotic disorders that can be treated according to the present invention include, but are not limited to, continuous or episodic schizophrenia of different types (for instance paranoid, hebephrenic, catatonic, undifferentiated, residual, and schizophreniform disorders); schizotypal disorders (such as borderline, latent, prepsychotic, prodromal, pseudoneurotic pseudopsychopathic schizophrenia and schizotypal personality disorder); persistent delusional disorders; acute, transient and persistent psychotic disorders; induced delusional disorders; schizoaffective disorders of different type (for instance manic depressive or mixed type); puerperal psychosis and other and unspecified nonorganic psychosis.

Examples of mental and behavioral disorders due to psychoactive substance use that can be treated according to the present invention include, but are not limited to, mental and behavioral disorders due to use of alcohol, opioids, cannabinoids, sedatives or hypnotics, cocaine; mental and behavioral disorders due to the use of other stimulants including caffeine, mental and behavioral disorders due to drug dependence and abuse (e.g., narcotic dependence, alcoholism, amphetamine and methamphetamine dependence, opioid dependence, cocaine addiction, nicotine dependence, and drug withdrawal syndrome, and relapse prevention), use of hallucinogens, tobacco (nicotine), volatile solvents and mental and behavioral disorders due to multiple drug use and use of other psychoactive substances including the following subtype symptoms: harmful use, dependence syndrome, withdrawal state, and withdrawal state with delirium.

Examples of dementia that can be treated according to the present invention include, but are not limited to, vascular dementia, dementia due to Creutzfeld-Jacob disease, HIV, head trauma, Parkinson's, Huntington's, Pick's disease, dementia of the Alzheimer's type.

In certain embodiments, the present invention is directed to methods for the treatment of schizophrenia by administration of a therapeutically effective amount of a tricyclic compound of the present invention to a patient in need thereof.

In certain other embodiments, the invention is further directed to a method for the treatment of cognitive impairment associated with schizophrenia by administration of a therapeutically effective amount of a tricyclic compound of the present invention to a patient in need thereof.

In addition to the central nervous system disorders mentioned above, there is extensive literature in the art describing the effects of PDE inhibitors on various autoimmune and inflammatory cell responses, which in addition to CAMP increase, include inhibition of superoxide production, degranulation, chemotaxis and tumor necrosis factor (TNF) release in eosinophils, neutrophils and monocytes. Therefore, the tricyclic compounds of the present invention may be useful for treating autoimmune and inflammatory diseases. (See: Schett, G. et al., Apremilast: *A novel PDE4 Inhibitor in the Treatment of Autoimmune and Inflammatory Diseases*, Ther. Adv. Musculoskeletal Dis. 2010; 2(5):271-278). For example, the compounds of the present invention may be useful for treatment of oral ulcers associated with Behçet's disease (ld.). The compounds of the present invention may also be useful for the treatment of pain associated with arthritis (See: Hess, A. et al., *Blockade of TNF-α rapidly inhibits pain responses in the central nervous system*, PNAS, vol. 108, no. 9, 3731-3736 (2011) or for the treatment of psoriasis or psoriatic arthritis (See: Schafer, P., *Apremilast mechanism of action and application to psoriasis and psoriatic arthritis*, Biochem. Pharmacol. (2012), 15; 83(12): 1583-90). Accordingly, tricyclic compounds of the present invention may also be useful for treatment of ankylosing spondylitis [see: Patan, E. et al., *Efficacy and safety of apremilast, an oral phosphodiesterase 4 inhibitor, in ankylosing spondylitis*, Ann. Rheum. Dis. (Sep. 14, 2102)]. Other conditions treatable by administration of the compounds of the present invention include, but are not limited to, acute and chronic airway diseases such as, but not limited to, asthma, chronic or acute bronchoconstriction, chronic bronchitis, bronchiectasis, small airways obstruction, emphysema, obstructive or inflammatory airways diseases, acute respiratory distress syndrome (ARDS), COPD, pneumoconiosis, seasonal allergic rhinitis or perennial allergic rhinitis or sinusitis, and acute lung injury (ALI)

In yet another embodiment, the compounds of the present invention may be useful for treating erectile dysfunction, rheumatoid arthritis, osteoarthritis, osteoporosis, gout, and fever, edema and pain associated with inflammation, eosinophil-related disorders, skin and connective tissue disorders such as dermatitis or eczema, urticaria, conjunctivitis, uveitis, psoriasis, inflammatory bowel disease, ulcerative colitis, sepsis, septic shock, liver injury, pulmonary hypertension, pulmonary edema, bone loss disease, foot ulcers and infection.

In yet another embodiment, the compounds of the present invention may be useful for treating cancer. For example, the compounds of the present invention may be useful for treatment of brain cancer (e.g., medulloblastoma) (See: Schmidt, A. L., *BDNF and PDE4, but not GRPR, Regulate Viability of Human Medulloblastoma Cells*, J. Mol. Neuroscience (2010) 40:303-310). The compounds of the present invention may also be useful for treating melanoma (See: Marquette, A. et al., *ERK and PDE4 cooperate to induce RAF isoform switching in melanoma*, Nature Structural & Molecular Biology, vol. 18, no. 5, 584-91, 2011). In certain embodiments, the compounds of the present invention may be useful for treating leukemia, e.g., chronic lymphocytic leukemia, (See: Kim, D. H. et al., *Type 4 Cyclic Adenosine Monophosphate Phosphodiesterase as a Therapeutic Target in Chronic Lymphocytic Leulemia*, Blood Journal of The American Society of Hematology, Oct. 1, 1998, vol. 92, no. 7 2484-2494).

In certain other embodiments, the compounds of the present invention may be useful for treating diabetes or diseases associated with diabetes (See: Vollert, S. et al., *The glucose-lowering effects of the PDE4 inhibitors roflumilast and roflumilast-N-Oxide in db/db mice*, Diabetologia (2012) 55:2779-2788. Wouters, E. F. M. et al., Effect of the Phosphodiesterase 4 *Inhibitor Roflumilast on Glucose Metabolism in Patients with Treatment-Naïve, Newly Diagnosed Type* 2 *Diabetes Mellitus*, Journal of Clinical Endocrinology and Metabolism 2012, 97, 1720-1725). Other examples include, but are not limited to, diabetic macular degeneration, diabetic neuropathy, obesity, Type I diabetes, Type II diabetes mellitus, idiopathic Type I diabetes (Type Ib), latent autoimmune diabetes in adults (LADA), early-onset Type II diabetes (EOD), youth-onset atypical diabetes (YOAD), maturity onset diabetes of the young (MODY), malnutrition-related diabetes, gestational diabetes, metabolic syndrome, syndrome X, impaired glucose metabolism, glucose intolerance, conditions of impaired glucose tolerance (IGT), conditions of impaired fasting plasma glucose, hyperglycemia, hyperinsulinemia, insulin resistance, metabolic acidosis, ketosis, urinary incontinence (e.g., bladder overactivity), diabetic macular edema, nephropathy and related health risks (e.g., diabetic nephropathy), symptoms or disorders. As such, the compounds can also be used to reduce body fat or body weight of an overweight or obese individual.

In certain other embodiments, the compounds of the present invention may be useful in the prevention and treatment of disorders associated with enhanced endothelial activity, impaired endothelial barrier function and/or enhanced neoangiogenesis, such as septic shock; angioedema, peripheral edema, communicating or non-communicating hydrocepahuls, vascular edema, cerebral edema; reduced natriuria pathology; inflammatory diseases, including asthma, rhinitis, arthritis and rheumatoid diseases and autoimmune diseases; acute and/or chronic renal or liver failure, glomerulosclerosis, liver dysfunction; non-alcoholic steatohepatitis (NASH), non-alcoholic fatty liver disease (NAFLD), psoriasis, Irritable Bowel Disease (IBD), Crohn's disease, and benign/malignant neoplasia.

In certain other embodiments, the compounds of the present invention may be useful for treating diseases of the spinal cord and/or peripheral nervous system, including spinal cord injury, spinal cord edema, spinal cord tumors, vascular malformations or anomalies of the spinal cord, syringomyelia, hydromyelia.

In certain other embodiments, the compounds described herein are further useful in the prevention and treatment of disorders associated with cardiovascular disease, thrombosis, embolism, or ischemic disorders including, but not limited to thrombosis induced tissue infarction in coronary artery disease, in cerebrovascular disease (including cerebral arteriosclerosis, cerebral amyloid angiopathy, hereditary cerebral hemorrhage, and brain hypoxia-ischemia) and/or in peripheral vascular disease; left ventricular hypertrophy, peripheral arterial disease, hyper apo B lipoproteinemia, hyperlipidemia, hypertriglyceridemia, dyslipidemia, postprandial lipemia, stable and unstable angina, angina pectoris, transient ischemic attacks, stroke, intermittent claudication, atherosclerosis, congestive heart failure, hypertension, myocardial infarct (e.g., necrosis and apoptosis), cerebral infarct, reperfusion injury (brain/cardiac), traumatic brain injury, subdural, epidural or subarachnoid hemorrhage, migraine, cluster and tension headaches, placenta insufficiency thrombosis after surgical procedures, such as bypass, angioplasty, restenosis after angioplasty, stent placement, heart valve replacement, cognitive decline or delirium postoperative or in association with intensive care therapy, brain or ophthalmologic tumors.

In certain other embodiments, the compounds described herein are further useful for treating pain conditions and disorders. Examples of such pain conditions and disorders include, but are not limited to, inflammatory pain, hyperalgesia, inflammatory hyperalgesia, migraine, cancer pain, osteoarthritis pain, post-surgical pain, non-inflammatory pain, neuropathic pain, sub-categories of neuropathic pain including peripheral neuropathic pain syndromes, chemotherapy-induced neuropathy, complex regional pain syndrome, HIV sensory neuropathy, neuropathy secondary to tumor infiltration, painful diabetic neuropathy, phantom limb pain, postherpetic neuralgia, postmastectomy pain, trigeminal neuralgia, central neuropathic pain syndromes, central post stroke pain, multiple sclerosis pain, Parkinson disease pain, and spinal cord injury pain.

In certain other embodiments, the compounds described herein are further useful for treating wounds or promoting wound healing, burns, scarring, and related conditions.

In certain other embodiments, the compounds described herein are further useful for treating neuronal damage disorders (including ocular damage, cataract, retinopathy including diabetic macular edema or macular degeneration of the eye, tinnitus, hearing impairment and loss, and brain edema).

In certain other embodiments, the compounds described herein are further useful for treating transplant rejection, allograft rejection, renal and liver failure, and restless leg syndrome.

The compounds of the invention are also useful in treating and/or preventing a disease or condition mediated by or otherwise associated with an IRAK enzyme; the method comprising administering to a subject in need thereof an effective amount of a compound of the invention.

The disease may be, but not limited to, one of the following classes: auto-immune diseases, inflammatory diseases, allergic diseases, metabolic diseases, infection-based diseases, trauma or tissue-injury based diseases, fibrotic diseases, genetic diseases, diseases driven by over-activity of IL1 pathways, cardiovascular diseases, vascular diseases, heart diseases, neurological diseases, neurodegenerative diseases, respiratory diseases, pulmonary diseases, airways diseases, renal diseases, skin and/or dermatological diseases, liver diseases, gastrointestinal diseases, oral diseases, pain and sensory diseases, hematopoietic diseases, joint diseases, muscle diseases, bone diseases, and ophthalmic and/or ocular diseases.

Specific autoimmune diseases include, but are not limited to: rheumatoid arthritis, osteoarthritis, psoriasis, allergic dermatitis, systemic lupus erythematosus (and resulting complications), Sjögren's syndrome, multiple sclerosis, asthma, glomerular nephritis, irritable bowel syndrome, inflammatory bowel disease, Crohn's disease, ankylosing spondylitis, Behçet's disease, lupus nephritis, scleroderma, systemic scleroderma, type 1 or juvenile on-set diabetes, alopecia universalis, acute disseminated encephalomyelitis, Addison's disease, antiphospholipid antibody syndrome, atrophic gastritis of pernicious anemia, autoimmune alopecia, autoimmune hemolytic anemia, autoimmune hepatitis, autoimmune encephalomyelitis, autoimmune thrombocytopenia, Bullous pemphigoid, Chagas disease, Celiac disease, chronic hepatitis, Cogan's syndrome, dermatomyositis, endometriosis, Goodpasture's syndrome, Graves' disease, Guillain-Barré syndrome, Hashimoto's disease (or Hashimoto's thyroiditis), hemolytic anemia, hidradentitis suppurativa, idiopathic thrombocytopenia purpura, interstitial cystitis, membranous glomerulopathy, morphea, mystenia gravis, narcolepsy, pemphigus, pernicous anemia, polyarteritis nodosa, polymyositis, primary biliary cirrhosis, Reiter's syndrome, schizophrenia, symphathetic opthalmia, systemic sclerosis, temporal arteritis, thyroiditis, vasculitis, vitiglio, vulvodynia, Wegner's granulomatosis, palmoplantar keratoderma, systemic-onset Juvenile Idiopathic Arthritis (SJIA), or an indication listed in a separate category herein.

Specific inflammatory diseases include, but are not limited to: chronic obstructive pulmonary diseases, airway hyper-responsiveness, cystic fibrosis, acute respiratory distress syndrome, sinusitis, rhinitis, gingivitis, atherosclerosis, chronic prostatitis, glomerular nephritis, ulcerative colitis, uveitis, periodontal disease, or an indication listed in a separate category herein.

Specific pain conditions include, but are not limited to: inflammatory pain, surgical pain, visceral pain, dental pain, premenstrual pain, central pain, pain due to burns, migraine or cluster headaches, nerve injury, interstitial cystitis, cancer pain, viral, parasitic or bacterial infection, post-traumatic injury, pain associated with irritable bowel syndrome, gout, pain associated with any of the other indications listed within this specification, or an indication listed in a separate category herein.

Specific respiratory, airway and pulmonary conditions include, but are not limited to: asthma (which may encompass chronic, late, bronchial, allergic, intrinsic, extrinsic or dust), chronic obstructive pulmonary disease, idiopathic pulmonary fibrosis, pulmonary arterial hypertension, cystic fibrosis, interstitial lung disease, acute lung injury, sarcoidosis, allergic rhinitis, chronic cough, bronchitis, recurrent airway obstruction, emphysema, or bronchospasm, or an indication listed in a separate disease category herein.

Specific gastrointestinal (GI) disorders include, but are not limited to: Irritable Bowel Syndrome (IBS), Inflammatory Bowel Disease (IBD), biliary colic and other biliary disorders, renal colic, diarrhea-dominant IBS, pain associated with GI distension, ulcerative colitis, Crohn's Disease, irritable bowel syndrome, Celiac disease, proctitis, eosinophilic gastroenteritis, mastocytosis, or an indication listed in a separate disease category herein.

Specific allergic diseases include, but are not limited to: anaphylaxis, allergic rhinitis, allergic dermatitis, allergic urticaria, angioedema, allergic asthma, allergic reactions to: food, drugs, insect bites, pollen; or an indication listed in a separate disease category herein.

Specific infection-based diseases include, but are not limited to: sepsis, septic shock, viral diseases, malaria, Lyme disease, ocular infections, conjunctivitis, Whipple Disease, or an indication listed in a separate disease category herein.

Specific trauma and tissue injury-based conditions include, but are not limited to: Renal glomerular damage, reperfusion injury (for example to heart, kidney, lung), spinal cord injury, tissue scarring, tissue adhesion, tissue repair, transplant rejection (for examples to heart, lung, bone marrow, cartilage, cornea, kidney, limb, liver, muscle, myoblast, pancreas, pancreatic islet, skin, nerve, small intestine, trachea), hypersensitivities, or an indication listed in a separate disease category herein.

Specific fibrotic diseases include, but are not limited to: Idiopathic pulmonary fibrosis, liver fibrosis, renal fibrosis, or an indication listed in a separate disease category herein.

Specific diseases considered to be driven by over-activity of IL1 pathways include, but are not limited to: Cryopyrin-associated periodic syndromes, myositis, and indications included in the following review article: C. A. Dinarello, A. Simon and J. W. M. van der Meer, Treating inflammation by blocking interleukin-1 in a broad spectrum of diseases, Nat Rev Drug Discov, 2012, 11(8), 633-652, http://dx.doi.org/10.1038/nrd3800 and supplementary information contained therein, or an indication listed in a separate disease category herein.

Specific ophthalmic/ocular diseases include, but are not limited to: uveitis, age-related macular degeneration, diabetic macular edema, keratoconjuctivitis, uveitis associated with Behçet's disease, vernal conjunctivitis, ketatitis, lens-induced uveitis, herpetic keratitis, conical keratitis, corneal epithelial dystrophy, ocular pemphigus, Mooren's ulcer, Scleritis, Graves' ophthalmopathy, Vogt-Koyanagi-Harada syndrome, keratoconjunctivitis sicca, phlyctenule, iridocyclitis, sympathetic ophthalmia, allergic conjunctivitis, ocular neovascularization, dry eye syndrome, or an indication listed in a separate disease category herein.

Specific joint, muscle and bone disorders include, but are not limited to: osteoarthritis, osteoporosis, rheumatoid arthritis, juvenile arthritis, psoriatic arthritis, erosive osteoarthritis of the hand, arthrofibrosis/traumatic knee injury, anterior cruciate knee ligament tear, relapsing polychondritis, recurrent multifocal osteomyelitis, Majeed Syndrome, ankylosing spondylitis, gout of the lumbar spine, antisynthetase syndrome, idiopathic inflammatory myopathies, articular chondrocalcinosis, systemic-onset Juvenile Idiopathic Arthritis (SJIA), gout and pyrophosphate crystal arthritis, or an indication listed in a separate disease category herein.

Specific skin/dermatological diseases include, but are not limited to: psoriasis, atopic dermatitis, cutaneous lupus, acne, dermatomyositis, eczema, pruritus, scleroderma, Sweet Syndrome/neutrophilic dermatosis, neutrophilic panniculitis, acrodermatitis (form of pustular psoriasis), or an indication listed in a separate disease category herein.

Specific renal diseases include, but are not limited to: acute kidney injury (AKI) (sepsis-AKI, coronary artery bypass graft-AKI, cardiac surgery-AKI, non-cardiac surgery-AKI, transplant surgery-AKI cisplatin-AKI, contrast/imaging agent induced-AKI), glomerulonephritis, IgA nephropathy, crescentic GN, lupus nephritis, HIV associated nephropathy, membraneous nephropathy, $C_3$ glomerulopathy, Dense deposit disease, ANCA vasculitis, diabetic nephropathy, hemolytic-uremic syndrome, atypical Hemolytic-uremic syndrome, nephrotic syndrome, nephritic syndrome, hypertensive nephrosclerosis, ApoL1 nephropathy, focal segmental glomerulosclerosis, Alport syndrome, Fanconi, syndrome, crystal nephropathy, nephrolithiasis, nephrotic syndrome, renal transplant rejection, amyloidosis, glomerulonephritis in SJIA, or an indication listed in a separate disease category herein.

Specific genetic diseases include, but are not limited to: Familial Mediterranean fever (FMF), CAPS (FCAS, Muckle-Wells Syndrome, NOMID/CINCA), male hypoinfertility in CAPS, NLRP12 Autoinflammatory Syndrome, or an indication listed in a separate disease category herein.

Specific hematopoietic diseases include, but are not limited to: hemolytic anemia, or an indication listed in a separate disease category herein.

Specific liver diseases include, but are not limited to: liver fibrosis, liver cirrhosis, nonalcoholic steatohepatitis (NASH), or an indication listed in a separate disease category herein.

Specific oral diseases include, but are not limited to: gingivitis, periodontal disease or an indication listed in a separate disease category herein.

Specific metabolic diseases include, but are not limited to: Type 2 diabetes (and resulting complications), gout and hyperuricemia, metabolic syndrome, insulin resistance, obesity, or an indication listed in a separate disease category herein.

Compounds of the current invention are also useful in the treatment of a proliferative disease selected from a benign or malignant tumor, solid tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma, gastrointestinal cancer, especially colon carcinoma or colorectal adenoma, a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, nonsmall-cell lung carcinoma, lymphomas, Hodgkins and Non-Hodgkins, a mammary carcinoma, follicular carcinoma, undifferentiated carcinoma, papillary carcinoma, seminoma, melanoma, smoldering of indolent multiple myeloma, or hematological malignancies (including leukemia, diffuse large B-cell lymphoma (DLBCL), ABC DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, Waldenstrom's macroglobulinemia (WM), splenic marginal zone lymphoma, multiple myeloma, plasmacytoma, intravascular large B-cell lymphoma), or an indication listed in a separate disease category herein.

Cardiovascular conditions include, but are not limited to coronary heart disease, acute coronary syndrome, ischaemic heart disease, first or recurrent myocardial infarction, secondary myocardial infarction, non-ST segment elevation myocardial infarction, or ST segment elevation myocardial infarction, ischemic sudden death, transient ischemic attack, peripheral occlusive arterial disease, angina, atherosclerosis, hypertension, heart failure (such as congestive heart failure), diastolic dysfunction (such as left ventricular diastolic dysfunction, diastolic heart failure, and impaired diastolic filling), systolic dysfunction (such as systolic heart failure with reduced ejection fraction), vasculitis, ANCA vasculitis, post-myocardial infarction cardiac remodeling atrial fibrillation, arrhythmia (ventricular), ischemia, hypertrophic cardiomyopathy, sudden cardiac death, myocardial and vascular fibrosis, impaired arterial compliance, myocardial necrotic lesions, vascular damage, left ventricular hypertrophy, decreased ejection fraction, cardiac lesions, vascular wall hypertrophy, endothelial thickening, fibrinoid necrosis of coronary arteries, adverse remodeling, stroke, and the like, or an indication listed in a separate disease category herein. Also, included are venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g., after a bypass) and reocclusion (e.g., during or after percutaneous transluminal coronary angioplasty).

Cardiovascular complications of type 2 diabetes are associated with inflammation, accordingly, the compounds of the present invention may be used to treat diabetes and diabetic complications such as macrovascular disease, hyperglycemia, metabolic syndrome, impaired glucose tolerance, hyperuricemia, glucosuria, cataracts, diabetic neuropathy, diabetic nephropathy, diabetic retinopathy, obesity, dyslipidemia, hypertension, hyperinsulinemia, and insulin resistance syndrome, or an indication listed in a separate disease category herein.

Linkage of innate immunity and inflammation to disease has been demonstrated in neuroinflammatory and neurodegenerative conditions. Therefore, the compounds of the present invention are particularly indicated for use in the treatment of neuroinflammatory and neurodegenerative conditions (i.e., disorders or diseases) in mammals including humans such as multiple sclerosis, migraine; epilepsy; Alzheimer's disease; Parkinson's disease; brain injury; stroke; cerebrovascular diseases (including cerebral arteriosclerosis, cerebral amyloid angiopathy, hereditary cerebral hemorrhage, and brain hypoxia-ischemia); cognitive disorders (including amnesia, senile dementia, HIV associated dementia, Alzheimer's associated dementia, Huntington's associated dementia, Lewy body dementia, vascular dementia, drug related dementia, delirium, and mild cognitive impairment); mental deficiency (including Down syndrome and fragile X syndrome); sleep disorders (including hypersomnia, circadian rhythm sleep disorder, insomnia, parasomnia, and sleep deprivation) and psychiatric disorders (such as anxiety (including acute stress disorder, generalized anxiety disorder, social anxiety disorder, panic disorder, post-traumatic stress disorder and obsessive-compulsive disorder); factitious disorder (including acute hallucinatory mania); impulse control disorders (including compulsive gambling and intermittent explosive disorder); mood disorders (including bipolar I disorder, bipolar II disorder, mania, mixed affective state, major depression, chronic depression, seasonal depression, psychotic depression, and postpartum depression); psychomotor disorder; psychotic disorders (including schizophrenia, schizoaffective disorder, schizophreniform, and delusional disorder); drug dependence (including narcotic dependence, alcoholism, amphetamine dependence, cocaine addiction, nicotine dependence, and drug withdrawal syndrome); eating disorders (including anorexia, bulimia, binge eating disorder, hyperphagia, and pagophagia); and pediatric psychiatric disorders (including attention deficit disorder, attention deficit/hyperactive disorder, conduct disorder, and autism), myotrophic lateral sclerosis, chronic fatigue syndrome, or an indication listed in a separate disease category herein.

Formulations

The compounds of the invention may be administered orally. Oral administration may involve swallowing, so that the compound enters the gastrointestinal tract, or buccal or sublingual administration may be employed by which the compound enters the blood stream directly from the mouth.

In another embodiment, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be formulated such that administration topically to the skin or mucosa (i.e., dermally or transdermally) leads to systemic absorption of the compound. In another embodiment, the compounds of the invention can also be formulated such that administration intranasally or by inhalation leads to systemic absorption of the compound. In another embodiment, the compounds of the invention may be formulated such that administration rectally or vaginally leads to systemic absorption of the compound.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, the total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing 0.01, 0.05, 0.1, 0.5, 1.0, 2.5, 5.0, 10.0, 15.0, 25.0, 50.0, 75.0, 100, 125, 150, 175, 200, 250 and 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises the use of one or more compounds of the invention for the preparation of a medicament for the treatment of the conditions recited herein.

For the treatment of the conditions referred to above, the compounds of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically (e.g., intranasal or ophthalmic).

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of the present invention are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneal injections, intramuscular injections, intrasternal injections, and infusion. Injectable preparations (i.e., sterile injectable aqueous or oleaginous suspensions) may be formulated according to the known art using suitable dispersing, wetting, and/or suspending agents, and include depot formulations.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound that enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, Finnin and Morgan, J. Pharm. Sci., 88 (10), 955-958 (1999).

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (e.g., absorbable gel sponges, collagen) and non-biodegradable (e.g., silicone) implants, wafers, lenses and particulate or vesicular systems, such as niosomes or liposomes. A polymer such as crossed-linked polyacrylic acid, polyvinyl alcohol, hyaluronic acid, a cellulosic polymer, for example, hydroxypropylmethyl cellulose, hydroxyethyl cellulose, or methyl cellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone; as a mixture, for example, in a dry blend with lactose; or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3, 3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pennsylvania, 1975; Liberman et al., Eds., Pharmaceutical Dosage Forms, Marcel Decker, New York, N.Y., 1980; and Kibbe et al., Eds., Handbook of Pharmaceutical Excipients (3$^{rd}$ Ed.), American Pharmaceutical Association, Washington, 1999.

The compounds of the present invention can be used, alone or in combination with other therapeutic agents, in the treatment of various conditions or disease states. The compound(s) of the present invention and other therapeutic agent(s) may be administered simultaneously (either in the same dosage form or in separate dosage forms) or sequentially. An exemplary therapeutic agent may be, for example, a metabotropic glutamate receptor agonist.

The administration of two or more compounds "in combination" means that the two compounds are administered closely enough in time that the presence of one alters the biological effects of the other. The two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination.

The present invention includes the use of a combination of a PDE4 inhibitor compound of the present invention and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of the present invention or a pharmaceutically acceptable salt of the compound; (b) a second pharmaceutically active agent; and (c) a pharmaceutically acceptable carrier, vehicle or diluent.

Various pharmaceutically active agents may be selected for use in conjunction with the compounds of the present invention, depending on the disease, disorder, or condition to be treated. Pharmaceutically active agents that may be used in combination with the compositions of the present invention include, without limitation:

(i) acetylcholinesterase inhibitors, such as donepezil hydrochloride (ARICEPT, MEMAC), physostigmine salicylate (ANTILIRIUM), physostigmine sulfate (ESERINE), metrifonate, neostigmine, ganstigmine, pyridostigmine (MESTINON), ambenonium (MYTELASE), demarcarium, Debio 9902 (also known as ZT-1; Debiopharm), rivastigmine (EXELON), ladostigil, NP-0361, galantamine hydrobromide (RAZADYNE, RIMINYL, NIVALIN), tacrine (COGNEX), tolserine, velnacrine maleate, memoquin, huperzine A (HUP-A; NeuroHitech), phenserine, edrophonium (ENLON, TENSILON), and INM-176;

(ii) amyloid-ß (or fragments thereof), such as Aß1-15 conjugated to pan HLA DR-binding epitope (PADRE), ACC-001 (Elan/Wyeth), ACI-01, ACI-24, AN-1792, Affitope AD-01, CAD106, and V-950;

(iii) antibodies to amyloid-ß (or fragments thereof), such as ponezumab, solanezumab, bapineuzumab (also known as AAB-001), AAB-002 (Wyeth/Elan), ACI-01-Ab7, BAN-2401, intravenous Ig (GAMMAGARD), LY2062430 (humanized m266; Lilly), R1450 (Roche), ACU-5A5, huC091, and those disclosed in International Patent Publication Nos WO04/032868, WO05/025616, WO06/036291, WO06/069081, WO06/118959, in US Patent Publication Nos US2003/0073655, US2004/0192898, US2005/0048049, US2005/0019328, in European Patent Publication Nos EP0994728 and 1257584, and in U.S. Pat. No. 5,750,349;

(iv) amyloid-lowering or -inhibiting agents (including those that reduce amyloid production, accumulation and fibrillization) such as dimebon, davunetide, eprodisate, leuprolide, SK-PC-B70M, celecoxib, lovastatin, anapsos, oxiracetam, pramiracetam, varenicline, nicergoline, colostrinin, bisnorcymserine (also known as BNC), NIC5-15 (Humanetics), E-2012 (Eisai), pioglitazone, clioquinol (also known as PBT1), PBT2 (Prana Biotechnology), flurbiprofen (ANSAID, FROBEN) and its R-enantiomer tarenflurbil (FLURIZAN), nitroflurbiprofen, fenoprofen (FENOPRON, NALFON), ibuprofen (ADVIL, MOTRIN, NUROFEN), ibuprofen lysinate, meclofenamic acid, meclofenamate sodium (MECLOMEN), indomethacin (INDOCIN), diclofenac sodium (VOLTAREN), diclofenac potassium, sulindac (CLINORIL), sulindac sulfide, diflunisal (DOLOBID), naproxen (NAPROSYN), naproxen sodium (ANAPROX, ALEVE), ARC031 (Archer Pharmaceuticals), CAD-106 (Cytos), LY450139 (Lilly), insulin-degrading enzyme (also known as insulysin), the gingko biloba extract EGb-761 (ROKAN, TEBONIN), tramiprosate (CEREBRIL, ALZHEMED), eprodisate (FIBRILLEX, KIACTA), compound W (3,5-bis(4-nitrophenoxy)benzoic acid), NGX-96992, neprilysin (also known as neutral endopeptidase (NEP)), scyllo-inositol (also known as scyllitol), atorvastatin (LIPITOR), simvastatin (ZOCOR), KLVFF-(EEX)3, SKF-74652, ibutamoren mesylate, BACE inhibitors such as ASP-1702, SCH-745966, JNJ-715754, AMG-0683, AZ-12304146, BMS-782450, GSK-188909, NB-533, E2609 and TTP-854; gamma secretase modulators such as ELND-007; and RAGE (receptor for advanced glycation end-products) inhibitors, such as TTP488 (Transtech) and TTP4000 (Transtech), and those disclosed in U.S. Pat. No. 7,285,293, including PTI-777;

(v) alpha-adrenergic receptor agonists, such as guanfacine (INTUNIV, TENEX), clonidine (CATAPRES), metaraminol (ARAMINE), methyldopa (ALDOMET, DOPAMET, NOVOMEDOPA), tizanidine (ZANAFLEX), phenylephrine (also known as neosynephrine), methoxamine, cirazoline, guanfacine (INTUNIV), lofexidine, xylazine, modafinil (PROVIGIL), adrafinil, and armodafinil (NUVIGIL);

(vi) beta-adrenergic receptor blocking agents (beta blockers), such as carteolol, esmolol (BREVIBLOC), labetalol (NORMODYNE, TRANDATE), oxprenolol (LARACOR, TRASACOR), pindolol (VISKEN), propanolol (INDERAL), sotalol (BETAPACE, SOTALEX, SOTACOR), timolol (BLOCADREN, TIMOPTIC), acebutolol (SECTRAL, PRENT), nadolol (CORGARD), metoprolol tartrate (LOPRESSOR), metoprolol succinate (TOPROL-XL), atenolol (TENORMIN), butoxamine, and SR 59230A (Sanofi);

(vii) anticholinergics, such as amitriptyline (ELAVIL, ENDEP), butriptyline, benztropine mesylate (COGENTIN), trihexyphenidyl (ARTANE), diphenhydramine (BENADRYL), orphenadrine (NORFLEX), hyoscyamine, atropine (ATROPEN), scopolamine (TRANSDERM-SCOP), scopolamine methylbromide (PAR- MINE), dicycloverine (BENTYL, BYCLOMINE, DIBENT, DILOMINE), tolterodine (DETROL), oxybutynin (DITROPAN, LYRINEL XL, OXYTROL), penthienate bromide, propantheline (PRO-BANTHINE), cyclizine, imipramine hydrochloride (TOFRANIL), imipramine maleate (SURMONTIL), lofepramine, desipramine (NORPRAMIN), doxepin (SINEQUAN, ZONALON), trimipramine (SURMONTIL), and glycopyrrolate (ROBINUL);

(viii) anticonvulsants, such as carbamazepine (TEGRETOL, CARBATROL), oxcarbazepine (TRILEPTAL), phenytoin sodium (PHENYTEK), fosphenytoin (CEREBYX, PRODILANTIN), divalproex sodium (DEPAKOTE), gabapentin (NEURONTIN), pregabalin (LYRICA), topiramate (TOPAMAX), valproic acid (DEPAKENE), valproate sodium (DEPACON), 1-benzyl-5-bromouracil, progabide, beclamide, zonisamide (TRERIEF, EXCEGRAN), CP-465022, retigabine, talampanel, and primidone (MYSOLINE);

(ix) antipsychotics, such as lurasidone (LATUDA, also known as SM-13496; Dainippon Sumitomo), aripiprazole (ABILIFY), chlorpromazine (THORAZINE), haloperidol (HALDOL), iloperidone (FANAPTA), flupentixol decanoate (DEPIXOL, FLUANXOL), reserpine (SERPLAN), pimozide (ORAP), fluphenazine decanoate, fluphenazine hydrochloride, prochlorperazine (COMPRO), asenapine (SAPHRIS), loxapine (LOXITANE), molindone (MOBAN), perphenazine, thioridazine, thiothixine, trifluoperazine (STELAZINE), ramelteon, clozapine (CLOZARIL), norclozapine (ACP-104), risperidone (RISPERDAL), paliperidone (INVEGA), melperone, olanzapine (ZYPREXA), quetiapine (SEROQUEL), talnetant, amisulpride, ziprasidone (GEODON), blonanserin (LONASEN), and ACP-103 (Acadia Pharmaceuticals);

(x) calcium channel blockers such as lomerizine, ziconotide, nilvadipine (ESCOR, NIVADIL), diperdipine, amlodipine (NORVASC, ISTIN, AMLODIN), felodipine (PLENDIL), nicardipine (CARDENE), nifedipine (ADALAT, PROCARDIA), MEM 1003 and its parent compound nimodipine (NIMOTOP), nisoldipine (SULAR), nitrendipine, lacidipine (LACIPIL, MOTENS), lercanidipine (ZANIDIP), lifarizine, diltiazem (CARDIZEM), verapamil (CALAN, VERELAN), AR-R 18565 (AstraZeneca), and enecadin;

(xi) catechol O-methyltransferase (COMT) inhibitors, such as nitecapone, tolcapone (TASMAR), entacapone (COMTAN), and tropolone;

(xii) central nervous system stimulants, such as atomoxetine, reboxetine, yohimbine, caffeine, phenmetrazine, phendimetrazine, pemoline, fencamfamine (GLUCOENERGAN, REACTIVAN), fenethylline (CAPTAGON), pipradol (MERETRAN), deanol (also known as dimethylaminoethanol), methylphenidate (DAYTRANA), methylphenidate hydrochloride (RITALIN), dexmethylphenidate (FOCALIN), amphetamine (alone or in combination with other CNS stimulants, e.g., ADDERALL (amphetamine aspartate, amphetamine sulfate, dextroamphetamine saccharate, and dextroamphetamine sulfate)), dextroamphetamine sulfate (DEXEDRINE, DEXTROSTAT), methamphetamine (DESOXYN), lisdexfetamine (VYVANSE), and benzphetamine (DIDREX);

(xiii) corticosteroids, such as prednisone (STERAPRED, DELTASONE), prednisolone (PRELONE), predisolone acetate (OMNIPRED, PRED MILD, PRED FORTE), prednisolone sodium phosphate (ORAPRED ODT), methylprednisolone (MEDROL); methylprednisolone acetate (DEPO-MEDROL), and methylprednisolone sodium succinate (A-METHAPRED, SOLU-MEDROL);

(xiv) dopamine receptor agonists, such as apomorphine (APOKYN), bromocriptine (PARLODEL), cabergoline (DOSTINEX), dihydrexidine, dihydroergocryptine, fenoldopam (CORLOPAM), lisuride (DOPERGIN), terguride spergolide (PERMAX), piribedil (TRIVASTAL, TRASTAL), pramipexole (MIRAPEX), quinpirole, ropinirole (REQUIP), rotigotine (NEUPRO), SKF-82958 (GlaxoSmithKline), cariprazine, pardoprunox and sarizotan;

(xv) dopamine receptor antagonists, such as chlorpromazine, fluphenazine, haloperidol, loxzpine, resperidone, thioridazine, thiothixene, trifluoperazine, tetrabenazine (NITOMAN, XENAZINE), 7-hydroxyamoxapine, droperidol (INAPSINE, DRIDOL, DROPLETAN), domperidone (MOTILIUM), L-741742, L-745870, raclopride, SB-277011A, SCH-23390, ecopipam, SKF-83566, and metoclopramide (REGLAN);

(xvi) dopamine reuptake inhibitors such as bupropion, safinamide, nomifensine maleate (MERITAL), vanoxerine (also known as GBR-12909) and its decanoate ester DBL-583, and amineptine;

(xvii) gamma-amino-butyric acid (GABA) receptor agonists, such as baclofen (LIORESAL, KEMSTRO), siclofen, pentobarbital (NEMBUTAL), progabide (GABRENE), and clomethiazole;

(xviii) histamine 3 (H3) antagonists such as ciproxifan, tiprolisant, S-38093, irdabisant, pitolisant, GSK-239512, GSK-207040, JNJ-5207852, JNJ-17216498, HPP-404, SAR-110894, trans-3-fluoro-3-(3-fluoro-4-pyrrolidin-1-ylmethyl-phenyl)-cyclobutane carboxylic acid ethylamide (PF-3654746 and those disclosed in US Patent Publication Nos US2005-0043354, US2005-0267095, US2005-0256135, US2008-0096955, US2007-1079175, and US2008-0176925; International Patent Publication Nos WO2006/136924, WO2007/063385, WO2007/069053, WO2007/088450, WO2007/099423, WO2007/105053, WO2007/138431, and WO2007/088462; and U.S. Pat. No. 7,115,600);

(xix) immunomodulators such as glatiramer acetate (also known as copolymer-1; COPAXONE), MBP-8298 (synthetic myelin basic protein peptide), dimethyl fumarate, fingolimod (also known as FTY720), roquinimex (LINOMIDE), laquinimod (also known as ABR-215062 and SAIK-MS), ABT-874 (human anti-IL-12 antibody; Abbott), rituximab (RITUXAN), leflunomide, ciclesonide, alemtuzumab (CAMPATH), daclizumab (ZENAPAX), and natalizumab (TYSABRI);

(xx) immunosuppressants such as methotrexate (TREXALL, RHEUMATREX), mitoxantrone (NOVANTRONE), teriflunomide, suplatast tosilate, mycophenolate mofetil (CELLCEPT), mycophenolate sodium (MYFORTIC), azathioprine (AZASAN, IMURAN), mercaptopurine (PURI-NETHOL), cyclophosphamide (NEOSAR, CYTOXAN), voclosporin, PUR-118, AMG 357, AMG 811, BCT197, chlorambucil (LEUKERAN), cladribine (LEUSTATIN, MYLINAX), alpha-fetoprotein, etanercept (ENBREL), leflunomide, ciclesonide chloroquine, hydroxychloroquine, d-penicillamine, auranofin, sulfasalazine, sodium aurothiomalate, cyclosporine, cromolyn, infliximab, adalimumab, certolizumab pegol, golimumab, rituximab, ocrelizumab, ofatumumab, and 4-benzyloxy-5-((5-undecyl-2H-pyrrol-2-ylidene)methyl)-2,2'-bi-1H-pyrrole (also known as PNU-156804);

(xxi) interferons, including interferon beta-1a (AVONEX, REBIF) and interferon beta-1b (BETASERON, BETAFERON);

(xxii) levodopa (or its methyl or ethyl ester), alone or in combination with a DOPA decarboxylase inhibitor (e.g., carbidopa (SINEMET, CARBILEV, PARCOPA), benserazide (MADOPAR), α-methyldopa, monofluromethyldopa, difluoromethyldopa, brocresine, or m-hydroxybenzylhydrazine);

(xxiii) N-methyl-D-aspartate (NMDA) receptor antagonists, such as memantine (NAMENDA, AXURA, EBIXA), amantadine (SYMMETREL), acamprosate (CAMPRAL), besonprodil, ketamine (KETALAR), delucemine, dexanabinol, dexefaroxan, dextromethorphan, dextrorphan, traxoprodil, CP-283097, himantane, idantadol, ipenoxazone, L-701252 (Merck), lancicemine, levorphanol (DROMORAN), LY-233536 and LY-235959 (both Lilly), methadone, (DOLOPHINE), neramexane, perzinfotel, phencyclidine, tianeptine (STABLON), dizocilpine (also known as MK-801), EAB-318 (Wyeth), ibogaine, voacangine, tiletamine, riluzole (RILUTEK), aptiganel (CERESOTAT), gavestinel, and remacimide;

(xxiv) monoamine oxidase (MAO) inhibitors, such as selegiline (EMSAM), selegiline hydrochloride (I-deprenyl, ELDEPRYL, ZELAPAR), dimethylselegilene, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), CHF-3381 (Chiesi Farmaceutici), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL);

(xxv) muscarinic receptor (particularly M1 subtype) agonists, such as cevimeline, levetiracetam, bethanechol chloride (DUVOID, URECHOLINE), itameline, pilocarpine (SALAGEN), NGX267, arecoline, L-687306 (Merck), L-689660 (Merck), furtrethonium iodide (FURAMON, FURANOL), furtrethonium benzensulfonate, furtrethonium p-toluenesulfonate, McN-A-343, oxotremorine, sabcomeline, AC-90222 (Acadia Pharmaceuticals), and carbachol (CARBASTAT, MIOSTAT, CARBOPTIC);

(xxvi) neuroprotective drugs such as bosutinib, condoliase, airmoclomol, lamotrigine, perampanel, aniracetam, minaprime, viluzole 2,3,4,9-tetrahydro-1H-carbazol-3-one oxime, desmoteplase, anatibant, astaxanthin, neuropeptide NAP (e.g., AL-108 and AL-208; both Allon Therapeutics), neurostrol, perampenel, ispronicline, bis(4-β-D-glucopyranosyloxybenzyl)-2-β-D-glucopyranosyl-2-isobutyltartrate (also known as dactylorhin B or DHB), formobactin, xaliproden (XAPRILA), lactacystin, dimeboline hydrochloride (DIMEBON), disufenton (CEROVIVE), arundic acid (ONO-2506, PROGLIA, CEREACT), citicoline (also known as cytidine 5'-diphosphocholine), edaravone (RADICUT), AEOL-10113 and AEOL-10150 (both Aeolus Pharmaceuticals), AGY-94806 (also known as SA-450 and Msc-1), granulocyte-colony stimulating factor (also known as AX-200), BAY-38-7271 (also known as KN-387271; Bayer AG), ancrod (VIPRINEX, ARWIN), DP-b99 (D-Pharm Ltd), HF-0220 (17-ß-hydroxyepiandrosterone; Newron Pharmaceuticals), HF-0420 (also known as oligotropin), pyridoxal 5'-phosphate (also known as MC-1), microplasmin, S-18986, piclozotan, NP031112, tacrolimus, L-seryl-L-methionyl-L-alanyl-L-lysyl-L-glutamyl-glycyl-L-valine, AC-184897 (Acadia Pharmaceuticals), ADNF-14 (National Institutes of Health), stilbazulenyl nitrone, SUN-N8075 (Daiichi Suntory Biomedical Research), and zonampanel;

(xxvii) nicotinic receptor agonists, such as epibatidine, bupropion, CP-601927, varenicline, ABT-089 (Abbott), ABT-594, AZD-0328 (AstraZeneca), EVP-6124, R3487 (also known as MEM3454; Roche/Memory Pharmaceuticals), R4996 (also known as MEM63908; Roche/Memory Pharmaceuticals), TC-4959 and TC-5619 (both Targacept), and RJR-2403;

(xxviii) norepinephrine (noradrenaline) reuptake inhibitors, such as atomoxetine (STRATTERA), doxepin (APONAL, ADAPIN, SINEQUAN), nortriptyline (AVENTYL, PAMELOR, NORTRILEN), amoxapine (ASENDIN, DEMOLOX, MOXIDIL), reboxetine (EDRONAX, VESTRA), viloxazine (VIVALAN), maprotiline (DEPRILEPT, LUDIOMIL, PSYMION), bupropion (WELLBUTRIN), and radaxafine;

(xxix) phosphodiesterase (PDE) inhibitors, including but not limited to, (a) PDE1 inhibitors (e.g., vinpocetine (CAVINTON, CERACTIN, INTELECTOL) and those disclosed in U.S. Pat. No. 6,235,742, (b) PDE2 inhibitors (e.g., erythro-9-(2-hydroxy-3-nonyl)adenine (EHNA), BAY 60-7550, and those described in U.S. Pat. No. 6,174,884), (c) PDE3 inhibitors (e.g., anagrelide, cilostazol, milrinone, olprinone, parogrelil, and pimobendan), (d) PDE4 inhibitors (e.g., apremilast, ibudilastroflumilast, rolipram, Ro 20-1724, ibudilast (KETAS), piclamilast (also known as RP73401), CDP840, cilomilast (ARIFLO), roflumilast, tofimilast, oglemilast (also known as GRC 3886), tetomilast (also known as OPC-6535), lirimifast, theophylline (UNIPHYL, THEOLAIR), arofylline (also known as LAS-31025), doxofylline, RPR-122818, or mesembrine), and (e) PDE5 inhibitors (e.g., sildenafil (VIAGRA, REVATIO), tadalafil (CIALIS), vardenafil (LEVITRA, VIVANZA), udenafil, avanafil, dipyridamole (PERSANTINE), E-4010, E-4021, E-8010, zaprinast, iodenafil, mirodenafil, DA-8159, and those disclosed in International Patent Applications WO2002/020521, WO2005/049616, WO2006/120552, WO2006/126081, WO2006/126082, WO2006/126083, and WO2007/122466), (f) PDE7 inhibitors; (g) PDE8 inhibitors; (h) PDE9 inhibitors (e.g., BAY 73-6691 (Bayer AG) and those disclosed in US Patent Publication Nos US2003/0195205, US2004/0220186, US2006/0111372, US2006/0106035, and U.S. Ser. No. 12/118,062 (filed May 9, 2008)), (i) PDE10 inhibitor such as 2-[4-(1-Methyl-4-pyridin-4-yl-1H-pyrazol-3-yl)phenoxymethyl]quinoline (PF-2545920), and SCH-1518291; and (j) PDE11 inhibitors;

(xxx) quinolines, such as quinine (including its hydrochloride, dihydrochloride, sulfate, bisulfate and gluconate salts), chloroquine, sontoquine, hydroxychloroquine (PLAQUENIL), mefloquine (LARIAM), and amodiaquine (CAMOQUIN, FLAVOQUINE); (xxxi) β-secretase inhibitors, such as ASP-1702, SCH-745966, JNJ-715754, AMG-0683, AZ-12304146, BMS-782450, GSK-188909, NB-533, LY-2886721, E-2609, HPP-854, (+)-phenserine tartrate (POSIPHEN), LSN-2434074 (also known as LY-2434074), KMI-574, SCH-745966, Ac-rER (N²-acetyl-D-arginyl-L-arginine), loxistatin (also known as E64d), and CA074Me;

(xxxii) γ-secretase inhibitors and modulators, such as BMS-708163 (Avagacest), WO20060430064 (Merck), DSP8658 (Dainippon), ITI-009, L-685458 (Merck), ELAN-G, ELAN-Z, 4-chloro-N-[2-ethyl-1(S)-(hydroxymethyl)butyl]benzenesulfonamide;

(xxxiii) serotonin (5-hydroxytryptamine) 1A (5-HT$_{1A}$) receptor antagonists, such as spiperone, levo-pindolol, BMY 7378, NAD-299, S(−)-UH-301, NAN 190, lecozotan;

(xxxiv) serotonin (5-hydroxytryptamine) 2C (5-HT2c) receptor agonists, such as vabicaserin, and zicronapine;

(xxxv) serotonin (5-hydroxytryptamine) 4 (5-HT$_4$) receptor agonists, such as PRX-03140 (Epix);

(xxxvi) serotonin (5-hydroxytryptamine) 6 (5-HT$_6$) receptor antagonists, such as A-964324, AVI-101, AVN-211, mianserin (TORVOL, BOLVIDON, NORVAL), methiothepin (also known as metitepine), ritanserin, ALX-1161, ALX-1175, MS-245, LY-483518 (also known as SGS518; Lilly), MS-245, Ro 04-6790, Ro 43-68544, Ro 63-0563, Ro 65-7199, Ro 65-7674, SB-399885, SB-214111, SB-258510, SB-271046, SB-357134, SB-699929, SB-271046, SB-742457 (GlaxoSmithKline), Lu AE58054 (Lundbeck A/S), and PRX-07034 (Epix);

(xxxvii) serotonin (5-HT) reuptake inhibitors such as alaproclate, citalopram (CELEXA, CIPRAMIL), escitalopram (LEXAPRO, CIPRALEX), clomipramine (ANAFRANIL), duloxetine (CYMBALTA), femoxetine (MALEXIL), fenfluramine (PONDIMIN), norfenfluramine, fluoxetine (PROZAC), fluvoxamine (LUVOX), indalpine, milnacipran (IXEL), paroxetine (PAXIL, SEROXAT), sertraline (ZOLOFT, LUSTRAL), trazodone (DESYREL, MOLIPAXIN), venlafaxine (EFFEXOR), zimelidine (NORMUD, ZELMID), bicifadine, desvenlafaxine (PRISTIQ), brasofensine, vilazodone, cariprazine, neuralstem and tesofensine;

(xxxviii) trophic factors, such as nerve growth factor (NGF), basic fibroblast growth factor (bFGF; ERSOFERMIN), neurotrophin-3 (NT-3), cardiotrophin-1, brain-derived neurotrophic factor (BDNF), neublastin, meteorin, and glial-derived neurotrophic factor (GDNF), and agents that stimulate production of trophic factors, such as propentofylline, idebenone, PYM50028 (COGANE; Phytopharm), and AIT-082 (NEOTROFIN);

(xxxix) Glycine transporter-1 inhibitors such as paliflutine, ORG-25935, JNJ-17305600, and ORG-26041;

(xl) AMPA-type glutamate receptor modulators such as perampanel, mibampator, selurampanel, GSK-729327, N-{(3S,4S)-4-[4-(5-cyanothiophen-2-yl)phenoxy]tetrahydro-furan-3-yl}propane-2-sulfonamide, and the like.

(xli) Janus kinase inhibitors (JAK) such as, but not limited to, tofacitinib, ruxolitinib, baricitinib, CYT387, GLPG0634, lestaurtinib, pacritinib, and TG101348.

In another embodiment of the present invention, a compound of Formula I may be co-administered with an anti-obesity agent where the anti-obesity agent is selected from the group consisting of gut-selective MTP inhibitors (e.g., dirlotapide, mitratapide and implitapide, R56918 (CAS No. 403987) and CAS No. 913541-47-6), CCKa agonists (e.g., N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide described in PCT Publication No. WO 2005/116034 or US Publication No. 2005-0267100 A1), 5HT2c agonists (e.g., lorcaserin), MCR4 agonist (e.g., compounds described in U.S. Pat. No. 6,818,658), lipase inhibitor (e.g., Cetilistat), PYY$_{3-36}$ (as used herein "PYY$_{3-36}$" includes analogs, such as peglated PYY$_{3-36}$ e.g., those described in US Publication 2006/0178501), opioid antagonists (e.g., naltrexone), the combination of naltrexone with buprorpion, oleoyl-estrone (CAS No. 180003-17-2), obinepitide (TM30338), pramlintide (Symlin®), tesofensine (NS2330), leptin, liraglutide, bromocriptine, orlistat, exenatide (Byetta®), AOD-9604 (CAS No. 221231-10-3) and sibutramine.

Other anti-obesity agents include 11β-hydroxy steroid dehydrogenase-1 (11β-HSD type 1) inhibitors, stearoyl-CoA desaturase-1 (SCD-1) inhibitor, cholecystokinin-A (CCK-A) agonists, monoamine reuptake inhibitors (such as sibutramine), sympathomimetic agents, ß3 adrenergic agonists, dopamine agonists (such as bromocriptine), melanocyte-stimulating hormone analogs, melanin concentrating hormone antagonists, leptin (the OB protein), leptin analogs, leptin agonists, galanin antagonists, lipase inhibitors (such as tetrahydrolipstatin, i.e. orlistat), anorectic agents (such as a bombesin agonist), neuropeptide-Y antagonists (e.g., NPY Y5 antagonists), thyromimetic agents, dehydroepiandrosterone or an analog thereof, glucocorticoid agonists or antagonists, orexin antagonists, glucagon-like peptide-1 agonists, ciliary neurotrophic factors (such as Axokine™ available from Regeneron Pharmaceuticals, Inc., Tarrytown, NY and Procter & Gamble Company, Cincinnati, OH), human agouti-related protein (AGRP) inhibitors, ghrelin antagonists, histamine 3 antagonists or inverse agonists, neuromedin U agonists, MTP/ApoB inhibitors (e.g., gut-selective MTP inhibitors, such as dirlotapide), opioid antagonist, orexin antagonist, the combination of naltrexone with buprorpion and the like.

In another embodiment of the present invention, a compound of Formula I may be co-administered with an anti-diabetic agent, where the anti-diabetic agent is selected from the group consisting of an acetyl-CoA carboxylase- (ACC) inhibitor such as those described in WO2009144554, WO2003072197, WO2009144555 and WO2008065508, a diacylglycerol O-acyltransferase 1 (DGAT-1) inhibitor, such as those described in WO09016462 or WO2010086820, AZD7687 or LCQ908, monoacylglycerol O-acyltransferase inhibitors, a phosphodiesterase (PDE)-10 inhibitor, an AMPK activator, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPARγ agonist (e.g., balaglitazone, ciglitazone, darglitazone, englitazone, isaglitazone, pioglitazone and rosiglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) modulator such as an agonist (e.g., exendin-3, exendin-4, ZYOG-1 and TTP273), liraglutide (Victoza®), albiglutide, exenatide (Byetta®, Bydureon®), albiglutide, lixisenatide, dulaglutide, semaglutide (NN-9924), TTP-054, a protein tyrosine phosphatase-1B (PTP-1B) inhibitor (e.g., trodusquemine, hyrtiosal extract, and compounds disclosed by Zhang, S., et al., *Drug Discovery Today,* 12 (9/10), 373-381 (2007)), SIRT-1 activator (e.g., resveratrol, GSK2245840 or GSK184072), a dipeptidyl peptidase IV (DPP-IV) inhibitor (e.g., those in WO2005116014, sitagliptin, vildagliptin, alogliptin, dutogliptin, linagliptin and saxagliptin), an insulin secreatagogue, a fatty acid oxidation inhibitor, an A2 antagonist, a c-jun amino-terminal kinase (JNK) inhibitor, glucokinase activators (GKa) such as those described in WO2010103437, WO2010103438, WO2010013161, WO2007122482, TTP-399, TTP-355, TTP-547, AZD1656, ARRY403, MK-0599, TAK-329, AZD5658 or GKM-001, insulin, an insulin mimetic, a glycogen phosphorylase inhibitor (e.g. GSK1362885), a VPAC2 receptor agonist, SGLT2 inhibitors, such as those described in E. C. Chao et al. Nature Reviews Drug Discovery 9, 551-559 (July 2010) including dapagliflozin, canagliflozin, empagliflozin, tofogliflozin (CSG452), ASP-1941, THR1474, TS-071, ISIS388626 and LX4211 as well as those in WO2010023594, a glucagon receptor modulator such as those described in Demong, D. E. et al. Annual Reports in Medicinal Chemistry 2008, 43, 119-137, GPR119 modulators, particularly agonists, such as those described in WO2010140092, WO2010128425, WO2010128414, WO2010106457, Jones, R. M. et al. in Medicinal Chemistry 2009, 44, 149-170 (e.g. MBX-2982, GSK1292263, APD597 and PSN821), FGF21 derivatives or analogs such as those described in Kharitonenkov, A. et al. et al., Current Opinion in Investigational Drugs 2009, 10(4) 359-364, TGR5 (also termed GPBAR1) receptor modulators, particularly agonists, such as those described in Zhong, M., Current Topics in Medicinal Chemistry, 2010, 10(4), 386-396 and INT777, GPR40 agonists, such as those described in Medina, J. C., Annual Reports in Medicinal Chemistry, 2008, 43, 75-85, including but not limited to TAK-875, GPR120 modulators, particularly agonists, high affinity nicotinic acid receptor (HM74A) activators, and SGLT1 inhibitors, such as GSK1614235, listing of anti-diabetic agents found at page 28, line 35 through page 30, line 19 of WO2011005611, inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCα, PKCβ1, PKCβ2, etc. . . . ), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostain receptors (e.g. SSTR1, SSTR2, SSTR3 and SSTR5), inhibitors or modulators of PDHK2 or PDHK4, inhibitors of MAP4K4, modulators of IL1 family including IL1beta, modulators of RXRalpha, suitable anti-diabetic agents include mechanisms listed by Carpino, P. A., Goodwin, B. Expert Opin. Ther. Pat, 2010, 20(12), 1627-51.

Preferred anti-diabetic agents are metformin and DPP-IV inhibitors (e.g., sitagliptin, vildagliptin, alogliptin, dutoglip-tin, linagliptin and saxagliptin). Other antidiabetic agents could include inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCα, PKCβ, PKCγ), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostain receptors (e.g. SSTR1, SSTR2, SSTR3 and SSTR5), inhibitors or modulators of PDHK2 or PDHK4, inhibitors of MAP4K4, modulators of IL1 family including IL1beta, modulators of RXRalpha.

In another embodiment of the present invention, a compound of Formula I may be co-administered with a cholesterol/lipid modulating agent, where the cholesterol/lipid modulating agent is selected from the group consisting of HMG-COA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)); HMG-COA reductase gene expression inhibitor; squalene synthetase inhibitors; a squalene epoxidase inhibitor; a squalene cyclase inhibitor; a combined squalene epoxidase/squalene cyclase inhibitor a CETP inhibitor; fibrates; niacin, an ion-exchange resin, an antioxidant; bile acid sequestrants (such as questran); ACAT inhibitors; MTP/APO ß secretion inhibitors; lipooxygenase inhibitors; cholesterol absorption inhibitors; cholesteryl ester transfer protein inhibitors; an agent such as mipomersen; and or atherosclerotic agents including PCSK9 modulators.

In another embodiment, a compound of Formula I may be co-administered with agents for the treatment of non-alcoholic steatohepatitis (NASH) and/or non-alcoholic fatty liver disease (NAFLD), such as Orlistat, TZDs and other insulin sensitizing agents, FGF21 analogs, Metformin, Omega-3-acid ethyl esters (e.g. Lovaza), Fibrates, HMG CoA-reductase Inhibitors, Ezitimbe, Probucol, Ursodeoxycholic acid, TGR5 agonists, FXR agonists, Vitamin E, Betaine, Pentoxifylline, CB1 antagonists, Carnitine, N-acetylcysteine, Reduced glutathione, lorcaserin, the combination of naltrexone with buproprion, SGLT2 Inhibitors, Phentermine, Topiramate, Incretin (GLP and GIP) analogs and Angiotensin-receptor blockers.

Additional therapeutic agents include anti-coagulant or coagulation inhibitory agents, anti-platelet or platelet inhibitory agents, thrombin inhibitors, thrombolytic or fibrinolytic agents, anti-arrythmic agents, anti-hypertensive agents, calcium channel blockers (L-type and T-type), cardiac glycosides, diruetics, mineralocorticoid receptor antagonists, NO donating agents such as organonitrates, NO promoting agents such as phosphodiesterase inhibitors, cholesterol/lipid lowering agents and lipid profile therapies, anti-diabetic agents, anti-depressants, anti-inflammatory agents (steroidal and non-steroidal), anti-osteoporosis agents, hormone replacement therapies, oral contraceptives, anti-obesity agents, anti-anxiety agents, anti-proliferative agents, anti-tumor agents, anti-ulcer and gastroesophageal reflux disease agents, growth hormone and/or growth hormone secretagogues, thyroid mimetics (including thyroid hormone receptor antagonist), anti-infective agents, anti-viral agents, anti-bacterial agents, and anti-fungal agents. Examples of suitable mineralocorticoid receptor antagonists include sprionolactone and eplerenone.

Those skilled in the art will recognize that the compounds of this invention may also be used in conjunction with other cardiovascular or cerebrovascular treatments including PCI, stenting, drug eluting stents, stem cell therapy and medical devices, such as implanted pacemakers, defibrillators, or cardiac resynchronization therapy.

Agents used in an ICU setting are included, for example, dobutamine, dopamine, epinephrine, nitroglycerin, nitroprusside etc.

Combination agents useful for treating vasculitis are included, for example, azathioprine, cyclophosphamide, mycophenolate, mofetil, rituximab etc.

In another embodiment, the present invention provides a combination wherein the second agent is at least one agent selected from a factor Xa inhibitor, an anti-coagulant agent, an anti-platelet agent, a thrombin inhibiting agent, a thrombolytic agent, and a fibrinolytic agent. Exemplary factor Xa inhibitors include apixaban and rivaroxaban. Examples of suitable anti-coagulants for use in combination with the compounds of the present invention include heparins (e.g., unfractioned and low molecular weight heparins such as enoxaparin and dalteparin).

In another preferred embodiment the second agent is at least one agent selected from warfarin, dabigatran, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

A preferred second agent is at least one anti-platelet agent. Especially preferred anti-platelet agents are aspirin and clopidogrel.

The term anti-platelet agents (or platelet inhibitory agents), as used herein, denotes agents that inhibit platelet function, for example by inhibiting the aggregation, adhesion or granular secretion of platelets. Agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicyclic acid or ASA) and COX-2 inhibitors such as CELEBREX or piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, PDE-III inhibitors (e.g., Pletal, dipyridamole), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticagrelor, prasugrel, ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastrointestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, dabigatran, heparins, hirudin, argatroban, and melagatran, including pharmaceutically acceptable salts and prodrugs thereof. Boroarginine derivatives and boropeptides include N-acetyl and peptide derivatives of boronic acid, such as C-terminal alpha-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. The term thrombolytics or fibrinolytic agents (or thrombolytics or fibrinolytics), as used herein, denote agents that lyse blood clots (thrombi). Such agents include tissue plasminogen activator (natural or recombinant) and modified forms thereof, anistreplase, urokinase, streptokinase, tenecteplase (TNK), lanoteplase (nPA), factor VIIa inhibitors, PAI-1 inhibitors (i.e., inactivators of tissue plasminogen activator inhibitors), alpha2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase.

Examples of suitable anti-arrythmic agents include: Class I agents (such as propafenone); Class II agents (such as metoprolol, atenolol, carvadiol and propranolol); Class III agents (such as sotalol, dofetilide, amiodarone, azimilide and ibutilide); Class IV agents (such as ditiazem and verapamil); K$^+$ channel openers such as $I_{Ach}$ inhibitors, and $I_{Kur}$ inhibitors (e.g., compounds such as those disclosed in WO01/40231).

The compounds of the present invention may be used in combination with antihypertensive agents and such antihypertensive activity is readily determined by those skilled in the art according to standard assays (e.g., blood pressure measurements). Examples of suitable anti-hypertensive agents include: alpha adrenergic blockers; beta adrenergic blockers; calcium channel blockers (e.g., diltiazem, verapamil, nifedipine and amlodipine); vasodilators (e.g., hydralazine), diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, torsemide, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., gemopatrilat and nitrates). An exemplary antianginal agent is ivabradine.

Examples of suitable calcium channel blockers (L-type or T-type) include diltiazem, verapamil, nifedipine and amlodipine and mybefradil.

Examples of suitable cardiac glycosides include digitalis and ouabain.

In one embodiment, a Formula I compound may be co-administered with one or more diuretics. Examples of suitable diuretics include (a) loop diuretics such as furosemide (such as LASIX™), torsemide (such as DEMADEX™), bemetanide (such as BUMEX™), and ethacrynic acid (such as EDECRIN™); (b) thiazide-type diuretics such as chlorothiazide (such as DIURIL™, ESIDRIX™ or HYDRODIURIL™), hydrochlorothiazide (such as MICROZIDE™ or ORETIC™), benzthiazide, hydroflumethiazide (such as SALURON™), bendroflumethiazide, methychlorthiazide, polythiazide, trichlormethiazide, and indapamide (such as LOZOL™); (c) phthalimidine-type diuretics such as chlorthalidone (such as HYGROTON™), and metolazone (such as ZAROXOLYN™); (d) quinazoline-type diuretics such as quinethazone; and (e) potassium-sparing diuretics such as triamterene (such as DYRENIUM™), and amiloride (such as MIDAMOR™ or MODURETIC™).

In another embodiment, a compound of Formula I may be co-administered with a loop diuretic. In still another embodiment, the loop diuretic is selected from furosemide and torsemide. In still another embodiment, one or more compounds of Formula I may be co-administered with furosemide. In still another embodiment, one or more compounds of Formula I may be co-administered with torsemide which may optionally be a controlled or modified release form of torsemide.

In another embodiment, a compound of Formula I may be co-administered with a thiazide-type diuretic. In still another embodiment, the thiazide-type diuretic is selected from the group consisting of chlorothiazide and hydrochlorothiazide. In still another embodiment, one or more compounds of Formula I may be co-administered with chlorothiazide. In still another embodiment, one or more compounds of Formula I may be co-administered with hydrochlorothiazide.

In another embodiment, one or more compounds of Formula I may be co-administered with a phthalimidine-type diuretic. In still another embodiment, the phthalimidine-type diuretic is chlorthalidone.

In another embodiment, compounds of the present invention may also be co-administered together with:

Antidiarrheals, such as diphenoxylate (Lomotil) and loperamide (Imodium);

Bile acid binding agents, such as cholestyramine, alosetron (Lotronex) and ubiprostone (Amitiza);

Laxatives, such as Milk of Magnesia, polyethylene glycol (MiraLax), Dulcolax, Correctol and Senokot, and anticholinergics or antispasmodics such as dicyclomine (Bentyl);

lymphocyte activation inhibitors, including but not limited to, abatacept:

Anti-IL1 treatments, including but not limited to, anakinra, rilonacept, canakinumab, gevokizumab, MABp1 and MEDI-8968;

Glucocorticoid receptor modulators that may be dosed orally, by inhalation, by injection, topically, rectally, by ocular delivery, including but not limited to, betamethasone, prednisone, hydrocortisone, prednisolone, flunisolide, triamcinoline acetonide, beclomethasone, dipropionate, budesonide, fluticasone propionate, ciclesonide, mometasone furoate, fluocinonide, desoximetasone, methylprednisolone or PF-04171327; Aminosalicyic acid derivatives, including but not limited to, sulfasalazine and mesalazine; Anti-α4 integrin agents, including but not limited to, natalizumab;

α1- or α2-adrenergic agonist agents including but not limited to: propylhexidrine, phenylephrine, phenylpropanolamine, pseudoephedrine or naphazoline hydrochloride, oxymetazoline hydrochloride, tetrahydrozoline hydrochloride, xylometazoline hydrochloride or ethylnorepinephrine hydrochloride;

α-adrenergic agonists, including but not limited to, metaproterenol, isoprotenerol, isoprenaline, albuterol, salbutamol, formoterol, salmeterol, terbutaline, orciprenaline, botolterol mesylate, pirbuterol;

Anticholinergic agents, including but not limited to, ipratropium bromide, tiotropium bromide, oxitropium bromide, aclindinium bromide, glycopyrrolate, pirenzipine or telenzepine;

The present invention further comprises kits that are suitable for use in performing the methods of treatment described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of the invention.

The compounds of the invention, or their pharmaceutically acceptable salts, may be prepared by a variety of methods that are analogously known in the art. The reaction Schemes described below, together with synthetic methods known in the art of organic chemistry, or modifications and derivatizations that are familiar to those of ordinary skill in the art, illustrate methods for preparing the compounds. Others, including modifications thereof, will be readily apparent to one skilled in the art.

The starting materials used herein are commercially available or may be prepared by routine methods known in the art (such as those methods disclosed in standard reference books such as the COMPENDIUM OF ORGANIC SYNTHETIC METHODS, Vol. I-XII (published by Wiley-Interscience)). Preferred methods include, but are not limited to, those described below.

During any of the following synthetic sequences, it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999; and T. W. Greene and P. G. M. Wuts, Protective Groups in Organic Chemistry, John Wiley & Sons, 2007, which are hereby incorporated by reference.

Compounds of the present invention or their pharmaceutically acceptable salts of said compounds or tautomers and radioisotopes, can be prepared according to the reaction Schemes discussed herein below. Unless otherwise indicated, the substituents in the Schemes are defined as above. Isolation and purification of the products is accomplished by standard procedures, which are known to a chemist of ordinary skill.

One skilled in the art will recognize that in some cases, the compounds in Schemes 1 through 11 will be generated as a mixture of diastereomers and/or enantiomers; these may be separated at various stages of the synthetic Scheme using conventional techniques or a combination of such techniques, such as, but not limited to, crystallization, normal-phase chromatography, reversed phase chromatography and chiral chromatography, to afford the single enantiomers of the invention.

It will be understood by one skilled in the art that the various symbols, superscripts and subscripts used in the Scheme, methods and examples are used for convenience of representation and/or to reflect the order in which they are introduced in the Scheme, and are not intended to necessarily correspond to the symbols, superscripts or subscripts in the appended claims. The Schemes are representative of methods useful in synthesizing the compounds of the present invention. They are not to constrain the scope of the invention in any way.

Scheme 1 below illustrates one synthetic sequence for the preparation of compounds of Formula I, as depicted above, wherein A is a fused oxygen-containing heterocycloalkyl, a fused phenyl or a fused heteroaryl ring; and the piperazinyl ring is saturated (bond between $C_6$ and $C_7$ is a single bond).

The initial step in the synthesis, as depicted, utilizes heterocycles of Formula 1 as an initial starting material. Heterocycles of Formula 1 undergo alkylation via alkyl halides in the presence of base as a proton scavenger or via the alkyl alcohol under Mitsunobu conditions. During the alkylation step, Z is represented by an appropriate leaving group, the $R^{3a}$, $R^{3b}$, $R^{4a}$, $R^{4b}$ substituents and n of Formula 2 should be represented by the same moieties as desired in the final product or protected variation thereof. For example, the final product of Example 2 can be prepared utilizing reaction Scheme 1, where the $R^{3a}$, $R^{3b}$, $R^{4a}$, and $R^{4b}$ substituents of Formula 2 are each represented by hydrogen and n is 1.

The next step of the sequence is $S_N2$ displacement of a halide of Formula II with an amine of Formula 3 in the presence of base as a proton scavenger, at temperature from room temperature to 60° C., to afford amines of Formula III. During the $S_N2$ reaction step, the $R^2$ substituent on the amine nucleophile of Formula 3 should be represented by the same moiety as is desired in the final product. For example, the final product of Example 2 can be prepared utilizing reaction Scheme 1, where $R^2$ of the amine nucleophile of Formula 3 is represented by cyclopropylamine.

In the next step, the tricyclic ring system of Formula IV can be formed via intermolecular amine addition to the ethyl ester of Formula III under a variety of conditions such as $K_2CO_3$ in acetonitrile (ACN), $Mg(OMe)_2$ in MeOH, or $CaCl_2$) in MeOH, at temperatures from room temperature to 80° C.

In the final step of Scheme 1, conversion of compounds of Formula IV to compounds of Formula I can be accomplished via an electrophilic bromination followed by Suzuki coupling. The resulting bromide undergoes Suzuki coupling with boronic acids of Formula 4 in the presence of base, a metal catalyst (Pd, Ni, Cu), a phosphine ligand, at temperatures from room temperature to 100° C. to afford the desired ring system Formula I (see de Vries, J. G. *Topics in Organometallic Chemistry* 2012, 42, pg 12-20 reference and references contained therein). During the Suzuki coupling, the $R^1$ substituent of the boronic acid of the Formula 4 should be represented by the same moiety as is desired in the final product or protected variation thereof. For example, the final product of Example 2 mentioned above can be prepared utilizing reaction Scheme 1, where $R^1$ of the boronic acid of Formula 4 is represented by 4-chlorophenyl.

Scheme 1

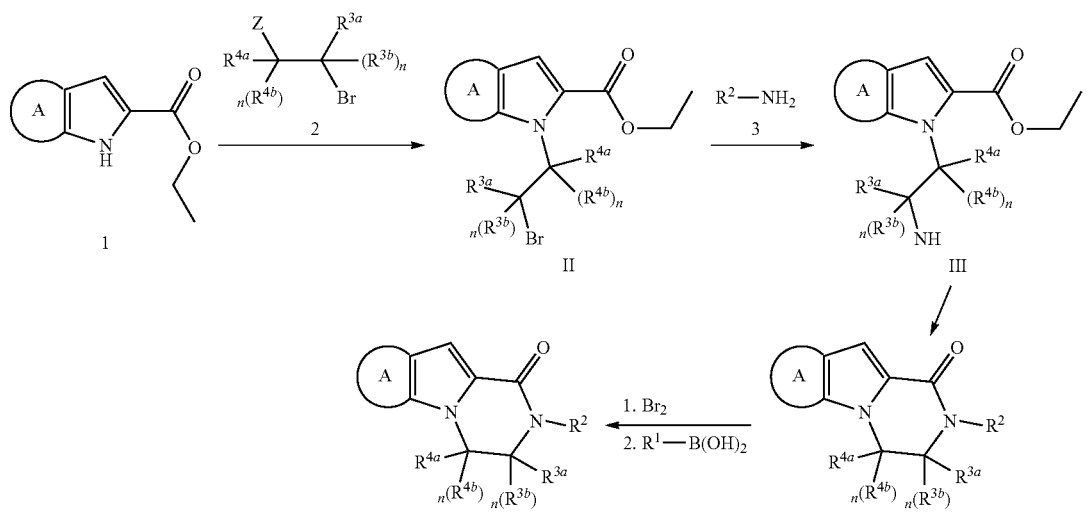

Scheme 2 below describes an alternate synthetic sequence for the preparation of compounds of Formula I, wherein A is a fused oxygen-containing heterocycloalkyl, a fused phenyl or a fused heteroaryl ring; and the piperazinyl ring is saturated (bond between $C_6$ and $C_7$ is a single bond).

The initial step in the synthesis, as depicted, utilizes heterocycles of Formula 1 as an initial starting material. The heterocycles of Formula 1 undergo electrophilic bromination followed by Suzuki coupling with boronic acids of Formula 4 in the presence of base, a metal catalyst (Pd, Ni, Cu), a phosphine ligand, at temperature from room temperature to 100° C. to afford compounds of the Formula V. During the coupling, the $R^1$ substituent of the boronic acid of the Formula 4 should be represented by the same moiety as is desired in the final product or protected variation thereof.

Following the Suzuki coupling step, the compounds of Formula VI can be prepared via alkylation with silyl ether functionalized alkyl halides of Formula 5 under standard conditions. During the alkylation step, the $R^{3a}$, $R^{3b}$, $R^{4a}$, and $R^{4b}$ substituents and n of Formula 5 should be represented by the same moieties as desired in the final product or protected variation thereof.

In the next step, the lactone of Formula VII can be generated by silyl deprotection and subsequent lactone formation of compounds of formula VI under acidic conditions, at temperatures from room temperature to 100° C.

Following the alkylation step, the compounds of Formula VIII can be generated by reduction of the lactone to the hemiacetal in the presence of amines with Formula 3. During the course of the addition, the $R^2$ substituent of the amine of the Formula 3 should be represented by the same moiety as is desired in the final product or protected variation thereof.

In the final step of Scheme 2, conversion of the compounds of Formula VIII to the compounds of Formula I can be accomplished under standard Mitsunobu conditions (see Mitsunobu, O. *Synthesis* 1981, 1, pg 1-28 reference and references contained therein).

should be represented by the same moiety as is desired in the final product or protected variation thereof.

In the final step of Scheme 3, the compounds of Formula IX can be alkylated by substituted bishalide of the Formula 6 in the presence of a base, at temperatures of 100° C. to generate compounds of formula I. During the alkylation step, the $R^{3a}$, $R^{3b}$, $R^{4a}$, and $R^{4b}$ substituents and n of Formula 6 should be represented by the same moieties as desired in the final product or protected variation thereof.

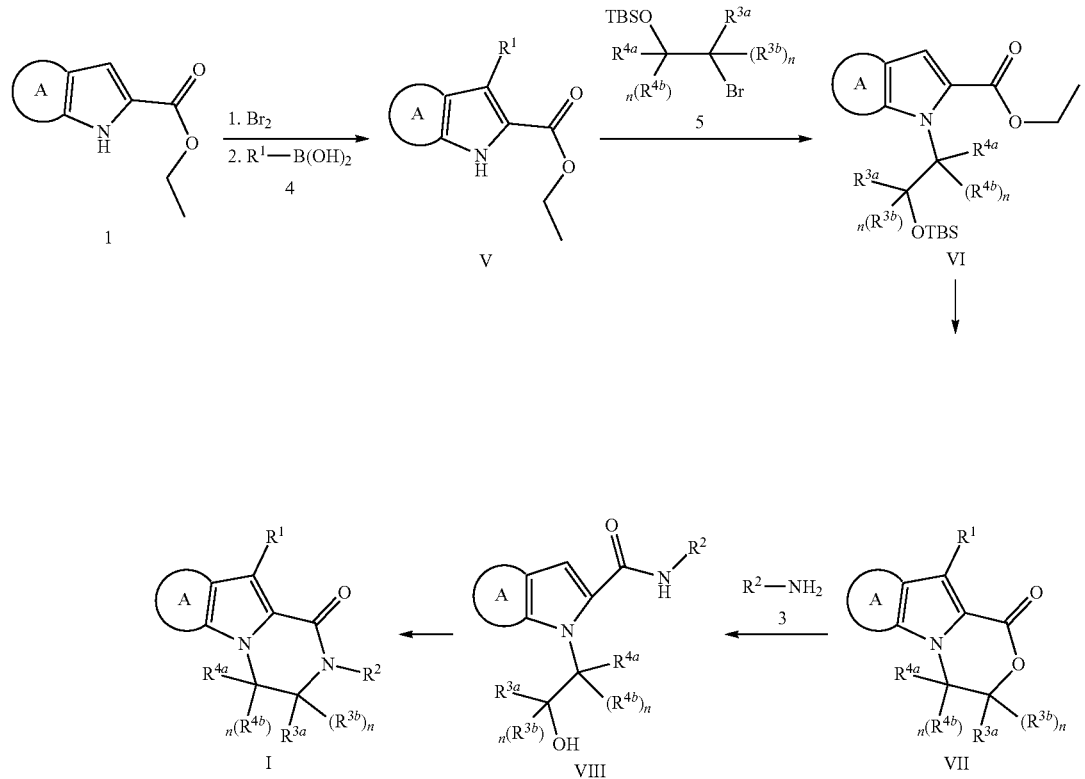

Scheme 2

Scheme 3 below describes an alternate synthetic sequence for the preparation of compounds of the Formula I, wherein A is a fused oxygen-containing heterocycloalkyl, a fused phenyl or a fused heteroaryl ring; and the piperazinyl ring is saturated (bond between $C_6$ and $C_7$ is a single bond).

The initial step in the synthesis, as depicted, utilizes compounds of Formula V as an initial starting material. The compounds of Formula V can undergo direct conversion to the desired amide through various conditions; some of which are described in the synthesis of Formula IV in Scheme 1. Alternatively, compounds depicted by Formula V can undergo saponification to generate carboxylic acids under acidic or basic conditions, at temperatures from room temperature to 80° C. which can then be coupled with amines of Formula 3 in the presence of an amide coupling or dehydrating agent, such as, 2,4,6-Tripropyl-1,3,5,2,4,6-trioxatriphosphinane 2,4,6-trioxide (T3P), O-(7-azabenzotriazol-1-yl)-N,N,N',N'-tetramethyluronium hexafluorophosphate (HATU), dicyclohexylcarbodiimide (DCC), etc., at temperatures ranging from −20° C. to 100° C. During the coupling, the $R^2$ substituent of the amine of the Formula 3

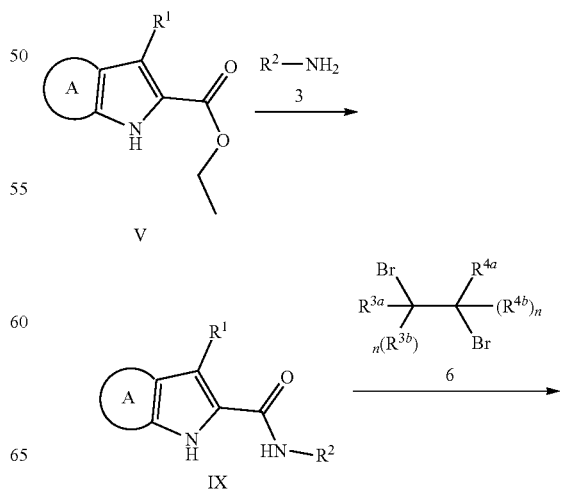

Scheme 3

-continued

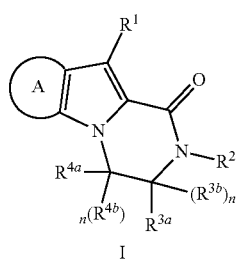

I

-continued

Ia¹

XI

Scheme 4 below describes a potential synthetic sequence for the preparation of compounds of Formula Ia¹, which is a subset of Formula I, wherein A is a fused pyridinyl ring; and the piperazinyl ring is saturated (bond between $C_6$ and $C_7$ is a single bond).

The initial step in the synthesis, as depicted, utilizes 2,3-dibromopyridine of Formula 7 as an initial starting material. The 2,3-dibromopyridine of Formula 7 undergoes a metal-halogen exchange at the 2 position in the presence of a lithium source such as $TMSCH_2Li$ and LiDMEA followed by addition of the resulting anion to electrophiles such as aldehydes of Formula 8, to afford alcohols of Formula X. During the anion addition step to the electrophile, the $R^1$ substituent of the aldehydes of the Formula 8 should be represented by the same moiety as is desired in the final product or protected variation thereof.

In the next step, compounds of Formula XI can be generated by oxidation of the alcohol of Formula X with standard oxidation conditions such as $MnO_2$, Swern oxidations, or Dess-Martin periodinanes.

In the final step of Scheme 4, conversion of compounds of Formula XI to compounds of Formula Ia¹ is performed by metal catalyzed coupling. Formula XI undergoes metal-mediated Buchwald-Hartwig type coupling with substituted piperazine-2-ones of Formula 9 in the presence of base, a metal catalyst (Pd, Ni, Cu), a phosphine ligand, at temperatures from room temperature to 100° C. to afford Formula Ia¹ (see Buchwald, S. L. et al. *Current Organic Synthesis* 2011, 8(1), pg 53-78 reference and references contained therein). During the metal-mediated coupling, the $R^2$, $R^{3a}$, $R^{3b}$, $R^{4a}$, and $R^{4b}$ substituents and n of the piperazine-2-ones of Formula 9 should be represented by the same moieties as is desired in the final product or protected variation thereof.

Scheme 5 below describes an alternate synthetic sequence for the preparation of compounds of Formula Ia¹, which is a subset of Formula I, wherein A is a fused pyridinyl ring; and the piperazinyl ring is saturated (bond between $C_6$ and $C_7$ is a single bond).

The initial step in the synthesis, as depicted, utilizes 2-bromo-3-halopyridine of Formula 10 as an initial starting material. The 2-bromo-3-halopyridine of Formula 10 undergoes metal catalyzed coupling with substituted piperazine-2-ones of Formula 9 in the presence of base, a metal catalyst (Pd, Ni, Cu), a phosphine ligand, at temperature from room temperature to 100° C. to afford compounds of the Formula XII. During this transformation, X is represented by an appropriate leaving group, the $R^2$, $R^{3a}$, $R^{3b}$, $R^{4a}$, and $R^{4b}$ substituents and n of the piperazine-2-ones of the Formula 9 should be represented by the same moieties as is desired in the final product or protected variation thereof.

In the next step compounds of Formula XIII can be prepared from compounds of Formula XII by addition of diethyl chlorophosphate in the presence of a base, at temperatures from 0 to −78° C.

In the next step compounds of Formula XIV can be generated by the condensation of compounds of Formula XIII and aldehydes of Formula 8 utilizing a Homer-Wadsworth-Emmons reaction (see Maryanoff, B. E. et al. *Chemical Review* 1989, 89, pg 863-927 reference and references contained therein). During the Horner-Wadsworth-Emmons reaction, the $R^1$ substituent of the aldehyde of Formula 8 should be represented by the same moiety as is desired in the final product or protected variation thereof.

In the final step of Scheme 5, compounds of Formula Ia¹ can be prepared via an intramolecular Heck reaction of compounds of Formula XIV, in the presence of a base, a metal catalyst, a phosphine ligand, at temperature from 50 to 100° C. (see de Vries, J. G. *Topics in Organometallic Chemistry* 2012, 42, pg 3-11 reference and references contained therein).

Scheme 4

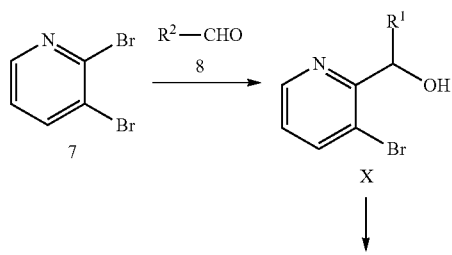

Scheme 5

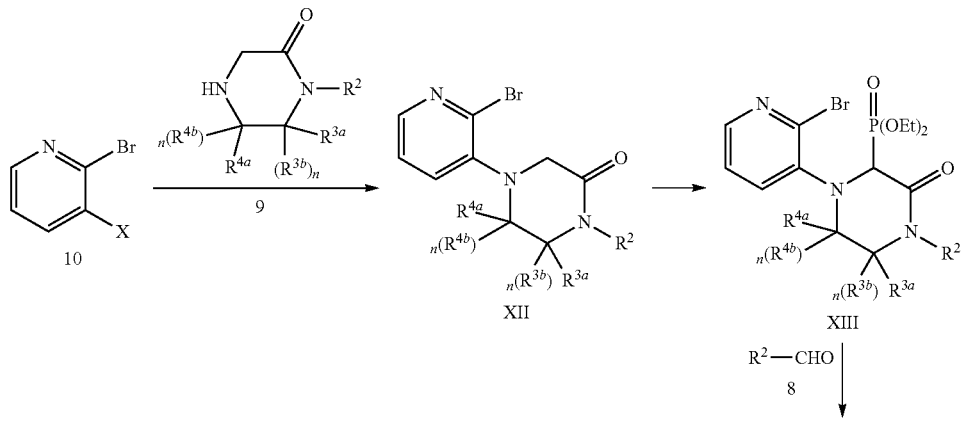

Scheme 6 below describes a synthetic sequence for compounds of Formula Ia², which is a subset of Formula I, wherein A is a "reverse" fused pyridine ring; and the piperazinyl ring is saturated (bond between $C_6$ and $C_7$ is a single bond).

The initial step in the synthesis, as depicted, utilizes 2,3-dibromopyrimidine of Formula 7 as an initial starting material. The 2,3-dibromopyrimidine of Formula 7 undergoes metal exchange followed by addition of the corresponding anion to aldehydes of Formula 8, to afford alcohols of Formula XV (see Trécourt, F *Tetrahedron* 2000, 56(10), 1349-1360). During the anion addition, the $R^1$ substituent of the aldehyde of the Formula 8 should be represented by the same moiety as is desired in the final product or protected variation thereof.

In the next step, compounds of Formula XVI can be generated by oxidation of the alcohols of Formula XV at room temperature.

In the final step of Scheme 6, conversion of compounds of Formula XVI to compounds of Formula Ia² occurs by a metal catalyzed coupling reaction. Formula XVI undergoes metal coupling with piperazine-2-ones of Formula 9 in the presence of base, a metal catalyst (Pd, Ni, Cu), a phosphine ligand, at temperatures from room temperature to 100° C. to afford Formula Ia². During the metal coupling, the $R^2$, $R^{3a}$, $R^{3b}$, $R^{4a}$, and $R^{4b}$ substituent and n of the piperazine-2-ones of Formula 9 should be represented by the same moieties as is desired in the final product or protected variation thereof.

Scheme 6

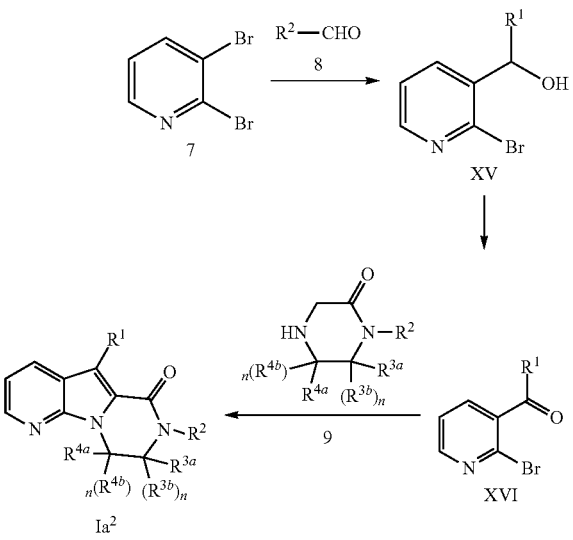

Scheme 7 describes a synthetic sequence for the preparation of compounds of Formula I, wherein A is a fused oxygen-containing heterocycloalkyl, phenyl or heteroaryl ring; the piperazinyl ring is saturated or unsaturated (bond between $C_6$ and $C_7$ is a single or double bond); $R^{3a}$, $R^{3b}$, $R^{4a}$, and $R^{4b}$ are hydrogen and n is when bond between $C_6$ and $C_7$ is a single bond; or $R^{3a}$ and $R^{4a}$ are hydrogen, $R^{3b}$ and $R^{4b}$ are absent and n is 0 when the bond between $C_6$ and $C_7$ is a double bond.

The initial step in the synthesis, as depicted, utilizes compounds of Formula V as an initial starting material. Compounds of Formula V undergo alkylation with allyl alcohol via Mitsunobu conditions (see: Current Organic Chemistry (2009), 13(16), 1610-1632) or with allyl halides via $S_N2$ conditions to afford allyl pyrrolopyridines of Formula XVII. During the alkylation step the $R^1$ substituent of Formula V should be represented by the same moiety as is desired in the final product or protected variation thereof.

In the next step, compounds of Formula XVIII can be generated from Formula XVII, under oxidative conditions such as $OsO_4$.

Following oxidation of the alkene, the compounds of Formula XIX can be prepared by oxidative cleavage of the diol utilizing reagents such as $NaIO_4$ etc to afford compounds of Formula XVIII.

In the next step, compounds of Formula XX can be generated by the combination of compounds of Formula XIX and amines of Formula 3 under reductive amination conditions, at temperature from room temperature to 80° C. During the reductive amination, the $R^2$ substituent of the amine of the Formula 3 should be represented by the same moiety as is desired in the final product or protected variation thereof.

In the final step of Scheme 7, conversion of the compounds of Formula XX to a mixture of compounds of Formula I can be accomplished by treatment with a Lewis acid in a polar protic solvent. The compounds of Formula I (saturated and unsaturated) can then be separated by chromatography methods.

Scheme 8 below describes an alternate synthetic sequence for the preparation of compound of Formula I (wherein A is a fused oxygen-containing heterocycloalkyl, a fused phenyl or a fused heteroaryl ring; the piperazinyl ring is unsaturated; $R^{3b}$ and $R^{4b}$ are absent; and n is 0.

The initial step in the synthesis, as depicted, utilizes compounds of Formula XVII (Scheme 7) as an initial starting material. Compounds of Formula XVII undergo amide formation either by direct conversion of the ester by treatment with the appropriate amines in the presence of Lewis acids or a two-step method of saponification under acidic or basic conditions to afford the carboxylic acid which can be mixed with amines of Formula 3 in the presence of an amide coupling or dehydrating agent, such as, 2,4,6-Tripropyl-1,3,5,2,4,6-trioxatriphosphinane 2,4,6-trioxide (T3P), O-(7-azabenzotriazol-1-yl)-N,N,N',N'-tetramethyluronium hexafluorophosphate (HATU), dicyclohexylcarbodiimide (DCC), etc., at temperatures ranging from −20° C. to 100° C. to generate compounds of Formula XXI. During the coupling, the $R^1$, $R^{3a}$, and $R^{4a}$ substituents of Formula XVII and the $R^2$ substituent of the amine of the Formula 3 should be represented by the same moiety as is desired in the final product or protected variation thereof.

Following the amide coupling step, the compounds of Formula XXII can be prepared by an oxidative cleavage of the alkene moiety of compounds of Formula XXI.

In the final step of Scheme 8, the compounds of Formula I can be accomplished by dehydration under acidic conditions on compounds of Formula XXII to generate compounds of Formula I.

Scheme 7

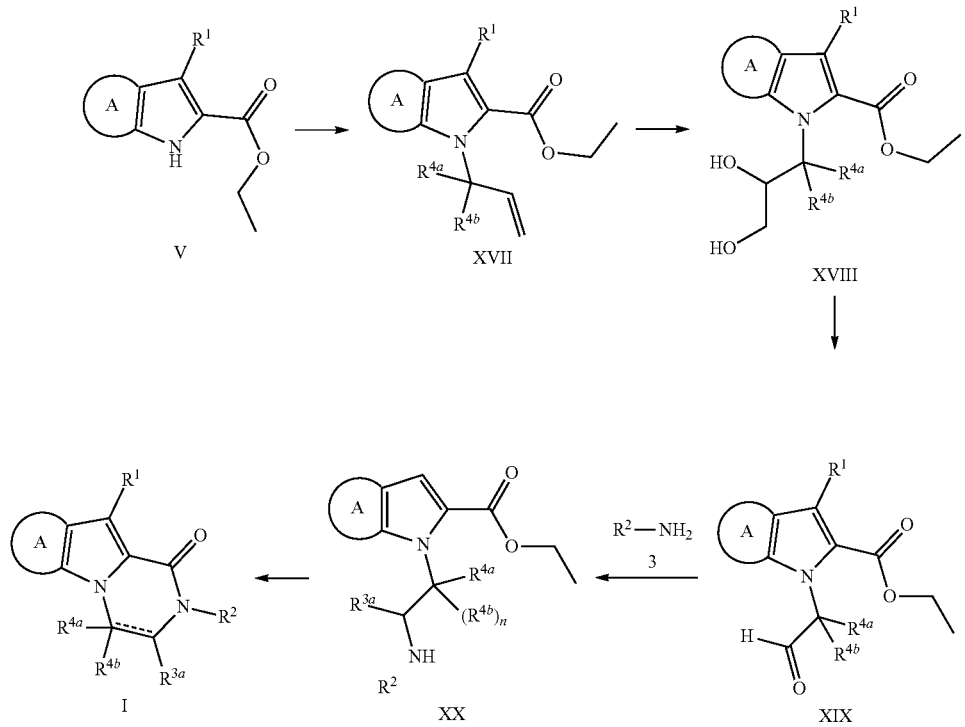

----- = absent or a bond

Scheme 8

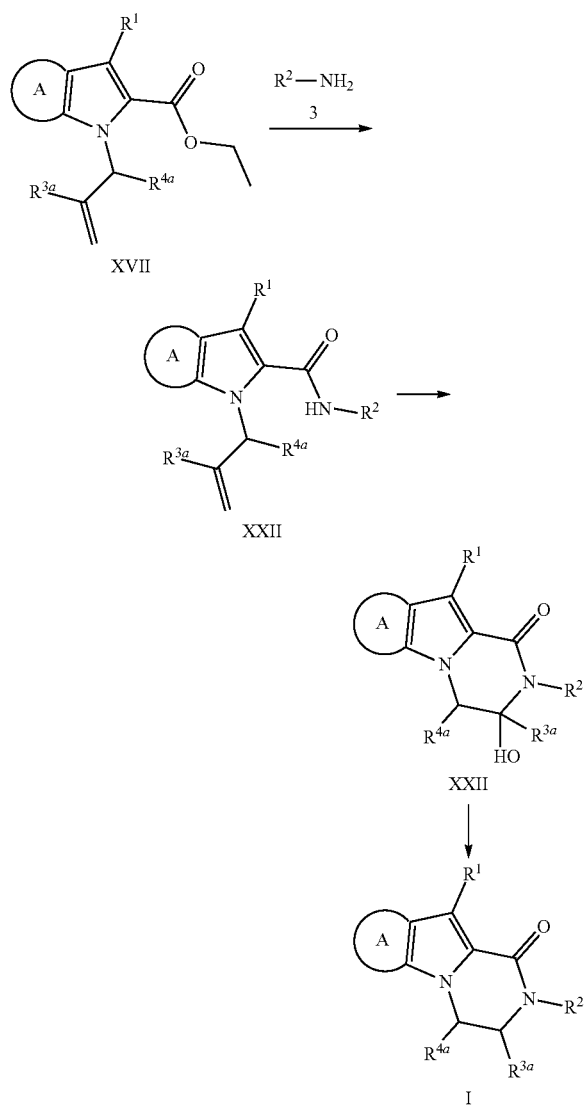

Scheme 9 below describes the synthesis of the fused amides of Formula Ib, which is another subset of Formula I, wherein A is a fused oxygen-containing heterocycloalkyl, a fused phenyl or a fused heteroaryl ring; $R^2$ and $R^{3a}$ together with the nitrogen to which they are attached form a (4- to 6-membered) heterocycloalkane ring; $R^{4a}$ is hydrogen; the piperazinyl ring is saturated; and Y can be —CH$_2$—, —CH$_2$—CH$_2$—, —CH$_2$—CH$_2$—CH$_2$— or —CH$_2$—CH$_2$—O—). The initial step in the synthesis, as depicted, utilizes compounds of Formula 1 as an initial starting material. The compounds of Formula 1 undergo alkylation with alcohols of Formula 11 under standard Mitsunobu conditions to afford compounds of Formula XXIII. During the Mitsunobu step, the Y substituent on the alcohol of Formula 11 should be represented by the same moiety as is desired in the final product or products thereof.

Next, the compounds of Formula XXIII were deprotected under acidic conditions followed by intra molecular amine addition to the ethyl ester catalyzed by Mg(OMe)$_2$ to afford the fused amides of Formula XXIV.

In the final step of Scheme 9, conversion of compounds of Formula XXIV to compounds of Formula Ib can be accomplished via electrophilic bromination followed by Suzuki coupling. Compounds of Formula XXIV undergo electrophilic bromination to afford the aryl/heteroaryl bromide which undergoes Suzuki coupling with boronic acids of Formula 4 in the presence of base, a metal catalyst (Pd, Ni, Cu), a phosphine ligand, at temperatures from room temperature to 100° C. to afford the desired ring system Formula Ib. During the Suzuki coupling, the $R^1$ substituent of the boronic acid of the Formula 4 should be represented by the same moiety as is desired in the final product or protected variation thereof.

Scheme 9

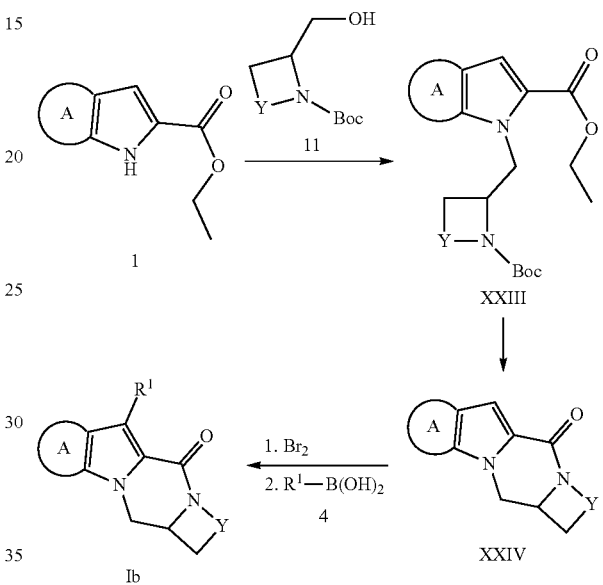

Scheme 10 below describes the synthetic sequence for the preparation of compounds of Formula Ic, which is another subset of Formula I, wherein A is a fused oxygen-containing heterocycloalkyl, a fused phenyl or a fused heteroaryl ring; and the piperazinyl ring is saturated (bond between $C_6$ and $C_7$ is a single bond). Starting from compounds of Formula XXV, which can be prepared via Schemes 1-3, displacement of the nitro group of compounds of Formula XXV with [$^{18}$F]fluoride anion in the presence of a base, such as, K$_2$CO$_3$ or KOAc, afford compounds of Formula Ic.

Scheme 10

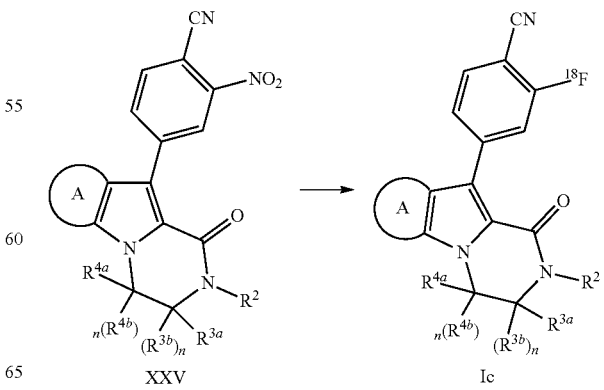

Scheme 11 below describes a potential synthetic sequence for the preparation of compounds of Formula Ia$^5$, which is another subset of Formula I, wherein A is a fused tetrahydropyran ring; and the piperazinyl ring is saturated. The initial step in the synthesis, as depicted, utilizes methyl 1H-pyrrole-2-carboxylate of Formula 12 as an initial starting material. The methyl 1H-pyrrole-2-carboxylate of Formula 12 undergoes alkylation via alkyl halides of Formula 2 in the presence of base as a proton scavenger or via the alkyl alcohol under Mitsunobu conditions to form the compounds of Formula XXVI. During the alkylation step, Z is represented by an appropriate leaving group, the $R^{3a}$, $R^{3b}$, $R^{4a}$, and $R^{4b}$ substituents and n of Formula 2 should be represented by the same moieties as desired in the final product or protected variation thereof. The next step of the sequence is $S_N2$ displacement of a halide with an amine in the presence of base as a proton scavenger, at temperature from room temperature to 60° C., to afford amines of Formula XXVII. During the $S_N2$ reaction step, the $R^2$ substituent on the amine nucleophile of Formula 3 should be represented by the same moiety as is desired in the final product.

In the next step, the lactam of formula XXVIII can be formed via intermolecular amine addition to the methyl ester under a variety of conditions such as $K_2CO_3$ in acetonitrile (ACN), Mg(OMe)$_2$ in MeOH, or CaCl$_2$) in MeOH, at temperatures from room temperature to 80° C.

In the next step of Scheme 11, compounds of Formula XXIX can be prepared via formylation of compounds of Formula XXVIII in the presence of POCl$_3$ and N, N-dimethyl formamide.

Following the formylation step, the compounds of Formula XXX can be prepared utilizing a Horner-Wadsworth-Emmons or Wittig reaction on compounds of formula XXIX followed by reduction of the resulting alkene in the presence of a metal catalyst (Pd, Pt, etc) and hydrogen.

In the next step, compounds of Formula XXXI can be accomplished via an electrophilic bromination (such as NBS or Br$_2$) followed by reduction of the ester with a metal hydride (LiBH$_4$, LiAlH$_4$, etc).

Next, compounds of Formula XXXII were prepared utilizing an intramolecular ring closure of compounds of Formula XXXI, in the presence of a base, a metal catalyst (Cu, Pt), at temperature from 100 to 120° C.

In the final step of Scheme 11, conversion of compounds of Formula XXXII to compounds of Formula Ia$^5$ can be accomplished via electrophilic bromination (NBS or Br$_2$) followed by Suzuki coupling. The compounds of Formula XXXII undergo electrophilic bromination to afford the heteroaryl bromide which undergoes Suzuki coupling with boronic acids of Formula 4 in the presence of base, a metal catalyst (Pd, Ni, Cu), a phosphine ligand, at temperatures from room temperature to 100° C. to afford the desired ring system Formula Ia$^5$ (see de Vries, J. G. *Topics in Organometallic Chemistry* 2012, 42, pg 12-20 reference and references contained therein). During the Suzuki coupling, the $R^1$ substituent of the boronic acid of the Formula 4 should be represented by the same moiety as is desired in the final product or protected variation thereof.

Scheme 11

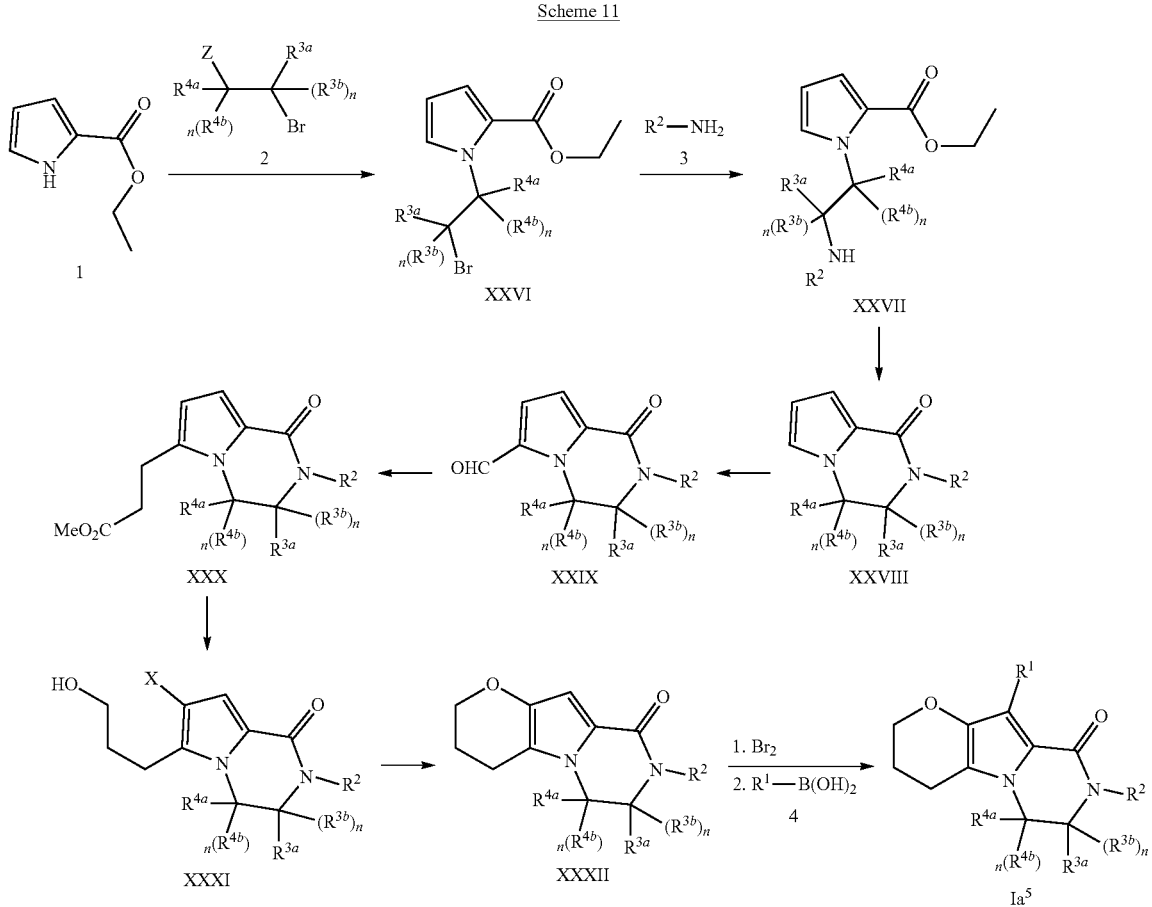

Scheme P1 below describes the synthetic sequence for the preparation of compounds of Formula P1, where U can be either carbon, or nitrogen. The synthesis of compounds of Formula P1 is one synthetic sequence utilized for preparing compounds of Formula 1 as depicted above in Schemes 1, 2, and 9. The initial step in the synthesis, as depicted, utilizes heterocycles of Formula 13 as an initial starting material. The heterocycles of Formula 13 undergo condensation with 2-oxopropanoate Formula 14 in the presence of catalytic amount of acid to afford compounds of Formula XXXIII (see Trécourt, F *Tetrahedron* 2000, 56(10), 1349-1360).

In the next step, compounds of Formula P1 can be generated via an intramolecular Heck reaction of compounds of Formula XXXIII in the presence of a base, a metal catalyst, at temperatures from 100° C. to 140° C.

Scheme P1

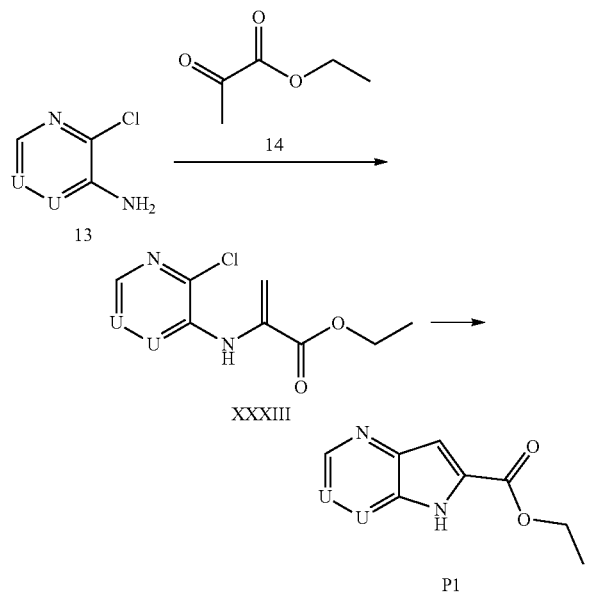

Scheme P2 below describes the synthetic sequence for the preparation of compounds of Formula P2. The synthesis of compounds of Formula P2 is another synthetic sequence utilized for preparing compounds of Formula 1 as depicted above in Schemes 1, 2, and 9. The initial step in the synthesis, as depicted, utilizes heterocycles of Formula 15 as an initial starting material. The heterocycles of Formula 15 undergo condensation with ethyl 2-azidoacetate Formula 16 in the presence of a base to afford compounds of Formula XXXIV.

In the next step, compounds of Formula P2 can be generated via a cyclization reaction of compounds of Formula XXXIV at temperatures from 100° C. to 140° C.

Scheme P2

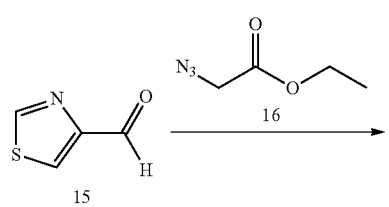

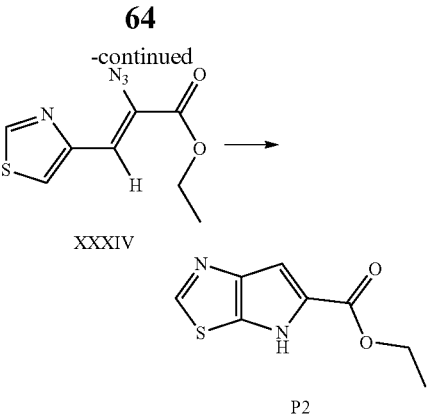

Experimental Procedures and Working Examples

The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification. Anhydrous solvents were employed where appropriate, generally AcroSeal® products from Acros Organics or DriSolv® products from EMD Chemicals. In other cases, commercial solvents were passed through columns packed with 4 Å molecular sieves, until the following QC standards for water were attained: a) <100 ppm for dichloromethane, toluene, N,N-dimethylformamide and tetrahydrofuran; b) <180 ppm for methanol, ethanol, 1,4-dioxane and diisopropylamine. For very sensitive reactions, solvents were further treated with metallic sodium, calcium hydride or molecular sieves, and distilled just prior to use. Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed. In some examples, chiral separations were carried out to separate enantiomers or atropisomers (or atropenantiomers) of certain compounds of the invention (in some examples, the separated atropisomers are designated as ENT-1 and ENT-2, according to their order of elution). In some examples, the optical rotation of an enantiomer or atropisomer was measured using a polarimeter. According to its observed rotation data (or its specific rotation data), an enantiomer or atropisomer (or atropenantiomer) with a clockwise rotation was designated as the (+)-enantiomer or (+)-atropisomer [or the (+) atropenantiomer] and an enantiomer or atropisomer (or atropenantiomer) with a counterclockwise rotation was designated as the (−)-enantiomer or (−)-atropisomer [or the (−) atropenantiomer].

Reactions proceeding through detectable intermediates were generally followed by LCMS, and allowed to proceed to full conversion prior to addition of subsequent reagents. For syntheses referencing procedures in other Examples or Methods, reaction conditions (reaction time and temperature) may vary. In general, reactions were followed by thin-layer chromatography or mass spectrometry, and subjected to work-up when appropriate. Purifications may vary between experiments: in general, solvents and the solvent ratios used for eluents/gradients were chosen to provide appropriate $R_f$s or retention times.

Example 1

10-(4-Chlorophenyl)-8-(pyrimidin-2-yl)-7,8-dihydropyrido[2', 3': 4,5]pyrrolo[1,2-a]pyrazin-9(6H)-one (1)

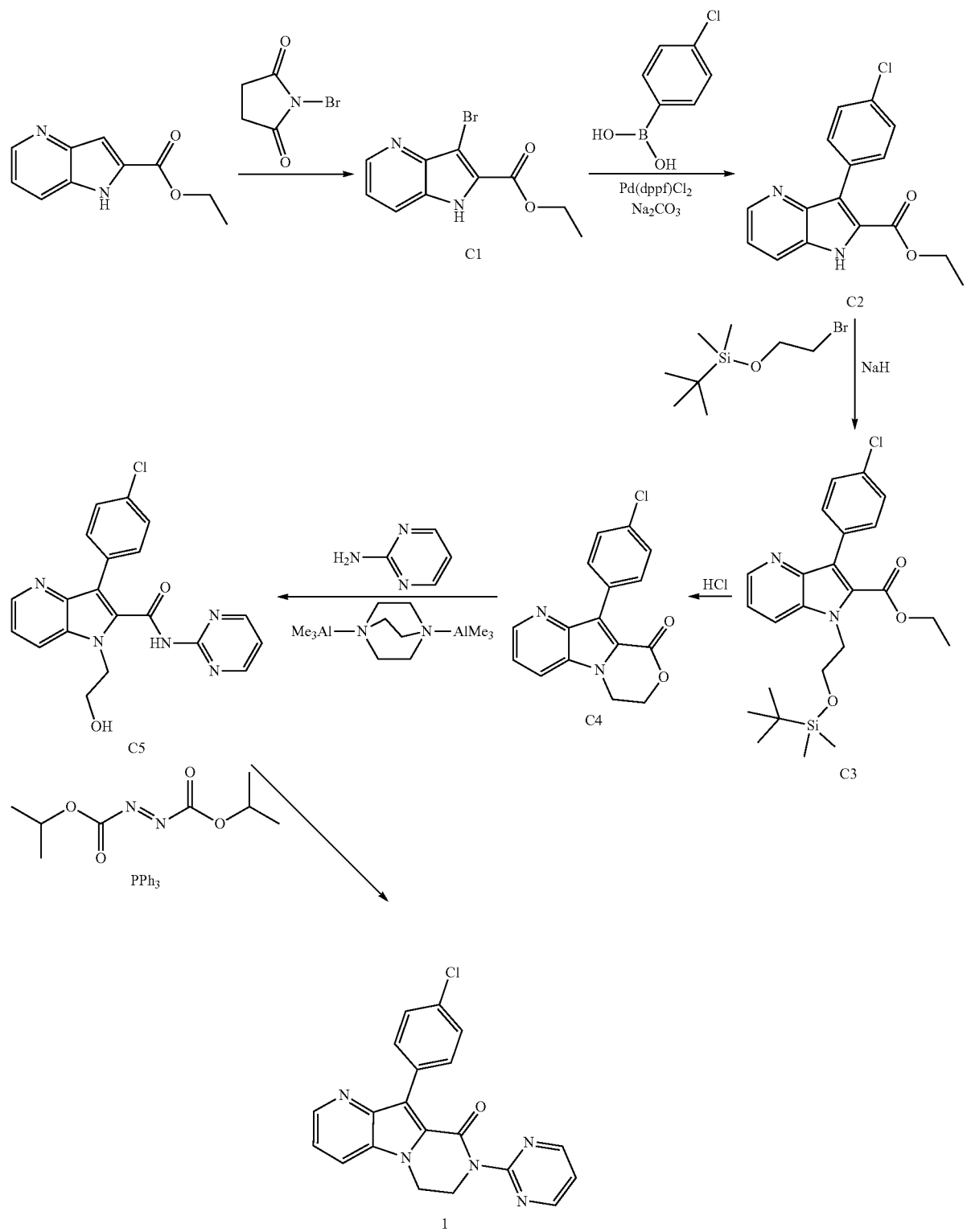

Step 1. Synthesis of ethyl 3-bromo-1H-pyrrolo[3,2-b]pyridine-2-carboxylate (C1)

N-Bromosuccinimide (15.4 g, 86.5 mmol) was added to a 0° C. solution of ethyl 1H-pyrrolo[3,2-b]pyridine-2-carboxylate (15.0 g, 78.9 mmol) in dichloromethane (150 mL), and the reaction mixture was stirred at room temperature for 16 hours. After addition of dichloromethane (150 mL) and water (200 mL), the aqueous layer was extracted with dichloromethane (3×150 mL). The combined organic layers were washed with saturated aqueous sodium chloride solution (5×50 mL), dried over sodium sulfate, filtered, and concentrated in vacuo. Silica gel chromatography (Gradient: 0% to 50% ethyl acetate in petroleum ether) afforded the product as a yellow solid. Yield: 13 g, 48 mmol, 61%. $^1$H NMR (400 MHZ, CDCl$_3$) δ 9.94 (br s, 1H), 8.65 (dd, J=4.5, 1.1 Hz, 1H), 7.78 (dd, J=8.4, 1.0 Hz, 1H), 7.31 (dd, J=8.4, 4.5 Hz, 1H), 4.49 (q, J=7.1 Hz, 2H), 1.45 (t, J=7.1 Hz, 3H).

Step 2. Synthesis of ethyl 3-(4-chlorophenyl)-1H-pyrrolo[3,2-b]pyridine-2-carboxylate (C2)

This experiment was carried out five times. To a mixture of C$_1$ (1.08 g, 4.01 mmol), (4-chlorophenyl)boronic acid (936 mg, 5.99 mmol) and sodium carbonate (1.27 g, 12.0 mmol) in 1,4-dioxane (20 mL) and water (2 mL) was added [1,1'-bis(diphenylphosphino)ferrocene]dichloropalladium (II) (146 mg, 200 umol). The reaction mixture was stirred at 100° C. for 18 hours, and then concentrated in vacuo. Water (30 mL) was added, and the mixture was extracted with ethyl acetate (3×30 mL). The combined organic layers were washed with saturated aqueous sodium chloride solution (3×20 mL), dried over sodium sulfate, filtered, concentrated under reduced pressure, and purified by silica gel chromatography (Gradient: 0% to 30% ethyl acetate in petroleum ether) to provide the product as a yellow solid. Total yield: 5.2 g, 17 mmol, 85%. $^1$H NMR (400 MHZ, CDCl$_3$) δ 9.25 (br s, 1H), 8.62 (dd, J=4.5, 1.4 Hz, 1H), 7.78 (dd, J=8.3, 1.3 Hz, 1H), 7.66 (br d, J=8.7 Hz, 2H), 7.43 (br d, J=8.5 Hz, 2H), 7.30 (dd, J=8.3, 4.5 Hz, 1H), 4.36 (q, J=7.2 Hz, 2H), 1.29 (t, J=7.2 Hz, 3H).

Step 3. Synthesis of ethyl 1-(2-{[tert-butyl(dimethyl)silyl]oxy}ethyl)-3-(4-chlorophenyl)-1H-pyrrolo[3,2-b]pyridine-2-carboxylate (C3)

A mixture of sodium hydride (60% in mineral oil, 1.4 g, 35 mmol) and N,N-dimethylformamide (30 mL) was cooled to 0° C. and treated in a drop-wise fashion with a solution of C2 (7.00 g, 23.3 mmol) in N,N-dimethylformamide (40 mL). This was stirred at room temperature for 1 hour, then cooled to 0° C. After addition of (2-bromoethoxy)(tert-butyl)dimethylsilane (11.2 g, 46.8 mmol), the reaction mixture was allowed to stir at room temperature for 16 hours, and was then quenched with water (150 mL). The mixture was extracted with ethyl acetate (3×150 mL), and the combined organic layers were washed with saturated aqueous sodium chloride solution (5×50 mL), dried over sodium sulfate, filtered, and concentrated in vacuo. Silica gel chromatography (Gradient: 0% to 10% ethyl acetate in petroleum ether) provided the product as a yellow oil. Yield: 6.8 g, 15 mmol, 64%. $^1$H NMR (400 MHZ, CDCl$_3$) δ 8.57 (dd, J=4.4, 1.4 Hz, 1H), 7.86 (dd, J=8.5, 1.4 Hz, 1H), 7.45 (br AB quartet, $J_{AB}$=8.6 Hz, $\Delta_{VAB}$=22.3 Hz, 4H), 7.26 (dd, J=8.4, 4.5, 1H, assumed; partially obscured by solvent peak), 4.65-4.71 (m, 2H), 4.23 (q, J=7.2 Hz, 2H), 3.98-4.03 (m, 2H), 1.12 (t, J=7.1 Hz, 3H), 0.73 (s, 9H), −0.20 (s, 6H).

Step 4. Synthesis of 10-(4-chlorophenyl)-6,7-dihydro-9H-pyrido[2',3':4,5]pyrrolo[2,1-c][1,4]oxazin-9-one (C4)

A solution of C3 (6.5 g, 14 mmol) in 6 M aqueous hydrochloric acid (78 mL) and tetrahydrofuran (156 mL) was heated at 70° C. for 3 hours. After removal of tetrahydrofuran in vacuo, the aqueous residue was slowly poured into saturated aqueous sodium bicarbonate solution and extracted with dichloromethane (3×100 mL). The combined organic layers were washed with saturated aqueous sodium chloride solution (2×50 mL), dried over sodium sulfate, filtered, concentrated under reduced pressure, and purified by silica gel chromatography (Gradient: 0% to 70% ethyl acetate in petroleum ether), affording the product as a white solid. Yield: 3.23 g, 10.8 mmol, 77%. $^1$H NMR (400 MHZ, CDCl$_3$) δ 8.69 (dd, J=4.5, 1.3 Hz, 1H), 7.81 (br d, J=8.7 Hz, 2H), 7.75 (dd, J=8.5, 1.3 Hz, 1H), 7.47 (br d, J=8.7 Hz, 2H), 7.39 (dd, J=8.5, 4.5 Hz, 1H), 4.79-4.84 (m, 2H), 4.40-4.45 (m, 2H).

Step 5. Synthesis of 3-(4-chlorophenyl)-1-(2-hydroxyethyl)-N-(pyrimidin-2-yl)-1H-pyrrolo[3,2-b]pyridine-2-carboxamide (C5)

To a solution of pyrimidin-2-amine (72.7 mg, 0.764 mmol) in tetrahydrofuran (9 mL) was added bis(trimethylaluminum)-1,4-diazabicyclo[2.2.2]octane adduct (97%, 202 mg, 0.764 mmol) at room temperature, in three portions over 2 minutes. This mixture was stirred for 5 minutes, and then treated with C4 (114 mg, 0.382 mmol) in one portion. The reaction mixture was heated for 20 hours at 70° C. and then cooled to room temperature; at this point, a mixture of additional pyrimidin-2-amine (35 mg, 0.37 mmol) and bis(trimethylaluminum)-1,4-diazabicyclo[2.2.2]octane adduct (97%, 100 mg, 0.38 mmol) that had been stirred in tetrahydrofuran (2 mL) for 5 minutes was added, and the reaction mixture was heated at 70° C. for an additional 3.5 hours. After it had cooled to ambient temperature, the reaction mixture was treated with 1 M aqueous sodium hydroxide solution until it was strongly basic; this mixture was extracted three times with dichloromethane. The aqueous phase was acidified to a pH of approximately 5-6 with 1 M aqueous hydrochloric acid, and subsequently extracted three times with dichloromethane. The combined organic layers from the acidic extractions were dried over magnesium sulfate, filtered, and concentrated in vacuo to provide the product as an off-white solid. Yield: 119 mg, 0.302 mmol, 79%. LCMS m/z 394.1, 396.2 [M+H]$^+$. $^1$H NMR (400 MHZ, CDCl$_3$) δ 8.62 (dd, J=4.5, 1.4 Hz, 1H), 8.51 (br d, J=4.8 Hz, 2H), 8.32 (br s, 1H), 7.86 (dd, J=8.5, 1.4 Hz, 1H), 7.57 (br d, J=8.5 Hz, 2H), 7.42 (br d, J=8.6 Hz, 2H), 7.32 (dd, J=8.5, 4.5 Hz, 1H), 7.02 (t, J=4.9 Hz, 1H), 4.68-4.73 (m, 2H), 4.08-4.14 (m, 2H).

Step 6. Synthesis of 10-(4-chlorophenyl)-8-(pyrimidin-2-yl)-7,8-dihydropyrido[2',3':4,5]pyrrolo[1,2-a]pyrazin-9(6H)-one (1)

To a solution of C5 (117 mg, 0.297 mmol) in tetrahydrofuran (2 mL) were added diisopropyl azodicarboxylate (0.147 mL, 0.742 mmol) and polymer-supported triphenylphosphine (1.6 mmol/g, 464 mg, 0.742 mmol). After the reaction mixture had stirred at room temperature for 1.5 hours, it was diluted with ethyl acetate, and the supernatant was passed through a disposable syringe equipped with an Acrodisc® filter. The filtrate was washed with water, dried over magnesium sulfate, and concentrated in vacuo. Silica gel chromatography (Gradient: 0% to 4% methanol in dichloromethane) provided the product as a white foam. Yield: 99 mg, 0.26 mmol, 88%. LCMS m/z 376.1, 378.1 [M+H]$^+$. $^1$H NMR (400 MHz, CDCl$_3$) δ 8.76 (d, J=4.8 Hz, 2H), 8.66 (dd, J=4.4, 1.4 Hz, 1H), 7.74-7.79 (m, 3H), 7.41 (br d, J=8.8 Hz, 2H), 7.36 (dd, J=8.4, 4.5 Hz, 1H), 7.15 (t, J=4.8 Hz, 1H), 4.57-4.62 (m, 2H), 4.49-4.54 (m, 2H).

Example 2

10-(4-Chlorophenyl)-8-cyclopropyl-7,8-dihydro-pyrido[2',3':4,5]pyrrolo[1,2-a]pyrazin-9(6H)-one (2)

Step 2. Synthesis of ethyl 1-[2-(cyclopropylamino)ethyl]-1H-pyrrolo[3,2-b]pyridine-2-carboxylate (C7)

Potassium carbonate (17.4 g, 0.126 mol) was added to a solution of C6 (25 g, 84 mmol) in acetonitrile (400 mL), followed by cyclopropylamine (192 g, 3.36 mol). The reaction mixture was stirred for 16 hours at 60° C., whereupon it was filtered and then concentrated under reduced pressure, to provide the product as a yellow semi-solid (23 g). By LCMS analysis, both the intended product C7 (m/z 273.9 [M+H]$^+$) and C8, the tricyclic compound resulting from intramolecular cyclization (m/z 227.8 [M+H]$^+$), were present. This material was used for the following step without further purification.

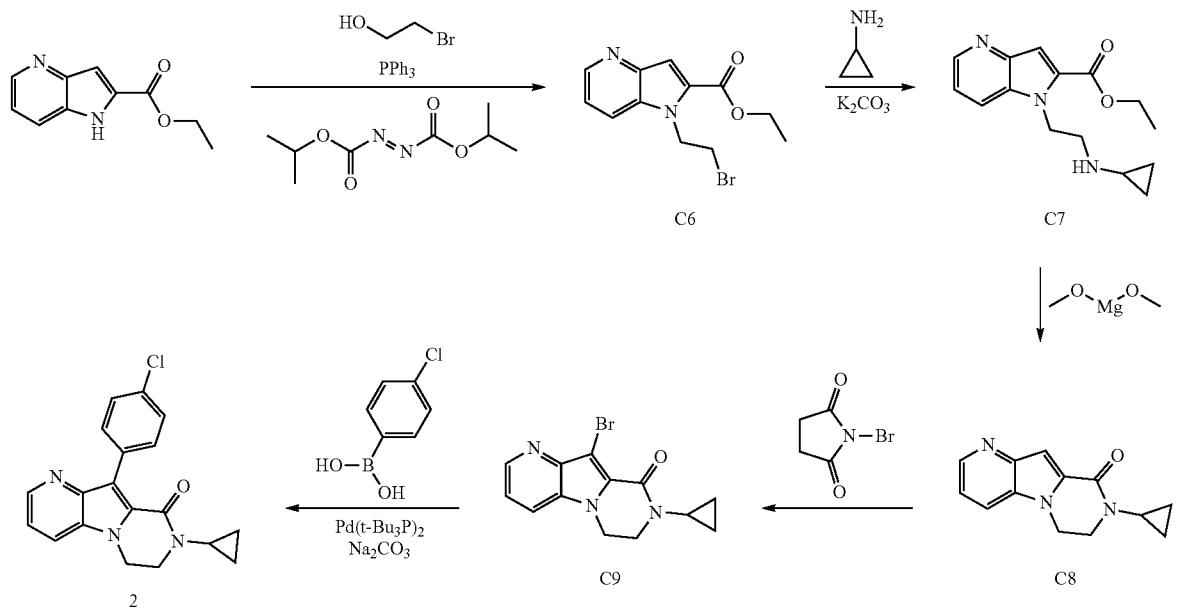

Step 1. Synthesis of ethyl 1-(2-bromoethyl)-1H-pyrrolo[3,2-b]pyridine-2-carboxylate (C6)

A solution of ethyl 1H-pyrrolo[3,2-b]pyridine-2-carboxylate (23 g, 0.12 mol), 2-bromoethanol (37.9 g, 0.303 mol) and triphenylphosphine (79.4 g, 0.303 mol) in tetrahydrofuran was cooled to 0° C. Diisopropyl azodicarboxylate (61.2 g, 0.303 mol) was added drop-wise over 20 minutes and the resulting mixture was warmed to 25° C. and stirred for 18 hours. After the solvent had been removed under reduced pressure, the residue was diluted with ethyl acetate (300 mL) and extracted with aqueous hydrochloric acid (1 M, 3×100 mL). The combined aqueous extracts were basified to pH 8-9 using saturated aqueous sodium carbonate solution, and the resulting mixture was extracted with ethyl acetate (3×100 mL). The combined organic layers were concentrated in vacuo; silica gel chromatography (Eluent: 5:1 petroleum ether/ethyl acetate) provided the product as a white solid. Yield: 25 g, 84 mmol, 70%. $^1$H NMR (400 MHZ, CDCl$_3$) δ 8.59 (dd, J=4.5, 1.3 Hz, 1H), 7.81 (br d, J=8.5 Hz, 1H), 7.50 (br s, 1H), 7.28 (dd, J=8.5, 4.5 Hz, 1H), 4.92 (t, J=6.7 Hz, 2H), 4.42 (q, J=7.2 Hz, 2H), 3.73 (t, J=6.7 Hz, 2H), 1.44 (t, J=7.2 Hz, 3H).

Step 3. Synthesis of 8-cyclopropyl-7,8-dihydro-pyrido[2',3':4,5]pyrrolo[1,2-a]pyrazin-9(6H)-one (C8)

Magnesium methoxide (7.26 g, 84.1 mmol) was added to a solution of C7 (from the previous step, 23 g, ≤84 mmol) in methanol (350 mL). After the reaction mixture had been stirred for 1 hour at 80° C., solids were removed via filtration and the filtrate was concentrated under reduced pressure. Purification via silica gel chromatography (Eluent: 1:1 petroleum ether/ethyl acetate) afforded the product as a white solid. Yield: 18.5 g, 81.4 mmol, 97% over 2 steps. $^1$H NMR (400 MHZ, CDCl$_3$) δ 8.51 (dd, J=4.5, 1.3 Hz, 1H), 7.59 (br d, J=8.5 Hz, 1H), 7.40 (br s, 1H), 7.19 (dd, J=8.5, 4.5 Hz, 1H), 4.18-4.23 (m, 2H), 3.80-3.85 (m, 2H), 2.81-2.88 (m, 1H), 0.93-0.99 (m, 2H), 0.74-0.80 (m, 2H).

Step 4. Synthesis of 10-bromo-8-cyclopropyl-7,8-dihydropyrido[2',3':4,5]pyrrolo[1,2-a]pyrazin-9(6H)-one (C9)

N-Bromosuccinimide (17.4 g, 97.8 mmol) was added to a solution of C8 (18.5 g, 81.4 mmol) in dichloromethane (400 mL), and the reaction mixture was stirred for 1 hour at 25° C. It was then concentrated under reduced pressure, cooled, and treated with saturated aqueous sodium thiosulfate solution (100 mL). The mixture was extracted with dichloromethane (3×100 mL), and the combined organic layers were dried, filtered, and concentrated in vacuo. Silica gel chromatography (Eluent: 20:1 dichloromethane/methanol) provided the product as a light yellow solid. Yield: 17.9 g, 58.5 mmol, 72%. LCMS m/z 307.9 [M+H]$^+$. $^1$H NMR (400 MHZ, CDCl$_3$) δ 8.61 (br d, J=4.5 Hz, 1H), 7.63 (br d, J=8.4 Hz, 1H), 7.29 (dd, J=8.4, 4.5 Hz, 1H, assumed; partially obscured by solvent peak), 4.23-4.28 (m, 2H), 3.82-3.87 (m, 2H), 2.82-2.89 (m, 1H), 0.95-1.02 (m, 2H), 0.77-0.83 (m, 2H).

Step 5. Synthesis of 10-(4-chlorophenyl)-8-cyclopropyl-7,8-dihydropyrido[2',3':4,5]pyrrolo[1,2-a]pyrazin-9(6H)-one (2)

This reaction was carried out four times. Bis(tri-tert-butylphosphine)palladium(0) (83 mg, 0.16 mmol) was added to a mixture of C9 (500 mg, 1.63 mmol), (4-chlorophenyl)boronic acid (509 mg, 3.26 mmol), 1,4-dioxane (15 mL), and sodium carbonate (864 g, 8.15 mmol, as a 3 M solution in water). The reaction mixture was stirred at 90° C. for 16 hours, then diluted with water (50 mL) and ethyl acetate (50 mL). After extraction of the aqueous layer with ethyl acetate (3×30 mL), the combined organic layers were washed with saturated aqueous sodium chloride solution, dried over sodium sulfate, filtered, and concentrated in vacuo. Purification of the combined crude products via silica gel chromatography (Gradient: 0% to 100% ethyl acetate in petroleum ether) provided the product as a yellow solid. Yield: 870 mg, 2.58 mmol, 39%. LCMS m/z 337.8 [M+H]$^+$. $^1$H NMR (400 MHZ, CDCl$_3$) δ 8.60 (dd, J=4.5, 1.4 Hz, 1H), 7.76 (br d, J=8.5 Hz, 2H), 7.67 (dd, J=8.4, 1.4 Hz, 1H), 7.43 (br d, J=8.4 Hz, 2H), 7.29 (dd, J=8.4, 4.5 Hz, 1H), 4.27-4.32 (m, 2H), 3.86-3.92 (m, 2H), 2.81-2.87 (m, 1H), 0.92-0.99 (m, 2H), 0.73-0.80 (m, 2H).

Alternate Synthesis of Example 2

10-(4-Chlorophenyl)-8-cyclopropyl-7,8-dihydropyrido[2',3':4,5]pyrrolo[1,2-a]pyrazin-9(6H)-one (2)

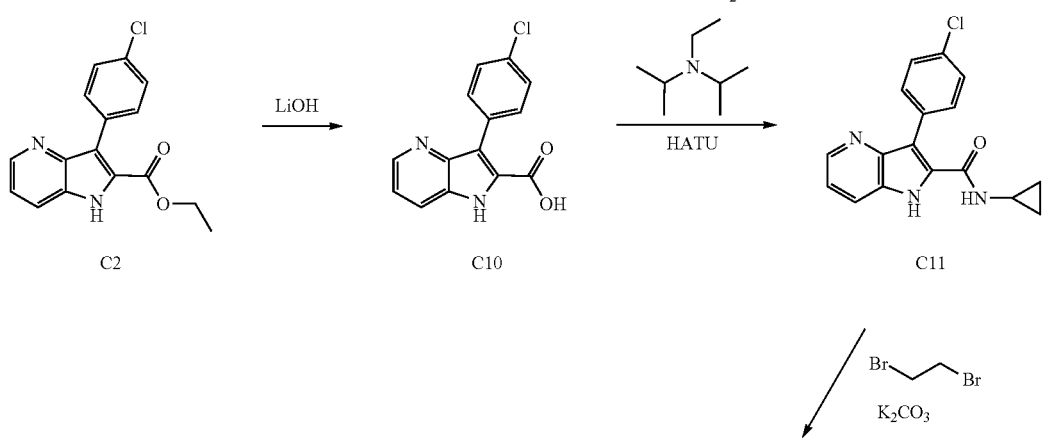

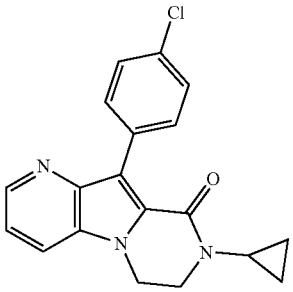

2

Step 1. Synthesis of 3-(4-chlorophenyl)-1H-pyrrolo[3,2-b]pyridine-2-carboxylic acid (C10)

A mixture of C2 (300 mg, 1.0 mmol) and lithium hydroxide monohydrate (126 mg, 3.00 mmol) in ethanol (10 mL) and water (1 mL) was stirred at room temperature for 3 hours. The reaction mixture was diluted with water and acidified with aqueous hydrochloric acid to a pH of less than 5. Removal of ethanol in vacuo, followed by lyophilization, afforded the product as a yellow solid. Yield: 300 mg, assumed quantitative.

Step 2. Synthesis of 3-(4-chlorophenyl)-N-cyclopropyl-1H-pyrrolo[3,2-b]pyridine-2-carboxamide (C11)

To a solution of C10 (200 mg, 0.73 mmol) and O-(7-azabenzotriazol-1-yl)-N,N,N',N'-tetramethyluronium hexafluorophosphate (HATU, 555 mg, 1.46 mmol) in N,N-dimethylformamide (6 mL) was added N,N-diisopropylethylamine (0.40 mL, 2.3 mmol), and the resulting mixture was stirred at room temperature for 10 minutes. Cyclopropylamine (63 mg, 1.1 mmol) was added, and the reaction mixture was stirred at room temperature for 3 hours, then diluted with water and extracted with ethyl acetate (4×25 mL). The combined organic layers were concentrated in vacuo and purified by high-performance liquid chromatography (HPLC) (Column: DIKMA Diamonsil (2) C18, 5 um; Mobile phase A: 0.225% formic acid in water; Mobile phase B: acetonitrile; Gradient: 10% to 30% B) to provide the product as a white solid. Yield: 20 mg, 64 umol, 9%. LCMS m/z 311.9 [M+H]$^+$. $^1$H NMR (400 MHz, DMSO-d$_6$) δ 12.26 (br s, 1H), 8.48 (d, J=4.3 Hz, 1H), 8.32 (br d, J=3.8 Hz, 1H), 7.95-8.02 (m, 1H), 7.75 (d, J=8.3 Hz, 2H), 7.50 (d, J=8.5 Hz, 2H), 7.32-7.39 (m, 1H), 2.78-2.87 (m, 1H), 0.66-0.73 (m, 2H), 0.44-0.50 (m, 2H).

Step 3. Synthesis of 10-(4-chlorophenyl)-8-cyclopropyl-7,8-dihydropyrido[2',3':4,5]pyrrolo[1,2-a]pyrazin-9(6H)-one (2)

A solution of C11 (25 mg, 80 umol), potassium carbonate (98 mg, 0.71 mmol) and 1,2-dibromoethane (0.5 mL) in acetonitrile (2.5 mL) was stirred at 100° C. for 4 hours. After filtration of the mixture, the filtrate was concentrated under reduced pressure and purified by reversed phase HPLC (Column: Kromasil Eternity-5-C18, 5 um; Mobile phase A: 0.225% formic acid in water; Mobile phase B: acetonitrile; Gradient: 15% to 35% B) to afford the product as a yellow solid. Yield: 9.9 mg, 29 umol, 36%. LCMS m/z 338.0 [M+H]$^+$. $^1$H NMR (400 MHz, DMSO-d$_6$) δ 8.48 (br d, J=4.3 Hz, 1H), 8.06 (br d, J=8.3 Hz, 1H), 7.77 (br d, J=8.5 Hz, 2H), 7.44 (br d, J=8.8 Hz, 2H), 7.36 (dd, J=8.4, 4.6 Hz, 1H), 4.35-4.41 (m, 2H), 3.78-3.83 (m, 2H), 2.82-2.90 (m, 1H), 0.71-0.83 (m, 4H).

Example 3

(6aR)-12-(4-Chlorophenyl)-6a,7,8,9-tetrahydro-6H,11H-pyrido[2',3':4,5]pyrrolo[1,2-a]pyrrolo[1,2-d]pyrazin-11-one, trifluoroacetate salt (3)

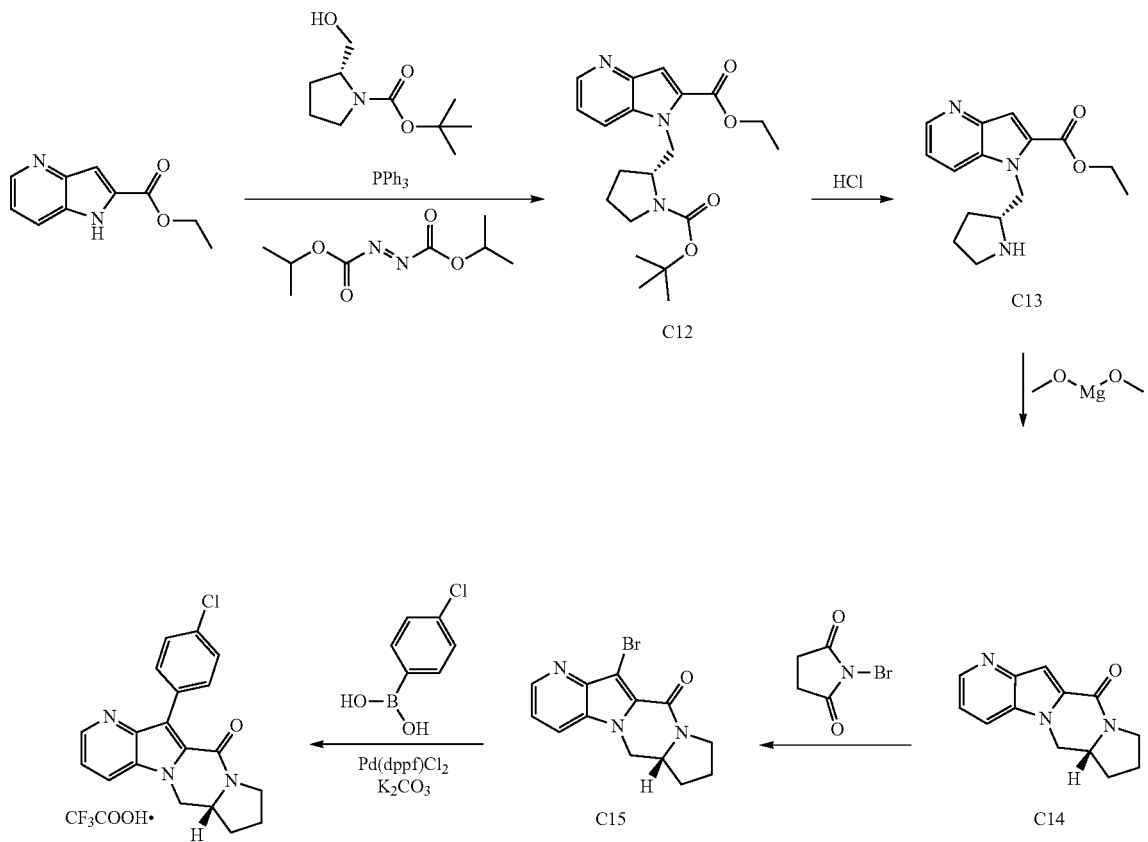

Step 1. Synthesis of ethyl 1-{[(2R)-1-(tert-butoxy-carbonyl)pyrrolidin-2-yl]methyl}-1H-pyrrolo[3,2-b]pyridine-2-carboxylate (C12)

Ethyl 1H-pyrrolo[3,2-b]pyridine-2-carboxylate (200 mg, 1.05 mmol), tert-butyl (2R)-2-(hydroxymethyl)pyrrolidine-1-carboxylate (529 mg, 2.63 mmol), and triphenylphosphine (690 mg, 2.63 mmol) were dissolved in tetrahydrofuran (200 mL) and cooled to 0° C. Diisopropyl azodicarboxylate (0.521 mL, 2.63 mmol) was added drop-wise over 20 minutes, and the reaction mixture was allowed to warm to room temperature and stir for 18 hours. Solvent was removed in vacuo, and purification via silica gel chromatography (Gradient: 0% to 100% ethyl acetate in heptane) provided product (500 mg) still containing contaminants. This material was taken directly to the following step. LCMS m/z 374.3 [M+H]$^+$.

Step 2. Synthesis of ethyl 1-[(2R)-pyrrolidin-2-ylmethyl]-1H-pyrrolo[3,2-b]pyridine-2-carboxylate (C13)

A solution of C12 (from the previous step, ≤1.05 mmol) in diethyl ether was treated with a solution of hydrogen chloride in diethyl ether (4 M, 5 mL), and the reaction mixture was allowed to stir for 3 days. The reaction mixture was analyzed by LCMS and was found to consist predominantly of compound C13: m/z 274.2 [M+H]$^+$. Solvent was removed in vacuo, and the residue was mixed with water and extracted with ethyl acetate. The aqueous layer was basified via addition of saturated aqueous sodium carbonate solution and then extracted with ethyl acetate (2×100 mL). These two organic layers were combined and dried over magnesium sulfate, filtered, and concentrated under reduced pressure to provide a product (90 mg) that by NMR analysis had essentially completely cyclized to C14, the product of step 3. This material was nonetheless subjected to the following step.

Step 3. Synthesis of (6aR)-6a, 7,8,9-tetrahydro-6H, 11H-pyrido[2',3':4,5]pyrrolo[1,2-a]pyrrolo[1,2-d]pyrazin-11-one (C14)

The material from the previous step (90 mg) was mixed with a solution of magnesium methoxide in methanol (6-10% solution, 4 mL) and the reaction mixture was heated to reflux for 18 hours. Evaporation of solvent under reduced pressure was followed by addition of water and extraction with ethyl acetate (2×100 mL). The combined organic layers were dried over magnesium sulfate, filtered, and concentrated in vacuo; silica gel chromatography (Gradient: 0% to 10% methanol in dichloromethane) afforded the product. Yield: 70 mg, 0.31 mmol, 30% over 3 steps. LCMS m/z 228.1 [M+H]$^+$. $^1$H NMR (400 MHZ, CD$_3$OD) δ 8.43 (dd, J=4.6, 1.3 Hz, 1H), 8.00 (ddd, J=8.5, 1.2, 1.1 Hz, 1H), 7.36 (dd, J=8.4, 4.7 Hz, 1H), 7.25 (br s, 1H), 4.85 (dd, J=12.1, 4.5 Hz, 1H, assumed; partially obscured by water peak), 4.19-4.29 (m, 1H), 3.87 (dd, J=12.1, 12.1 Hz, 1H), 3.77-3.84 (m, 1H), 3.60-3.69 (m, 1H), 2.36-2.44 (m, 1H), 2.17-2.25 (m, 1H), 1.98-2.11 (m, 1H), 1.87-1.98 (m, 1H).

Step 4. Synthesis of (6aR)-12-bromo-6a,7,8,9-tetrahydro-6H, 11H-pyrido[2',3':4,5]pyrrolo[1,2-a]pyrrolo[1,2-d]pyrazin-11-one (C15)

Compound C14 was converted to the product according to the method described for synthesis of C1 in Example 1. In this case, the chromatographic purification was carried out with 5% methanol in dichloromethane as eluent. Yield: 70 mg, 0.23 mmol, 58%. LCMS m/z 306.0, 308.0 [M+H]$^+$. $^1$H NMR (400 MHZ, CD$_3$OD) δ 8.49 (dd, J=4.6, 1.3 Hz, 1H), 8.02 (dd, J=8.5, 1.3 Hz, 1H), 7.43 (dd, J=8.5, 4.6 Hz, 1H), 4.87 (dd, J=12.1, 4.3 Hz, 1H), 4.16-4.25 (m, 1H), 3.88 (dd, J=12.0, 12.0 Hz, 1H), 3.75-3.82 (m, 1H), 3.59-3.68 (m, 1H), 2.35-2.42 (m, 1H), 2.16-2.25 (m, 1H), 1.97-2.10 (m, 1H), 1.86-1.97 (m, 1H).

Step 5. Synthesis of (6aR)-12-(4-chlorophenyl)-6a, 7,8,9-tetrahydro-6H, 11H-pyrido[2',3':4,5]pyrrolo[1,2-a]pyrrolo[1,2-d]pyrazin-11-one, trifluoroacetate salt (3)

Compound C15 was converted to the product according to the general method described for synthesis of C2 in Example 1. Purification in this case was carried out by reversed phase HPLC (Column: Waters Sunfire C18, 5 um; Mobile phase A: 0.05% trifluoroacetic acid in water (v/v); Mobile phase B: 0.05% trifluoroacetic acid in acetonitrile (v/v); Gradient: 10% to 30% B) to provide the product. Yield: 33 mg, 73 umol, 74%. LCMS m/z 338.0, 340.0 [M+H]$^+$. $^1$H NMR (600 MHZ, DMSO-d$_6$) δ 8.48 (dd, J=4.4, 1.4 Hz, 1H), 8.04 (br d, J=8.4 Hz, 1H), 7.84 (br d, J=8.6 Hz, 2H), 7.44 (br d, J=8.7 Hz, 2H), 7.37 (dd, J=8.4, 4.4 Hz, 1H), 4.89 (dd, J=12.1, 3.9 Hz, 1H), 4.16-4.22 (m, 1H), 3.87 (dd, J=12.1, 12.0 Hz, 1H), 3.60-3.65 (m, 1H), 3.46-3.52 (m, 1H), 2.25-2.31 (m, 1H), 2.03-2.10 (m, 1H), 1.87-1.95 (m, 1H), 1.78-1.87 (m, 1H).

Example 4

4-(8-Cyclopropyl-9-oxo-6,7,8,9-tetrahydropyrido[2',3':4,5]pyrrolo[1,2-a]pyrazin-10-yl)-2-fluorobenzonitrile (4)

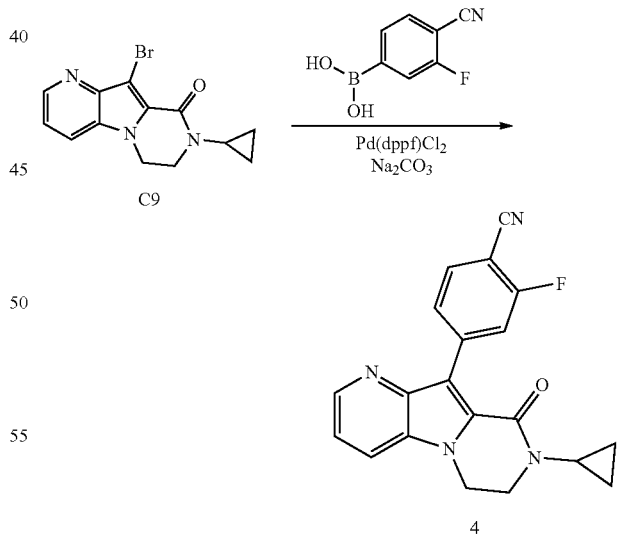

[1,1'-Bis(diphenylphosphino)ferrocene]dichloropalladium(II) (242 mg, 0.331 mmol) was added to a mixture of sodium carbonate (1.04 g, 9.81 mmol, as a 3 M solution in water), C9 (1.0 g, 3.3 mmol), and (4-cyano-3-fluorophenyl) boronic acid (592 mg, 3.59 mmol) in 1,4-dioxane (30 mL). The reaction mixture was stirred at 90° C. for 16 hours, whereupon it was diluted with water (30 mL) and ethyl acetate (30 mL). The aqueous layer was extracted with ethyl acetate (3×30 mL), and the combined organic layers were washed with saturated aqueous sodium chloride solution, dried over sodium sulfate, filtered, and concentrated in vacuo. Chromatographic purification on silica gel (Gradient: 0% to 75% ethyl acetate in petroleum ether, followed by a second column using 80% ethyl acetate in heptane as eluent) afforded a solid, which was slurried in diethyl ether, stirred for 30 minutes, and collected via filtration to afford the product as a white solid. Yield: 590 mg, 1.70 mmol, 52%. LCMS m/z 347.2 [M+H]$^+$. $^1$H NMR (400 MHZ, CDCl$_3$) δ 8.62 (br d, J=4.4 Hz, 1H), 7.76-7.81 (m, 2H), 7.73 (br d, J=8.4 Hz, 1H), 7.67 (dd, J=7.9, 7.0 Hz, 1H), 7.34 (dd, J=8.4, 4.5 Hz, 1H), 4.30-4.36 (m, 2H), 3.90-3.95 (m, 2H), 2.83-2.90 (m, 1H), 0.96-1.02 (m, 2H), 0.75-0.81 (m, 2H).

Example 4a 4-(8-Cyclopropyl-9-oxo-6,7,8,9-tetrahydropyrido[2',3':4,5]pyrrolo[1,2-a]pyrazin-10-yl)-2-($^{18}$F)fluorobenzonitrile (4a)

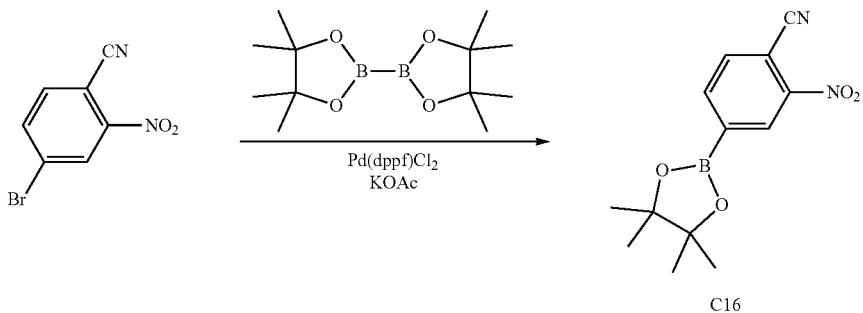

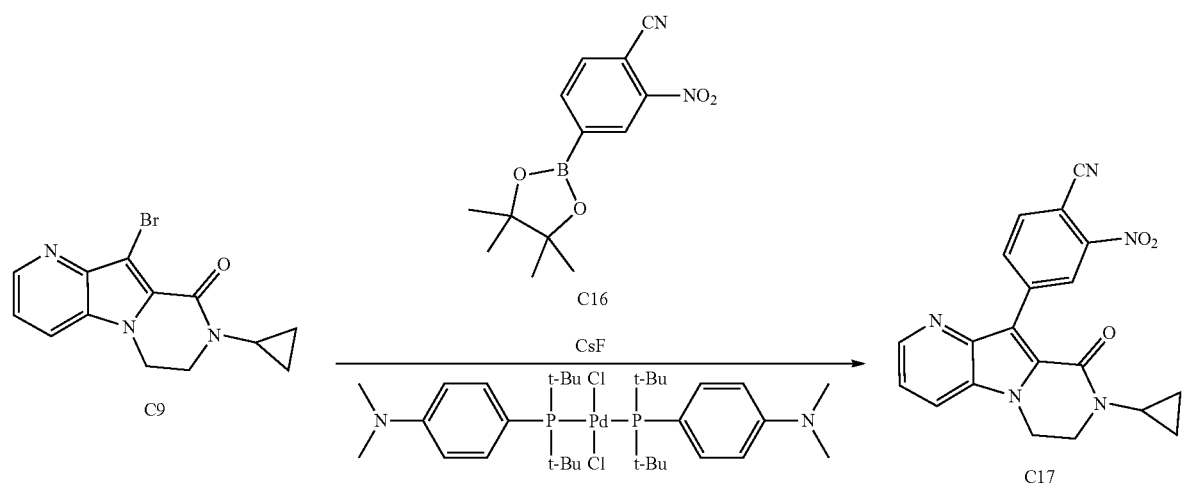

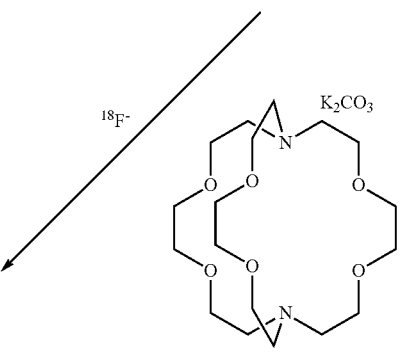

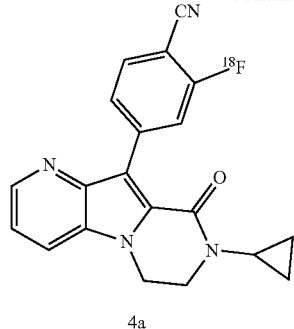

4a

Step 1. Synthesis of 2-nitro-4-(4,4,5,5-tetramethyl-1,3,2-dioxaborolan-2-yl)benzonitrile (C16)

4-Bromo-2-nitrobenzonitrile (800 mg, 3.52 mmol), 4,4,4',4',5,5,5',5'-octamethyl-2,2'-bi-1,3,2-dioxaborolane (940 mg, 3.70 mmol), and potassium acetate (1.0 g, 10 mmol) were combined in 1,4-dioxane (35 mL), and the mixture was degassed for 15 minutes. [1,1'-Bis(diphenylphosphino)ferrocene]dichloropalladium(II) (120 mg, 0.16 mmol) was added, and the reaction mixture was heated at 100° C. for 2 hours. After it had cooled to room temperature, solvent was removed in vacuo, and the residue was purified via chromatography on silica gel (Eluent: dichloromethane), providing the product as a brownish-yellow solid. Yield: 940 mg, 3.43 mmol, 97%. $^1$H NMR (400 MHZ, CDCl$_3$) δ 8.69 (br s, 1H), 8.18 (dd, J=7.6, 1.0 Hz, 1H), 7.90 (d, J=7.6 Hz, 1H), 1.38 (s, 12H).

Step 2. Synthesis of 4-(8-cyclopropyl-9-oxo-6,7,8,9-tetrahydropyrido[2',3':4,5]pyrrolo[1,2-a]pyrazin-10-yl)-2-nitrobenzonitrile (C17)

Reaction of C9 with C16 was carried out using the method described for synthesis of C49 in Example 13. The product was obtained as a yellow solid. Yield: 315 mg, 0.844 mmol, 98%. LCMS m/z 374.2 [M+H]$^+$. $^1$H NMR (500 MHZ, CDCl$_3$) δ 8.90 (d, J=1.5 Hz, 1H), 8.56 (dd, J=4.4, 1.2 Hz, 1H), 8.36 (dd, J=7.9, 1.6 Hz, 1H), 7.85 (d, J=8.0 Hz, 1H), 7.78 (dd, J=8.5, 1.2 Hz, 1H), 7.33 (dd, J=8.3, 4.4 Hz, 1H), 4.33-4.40 (m, 2H), 3.90-3.97 (m, 2H), 2.82-2.89 (m, 1H), 0.91-0.99 (m, 2H), 0.73-0.81 (m, 2H). HRMS (m/z): [M+H]$^+$ calcd for C$_{20}$H$_{15}$N$_5$O$_3$, 374.1248; found, 374.1246.

Step 3. Synthesis of 4-(8-cyclopropyl-9-oxo-6,7,8,9-tetrahydropyrido[2',3':4,5]pyrrolo[1,2-a]pyrazin-10-yl)-2-($^{18}$F)fluorobenzonitrile (4a)

[$^{18}$F]Fluoride in water was produced in a $^{18}$O(p,n)$^{18}$F nuclear reaction on a CTI RDS-111 cyclotron. The starting material for the p/n reaction was 97% O-18 enriched water from Huayi/Isoflex; irradiation was performed on the beamline 2 F-18 HP target (volume=2.4 mL), for 30 minutes at 60 μamp. The semi-preparative HPLC column was equilibrated with the mobile phase for 15 minutes at 3 mL/minute prior to the start of the experiment.

The activity was unloaded from the target and delivered straight to the glass V-vial on a General Electric FX-FN synthesis module. The [$^{18}$F]fluoride was passed through a Chromafix PS-HCO$_3$ cartridge (Macherey-Nagel), which had been pre-treated with ethanol (1 mL) followed by water (1 mL), with the water then drained off using a syringe. The fluoride was eluted with a solution of potassium carbonate (3 mg, 20 umol) in water (0.5 mL), followed by a solution of 4,7,13,16,21,24-hexaoxa-1,10-diazabicyclo[8.8.8]hexacosane (Kryptofix® 222, 20 mg, 53 umol) in acetonitrile (1 mL). After drying of the F-18/Kryptofix mixture, the residue was dissolved in a solution of C17 (2 mg, 6 umol) in anhydrous N,N-dimethylformamide (0.5 mL) and heated at 130° C. for 10 minutes. The reaction mixture was cooled to 35° C., then diluted with 30% acetonitrile in 0.05 M ammonium acetate (4.5 mL). The resulting light yellow solution was passed through a Waters Alumina N Sep-Pak Light cartridge [pre-conditioned with water (10 mL)] into an intermediate vial. The crude reaction mixture was then purified by semi-preparative HPLC (Column: Phenomenex Luna Phenyl-Hexyl, 10×250 mm, 5 μm; Eluent: 30% acetonitrile in 0.05 M aqueous ammonium acetate; Flow rate: 6.0 mL/minute) by automated filling of a 5.0 mL Rheodyne loop, followed by injection onto the column. The activity associated with 4a eluted from 33 minutes to 36 minutes (14000 cps), and the 4a collection started at 2000 cps and stopped at 6000 cps. The retention time of 4a was 34 minutes. The HPLC eluent associated with this collection was diluted with water (50 mL) containing ascorbic acid (12 mg), followed by trapping on a conditioned Phenomenex Strata® C18-E 50 mg cartridge. The cartridge was washed with water (3 mL), then eluted with ethanol (0.5 mL) and saline solution (4.5 mL). Specific activity of 4a at end of synthesis: 14305 Ci/mmol; Product activity: 289 mCi; Radiochemical purity of 4a: >99%; Chemical purity: >99%.

Compound 4a coeluted with the compound of Example 4 by analytical HPLC (Column: Phenomenex Gemini® C18, 150×4.6 mm, 4 μm; Eluent: 45:55 acetonitrile/water; Flow rate: 1.0 mL/min), with a retention time of 7.8 minutes.

Examples 5 and 6
10-(4-Chlorophenyl)-8-(4H-1,2,4-triazol-3-yl)-7,8-dihydropyrido[2',3':4,5]pyrrolo[1,2-a]pyrazin-9(6H)-one (5) and 10-(4-Chlorophenyl)-8-(4H-1,2,4-triazol-3-yl)pyrido[2',3':4,5]pyrrolo[1,2-a]pyrazin-9(8H)-one (6)
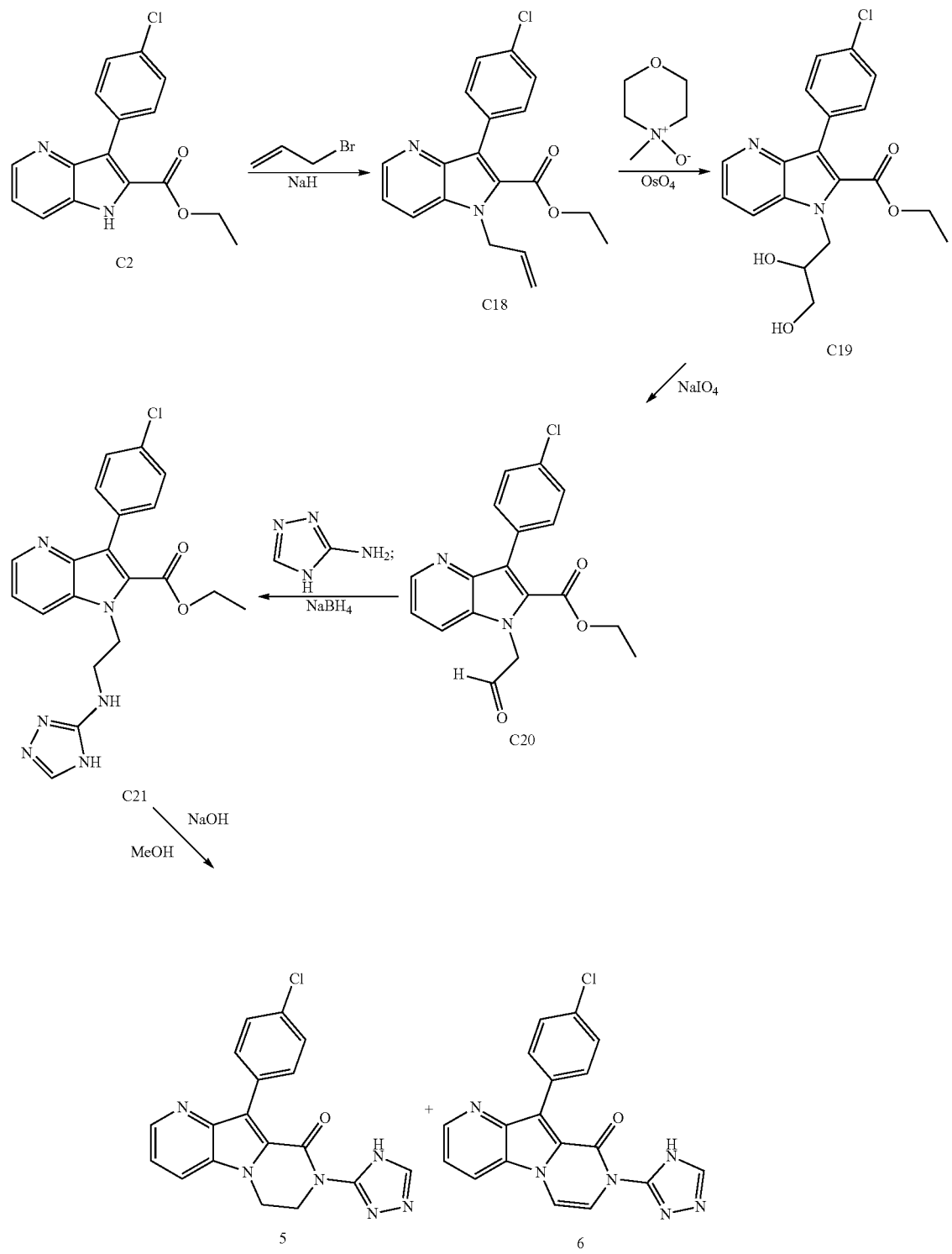

Step 1. Synthesis of ethyl 3-(4-chlorophenyl)-1-(prop-2-en-1-yl)-1H-pyrrolo[3,2-b]pyridine-2-carboxylate (C18)

Sodium hydride (60% in mineral oil, 150 mg, 3.75 mmol) was slowly added to a 0° C. solution of C2 (750 mg, 2.49 mmol) in N,N-dimethylformamide (10 mL). After 10 minutes, 3-bromoprop-1-ene (99%, 0.432 mL, 4.98 mmol) was added drop-wise, and the cooling bath was removed. After 4.5 hours, the reaction mixture was poured into water (25 mL) and diluted with ethyl acetate (100 mL). The organic layer was washed with half-saturated aqueous sodium chloride solution (4×50 mL), then with saturated aqueous sodium chloride solution (50 mL), dried over sodium sulfate, filtered, and concentrated in vacuo. The residue was subjected to silica gel chromatography (Gradient: 5% to 50% ethyl acetate in heptane), affording the product as a yellow oil (900 mg). This material was taken directly to the following step. $^1$H NMR (400 MHZ, CDCl$_3$) δ 8.61 (dd, J=4.5, 1.3 Hz, 1H), 7.76 (dd, J=8.5, 1.3 Hz, 1H), 7.48 (br AB quartet, J$_{AB}$=8.7 Hz, Δ$_{VAB}$=33.5 Hz, 4H), 7.30 (dd, J=8.5, 4.5 Hz, 1H), 5.98-6.09 (m, 1H), 5.17-5.22 (m, 3H), 4.99-5.06 (m, 1H), 4.25 (q, J=7.1 Hz, 2H), 1.14 (t, J=7.1 Hz, 3H).

Step 2. Synthesis of ethyl 3-(4-chlorophenyl)-1-(2,3-dihydroxypropyl)-1H-pyrrolo[3,2-b]pyridine-2-carboxylate (C19)

4-Methylmorpholine N-oxide monohydrate (674 mg, 4.99 mmol) was added to a solution of C18 (from the previous step, 900 mg, ≤2.49 mmol) in tetrahydrofuran (35 mL). After 20 minutes, osmium tetroxide (2.5 weight percent solution in tert-butanol, 0.94 mL, 75 umol) was added to the mixture. After 4.5 hours, the reaction was quenched via addition of 10% aqueous sodium thiosulfate solution (20 mL), and the mixture was allowed to stir for 20 minutes, whereupon it was extracted with ethyl acetate (4×45 mL). The combined organic layers were washed with aqueous sodium thiosulfate solution and with saturated aqueous sodium chloride solution, dried over sodium sulfate, filtered, and concentrated in vacuo, providing the product as a white solid. Yield: 850 mg, 2.27 mmol, 91% over 2 steps. $^1$H NMR (400 MHZ, CD$_3$OD) δ 8.41 (dd, J=4.6, 1.4 Hz, 1H), 8.06 (dd, J=8.5, 1.3 Hz, 1H), 7.38-7.44 (m, 4H), 7.32 (dd, J=8.6, 4.6 Hz, 1H), 4.73 (dd, J=14.5, 4.1 Hz, 1H), 4.55 (dd, J=14.5, 7.9 Hz, 1H), 4.20 (q, J=7.1 Hz, 2H), 3.99-4.05 (m, 1H), 3.61 (dd, half of ABX pattern, J=11.3, 4.7 Hz, 1H), 3.55 (dd, half of ABX pattern, J=11.3, 5.2 Hz, 1H), 1.08 (t, J=7.1 Hz, 3H).

Step 3. Synthesis of ethyl 3-(4-chlorophenyl)-1-(2-oxoethyl)-1H-pyrrolo[3,2-b]pyridine-2-carboxylate (C20)

Compound C19 (from a reaction sequence similar to steps 1 and 2 above, ≤2.49 mmol) was dissolved in a 1:1 mixture of ethyl acetate and tetrahydrofuran (50 mL), and treated drop-wise with a solution of sodium periodate (815 mg, 4.27 mmol) in water (30 mL). After stirring at room temperature for 18 hours, the reaction mixture was treated with additional sodium periodate (815 mg, 4.27 mmol) and allowed to react until, by LCMS analysis, the starting material had been consumed. An aqueous solution of sodium bisulfite (10%, 30 mL) was added, and the aqueous layer was extracted with ethyl acetate (2×250 mL). The combined organic layers were dried over magnesium sulfate, filtered, and concentrated in vacuo; purification via silica gel chromatography (Gradient: 0% to 70% ethyl acetate in heptane) afforded the product as a solid. Yield: 290 mg, 0.846 mmol, ≥34%. LCMS m/z 341.1, 343.1 [M−1]. $^1$H NMR (400 MHZ, CDCl$_3$) δ 9.79 (s, 1H), 8.60 (dd, J=4.5, 1.4 Hz, 1H), 7.63 (dd, J=8.5, 1.3 Hz, 1H), 7.45 (br AB quartet, J$_{AB}$=8.4 Hz, Δ$_{VAB}$=33 Hz, 4H), 7.30 (dd, J=8.5, 4.5 Hz, 1H), 4.87-5.04 (m, 2H), 4.20 (q, J=7.1 Hz, 2H), 1.10 (t, J=7.1 Hz, 3H).

Step 4. Synthesis of ethyl 3-(4-chlorophenyl)-1-[2-(4H-1,2,4-triazol-3-ylamino)ethyl]-1H-pyrrolo[3,2-b]pyridine-2-carboxylate (C21)

Compound C20 (200 mg, 0.58 mmol), 4H-1,2,4-triazol-3-amine (65.0 mg, 0.773 mmol) and a 5:1 mixture of ethanol and toluene (15 mL) were combined in a vial and heated at 80° C. for 4 hours. At this point, the cap was removed, and the reaction mixture was heated at 100° C. until 80% of the solvent had evaporated. After cooling to room temperature, the mixture was treated with sodium borohydride (73.1 mg, 1.93 mmol) and methanol (10 mL) and allowed to stir at room temperature for 18 hours. Saturated aqueous sodium bicarbonate solution (10 mL) was added, and stirring was continued for 30 minutes. The mixture was then partitioned between ethyl acetate (100 mL) and water (30 mL), and the organic layer was washed with saturated aqueous sodium chloride solution (30 mL), dried over magnesium sulfate, filtered, and concentrated in vacuo to afford the crude product (265 mg), which was taken into the following step without purification.

Step 5. Synthesis of 10-(4-chlorophenyl)-8-(4H-1,2,4-triazol-3-yl)-7,8-dihydropyrido[2',3':4,5]pyrrolo[1,2-a]pyrazin-9(6H)-one (5) and 10-(4-chlorophenyl)-8-(4H-1,2,4-triazol-3-yl)pyrido[2',3':4,5]pyrrolo[1,2-a]pyrazin-9(8H)-one (6)

Compound C21 (from the preceding step, ≤0.58 mmol) was dissolved in methanol (15 mL) and treated with aqueous sodium hydroxide solution (2 M, 2 mL). After 6 hours at room temperature, LCMS analysis indicated the presence of both the expected product 5 and the unsaturated analogue 6. The reaction mixture was partitioned between ethyl acetate (130 mL) and water (10 mL), and the organic layer was dried over magnesium sulfate, filtered, and concentrated in vacuo. The crude product was combined with that obtained from a similar reaction carried out on C21 (78 mg, ≤0.19 mmol) to afford 250 mg of material. One-third of this was subjected to reversed phase HPLC (Column: Waters XBridge C18, 5 um; Mobile phase A: 0.03% ammonium hydroxide in water (v/v); Mobile phase B: 0.03% ammonium hydroxide in acetonitrile (v/v); Gradient: 20% to 30% B) to provide 5. Yield: 4.0 mg, 11 umol, 4% over two steps. 5: LCMS m/z 365.1, 367.1 [M+H]$^+$. $^1$H NMR (600 MHz, DMSO-d$_6$), characteristic peaks: δ 8.54 (d, J=4 Hz, 1H), 8.14 (d, J=8 Hz, 1H), 7.84 (br s, 1H), 7.78 (br d, J=8.4 Hz, 2H), 7.49 (br d, J=8 Hz, 2H), 7.44 (dd, J=8.4, 4.4 Hz, 1H), 4.62 (br s, 2H).

Another one-third of the crude product was purified using reversed phase HPLC (Column: Waters XBridge C18, 5 um; Mobile phase A: 0.03% ammonium hydroxide in water (v/v); Mobile phase B: 0.03% ammonium hydroxide in acetonitrile (v/v); Gradient: 20% to 30% B) to provide 6. Yield: 2.6 mg, 7.2 umol, 3% over two steps. 6: LCMS m/z 363.1, 365.1 [M+H]$^+$. $^1$H NMR (600 MHZ, DMSO-d$_6$) δ 8.72 (dd, J=4.4, 1 Hz, 1H), 8.64 (br d, J=8.4 Hz, 1H), 8.46 (br s, 1H), 8.12 (d, J=5.7 Hz, 1H), 7.80 (br d, J=8.4 Hz, 2H), 7.56 (dd, J=8.4, 4.4 Hz, 1H), 7.49 (br d, J=8.4 Hz, 2H), 7.28 (br d, J=5.7 Hz, 1H).

Example 7

10-(4-Chloro-3-fluorophenyl)-8-cyclopropyl-7,8-dihydropyrazino[1',2':1,5]pyrrolo[3,2-d]pyrimidin-9(6H)-one (7)

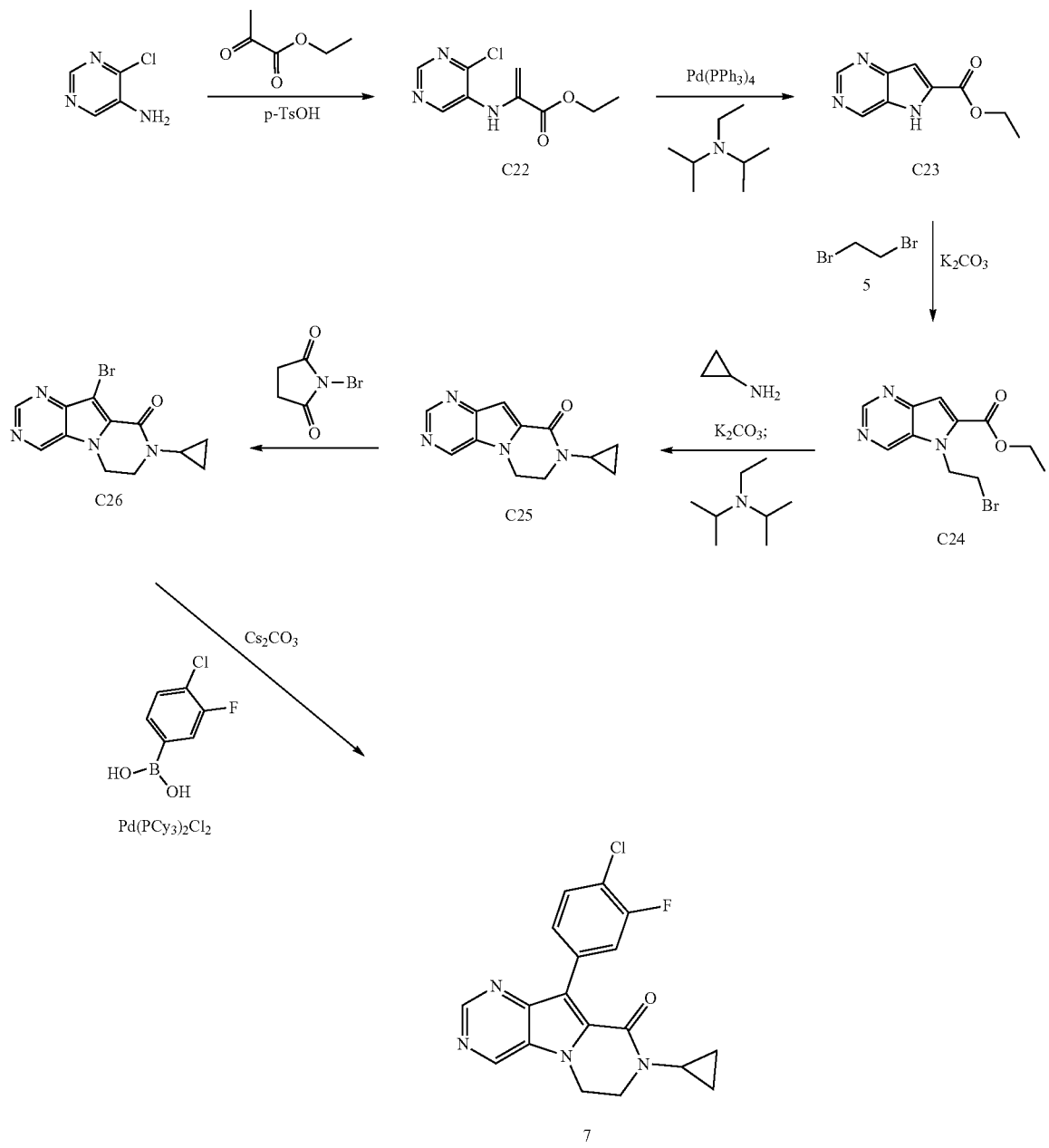

Step 1. Synthesis of ethyl 2-[(4-chloropyrimidin-5-yl)amino]prop-2-enoate (C22)

A mixture of 4-chloropyrimidin-5-amine (8.0 g, 62 mmol), ethyl 2-oxopropanoate (14.4 g, 124 mmol) and p-toluenesulfonic acid monohydrate (0.90 g, 4.7 mmol) in toluene (100 mL) was stirred at reflux for 3 hours, while water was azeotropically removed with a Dean-Stark trap. The mixture was subsequently concentrated to a small volume and purified by silica gel chromatography (Gradient: 0% to 30% ethyl acetate in petroleum ether) to afford the product as a yellow solid. Yield: 2.1 g, 9.2 mmol, 15%.

Step 2. Synthesis of ethyl 5H-pyrrolo[3,2-d]pyrimidine-6-carboxylate (C23)

A mixture of C22 (2.1 g, 9.2 mmol), N,N-diisopropylethylamine (3 mL), and tetrakis(triphenylphosphine)palladium (0) (0.2 g, 0.2 mmol) in pyridine (25 mL) was degassed several times with nitrogen and stirred at 140° C. for 4 hours.

After removal of solvent in vacuo, the residue was purified by silica gel chromatography (Gradient: 0% to 100% ethyl acetate in petroleum ether) to provide the product as a brown solid. Yield: 500 mg, 2.6 mmol, 28%. ¹H NMR (400 MHZ, CDCl₃) δ 9.33 (br s, 1H), 9.12 (s, 1H), 9.05 (d, J=0.5 Hz, 1H), 7.34-7.36 (m, 1H), 4.50 (q, J=7.2 Hz, 2H), 1.47 (t, J=7.2 Hz, 3H).

Step 3. Synthesis of ethyl 5-(2-bromoethyl)-5H-pyrrolo[3,2-d]pyrimidine-6-carboxylate (C24)

A mixture of C23 (400 mg, 2.1 mmol), 1,2-dibromoethane (1.57 g, 8.36 mmol) and potassium carbonate (1.1 g, 8.0 mmol) in acetonitrile (20 mL) was heated at 50° C. for 18 hours. After the reaction mixture had been cooled to room temperature and poured into water (20 mL), it was concentrated under reduced pressure to remove acetonitrile. The aqueous residue was extracted with ethyl acetate (3×20 mL), and the combined organic layers were washed with saturated aqueous sodium chloride solution, dried over sodium sulfate, filtered, and concentrated in vacuo to afford the product as a brown solid. Yield: 350 mg, 1.2 mmol, 57%. ¹H NMR (400 MHZ, CDCl₃) δ 9.12 (s, 2H), 7.45 (s, 1H), 5.01 (t, J=6.2 Hz, 2H), 4.46 (q, J=7.1 Hz, 2H), 3.80 (t, J=6.3 Hz, 2H), 1.46 (t, J=7.1 Hz, 3H).

Step 4. Synthesis of 8-cyclopropyl-7,8-dihydropyrazino[1',2': 1,5]pyrrolo[3,2-d]pyrimidin-9(6H)-one (C25)

To a solution of C24 (300 mg, 1.0 mmol) and cyclopropylamine (3.0 g, 52 mmol) in acetonitrile (10 mL) was added potassium carbonate (284 mg, 2.05 mmol), and the reaction mixture was stirred at 80° C. for 18 hours. Volatiles were removed in vacuo, and the residue was mixed with acetonitrile (15 mL) and N,N-diisopropylethylamine (5 mL), and was stirred at 80° C. for 3 hours. The reaction mixture was filtered and the filtrate was concentrated under reduced pressure to provide the product as a brown solid. Yield: 180 mg, 0.79 mmol, 79%. ¹H NMR (400 MHZ, CDCl₃) δ 9.07 (s, 1H), 8.91 (d, J=0.6 Hz, 1H), 7.38 (d, J=0.7 Hz, 1H), 4.33-4.38 (m, 2H), 3.87-3.92 (m, 2H), 2.86-2.93 (m, 1H), 0.98-1.04 (m, 2H), 0.78-0.84 (m, 2H).

Step 5. Synthesis of 10-bromo-8-cyclopropyl-7,8-dihydropyrazino[1',2':1,5]pyrrolo[3,2-d]pyrimidin-9(6H)-one (C26)

Compound C25 was converted to the product using the method described for synthesis of C1 in Example 1, except that no chromatographic purification was carried out in this case. The product was obtained as a brown solid. Yield: 500 mg, 1.6 mmol, 91%. 1H NMR (400 MHZ, CDCl₃) δ 9.15 (s, 1H), 9.00 (s, 1H), 4.39-4.44 (m, 2H), 3.88-3.93 (m, 2H), 2.86-2.92 (m, 1H), 0.99-1.05 (m, 2H), 0.80-0.85 (m, 2H).

Step 6. Synthesis of 10-(4-chloro-3-fluorophenyl)-8-cyclopropyl-7,8-dihydropyrazino[1',2':1,5]pyrrolo[3,2-d]pyrimidin-9(6H)-one (7)

Compound C26 (400 mg, 1.3 mmol), (4-chloro-3-fluorophenyl)boronic acid (341 mg, 1.96 mmol) and cesium carbonate (1.0 g, 3.1 mmol) were combined in a mixture of 1,4-dioxane (20 mL) and water (2 mL), and degassed with nitrogen for 2 minutes. Dichlorobis(tricyclohexylphosphine)-palladium(II) (20 mg, 27 umol) was added, and the reaction mixture was heated to 100° C. for 18 hours, then concentrated in vacuo, diluted with water (50 mL), and extracted with ethyl acetate (3×30 mL). The combined organic layers were concentrated under reduced pressure and purified via reversed phase high-performance liquid chromatography (Column: Phenomenex Gemini C18, 8 um; Mobile phase A: aqueous ammonia, pH 10; Mobile phase B: acetonitrile; Gradient: 36% to 56% B) to provide the product as a yellow solid. Yield: 30 mg, 84 umol, 6%. LCMS m/z 357.1 [M+H]⁺. ¹H NMR (400 MHZ, CDCl₃) δ 9.12 (s, 1H), 8.98 (s, 1H), 7.65 (dd, J=10.2, 1.7 Hz, 1H), 7.56 (br dd, J=8.4, 1.5 Hz, 1H), 7.48 (dd, J=8.2, 7.8 Hz, 1H), 4.39-4.45 (m, 2H), 3.92-3.98 (m, 2H), 2.85-2.92 (m, 1H), 0.97-1.04 (m, 2H), 0.77-0.83 (m, 2H).

Example 8

10-(4-Chloro-3-fluorophenyl)-8-cyclopropyl-7,8-dihydropyrrolo[1,2-a:4,5-b']dipyrazin-9(6H)-one (8)

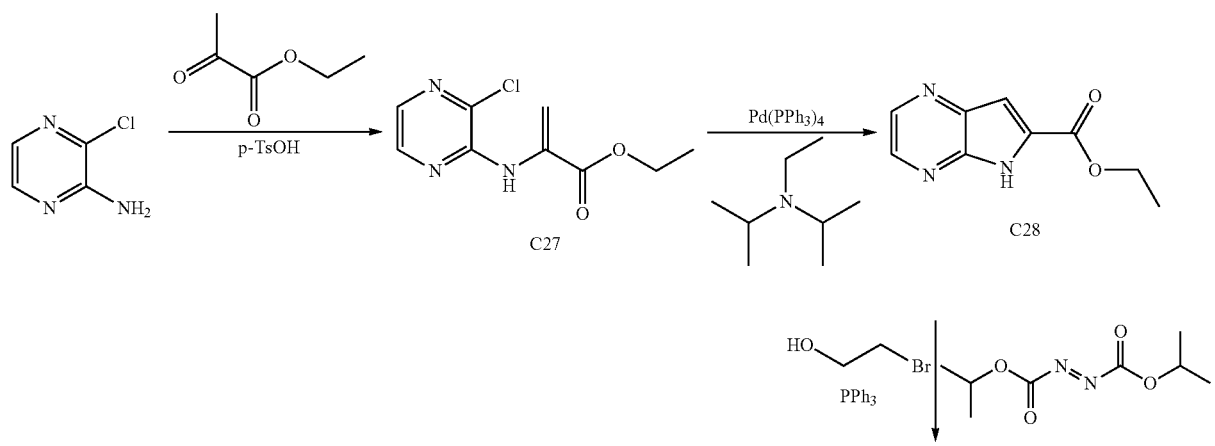

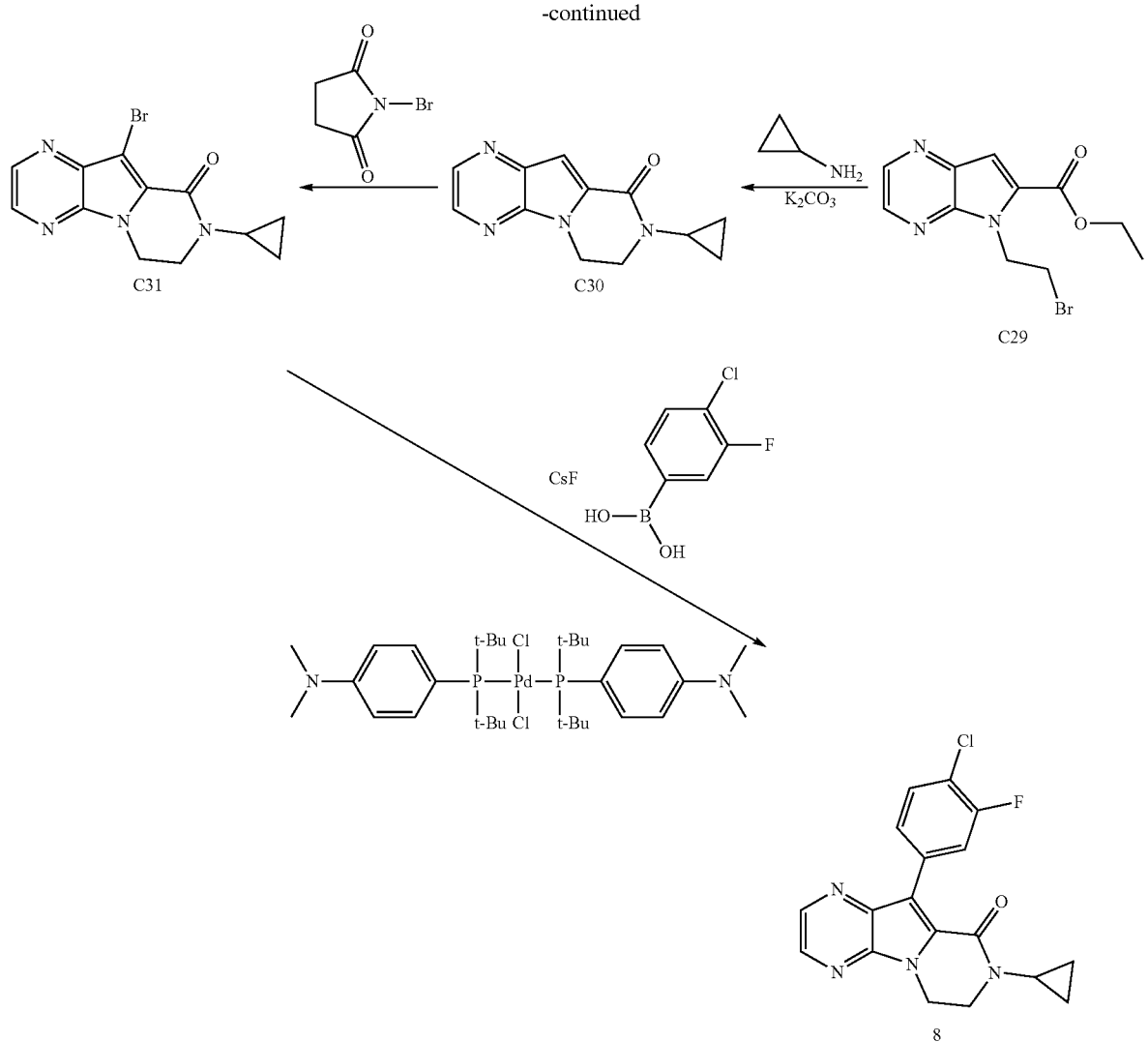

Step 1. Synthesis of ethyl 2-[(3-chloropyrazin-2-yl)amino]prop-2-enoate (C27)

3-Chloropyrazin-2-amine was converted to the product using the method described for synthesis of C22 in Example 7. The product was isolated as a white solid. Yield: 14.0 g, 61.5 mmol, 77%. $^1$H NMR (400 MHZ, CDCl$_3$) δ 8.11 (br s, 1H), 8.09 (d, J=2.8 Hz, 1H), 7.78 (d, J=2.6 Hz, 1H), 6.70 (s, 1H), 5.87 (d, J=1.4 Hz, 1H), 4.36 (q, J=7.2 Hz, 2H), 1.39 (t, J=7.2 Hz, 3H).

Step 2. Synthesis of ethyl 5H-pyrrolo[2,3-b]pyrazine-6-carboxylate (C28)

Compound C27 was converted to the product according to the method described for synthesis of C23 in Example 7. The product was obtained as a yellow solid. Yield: 7.6 g, 40 mmol, 83%. LCMS m/z 191.9 [M+H]$^+$. $^1$H NMR (400 MHZ, CDCl$_3$) δ 11.43 (br s, 1H), 8.63 (d, J=2.5 Hz, 1H), 8.55 (d, J=2.5 Hz, 1H), 7.39 (d, J=2.1 Hz, 1H), 4.51 (q, J=7.2 Hz, 2H), 1.48 (t, J=7.2 Hz, 3H).

Step 3. Synthesis of ethyl 5-(2-bromoethyl)-5H-pyrrolo[2,3-b]pyrazine-6-carboxylate (C29)

Compound C28 was reacted with 2-bromoethanol using the method described for synthesis of C12 in Example 3. In this case, chromatography was carried out using a gradient of 10% to 40% ethyl acetate in petroleum ether, and the product was obtained as a white solid. Yield: 2.0 g, 6.7 mmol, 64%. $^1$H NMR (400 MHZ, CDCl$_3$) δ 8.58 (d, J=2.4 Hz, 1H), 8.42 (d, J=2.4 Hz, 1H), 7.46 (s, 1H), 5.13 (t, J=7.1 Hz, 2H), 4.46 (q, J=7.2 Hz, 2H), 3.74 (t, J=7.0 Hz, 2H), 1.46 (t, J=7.2 Hz, 3H).

Step 4. Synthesis of 8-cyclopropyl-7,8-dihydropyrrolo[1,2-a:4,5-b']dipyrazin-9(6H)-one (C30)

To a solution of C29 (2.0 g, 6.7 mmol) and cyclopropylamine (33 mL) in acetonitrile (100 mL) was added potassium carbonate (2.8 g, 20 mmol), and the reaction mixture was stirred at 80° C. for 18 hours. After removal of volatiles under reduced pressure, the residue was partitioned between dichloromethane and water. The organic phase was separated, the aqueous phase was extracted with dichloromethane (2×80 mL), and the combined organic layers were washed with saturated aqueous sodium chloride solution (50 mL), dried over sodium sulfate, and concentrated in vacuo. Silica gel chromatography (Gradient: 70% to 100% ethyl acetate in petroleum ether) afforded the product as a yellow solid. Yield: 665 mg, 2.91 mmol, 43%. LCMS m/z 228.9 [M+H]$^+$. $^1$H NMR (400 MHZ, CDCl$_3$) δ 8.53 (d, J=2.5 Hz, 1H), 8.35 (d, J=2.5 Hz, 1H), 7.40 (s, 1H), 4.40-4.45 (m, 2H), 3.84-3.89 (m, 2H), 2.87-2.94 (m, 1H), 0.97-1.04 (m, 2H), 0.78-0.84 (m, 2H).

Step 5. Synthesis of 10-bromo-8-cyclopropyl-7,8-dihydropyrrolo[1,2-a:4,5-b']dipyrazin-9(6H)-one (C31)

Conversion of C30 to the product was carried out via the method described for synthesis of C1 in Example 1. In this case, the chromatographic gradient employed was 0% to 9% methanol in dichloromethane, providing the product as a yellow solid, which by 1H NMR retained a number of impurities. Yield: 3.0 g, 9.8 mmol, <75%. $^1$H NMR (400 MHZ, CDCl$_3$) δ 8.55 (d, J=2.4 Hz, 1H), 8.39 (d, J=2.4 Hz, 1H), 4.44-4.48 (m, 2H), 3.84-3.89 (m, 2H), 2.86-2.93 (m, 1H), 0.97-1.04 (m, 2H), 0.79-0.86 (m, 2H).

Step 6. Synthesis of 10-(4-chloro-3-fluorophenyl)-8-cyclopropyl-7,8-dihydropyrrolo[1,2-a:4,5-b']dipyrazin-9(6H)-one (8)

A mixture of C31 (190 mg, 0.62 mmol), (4-chloro-3-fluorophenyl)boronic acid (220 mg, 1.26 mmol) and cesium fluoride (380 mg, 2.50 mmol) in 1,4-dioxane (8 mL) was degassed with nitrogen for 2 minutes. After addition of bis[di-tert-butyl(4-dimethylaminophenyl)phosphine]dichloropalladium(II) (22 mg, 31 umol), the reaction mixture was stirred at 100° C. for 18 hours. Volatiles were removed in vacuo, and the residue was subjected to silica gel chromatography (Gradient: ethyl acetate in petroleum ether) followed by preparative thin layer chromatography on silica gel (Eluent: 1:1 petroleum ether/ethyl acetate) to afford the product as a yellow solid. Yield: 32.2 mg, 90.2 umol, 15%. LCMS m/z 356.8 [M+H]$^+$. $^1$H NMR (400 MHZ, CDCl$_3$) δ 8.57 (d, J=2.4 Hz, 1H), 8.42 (d, J=2.4 Hz, 1H), 7.69 (dd, J=10.4, 1.9 Hz, 1H), 7.60 (br dd, J=8.3, 1.5 Hz, 1H), 7.47 (dd, J=8.0, 7.9 Hz, 1H), 4.46-4.52 (m, 2H), 3.87-3.93 (m, 2H), 2.85-2.92 (m, 1H), 0.96-1.02 (m, 2H), 0.76-0.83 (m, 2H).

Example 9

5-(4-Chlorophenyl)-7-cyclopropyl-8,9-dihydropyrido[3',2':4,5]pyrrolo[1,2-a]pyrazin-6(7H)-one (9)

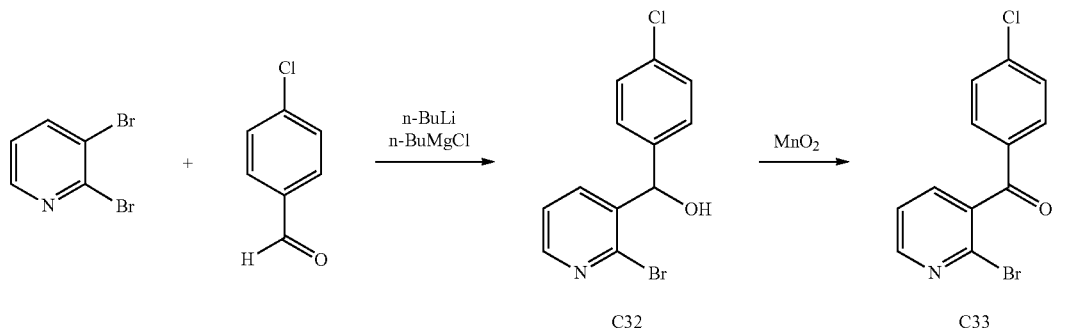

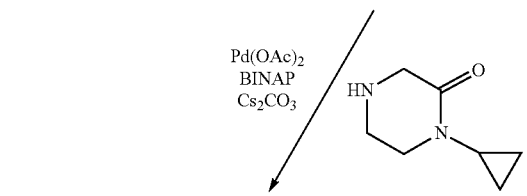

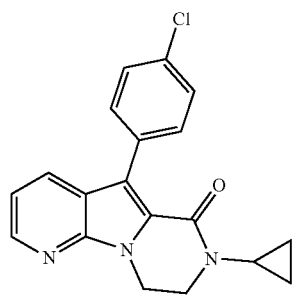

9

Step 1. Synthesis of (2-bromopyridin-3-yl)(4-chlorophenyl)methanol (C32)

n-Butyllithium (2.5 M in hexanes, 0.56 mL, 1.4 mmol) was added drop-wise to a 0° C. solution of n-butylmagnesium chloride (2.0 M in diethyl ether, 0.35 mL, 0.70 mmol) in tetrahydrofuran (2 mL). After it had stirred for 10 minutes, the mixture was cooled to −78° C. and treated drop-wise with a solution of 2,3-dibromopyridine (474 mg, 2.00 mmol) in tetrahydrofuran (2 mL). The reaction mixture was allowed to stir at −78° C. for 30 minutes, whereupon 4-chlorobenzaldehyde (422 mg, 3.00 mmol) was added; stirring was continued at −78° C. for 10 minutes, then at 0° C. for 10 minutes. Saturated aqueous sodium bicarbonate solution was added, and the mixture was extracted with ethyl acetate. The combined organic layers were dried over magnesium sulfate, filtered, and concentrated in vacuo. Silica gel chromatography (Gradient: 5% to 45% ethyl acetate in heptane) afforded the product as a colorless gum. Yield: 0.28 g, 0.94 mmol, 47%. LCMS m/z 297.9, 299.9, 301.9 [M+H]$^+$. 1H NMR (400 MHZ, CDCl$_3$) δ 8.31 (ddd, J=4.7, 2.0, 0.3 Hz, 1H), 7.90 (ddd, J=7.7, 2.0, 0.6 Hz, 1H), 7.34-7.35 (m, 4H), 7.33 (ddd, J=7.7, 4.7, 0.5 Hz, 1H), 6.13 (br s, 1H).

Step 2. Synthesis of (2-bromopyridin-3-yl)(4-chlorophenyl)methanone (C33)

A mixture of C32 (0.28 g, 0.94 mmol) and manganese (IV) oxide (815 mg, 9.37 mmol) in dichloromethane (5 mL) was stirred at room temperature for 16 hours. The reaction mixture was then filtered through diatomaceous earth using additional dichloromethane, and the filtrate was concentrated in vacuo. Silica gel chromatography (Gradient: 0% to 40% ethyl acetate in heptane) provided the product as a white solid. Yield: 203 mg, 0.684 mmol, 73%. LCMS m/z 295.9, 297.9, 299.9 [M+H]$^+$. 1H NMR (400 MHZ, CDCl$_3$) δ 8.55 (dd, J=4.8, 2.0 Hz, 1H), 7.76 (br d, J=8.5 Hz, 2H), 7.67 (dd, J=7.5, 2.0 Hz, 1H), 7.48 (br d, J=8.5 Hz, 2H), 7.44 (dd, J=7.5, 4.8 Hz, 1H).

Step 3. Synthesis of 5-(4-chlorophenyl)-7-cyclopropyl-8,9 dihydropyrido[3',2':4,5]-pyrrolo[1,2-a]pyrazin-6(7H)-one (9)

A mixture of C33 (137 mg, 0.462 mmol), 1-cyclopropylpiperazin-2-one (97.9 mg, 0.554 mmol) and cesium carbonate (903 mg, 2.77 mmol) in toluene (1 mL) was treated with a mixture of palladium(II) acetate (5.2 mg, 23 umol) and 1,1'-binaphthalene-2,2'-diylbis(diphenylphosphane) (BINAP, 14.3 mg, 23.0 umol) in toluene (0.5 mL) that had been stirred at room temperature for 10 minutes. The reaction mixture was heated at 120° C. for 16 hours, then filtered. The filtrate was purified via silica gel chromatography (Gradient: 10% to 100% ethyl acetate in heptane); subsequent crystallization from ethyl acetate/heptane afforded the product as a white solid. Yield: 83 mg, 0.25 mmol, 54%. LCMS m/z 338.1, 340.1 [M+H]$^+$. 1H NMR (400 MHZ, DMSO-d$_6$) δ 8.48 (dd, J=4.6, 1.5 Hz, 1H), 8.00 (dd, J=8.0, 1.5 Hz, 1H), 7.54 (br AB quartet, J$_{AB}$=8.7 Hz, Δ$_{VAB}$=44.1 Hz, 4H), 7.22 (dd, J=8.0, 4.6 Hz, 1H), 4.38-4.44 (m, 2H), 3.76-3.82 (m, 2H), 2.80-2.87 (m, 1H), 0.69-0.82 (m, 4H).

Example 10

(7R)-10-(4-Chlorophenyl)-8-cyclopropyl-7-methyl-7,8-dihydropyrido[2',3':4,5]pyrrolo[1,2-a]pyrazin-9 (6H)-one (10)

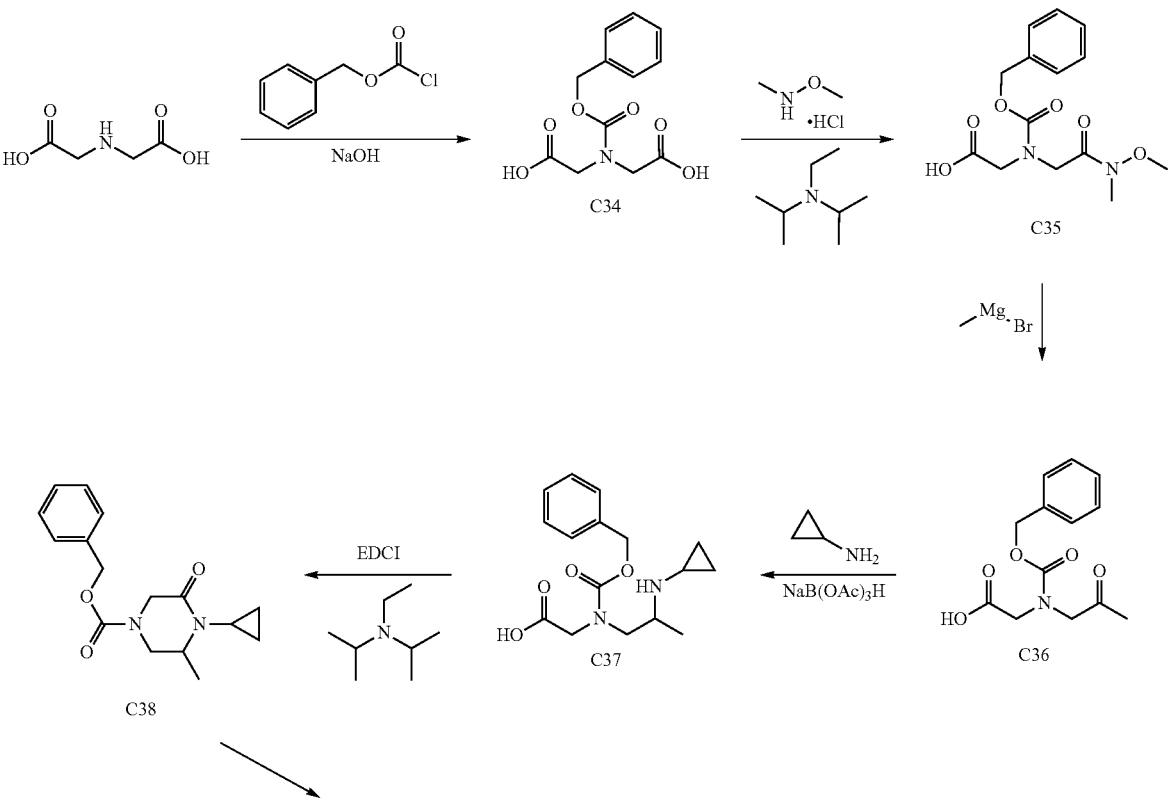

-continued

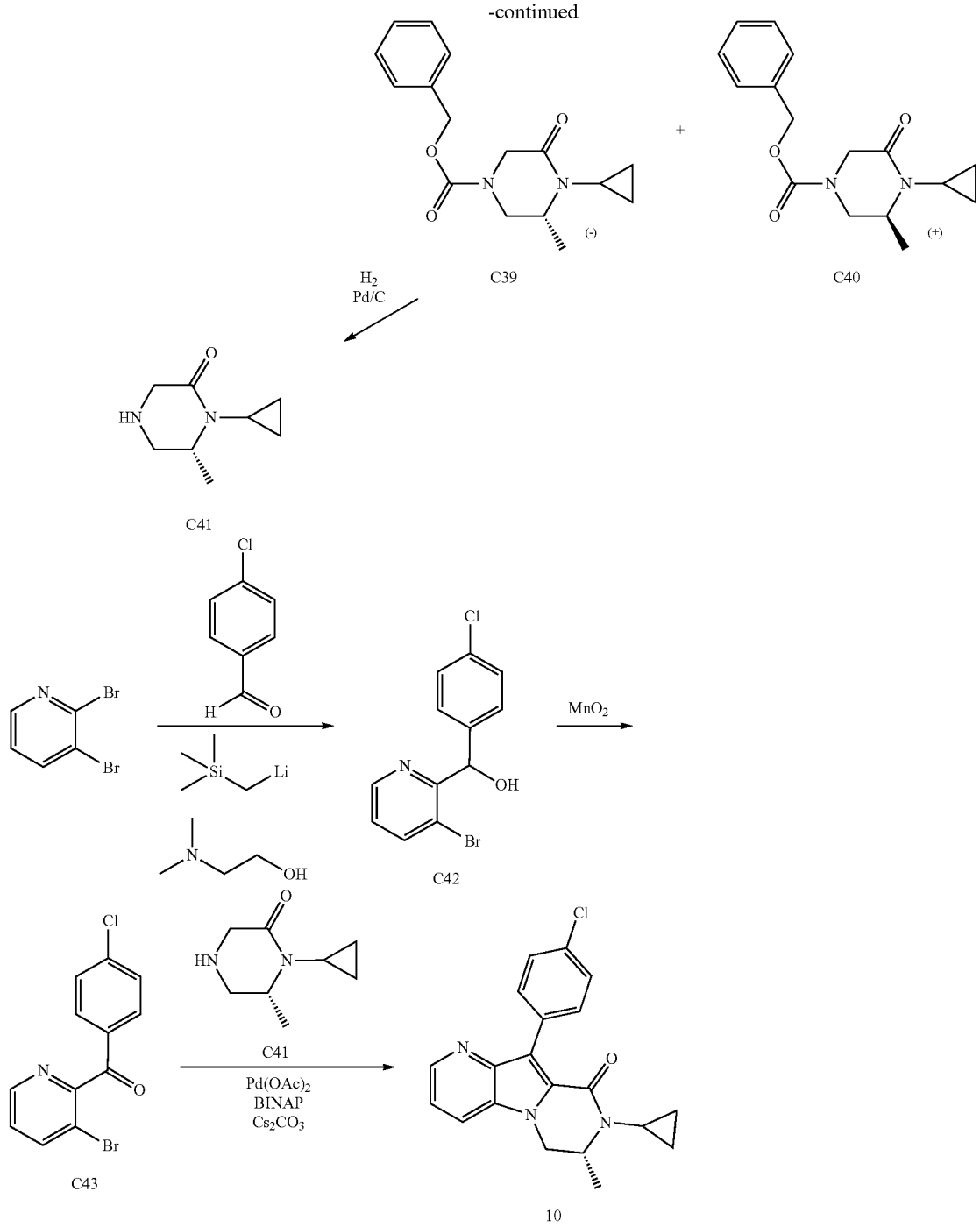

Step 1. Synthesis of 2,2'-{[(benzyloxy)carbonyl]imino}diacetic acid (C34)

A mixture of 2,2'-iminodiacetic acid (150 g, 1.13 mol) and aqueous sodium hydroxide solution (2 N, 1.5 L, 3 mol) was stirred at 0° C. for 30 minutes. After drop-wise addition of benzyl chloroformate (211 g, 1.24 mol) at 0° C., the reaction mixture was stirred at 10° C. for 18 hours. The reaction mixture was then washed with ethyl acetate (1 L), and the aqueous layer was acidified to a pH of approximately 2 and extracted with ethyl acetate (2×1 L). These two organic layers were combined, dried over sodium sulfate, filtered, and concentrated in vacuo to provide the product as a yellow gum. Yield: 180 g, 0.674 mol, 60%. $^1$H NMR (400 MHZ, CDCl$_3$) δ 8.07 (br s, 2H), 7.27-7.37 (m, 5H), 5.16 (s, 2H), 4.19 (br s, 2H), 4.13 (br s, 2H).

Step 2. Synthesis of ([(benzyloxy)carbonyl]{2-[methoxy(methyl)amino]-2-oxoethyl}amino)acetic acid (C35)

To a solution of C34 (180 g, 0.674 mol) in N,N-dimethylformamide (900 mL) was added 1-[3-(dimethylamino)propyl]-3-ethylcarbodiimide hydrochloride (EDCl, 97 g, 0.51 mol), N,N-diisopropylethylamine (65 g, 0.50 mol) and N,O-dimethylhydroxylamine hydrochloride (46 g, 0.47 mol), and the reaction mixture was stirred at 10° C. for 18 hours. After removal of solvent in vacuo, the residue was dissolved in ethyl acetate (2 L), washed with 1 N aqueous hydrochloric acid, and extracted with aqueous sodium bicarbonate solution. The aqueous sodium bicarbonate phase was adjusted to a pH of approximately 2 with aqueous hydrochloric acid and then extracted with ethyl acetate (2 L). The combined organic layers were washed with saturated aqueous sodium chloride solution, dried over sodium sulfate, filtered, and concentrated under reduced pressure to afford the product as a yellow gum (155 g), which was presumed to consist of a mixture of rotamers from examination of its $^1$H NMR spectrum. This material was taken directly to the following step. $^1$H NMR (400 MHZ, CDCl$_3$), characteristic peaks: δ 7.29-7.40 (m, 5H), 5.14-5.21 (m, 2H), 3.51 and 3.81 (2 s, total 3H), 3.30 and 3.21 (2 s, total 3H).

Step 3. Synthesis of N-[(benzyloxy)carbonyl]-N-(2-oxopropyl)glycine (C36)

Methylmagnesium bromide (3.0 M solution in diethyl ether, 670 mL, 2.0 mol) was added drop-wise to a 0° C. solution of C35 (from the previous reaction, 155 g, ≤0.47 mol) in tetrahydrofuran (2 L), and the resulting mixture was allowed to warm slowly to 12° C. and stir at that temperature for 18 hours. The reaction mixture was quenched by addition of saturated aqueous ammonium chloride solution, adjusted to a pH of approximately 2 with aqueous hydrochloric acid, and extracted with ethyl acetate. The organic layer was basified via addition of 1 N aqueous sodium hydroxide solution; the basic aqueous phase was washed with ethyl acetate, then acidified with aqueous hydrochloric acid to a pH of approximately 2 and extracted with ethyl acetate (2 L). This organic extract was washed with saturated aqueous sodium chloride solution, dried over sodium sulfate, filtered, and concentrated in vacuo to provide the crude product (60 g) as a red oil, which was used directly in the following step.

Step 4. Synthesis of N-[(benzyloxy)carbonyl]-N-[2-(cyclopropylamino)propyl]glycine (C37)

To a solution of C36 (60 g, ≤230 mmol) in dichloromethane (2 L) were added cyclopropylamine (39 g, 0.68 mol), sodium triacetoxyborohydride (145 g, 0.684 mol) and acetic acid (20 mL), and the reaction mixture was stirred at 13° C. for 3 days. Removal of solvents in vacuo afforded the crude product as an orange oil, which was used directly in the next step.

Step 5. Synthesis of benzyl 4-cyclopropyl-3-methyl-5-oxopiperazine-1-carboxylate (C38)

1-[3-(Dimethylamino)propyl]-3-ethylcarbodiimide hydrochloride (EDCl, 200 g, 1.04 mol) and N,N-diisopropylethylamine (215 g, 1.66 mol) were added to a solution of C37 (from the previous step) in N,N-dimethylformamide (2 L), and the reaction mixture was stirred at 14° C. for 18 hours. The reaction mixture was concentrated under reduced pressure, and the residue was dissolved in ethyl acetate (1.5 L), washed sequentially with 1 N aqueous hydrochloric acid, saturated aqueous sodium bicarbonate solution, and saturated aqueous sodium chloride solution, dried over sodium sulfate, filtered, and concentrated in vacuo. Purification via silica gel chromatography (Gradient: 30% to 100% ethyl acetate in petroleum ether) provided the product as a yellow oil. Yield: 18 g, 62.4 mmol, 13% over four steps. LCMS m/z 288.9 [M+H]$^+$. $^1$H NMR (400 MHZ, CDCl$_3$) δ 7.30-7.41 (m, 5H), 5.16 (AB quartet, J$_{AB}$=12.4 Hz, Δ$_{VAB}$=7.6 Hz, 2H), 4.23-4.36 (br m, 1H), 3.97 (d, J=18.2 Hz, 1H), 3.69-3.84 (br m, 1H), 3.36-3.60 (br m, 2H), 2.60-2.69 (m, 1H), 1.21-1.33 (br m, 3H), 1.00-1.10 (m, 1H), 0.69-0.80 (m, 2H), 0.48-0.61 (br m, 1H).

Step 6. Isolation of benzyl (3R)-4-cyclopropyl-3-methyl-5-oxopiperazine-1-carboxylate (C39) and benzyl (3S)-4-cyclopropyl-3-methyl-5-oxopiperazine-1-carboxylate (C40)

Compound C38 (2.60 g, 9.02 mmol) was separated into its component enantiomers via supercritical fluid chromatography (Column: Phenomenex Lux Cellulose-4; Eluent: 3:1 carbon dioxide/methanol). The first-eluting enantiomer, obtained as a solid that exhibited a negative (−) rotation, was designated as C39. Yield: 1.0 g, 3.5 mmol, 39%. The second-eluting enantiomer, obtained as a gum with a positive (+) rotation, was designated as C40. Yield: 1.0 g, 3.5 mmol, 39%. The absolute configuration of these two compounds was assigned as indicated on the basis of X-ray crystal structure determination on the product derived from C39; see X-ray data for Example 10 below. C39: LCMS m/z 289.2 [M+H]$^+$. 1H NMR (400 MHZ, CDCl$_3$) δ 7.30-7.41 (m, 5H), 5.16 (AB quartet, J$_{AB}$=12.5 Hz, Δ$_{VAB}$=7.0 Hz, 2H), 4.29 (br d, J=18.0 Hz, 1H), 3.96 (d, J=18.0 Hz, 1H), 3.70-3.84 (br m, 1H), 3.37-3.59 (br m, 2H), 2.60-2.69 (m, 1H), 1.21-1.33 (br m, 3H), 1.00-1.10 (m, 1H), 0.69-0.80 (m, 2H), 0.48-0.61 (br m, 1H). C40: LCMS m/z 289.2 [M+H]$^+$. $^1$H NMR (400 MHZ, CDCl$_3$) δ 7.30-7.41 (m, 5H), 5.16 (AB quartet, J$_{AB}$=12.4 Hz, Δ$_{VAB}$=7.0 Hz, 2H), 4.29 (br d, J=18 Hz, 1H), 3.96 (d, J=18.2 Hz, 1H), 3.70-3.84 (br m, 1H), 3.47-3.59 (br m, 1H), 3.42 (br d, J=13.5 Hz, 1H), 2.60-2.68 (m, 1H), 1.22-1.32 (br m, 3H), 1.00-1.10 (m, 1H), 0.69-0.79 (m, 2H), 0.49-0.60 (br m, 1H).

Step 7. Synthesis of (6R)-1-cyclopropyl-6-methylpiperazin-2-one (C41)

Palladium on carbon (10%, wet, 40 mg) was added to a solution of C39 (200 mg, 0.694 mmol) in ethanol (12 mL), and the reaction mixture was hydrogenated on a Parr shaker at 50 psi hydrogen for 18 hours, then filtered through diatomaceous earth. The filtrate was concentrated in vacuo to afford the product as an oil. Yield: 103 mg, 0.668 mmol, 96%. LCMS m/z 155.1 [M+H]$^+$. $^1$H NMR (400 MHZ, CDCl$_3$) δ 3.47 (AB quartet, J$_{AB}$=17.3 Hz, Δ$_{VAB}$=11.6 Hz, 2H), 3.41-3.49 (m, 1H), 3.13 (dd, J=13.2, 4.6 Hz, 1H), 2.77 (dd, J=13.0, 5.5 Hz, 1H), 2.56-2.63 (m, 1H), 1.31 (d, J=6.3 Hz, 3H), 1.02-1.11 (m, 1H), 0.66-0.76 (m, 2H), 0.53-0.62 (m, 1H).

Step 8. Synthesis of (3-bromopyridin-2-yl)(4-chlorophenyl)methanol (C42)

This compound was synthesized using the method of P. C. Gros and F. Elaachbouni, *Chem. Commun.* 2008, 4813-4815. [(Trimethylsilyl)methyl]lithium (1.0 M solution in pentane, 12.7 mL, 12.7 mmol) was added drop-wise to a 0° C. solution of 2-(dimethylamino)ethanol (423 μL, 4.22 mmol) in toluene (14 mL), and the mixture was stirred for 20 minutes. It was then cooled to −30° C. and treated with a solution of 2,3-dibromopyridine (1.0 g, 4.2 mmol) in toluene (6 mL). After the reaction mixture had been stirred for 40 minutes at −30° C., a solution of 4-chlorobenzaldehyde (99%, 899 mg, 6.33 mmol) in toluene (5 mL) was added in a drop-wise manner, and stirring was continued for 30 minutes at −30° C. At this point, the reaction was quenched via addition of saturated aqueous sodium bicarbonate solution (25 mL), and the mixture was allowed to warm to room temperature. It was extracted three times with ethyl acetate, and the combined organic layers were washed with saturated aqueous sodium chloride solution, dried over sodium sulfate, filtered, and concentrated in vacuo. Silica gel chromatography (Gradient: 0% to 40% ethyl acetate in heptane) afforded the product as a white solid. Yield: 949 mg, 3.18 mmol, 76%. LCMS m/z 298.0, 300.0, 302.0 [M+H]$^+$. $^1$H NMR (400 MHZ, CDCl$_3$) δ 8.60 (dd, J=4.7, 1.3 Hz, 1H), 7.88 (dd, J=8.0, 1.5 Hz, 1H), 7.26-7.32 (m, 4H), 7.20 (dd, J=8.0, 4.7 Hz, 1H), 5.95 (s, 1H), 5.27 (br s, 1H).

Step 9. Synthesis of (3-bromopyridin-2-yl)(4-chlorophenyl)methanone (C43)

Compound C42 was converted to the product according to the general procedure for the synthesis of C33 in Example 9, except that no chromatographic purification was carried out. The product was obtained as a white solid. Yield: 257 mg, 0.867 mmol, 98%. LCMS m/z 295.9, 297.9, 300.0 [M+H]$^+$. $^1$H NMR (400 MHZ, CDCl$_3$) δ 8.63 (dd, J=4.7, 1.3 Hz, 1H), 8.04 (dd, J=8.2, 1.3 Hz, 1H), 7.80 (br d, J=8.5 Hz, 2H), 7.46 (br d, J=8.6 Hz, 2H), 7.35 (dd, J=8.2, 4.7 Hz, 1H).

Step 10. Synthesis of (7R)-10-(4-chlorophenyl)-8-cyclopropyl-7-methyl-7,8-dihydropyrido[2',3':4,5]pyrrolo[1,2-a]pyrazin-9(6H)-one (10)

Compound C43 was reacted with C41 according to the general procedure for the synthesis of 9 in Example 9. In this case, after the silica gel chromatography, the resulting yellow glassy solid (155 mg) was treated with diethyl ether (1 mL) and concentrated in vacuo; the residue was mixed with diethyl ether (1 mL) and pentane (1 mL), and treated portion-wise with additional pentane until solid stopped precipitating from solution. Solvents were removed in vacuo, and residual material was rinsed into the product with ethyl acetate. Concentration under reduced pressure provided a light yellow solid (135 mg). This was mixed with pentane (1.5 mL), subjected to sonication for 3 minutes, then allowed to stand for 30 minutes. After removal of the pentane with a pipette, the residue was dried under vacuum to afford the product as a nearly white solid. Yield: 115 mg, 0.327 mmol, 57%. LCMS m/z 352.2, 354.0 [M+H]$^+$. $^1$H NMR (400 MHZ, CDCl$_3$) δ 8.62 (dd, J=4.5, 1.4 Hz, 1H), 7.78 (br d, J=8.5 Hz, 2H), 7.67 (dd, J=8.4, 1.4 Hz, 1H), 7.44 (br d, J=8.5 Hz, 2H), 7.30 (dd, J=8.4, 4.5 Hz, 1H), 4.28 (dd, half of ABX pattern, J=12.1, 4.1 Hz, 1H), 4.22 (dd, half of ABX pattern, J=12.1, 1.7 Hz, 1H), 4.02-4.10 (m, 1H), 2.80-2.86 (m, 1H), 1.39 (d, J=6.6 Hz, 3H), 1.09-1.17 (m, 1H), 0.87-0.94 (m, 1H), 0.78-0.86 (m, 1H), 0.57-0.64 (m, 1H).

A portion of compound 10 was recrystallized from tert-butyl methyl ether and hexanes. One of the resulting crystals was subjected to X-ray structural analysis, which established the absolute stereochemistry as shown. The crystallographic data is provided below.

Single Crystal X-Ray Analysis of Example 10

Data collection was performed on a Bruker APEX diffractometer at room temperature. Data collection consisted of omega and phi scans. The data collection was quite long, with the crystal small and weakly diffracting. The crystal was found to be twinned non-merohedrally, and was refined as such, separating the domains during integration.

The structure was solved by direct methods using SHELX software suite in the space group P1. The structure was subsequently refined by the full-matrix least squares method. All non-hydrogen atoms were found and refined using anisotropic displacement parameters. Overlaying the four molecules in the asymmetric unit shows them to be almost identical. Cell_now, platon and frame files suggest that the asymmetric unit is correctly identified, with four independent molecules.

All hydrogen atoms were placed in calculated positions and were allowed to ride on their carrier atoms. The final refinement included isotropic displacement parameters for all hydrogen atoms.

The absolute configuration is based on examination of the Flack parameter. In this case, the Flack parameter=0.0729 with esd 0.0197, within range for absolute configuration.

The final R-index was 4.8%. A final difference Fourier revealed no missing or misplaced electron density.

Pertinent crystal, data collection and refinement are summarized in Table 1. Atomic coordinates, bond lengths, bond angles, torsion angles and displacement parameters are listed in Tables 2-5.

SOFTWARE AND REFERENCES

SHELXTL, Version 5.1, Bruker A X S, 1997.

PLATON, A. L. Spek, *J. Appl. Cryst.* 2003, 36, 7-13.

MERCURY, C. F. Macrae, P. R. Edington, P. McCabe, E. Pidcock, G. P. Shields, R. Taylor, M. Towler and J. van de Streek, *J. Appl. Cryst.* 2006, 39, 453-457.

R. W. Hooft et al., *J. Appl. Cryst.* 2008, 41, 96-103.

H. D. Flack, *Acta Cryst.* 1983, A39, 867-881.

TABLE 1

| Crystal data and structure refinement for 10. | | |
|---|---|---|
| Empirical formula | C$_{20}$H$_{18}$ClN$_3$O | |
| Formula weight | 351.82 | |
| Temperature | 298(2) K | |
| Wavelength | 1.54178 Å | |
| Crystal system | Triclinic | |
| Space group | P1 | |
| Unit cell dimensions | a = 9.4957(5) Å | α = 111.160(3)°. |
| | b = 12.2095(7) Å | β = 91.353(3)°. |
| | c = 16.3038(9) Å | γ = 92.260(3)°. |
| Volume | 1759.95(17) Å$^3$ | |
| Z | 4 | |
| Density (calculated) | 1.328 Mg/m$^3$ | |
| Absorption coefficient | 2.017 mm$^{-1}$ | |
| F(000) | 736 | |
| Crystal size | 0.25 × 0.08 × 0.05 mm$^3$ | |
| Theta range for data collection | 2.91 to 54.36°. | |
| Index ranges | −10 <= h <= 9, −12 <= k <= 11, 0 <= l <= 17 | |
| Reflections collected | 4247 | |
| Independent reflections | 4247 [R(int) = 0.0000] | |
| Completeness to theta = 54.36° | 98.9% | |
| Absorption correction | Empirical | |
| Max. and min. transmission | 0.9059 and 0.6326 | |
| Refinement method | Full-matrix least-squares on F$^2$ | |

TABLE 1-continued

Crystal data and structure refinement for 10.

| | |
|---|---|
| Data/restraints/parameters | 4247/3/905 |
| Goodness-of-fit on $F^2$ | 1.038 |
| Final R indices [I > 2sigma(I)] | R1 = 0.0484, wR2 = 0.1173 |
| R indices (all data) | R1 = 0.0590, wR2 = 0.1241 |
| Absolute structure parameter | 0.07(2) |
| Largest diff. peak and hole | 0.429 and −0.183 e · Å$^{-3}$ |

TABLE 2

Atomic coordinates (×10$^4$) and equivalent isotropic displacement parameters (Å$^2$ × 10$^3$) for 10 U(eq) is defined as one third of the trace of the orthogonalized U$^{ij}$ tensor

| | x | y | z | U(eq) |
|---|---|---|---|---|
| C(1) | 2819(7) | 7758(6) | 1067(4) | 54(2) |
| C(2) | 2816(10) | 5873(8) | 971(7) | 92(2) |
| C(3) | 2645(10) | 5462(8) | 67(7) | 89(3) |
| C(4) | 2536(8) | 6217(7) | −379(5) | 71(2) |
| C(5) | 2627(7) | 7386(6) | 152(5) | 54(2) |
| C(6) | 2866(6) | 9029(6) | 1423(6) | 52(2) |
| C(7) | 2734(7) | 9361(6) | 697(4) | 52(2) |
| C(8) | 2841(7) | 10521(7) | 611(5) | 59(2) |
| C(9) | 1702(7) | 9531(6) | −857(4) | 60(2) |
| C(10) | 2456(8) | 8456(7) | −921(4) | 66(2) |
| C(11) | 2460(10) | 11682(8) | −280(6) | 90(3) |
| C(12) | 3770(12) | 12211(12) | −383(9) | 138(5) |
| C(13) | 2760(13) | 11790(10) | −1124(7) | 116(4) |
| C(14) | 149(8) | 9440(8) | −707(5) | 77(2) |
| C(15) | 2969(7) | 9747(6) | 2363(4) | 54(2) |
| C(16) | 2150(8) | 10699(7) | 2708(5) | 69(2) |
| C(17) | 2166(9) | 11365(7) | 3601(5) | 71(2) |
| C(18) | 3015(8) | 11071(6) | 4154(5) | 62(2) |
| C(19) | 3852(9) | 10122(7) | 3843(5) | 75(2) |
| C(20) | 3818(8) | 9464(6) | 2937(5) | 67(2) |
| C(21) | 5586(6) | 5928(6) | 8160(4) | 52(2) |
| C(22) | 5138(9) | 4040(8) | 7290(5) | 76(2) |
| C(23) | 5399(9) | 3643(7) | 7981(6) | 76(2) |
| C(24) | 5767(8) | 4431(7) | 8807(5) | 69(2) |
| C(25) | 5864(6) | 5605(6) | 8882(4) | 52(2) |
| C(26) | 5802(6) | 7201(6) | 8451(4) | 49(2) |
| C(27) | 6166(7) | 7559(6) | 9334(4) | 48(2) |
| C(28) | 6408(7) | 8757(6) | 10032(4) | 52(2) |
| C(29) | 7533(7) | 7741(6) | 10930(4) | 54(2) |
| C(30) | 6474(7) | 6728(6) | 10504(4) | 55(2) |
| C(31) | 7233(8) | 9958(6) | 11483(4) | 65(2) |
| C(32) | 8427(10) | 10740(7) | 11513(5) | 87(3) |
| C(33) | 8380(9) | 10184(7) | 12171(5) | 78(2) |
| C(34) | 9006(7) | 7443(6) | 10604(5) | 64(2) |
| C(35) | 5609(6) | 7899(6) | 7892(4) | 49(2) |
| C(36) | 6435(7) | 8917(6) | 7997(5) | 62(2) |
| C(37) | 6170(8) | 9578(6) | 7484(5) | 66(2) |
| C(38) | 5054(8) | 9268(7) | 6884(4) | 57(2) |
| C(39) | 4253(8) | 8265(7) | 6739(4) | 62(2) |
| C(40) | 4512(7) | 7591(6) | 7243(4) | 57(2) |
| C(41) | 450(6) | 8270(6) | 6292(5) | 57(2) |
| C(42) | 64(9) | 10131(9) | 7121(6) | 92(3) |
| C(43) | 254(9) | 10515(8) | 6433(7) | 88(3) |
| C(44) | 565(8) | 9732(7) | 5628(5) | 72(2) |
| C(45) | 687(7) | 8585(7) | 5561(5) | 59(2) |
| C(46) | 604(6) | 6999(7) | 6011(4) | 58(2) |
| C(47) | 914(6) | 6657(6) | 5134(4) | 53(2) |
| C(48) | 1088(7) | 5460(7) | 4467(4) | 58(2) |
| C(49) | 2132(7) | 6486(6) | 3549(4) | 55(2) |
| C(50) | 1170(7) | 7477(6) | 3961(4) | 59(2) |
| C(51) | 1900(8) | 4282(7) | 3051(5) | 70(2) |
| C(52) | 756(12) | 3406(9) | 2572(6) | 104(3) |
| C(53) | 1654(11) | 3987(8) | 2101(5) | 98(3) |
| C(54) | 3658(8) | 6818(8) | 3878(6) | 79(2) |
| C(55) | 468(6) | 6309(6) | 6583(4) | 57(2) |
| C(56) | 1320(7) | 5393(7) | 6514(5) | 64(2) |

TABLE 2-continued

Atomic coordinates (×10$^4$) and equivalent isotropic displacement parameters (Å$^2$ × 10$^3$) for 10 U(eq) is defined as one third of the trace of the orthogonalized U$^{ij}$ tensor

| | x | y | z | U(eq) |
|---|---|---|---|---|
| C(57) | 1140(8) | 4721(7) | 7017(5) | 68(2) |
| C(58) | 106(9) | 4950(8) | 7622(5) | 70(2) |
| C(59) | −746(8) | 5875(8) | 7715(5) | 73(2) |
| C(60) | −564(7) | 6568(7) | 7218(4) | 60(2) |
| C(61) | 7319(6) | 6558(6) | 3410(4) | 51(2) |
| C(62) | 7332(8) | 8464(8) | 3511(6) | 73(2) |
| C(63) | 7243(8) | 8859(7) | 4421(5) | 71(2) |
| C(64) | 7181(7) | 8088(6) | 4848(5) | 59(2) |
| C(65) | 7209(6) | 6900(6) | 4314(4) | 48(2) |
| C(66) | 7323(7) | 5319(6) | 3047(4) | 55(2) |
| C(67) | 7220(7) | 4967(6) | 3750(4) | 52(2) |
| C(68) | 7314(7) | 3788(7) | 3824(4) | 56(2) |
| C(69) | 6304(6) | 4683(6) | 5271(4) | 52(2) |
| C(70) | 7057(7) | 5842(6) | 5386(4) | 54(2) |
| C(71) | 7187(7) | 2650(6) | 4755(4) | 59(2) |
| C(72) | 8594(9) | 2202(7) | 4767(6) | 80(2) |
| C(73) | 7825(10) | 2666(8) | 5592(6) | 84(2) |
| C(74) | 4747(7) | 4639(7) | 5044(5) | 72(2) |
| C(75) | 7429(8) | 4579(6) | 2102(4) | 59(2) |
| C(76) | 6651(9) | 3514(7) | 1707(5) | 71(2) |
| C(77) | 6872(9) | 2797(7) | 847(5) | 77(2) |
| C(78) | 7815(9) | 3178(7) | 379(4) | 69(2) |
| C(79) | 8561(9) | 4217(7) | 732(5) | 74(2) |
| C(80) | 8367(8) | 4937(6) | 1586(4) | 63(2) |
| Cl(01) | 3045(3) | 11885(2) | 5266(1) | 93(1) |
| Cl(02) | 4685(3) | 10170(2) | 6283(1) | 98(1) |
| Cl(03) | 8100(3) | 2264(2) | −718(1) | 103(1) |
| Cl(04) | −200(3) | 4067(3) | 8219(2) | 103(1) |
| N(1) | 2891(7) | 7008(6) | 1502(4) | 76(2) |
| N(2) | 2559(5) | 8372(5) | −63(3) | 54(1) |
| N(3) | 2431(6) | 10554(5) | −181(3) | 58(1) |
| N(4) | 5237(6) | 5150(6) | 7352(3) | 63(2) |
| N(5) | 6246(5) | 6603(5) | 9589(3) | 51(1) |
| N(6) | 7041(6) | 8805(4) | 10786(3) | 52(1) |
| N(7) | 140(6) | 9025(7) | 7089(4) | 74(2) |
| N(8) | 975(5) | 7622(5) | 4871(4) | 56(1) |
| N(9) | 1583(6) | 5426(5) | 3682(3) | 56(1) |
| N(10) | 7372(6) | 7338(6) | 2994(4) | 65(2) |
| N(11) | 7132(5) | 5928(5) | 4522(3) | 49(1) |
| N(12) | 7051(5) | 3738(5) | 4626(3) | 51(2) |
| O(1) | 3294(6) | 11398(5) | 1227(3) | 82(2) |
| O(2) | 6008(5) | 9626(4) | 9901(3) | 68(1) |
| O(3) | 783(6) | 4578(5) | 4620(3) | 81(2) |
| O(4) | 7650(6) | 2929(5) | 3214(3) | 80(2) |

TABLE 3

Bond lengths [Å] and angles [°] for 10

| | |
|---|---|
| . C(1)—N(1) | 1.348(9) |
| C(1)—C(5) | 1.398(9) |
| C(1)—C(6) | 1.445(10) |
| C(2)—N(1) | 1.341(11) |
| C(2)—C(3) | 1.377(13) |
| C(3)—C(4) | 1.370(12) |
| C(4)—C(5) | 1.374(10) |
| C(5)—N(2) | 1.374(8) |
| C(6)—C(7) | 1.388(9) |
| C(6)—C(15) | 1.463(9) |
| C(7)—N(2) | 1.384(8) |
| C(7)—C(8) | 1.473(10) |
| C(8)—O(1) | 1.228(8) |
| C(8)—N(3) | 1.354(9) |
| C(9)—N(3) | 1.468(9) |
| C(9)—C(10) | 1.491(10) |
| C(9)—C(14) | 1.507(10) |
| C(10)—N(2) | 1.440(8) |
| C(11)—C(12) | 1.420(14) |
| C(11)—N(3) | 1.444(10) |
| C(11)—C(13) | 1.461(12) |
| C(12)—C(13) | 1.449(14) |

TABLE 3-continued

Bond lengths [Å] and angles [°] for 10

| | |
|---|---|
| C(15)—C(20) | 1.366(9) |
| C(15)—C(16) | 1.376(10) |
| C(16)—C(17) | 1.387(10) |
| C(17)—C(18) | 1.347(10) |
| C(18)—C(19) | 1.378(11) |
| C(18)—Cl(01) | 1.723(7) |
| C(19)—C(20) | 1.401(10) |
| C(21)—N(4) | 1.342(8) |
| C(21)—C(25) | 1.392(9) |
| C(21)—C(26) | 1.457(9) |
| C(22)—N(4) | 1.322(10) |
| C(22)—C(23) | 1.400(12) |
| C(23)—C(24) | 1.370(11) |
| C(24)—C(25) | 1.394(10) |
| C(25)—N(5) | 1.370(8) |
| C(26)—C(27) | 1.377(9) |
| C(26)—C(35) | 1.469(9) |
| C(27)—N(5) | 1.376(8) |
| C(27)—C(28) | 1.499(9) |
| C(28)—O(2) | 1.228(8) |
| C(28)—N(6) | 1.337(8) |
| C(29)—N(6) | 1.492(8) |
| C(29)—C(30) | 1.507(9) |
| C(29)—C(34) | 1.519(9) |
| C(30)—N(5) | 1.455(8) |
| C(31)—C(32) | 1.442(11) |
| C(31)—N(6) | 1.456(8) |
| C(31)—C(33) | 1.488(11) |
| C(32)—C(33) | 1.463(11) |
| C(35)—C(36) | 1.397(9) |
| C(35)—C(40) | 1.405(9) |
| C(36)—C(37) | 1.380(10) |
| C(37)—C(38) | 1.369(10) |
| C(38)—C(39) | 1.357(10) |
| C(38)—Cl(02) | 1.758(7) |
| C(39)—C(40) | 1.380(10) |
| C(41)—N(7) | 1.341(9) |
| C(41)—C(45) | 1.398(10) |
| C(41)—C(46) | 1.466(10) |
| C(42)—N(7) | 1.337(11) |
| C(42)—C(43) | 1.376(13) |
| C(43)—C(44) | 1.364(11) |
| C(44)—C(45) | 1.375(11) |
| C(45)—N(8) | 1.345(9) |
| C(46)—C(47) | 1.380(9) |
| C(46)—C(55) | 1.470(10) |
| C(47)—N(8) | 1.391(8) |
| C(47)—C(48) | 1.492(10) |
| C(48)—O(3) | 1.216(8) |
| C(48)—N(9) | 1.361(8) |
| C(49)—N(9) | 1.466(8) |
| C(49)—C(50) | 1.510(10) |
| C(49)—C(54) | 1.519(10) |
| C(50)—N(8) | 1.447(8) |
| C(51)—N(9) | 1.452(9) |
| C(51)—C(53) | 1.469(11) |
| C(51)—C(52) | 1.483(12) |
| C(52)—C(53) | 1.482(13) |
| C(55)—C(56) | 1.379(10) |
| C(55)—C(60) | 1.403(9) |
| C(56)—C(57) | 1.361(10) |
| C(57)—C(58) | 1.372(10) |
| C(58)—C(59) | 1.381(11) |
| C(58)—Cl(04) | 1.716(8) |
| C(59)—C(60) | 1.377(11) |
| C(61)—N(10) | 1.354(8) |
| C(61)—C(65) | 1.387(9) |
| C(61)—C(66) | 1.413(10) |
| C(62)—N(10) | 1.330(9) |
| C(62)—C(63) | 1.390(11) |
| C(63)—C(64) | 1.358(10) |
| C(64)—C(65) | 1.398(10) |
| C(65)—N(11) | 1.347(8) |
| C(66)—C(67) | 1.366(9) |
| C(66)—C(75) | 1.485(9) |
| C(67)—N(11) | 1.385(8) |
| C(67)—C(68) | 1.492(10) |
| C(68)—O(4) | 1.216(8) |
| C(68)—N(12) | 1.360(8) |
| C(69)—N(12) | 1.472(8) |
| C(69)—C(70) | 1.507(9) |
| C(69)—C(74) | 1.509(10) |
| C(70)—N(11) | 1.452(8) |
| C(71)—N(12) | 1.428(8) |
| C(71)—C(72) | 1.466(10) |
| C(71)—C(73) | 1.474(11) |
| C(72)—C(73) | 1.481(11) |
| C(75)—C(76) | 1.396(10) |
| C(75)—C(80) | 1.401(10) |
| C(76)—C(77) | 1.386(10) |
| C(77)—C(78) | 1.362(11) |
| C(78)—C(79) | 1.351(11) |
| C(78)—Cl(03) | 1.766(7) |
| C(79)—C(80) | 1.374(10) |
| N(1)—C(1)—C(5) | 123.1(7) |
| N(1)—C(1)—C(6) | 128.6(6) |
| C(5)—C(1)—C(6) | 108.3(6) |
| N(1)—C(2)—C(3) | 125.5(8) |
| C(4)—C(3)—C(2) | 121.4(8) |
| C(3)—C(4)—C(5) | 114.1(8) |
| N(2)—C(5)—C(4) | 130.0(7) |
| N(2)—C(5)—C(1) | 107.6(6) |
| C(4)—C(5)—C(1) | 122.3(7) |
| C(7)—C(6)—C(1) | 105.2(6) |
| C(7)—C(6)—C(15) | 130.1(6) |
| C(1)—C(6)—C(15) | 124.6(6) |
| N(2)—C(7)—C(6) | 109.8(6) |
| N(2)—C(7)—C(8) | 118.2(6) |
| C(6)—C(7)—C(8) | 131.8(6) |
| O(1)—C(8)—N(3) | 122.7(6) |
| O(1)—C(8)—C(7) | 121.0(6) |
| N(3)—C(8)—C(7) | 116.3(6) |
| N(3)—C(9)—C(10) | 108.8(5) |
| N(3)—C(9)—C(14) | 112.5(6) |
| C(10)—C(9)—C(14) | 113.7(6) |
| N(2)—C(10)—C(9) | 109.1(5) |
| C(12)—C(11)—N(3) | 119.5(9) |
| C(12)—C(11)—C(13) | 60.4(7) |
| N(3)—C(11)—C(13) | 121.1(8) |
| C(11)—C(12)—C(13) | 61.2(7) |
| C(12)—C(13)—C(11) | 58.4(7) |
| C(20)—C(15)—C(16) | 117.4(6) |
| C(20)—C(15)—C(6) | 121.6(6) |
| C(16)—C(15)—C(6) | 120.9(6) |
| C(15)—C(16)—C(17) | 122.6(7) |
| C(18)—C(17)—C(16) | 118.9(7) |
| C(17)—C(18)—C(19) | 120.8(6) |
| C(17)—C(18)—Cl(01) | 119.6(6) |
| C(19)—C(18)—Cl(01) | 119.6(6) |
| C(18)—C(19)—C(20) | 119.2(7) |
| C(15)—C(20)—C(19) | 121.1(7) |
| N(4)—C(21)—C(25) | 123.4(6) |
| N(4)—C(21)—C(26) | 128.9(6) |
| C(25)—C(21)—C(26) | 107.7(5) |
| N(4)—C(22)—C(23) | 125.3(7) |
| C(24)—C(23)—C(22) | 120.2(7) |
| C(23)—C(24)—C(25) | 115.1(7) |
| N(5)—C(25)—C(21) | 108.1(6) |
| N(5)—C(25)—C(24) | 130.6(7) |
| C(21)—C(25)—C(24) | 121.2(6) |
| C(27)—C(26)—C(21) | 104.9(5) |
| C(27)—C(26)—C(35) | 129.9(6) |
| C(21)—C(26)—C(35) | 125.2(6) |
| N(5)—C(27)—C(26) | 110.5(6) |
| N(5)—C(27)—C(28) | 117.6(5) |
| C(26)—C(27)—C(28) | 131.8(6) |
| O(2)—C(28)—N(6) | 123.5(6) |
| O(2)—C(28)—C(27) | 120.1(6) |
| N(6)—C(28)—C(27) | 116.4(6) |
| N(6)—C(29)—C(30) | 109.1(5) |
| N(6)—C(29)—C(34) | 112.2(5) |
| C(30)—C(29)—C(34) | 111.8(6) |
| N(5)—C(30)—C(29) | 108.1(5) |
| C(32)—C(31)—N(6) | 121.3(6) |
| C(32)—C(31)—C(33) | 59.9(6) |
| N(6)—C(31)—C(33) | 120.0(6) |

TABLE 3-continued

Bond lengths [Å] and angles [°] for 10

| | |
|---|---|
| C(31)—C(32)—C(33) | 61.6(6) |
| C(32)—C(33)—C(31) | 58.5(5) |
| C(36)—C(35)—C(40) | 116.6(6) |
| C(36)—C(35)—C(26) | 122.9(6) |
| C(40)—C(35)—C(26) | 120.3(6) |
| C(37)—C(36)—C(35) | 120.9(6) |
| C(38)—C(37)—C(36) | 120.3(7) |
| C(39)—C(38)—C(37) | 120.7(6) |
| C(39)—C(38)—Cl(02) | 120.0(6) |
| C(37)—C(38)—Cl(02) | 119.3(6) |
| C(38)—C(39)—C(40) | 119.5(6) |
| C(39)—C(40)—C(35) | 121.8(7) |
| N(7)—C(41)—C(45) | 124.5(7) |
| N(7)—C(41)—C(46) | 128.4(7) |
| C(45)—C(41)—C(46) | 107.1(6) |
| N(7)—C(42)—C(43) | 126.3(8) |
| C(44)—C(43)—C(42) | 119.6(8) |
| C(43)—C(44)—C(45) | 116.6(8) |
| N(8)—C(45)—C(44) | 130.9(7) |
| N(8)—C(45)—C(41) | 109.3(6) |
| C(44)—C(45)—C(41) | 119.8(7) |
| C(47)—C(46)—C(41) | 104.4(6) |
| C(47)—C(46)—C(55) | 130.5(7) |
| C(41)—C(46)—C(55) | 125.0(6) |
| C(46)—C(47)—N(8) | 110.6(6) |
| C(46)—C(47)—C(48) | 130.1(7) |
| N(8)—C(47)—C(48) | 119.2(6) |
| O(3)—C(48)—N(9) | 122.8(6) |
| O(3)—C(48)—C(47) | 121.4(6) |
| N(9)—C(48)—C(47) | 115.7(6) |
| N(9)—C(49)—C(50) | 109.4(5) |
| N(9)—C(49)—C(54) | 112.8(6) |
| C(50)—C(49)—C(54) | 112.3(6) |
| N(8)—C(50)—C(49) | 109.7(6) |
| N(9)—C(51)—C(53) | 121.3(7) |
| N(9)—C(51)—C(52) | 121.1(7) |
| C(53)—C(51)—C(52) | 60.3(6) |
| C(53)—C(52)—C(51) | 59.4(6) |
| C(51)—C(53)—C(52) | 60.3(6) |
| C(56)—C(55)—C(60) | 118.0(7) |
| C(56)—C(55)—C(46) | 122.2(6) |
| C(60)—C(55)—C(46) | 119.8(6) |
| C(57)—C(56)—C(55) | 121.7(6) |
| C(56)—C(57)—C(58) | 120.5(8) |
| C(57)—C(58)—C(59) | 119.0(7) |
| C(57)—C(58)—Cl(04) | 121.2(6) |
| C(59)—C(58)—Cl(04) | 119.7(6) |
| C(60)—C(59)—C(58) | 121.1(6) |
| C(59)—C(60)—C(55) | 119.7(7) |
| N(10)—C(61)—C(65) | 122.6(6) |
| N(10)—C(61)—C(66) | 129.0(6) |
| C(65)—C(61)—C(66) | 108.4(6) |
| N(10)—C(62)—C(63) | 124.3(7) |
| C(64)—C(63)—C(62) | 120.8(7) |
| C(63)—C(64)—C(65) | 115.7(6) |
| N(11)—C(65)—C(61) | 108.6(6) |
| N(11)—C(65)—C(64) | 130.5(7) |
| C(61)—C(65)—C(64) | 121.0(6) |
| C(67)—C(66)—C(61) | 105.0(6) |
| C(67)—C(66)—C(75) | 128.4(6) |
| C(61)—C(66)—C(75) | 126.6(6) |
| C(66)—C(67)—N(11) | 110.6(6) |
| C(66)—C(67)—C(68) | 131.7(6) |
| N(11)—C(67)—C(68) | 117.5(5) |
| O(4)—C(68)—N(12) | 121.6(6) |
| O(4)—C(68)—C(67) | 122.4(6) |
| N(12)—C(68)—C(67) | 116.0(6) |
| N(12)—C(69)—C(70) | 108.4(5) |
| N(12)—C(69)—C(74) | 113.0(6) |
| C(70)—C(69)—C(74) | 113.7(6) |
| N(11)—C(70)—C(69) | 107.7(5) |
| N(12)—C(71)—C(72) | 119.1(6) |
| N(12)—C(71)—C(73) | 118.8(6) |
| C(72)—C(71)—C(73) | 60.5(5) |
| C(71)—C(72)—C(73) | 60.0(5) |
| C(71)—C(73)—C(72) | 59.5(5) |
| C(76)—C(75)—C(80) | 118.0(6) |
| C(76)—C(75)—C(66) | 122.5(6) |
| C(80)—C(75)—C(66) | 119.5(7) |
| C(77)—C(76)—C(75) | 120.8(7) |
| C(78)—C(77)—C(76) | 118.7(7) |
| C(79)—C(78)—C(77) | 122.2(7) |
| C(79)—C(78)—Cl(03) | 119.1(6) |
| C(77)—C(78)—Cl(03) | 118.7(7) |
| C(78)—C(79)—C(80) | 120.1(7) |
| C(79)—C(80)—C(75) | 120.1(7) |
| C(2)—N(1)—C(1) | 113.6(7) |
| C(5)—N(2)—C(7) | 109.1(5) |
| C(5)—N(2)—C(10) | 128.9(6) |
| C(7)—N(2)—C(10) | 121.7(6) |
| C(8)—N(3)—C(11) | 118.0(6) |
| C(8)—N(3)—C(9) | 121.1(6) |
| C(11)—N(3)—C(9) | 119.7(6) |
| C(22)—N(4)—C(21) | 114.9(6) |
| C(25)—N(5)—C(27) | 108.8(5) |
| C(25)—N(5)—C(30) | 128.2(5) |
| C(27)—N(5)—C(30) | 122.3(5) |
| C(28)—N(6)—C(31) | 117.0(5) |
| C(28)—N(6)—C(29) | 122.8(5) |
| C(31)—N(6)—C(29) | 120.2(5) |
| C(42)—N(7)—C(41) | 113.1(7) |
| C(45)—N(8)—C(47) | 108.6(5) |
| C(45)—N(8)—C(50) | 130.0(6) |
| C(47)—N(8)—C(50) | 121.1(5) |
| C(48)—N(9)—C(51) | 117.2(5) |
| C(48)—N(9)—C(49) | 122.0(5) |
| C(51)—N(9)—C(49) | 118.9(5) |
| C(62)—N(10)—C(61) | 115.6(6) |
| C(65)—N(11)—C(67) | 107.5(5) |
| C(65)—N(11)—C(70) | 128.8(5) |
| C(67)—N(11)—C(70) | 123.6(5) |
| C(68)—N(12)—C(71) | 119.0(6) |
| C(68)—N(12)—C(69) | 119.9(5) |
| C(71)—N(12)—C(69) | 119.4(5) |

Symmetry transformations used to generate equivalent atoms.

TABLE 4

Anisotropic displacement parameters (Å² × 10³) for 10. The anisotropic displacement factor exponent takes the form: $-2\pi^2[h^2 a^{*2} U^{11} + \ldots + 2 h k a^* b^* U^{12}]$

| | U11 | U22 | U33 | U23 | U13 | U12 |
|---|---|---|---|---|---|---|
| C(1) | 63(4) | 55(5) | 47(4) | 19(4) | 17(3) | 8(3) |
| C(2) | 129(8) | 59(7) | 96(7) | 36(6) | 44(6) | 11(5) |
| C(3) | 111(7) | 48(5) | 98(7) | 14(5) | 37(5) | 3(4) |
| C(4) | 83(5) | 47(5) | 72(5) | 7(5) | 17(4) | 8(4) |
| C(5) | 55(4) | 46(5) | 60(5) | 16(4) | 17(3) | 12(3) |
| C(6) | 56(4) | 56(5) | 46(4) | 19(4) | 9(3) | 8(3) |
| C(7) | 67(4) | 52(5) | 36(4) | 13(4) | 6(3) | 5(3) |
| C(8) | 70(5) | 56(5) | 54(5) | 23(4) | 13(4) | 11(4) |
| C(9) | 66(5) | 78(5) | 37(4) | 23(4) | 0(3) | 10(4) |
| C(10) | 71(5) | 79(6) | 41(4) | 10(4) | 16(3) | 14(4) |
| C(11) | 105(7) | 91(7) | 81(6) | 42(5) | −5(5) | −3(5) |
| C(12) | 110(8) | 150(11) | 192(13) | 114(10) | −43(8) | −37(8) |
| C(13) | 170(10) | 103(8) | 99(8) | 71(6) | −11(7) | −24(7) |
| C(14) | 65(5) | 87(6) | 77(5) | 28(4) | 2(4) | 11(4) |
| C(15) | 66(4) | 59(5) | 42(4) | 23(4) | 6(3) | 8(3) |
| C(16) | 81(5) | 81(6) | 40(4) | 15(4) | 5(3) | 15(4) |
| C(17) | 89(5) | 72(5) | 51(5) | 20(4) | 12(4) | 19(4) |
| C(18) | 90(5) | 57(5) | 38(4) | 19(4) | 3(4) | −14(4) |
| C(19) | 101(6) | 73(6) | 61(5) | 40(5) | −10(4) | 1(5) |
| C(20) | 89(5) | 59(5) | 53(5) | 20(4) | −1(4) | 7(4) |
| C(21) | 49(4) | 67(5) | 38(4) | 15(4) | 16(3) | 4(3) |
| C(22) | 93(6) | 57(6) | 57(5) | −3(4) | 10(4) | −11(4) |
| C(23) | 96(6) | 46(5) | 68(5) | 2(4) | 14(4) | −15(4) |
| C(24) | 76(5) | 60(5) | 63(5) | 13(4) | 13(4) | −3(4) |
| C(25) | 48(4) | 46(5) | 53(4) | 8(4) | 10(3) | 0(3) |
| C(26) | 52(4) | 54(4) | 42(4) | 18(3) | 11(3) | 4(3) |
| C(27) | 59(4) | 52(4) | 42(4) | 26(3) | 6(3) | 6(3) |
| C(28) | 64(4) | 55(5) | 37(4) | 15(4) | 3(3) | 5(3) |
| C(29) | 70(4) | 55(4) | 39(4) | 23(3) | 2(3) | 0(3) |

TABLE 4-continued

Anisotropic displacement parameters (Å² × 10³) for 10. The anisotropic displacement factor exponent takes the form: $-2\pi^2[h^2 a^{*2}U^{11} + \ldots + 2 h k a^* b^* U^{12}]$

| | U11 | U22 | U33 | U23 | U13 | U12 |
|---|---|---|---|---|---|---|
| C(30) | 62(4) | 61(4) | 47(4) | 27(3) | 10(3) | 4(3) |
| C(31) | 84(5) | 47(4) | 50(4) | 2(4) | 7(4) | −1(4) |
| C(32) | 137(8) | 57(5) | 55(5) | 4(4) | 21(5) | −3(5) |
| C(33) | 115(7) | 65(5) | 47(4) | 13(4) | −6(4) | 1(4) |
| C(34) | 60(4) | 60(5) | 78(5) | 34(4) | 0(4) | 4(3) |
| C(35) | 47(4) | 54(4) | 43(4) | 15(3) | 13(3) | 10(3) |
| C(36) | 50(4) | 73(5) | 61(5) | 25(4) | −6(3) | −3(3) |
| C(37) | 77(5) | 58(5) | 71(5) | 35(4) | 1(4) | 3(4) |
| C(38) | 62(4) | 76(5) | 41(4) | 27(4) | 14(3) | 20(4) |
| C(39) | 64(4) | 89(6) | 32(4) | 22(4) | 0(3) | 10(4) |
| C(40) | 56(4) | 68(5) | 39(4) | 10(4) | 1(3) | −6(3) |
| C(41) | 50(4) | 65(5) | 49(5) | 12(4) | 1(3) | −2(3) |
| C(42) | 89(6) | 81(8) | 85(7) | 4(6) | 6(5) | 12(5) |
| C(43) | 91(6) | 65(6) | 99(7) | 21(6) | 6(5) | 8(4) |
| C(44) | 75(5) | 67(5) | 68(5) | 18(5) | 12(4) | 4(4) |
| C(45) | 58(4) | 59(5) | 57(5) | 17(4) | 5(3) | −2(3) |
| C(46) | 48(4) | 80(6) | 40(4) | 16(4) | 2(3) | −6(3) |
| C(47) | 53(4) | 60(5) | 44(4) | 17(4) | 5(3) | −7(3) |
| C(48) | 65(5) | 62(5) | 48(4) | 22(4) | 6(3) | −10(3) |
| C(49) | 59(4) | 68(5) | 43(4) | 24(4) | 9(3) | 4(3) |
| C(50) | 60(4) | 69(5) | 49(4) | 22(4) | 8(3) | −2(3) |
| C(51) | 86(5) | 64(5) | 56(5) | 17(4) | 6(4) | −6(4) |
| C(52) | 126(8) | 90(7) | 90(7) | 25(6) | −1(6) | 5(6) |
| C(53) | 144(8) | 84(6) | 56(5) | 11(5) | 29(5) | 7(6) |
| C(54) | 61(5) | 94(6) | 92(6) | 46(5) | −2(4) | −2(4) |
| C(55) | 48(4) | 75(5) | 42(4) | 16(4) | 2(3) | −2(4) |
| C(56) | 52(4) | 86(5) | 56(4) | 30(4) | 12(3) | −3(4) |
| C(57) | 68(5) | 82(5) | 54(5) | 25(4) | 10(4) | 2(4) |
| C(58) | 78(5) | 89(6) | 45(4) | 28(4) | 4(4) | −17(5) |
| C(59) | 53(4) | 113(7) | 50(5) | 27(5) | 10(3) | −4(4) |
| C(60) | 53(4) | 84(5) | 41(4) | 22(4) | 7(3) | 1(3) |
| C(61) | 52(4) | 57(5) | 52(4) | 28(4) | 8(3) | 3(3) |
| C(62) | 85(5) | 73(6) | 78(6) | 44(5) | 19(4) | 8(4) |
| C(63) | 86(5) | 55(5) | 75(6) | 24(4) | 20(4) | 9(4) |
| C(64) | 60(4) | 62(5) | 54(4) | 21(4) | 14(3) | 3(3) |
| C(65) | 45(4) | 60(5) | 43(4) | 21(4) | 13(3) | 5(3) |
| C(66) | 72(5) | 60(5) | 37(4) | 21(4) | 9(3) | 4(3) |
| C(67) | 59(4) | 59(5) | 41(4) | 20(4) | 10(3) | 2(3) |
| C(68) | 72(5) | 65(5) | 36(4) | 24(4) | 9(3) | −2(4) |
| C(69) | 61(4) | 60(4) | 44(4) | 28(3) | 19(3) | 12(3) |
| C(70) | 62(4) | 57(4) | 40(4) | 16(3) | 9(3) | −3(3) |
| C(71) | 70(5) | 57(5) | 60(5) | 34(4) | 3(3) | −6(3) |
| C(72) | 89(6) | 68(5) | 94(6) | 42(5) | 20(5) | 14(4) |
| C(73) | 123(7) | 70(6) | 69(5) | 36(5) | 14(5) | 12(5) |
| C(74) | 64(5) | 74(5) | 89(6) | 43(5) | 17(4) | −5(4) |
| C(75) | 79(5) | 54(5) | 47(4) | 21(4) | 11(3) | 21(4) |
| C(76) | 94(6) | 67(5) | 57(5) | 27(4) | 1(4) | −10(4) |
| C(77) | 119(7) | 67(5) | 44(5) | 18(4) | −6(4) | 0(4) |
| C(78) | 121(6) | 59(5) | 36(4) | 23(4) | 18(4) | 27(5) |
| C(79) | 99(6) | 72(6) | 62(5) | 33(5) | 29(4) | 26(5) |
| C(80) | 93(5) | 57(5) | 39(4) | 17(4) | 18(4) | 9(4) |
| Cl(01) | 151(2) | 75(1) | 49(1) | 20(1) | −1(1) | −27(1) |
| Cl(02) | 132(2) | 105(2) | 72(1) | 48(1) | 3(1) | 32(1) |
| Cl(03) | 170(2) | 84(2) | 49(1) | 13(1) | 24(1) | 41(1) |
| Cl(04) | 129(2) | 108(2) | 88(2) | 55(1) | 17(1) | −20(1) |
| N(1) | 95(5) | 64(5) | 78(4) | 33(4) | 32(3) | 10(3) |
| N(2) | 67(4) | 50(4) | 41(4) | 10(3) | 9(2) | 11(3) |
| N(3) | 76(4) | 60(4) | 44(4) | 25(3) | 2(3) | 4(3) |
| N(4) | 74(4) | 62(4) | 40(4) | 4(3) | 15(3) | −6(3) |
| N(5) | 58(3) | 53(4) | 41(3) | 17(3) | 6(2) | 3(3) |
| N(6) | 70(4) | 47(3) | 39(3) | 16(3) | 3(3) | 3(2) |
| N(7) | 73(4) | 84(5) | 53(4) | 11(4) | 4(3) | 5(3) |
| N(8) | 64(3) | 51(4) | 52(4) | 18(3) | 11(3) | −5(3) |
| N(9) | 75(4) | 48(4) | 46(3) | 17(3) | 16(3) | −5(3) |
| N(10) | 78(4) | 63(5) | 60(4) | 27(4) | 16(3) | 10(3) |
| N(11) | 61(3) | 53(4) | 33(3) | 17(3) | 10(2) | −5(2) |
| N(12) | 64(3) | 54(4) | 42(3) | 26(3) | 11(2) | 1(3) |
| O(1) | 125(5) | 54(3) | 58(3) | 13(3) | −2(3) | 3(3) |
| O(2) | 92(3) | 54(3) | 56(3) | 18(3) | −4(2) | 16(3) |
| O(3) | 120(4) | 61(3) | 63(3) | 26(3) | 13(3) | −30(3) |
| O(4) | 137(5) | 57(3) | 45(3) | 16(3) | 28(3) | 13(3) |

TABLE 5

Hydrogen coordinates (×10⁴) and isotropic displacement parameters (Å² × 10³) for 10.

| | x | y | z | U(eq) |
|---|---|---|---|---|
| H(076) | 2885 | 5316 | 1235 | 110 |
| H(085) | 2602 | 4656 | −246 | 106 |
| H(053) | 2411 | 5961 | −988 | 85 |
| H(088) | 1790 | 9639 | −1421 | 72 |
| H(05A) | 1944 | 7764 | −1330 | 80 |
| H(05B) | 3392 | 8500 | −1136 | 80 |
| H(062) | 1786 | 12231 | 71 | 108 |
| H(1A) | 4607 | 11770 | −413 | 166 |
| H(1B) | 3917 | 13055 | −86 | 166 |
| H(09A) | 2960 | 11081 | −1612 | 139 |
| H(09B) | 2268 | 12369 | −1284 | 139 |
| H(08C) | 21 | 9305 | −168 | 115 |
| H(08D) | −295 | 8798 | −1188 | 115 |
| H(08E) | −270 | 10159 | −669 | 115 |
| H(070) | 1562 | 10904 | 2328 | 83 |
| H(079) | 1600 | 12005 | 3814 | 85 |
| H(066) | 4432 | 9920 | 4228 | 90 |
| H(052) | 4383 | 8824 | 2724 | 80 |
| H(077) | 4873 | 3477 | 6742 | 91 |
| H(060) | 5323 | 2842 | 7880 | 91 |
| H(064) | 5939 | 4199 | 9283 | 82 |
| H(017) | 7563 | 7907 | 11565 | 64 |
| H(04A) | 6827 | 6010 | 10538 | 65 |
| H(04B) | 5593 | 6879 | 10805 | 65 |
| H(059) | 6358 | 10347 | 11693 | 78 |
| H(08F) | 8274 | 11575 | 11709 | 105 |
| H(08G) | 9104 | 10468 | 11055 | 105 |
| H(07D) | 8184 | 10671 | 12770 | 93 |
| H(07E) | 9016 | 9561 | 12116 | 93 |
| H(06A) | 8994 | 7234 | 9977 | 96 |
| H(06B) | 9309 | 6794 | 10751 | 96 |
| H(06C) | 9645 | 8114 | 10877 | 96 |
| H(063) | 7174 | 9152 | 8418 | 74 |
| H(073) | 6751 | 10237 | 7547 | 79 |
| H(083) | 3535 | 8034 | 6304 | 74 |
| H(041) | 3946 | 6915 | 7150 | 68 |
| H(098) | −137 | 10695 | 7660 | 110 |
| H(092) | 170 | 11304 | 6517 | 105 |
| H(074) | 690 | 9962 | 5148 | 86 |
| H(049) | 2100 | 6318 | 2914 | 66 |
| H(03A) | 1578 | 8201 | 3929 | 71 |
| H(03B) | 265 | 7303 | 3641 | 71 |
| H(057) | 2736 | 3945 | 3210 | 84 |
| H(09F) | 895 | 2585 | 2471 | 125 |
| H(09G) | −210 | 3637 | 2670 | 125 |
| H(09H) | 2339 | 3519 | 1710 | 118 |
| H(09I) | 1234 | 4570 | 1909 | 118 |
| H(07A) | 3720 | 7022 | 4505 | 118 |
| H(07B) | 3987 | 7478 | 3735 | 118 |
| H(07C) | 4229 | 6163 | 3602 | 118 |
| H(065) | 2036 | 5229 | 6114 | 77 |
| H(097) | 1723 | 4102 | 6950 | 81 |
| H(081) | −1454 | 6032 | 8120 | 87 |
| H(036) | −1123 | 7206 | 7302 | 72 |
| H(067) | 7365 | 9023 | 3247 | 88 |
| H(095) | 7226 | 9661 | 4742 | 86 |
| H(038) | 7124 | 8334 | 5456 | 70 |
| H(056) | 6394 | 4573 | 5836 | 62 |
| H(02A) | 6546 | 6486 | 5775 | 65 |
| H(02B) | 7998 | 5879 | 5642 | 65 |
| H(082) | 6421 | 2053 | 4493 | 71 |
| H(08A) | 9395 | 2673 | 4696 | 95 |
| H(08B) | 8685 | 1359 | 4509 | 95 |
| H(07F) | 7444 | 2107 | 5837 | 101 |
| H(07G) | 8155 | 3421 | 6024 | 101 |
| H(09C) | 4617 | 4742 | 4491 | 108 |
| H(09D) | 4308 | 5254 | 5496 | 108 |
| H(09E) | 4327 | 3891 | 5000 | 108 |
| H(080) | 5976 | 3283 | 2024 | 86 |
| H(099) | 6387 | 2070 | 594 | 93 |
| H(096) | 9207 | 4445 | 396 | 89 |
| H(072) | 8860 | 5663 | 1822 | 76 |

Example 11

(7S)-10-(4-Chlorophenyl)-8-cyclopropyl-7-methyl-7,8-dihydropyrido[2',3':4,5]pyrrolo[1,2-a]pyrazin-9(6H)-one (11)

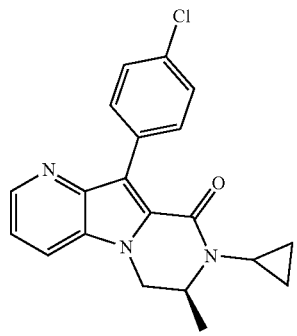

11

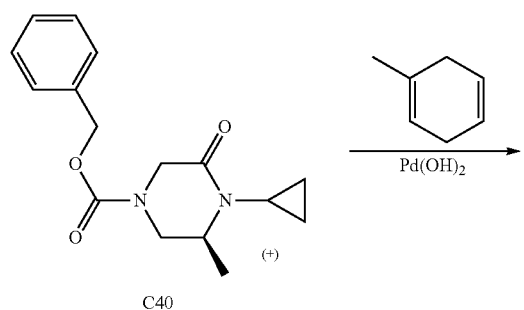

Step 1. Synthesis of (6S)-1-cyclopropyl-6-methylpiperazin-2-one (C44)

1-Methylcyclohexa-1,4-diene (1 mL) was added to a solution of C40 (255 mg, 0.884 mmol) in ethanol (4 mL), and the mixture was heated to 50° C. Palladium hydroxide on carbon (25 mg, 0.18 mmol) was added in one portion, and heating was continued at 70° C. for 3 hours. The reaction mixture was filtered through diatomaceous earth, and the filter cake was washed three times with ethanol; the combined filtrates were concentrated in vacuo to afford the product as an oil. Yield: 150 mg, assumed quantitative. $^1$H NMR (400 MHZ, CDCl$_3$) δ 3.46-3.57 (m, 3H), 3.19 (dd, J=13.0, 4.5 Hz, 1H), 2.81 (dd, J=13.1, 5.9 Hz, 1H), 2.56-2.64 (m, 1H), 1.33 (d, J=6.5 Hz, 3H), 1.03-1.12 (m, 1H), 0.67-0.79 (m, 2H), 0.55-0.64 (m, 1H).

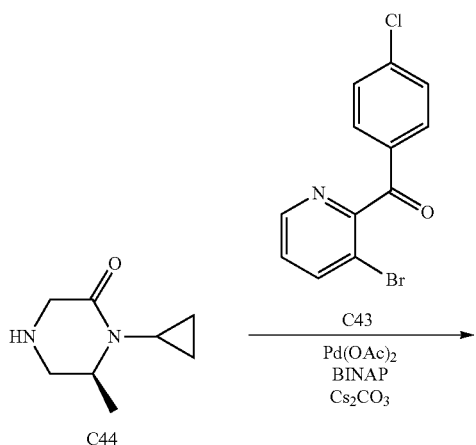

Step 2. Synthesis of (7S)-10-(4-chlorophenyl)-8-cyclopropyl-7-methyl-7,8-dihydropyrido[2',3':4,5]pyrrolo[1,2-a]pyrazin-9(6H)-one (11)

Compound C44 was reacted with C43 according to the general procedure for the synthesis of 9 in Example 9; the product was obtained as a white solid. Yield: 123 mg, 0.350 mmol, 39%. LCMS m/z 352.2. 354.1 [M+H]$^+$. $^1$H NMR (400 MHZ, CDCl$_3$) δ 8.63 (dd, J=4.6, 1.4 Hz, 1H), 7.78 (br d, J=8.6 Hz, 2H), 7.70 (dd, J=8.4, 1.4 Hz, 1H), 7.44 (br d, J=8.7 Hz, 2H), 7.32 (dd, J=8.4, 4.6 Hz, 1H), 4.29 (dd, half of ABX pattern, J=12.1, 4.0 Hz, 1H), 4.23 (dd, half of ABX pattern, J=12.1, 1.6 Hz, 1H), 4.02-4.10 (m, 1H), 2.80-2.86 (m, 1H), 1.39 (d, J=6.7 Hz, 3H), 1.09-1.18 (m, 1H), 0.78-0.94 (m, 2H), 0.57-0.65 (m, 1H).

Example 12

10-(4-Chlorophenyl)-2-cyclopropyl-3,4-dihydropy-razino[1,2-a]indol-1(2H)-one (12)

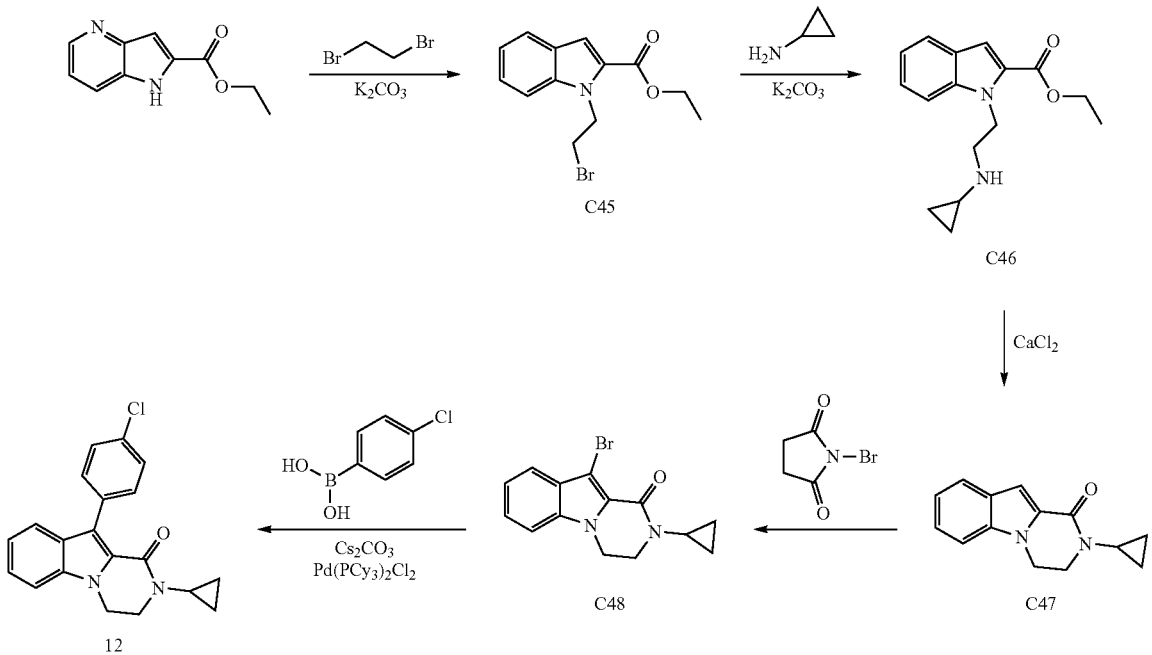

Step 1. Synthesis of ethyl 1-(2-bromoethyl)-1H-indole-2-carboxylate (C45)

Ethyl 1H-indole-2-carboxylate (4.12 g, 21.8 mmol), 1,2-dibromoethane (4.51 g, 24.0 mmol) and potassium carbonate (4.51 g, 32.6 mmol) were combined with N,N-dimethylformamide (100 mL) and heated at 100° C. for 18 hours. The reaction mixture was concentrated under reduced pressure to remove N,N-dimethylformamide, and the residue was diluted with water (100 mL) and extracted with ethyl acetate (3×200 mL). The combined organic layers were washed with saturated aqueous sodium chloride solution (100 mL), dried over sodium sulfate, filtered, and concentrated in vacuo; silica gel chromatography (Gradient: 5% to 9% ethyl acetate in petroleum ether) provided the product as a white solid. Yield: 544 mg, 1.84 mmol, 8%. $^1$H NMR (400 MHZ, CDCl$_3$) δ 7.69 (br d, J=8 Hz, 1H), 7.46 (br d, half of AB quartet, J=8.3 Hz, 1H), 7.34-7.42 (m, 2H), 7.15-7.22 (m, 1H), 4.93 (t, J=7.3 Hz, 2H), 4.40 (q, J=7 Hz, 2H), 3.70 (t, J=7.3 Hz, 2H), 1.43 (t, J=7.0 Hz, 3H).

Step 2. Synthesis of ethyl 1-[2-(cyclopropylamino)ethyl]-1H-indole-2-carboxylate (C46)

To a suspension of C45 (544 mg, 1.84 mmol) and potassium carbonate (381 mg, 2.76 mmol) in acetonitrile (15 mL) was added cyclopropylamine (4.2 g, 73.6 mmol), and the reaction vessel was sealed and heated at 60° C. for 18 hours, then at 80° C. for 4 hours. After solvent had been removed in vacuo, the residue was diluted with water (5 mL) and extracted with ethyl acetate (3×10 mL). The combined organic layers were washed with saturated aqueous sodium chloride solution (15 mL), dried over sodium sulfate, filtered, and concentrated under reduced pressure to afford the product as a white solid. Yield: 250 mg, 0.92 mmol, 50%. $^1$H NMR (400 MHz, CDCl$_3$) δ 7.68 (d, J=7.8 Hz, 1H), 7.47 (d, J=8 Hz, 1H), 7.31-7.38 (m, 2H), 7.16 (dd, J=7.5, 7.5 Hz, 1H), 4.70 (t, J=6.8 Hz, 2H), 4.38 (q, J=7.0 Hz, 2H), 3.11 (t, J=6.8 Hz, 2H), 2.13-2.20 (m, 1H), 1.42 (t, J=7.2 Hz, 3H), 0.40-0.47 (m, 2H), 0.29-0.35 (m, 2H).

Step 3. Synthesis of 2-cyclopropyl-3,4-dihydropyrazino[1,2-a]indol-1(2H)-one (C47)

To a solution of C46 (100 mg, 0.37 mmol) in methanol (5 mL) was added calcium chloride (41 mg, 0.37 mmol), and the reaction mixture was stirred at 80° C. for 2 days. The mixture was combined with an identical reaction mixture derived from 100 mg of C46 and concentrated in vacuo, providing a residue that was then diluted with water and extracted with dichloromethane (3×10 mL). The combined organic layers were washed with saturated aqueous sodium chloride solution (10 mL), dried over sodium sulfate, filtered, and concentrated under reduced pressure to provide the product as an off-white solid. Yield: 160 mg, 0.707 mmol, 96%. $^1$H NMR (400 MHz, DMSO-d$_6$) δ 7.66 (d, J=7.8 Hz, 1H), 7.52 (d, J=8.4 Hz, 1H), 7.26-7.31 (m, 1H), 7.10 (dd, J=7.4, 7.4 Hz, 1H), 7.03 (s, 1H), 4.26-4.30 (m, 2H), 3.73-3.77 (m, 2H), 2.81-2.88 (m, 1H), 0.78-0.84 (m, 2H), 0.70-0.76 (m, 2H).

Step 4. Synthesis of 10-bromo-2-cyclopropyl-3,4-dihydropyrazino[1,2-a]indol-1(2H)-one (C48)

To a −50° C. solution of C47 (200 mg, 0.88 mmol) in dichloromethane (20 mL) was added N-bromosuccinimide (180 mg, 1.01 mmol). After 5 minutes, the mixture was washed with water (10 mL) and extracted with dichloromethane (3×10 mL). The combined organic layers were washed with saturated aqueous sodium chloride solution (10 mL), dried over sodium sulfate, filtered, and concentrated in vacuo to afford the product as a white solid. Yield: 200 mg, 0.655 mmol, 74%. $^1$H NMR (400 MHz, CDCl$_3$) δ 7.70 (d, J=8.0 Hz, 1H), 7.37-7.42 (m, 1H), 7.28-7.31 (m, 1H), 7.22-7.27 (m, 1H, assumed; partially obscured by solvent peak), 4.22-4.27 (m, 2H), 3.79-3.84 (m, 2H), 2.81-2.87 (m, 1H), 0.94-1.01 (m, 2H), 0.76-0.82 (m, 2H).

Step 5. Synthesis of 10-(4-chlorophenyl)-2-cyclopropyl-3,4-dihydropyrazino[1,2-a]indol-1(2H)-one (12)

A mixture of C48 (100 mg, 0.33 mmol), (4-chlorophenyl) boronic acid (52 mg, 0.33 mmol), and cesium carbonate (210 mg, 0.644 mmol) in 1,4-dioxane (4 mL) and water (0.5 mL) was degassed with nitrogen for 2 minutes. Dichlorobis(tricyclohexylphosphine)palladium(II) (36 mg, 49 umol) was added in one portion, and the reaction vessel was sealed and heated at 90° C. for 18 hours. The reaction mixture was concentrated to dryness and the residue was purified by preparative thin layer chromatography; further purification was carried out using reversed phase HPLC (Column: Phenomenex Gemini C18, 5 um; Mobile phase A: ammonia in water, pH 10; Mobile phase B: acetonitrile; Gradient: 50% to 70% B) to provide the product as a white solid. Yield: 13.5 mg, 40.1 umol, 12%. LCMS m/z 336.9 [M+H]$^+$. $^1$H NMR (400 MHZ, CDCl$_3$) δ 7.65 (d, J=8.0 Hz, 1H), 7.59 (br d, J=8.5 Hz, 2H), 7.42 (br d, J=8.3 Hz, 2H), 7.33-7.40 (m, 2H), 7.18 (dd, J=7.3, 7.3 Hz, 1H), 4.26-4.32 (m, 2H), 3.83-3.89 (m, 2H), 2.77-2.84 (m, 1H), 0.90-0.97 (m, 2H), 0.71-0.78 (m, 2H).

Example 13

8-Cyclopropyl-10-(4-methylphenyl)pyrido[2',3':4,5]pyrrolo[1,2-a]pyrazin-9(8H)-one (13)

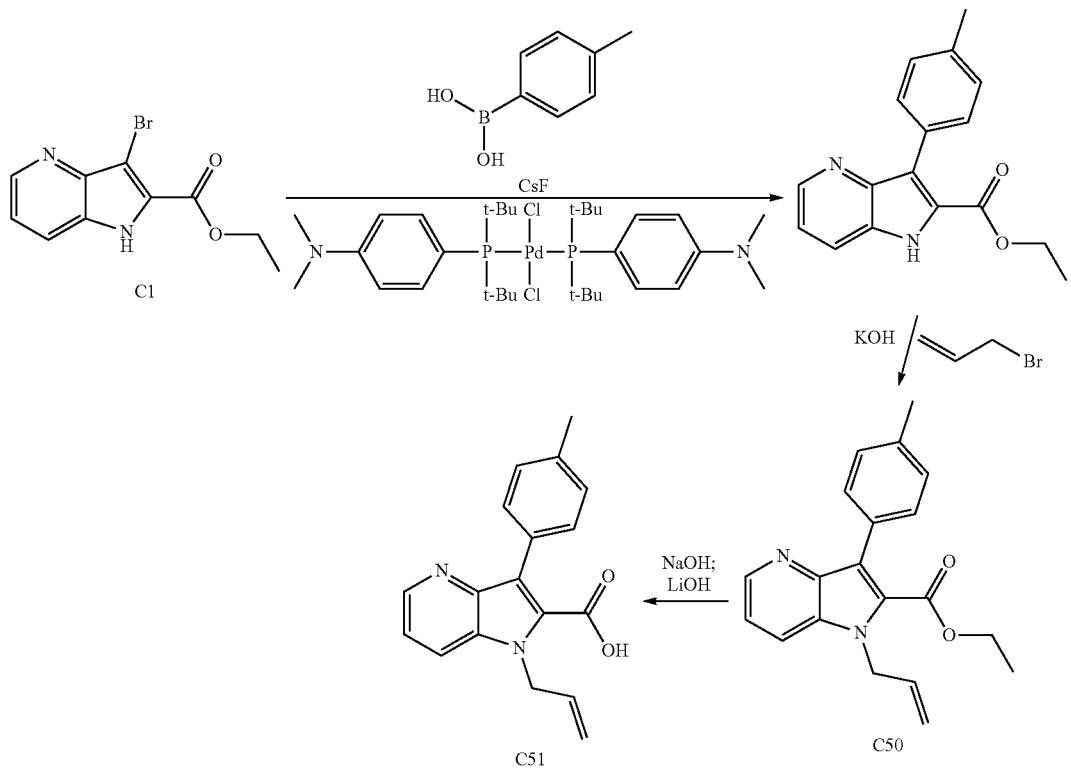

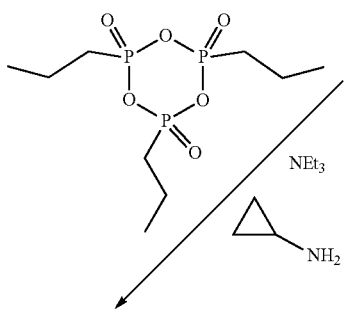

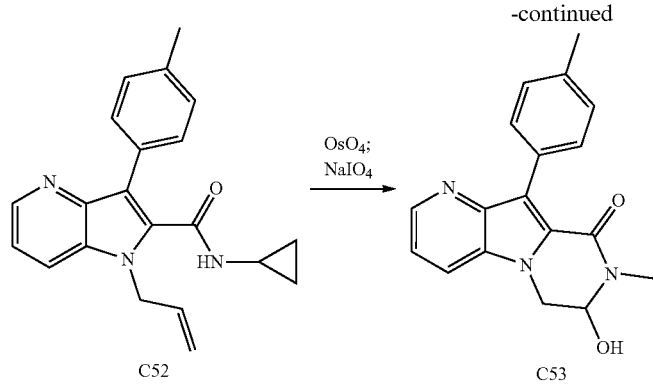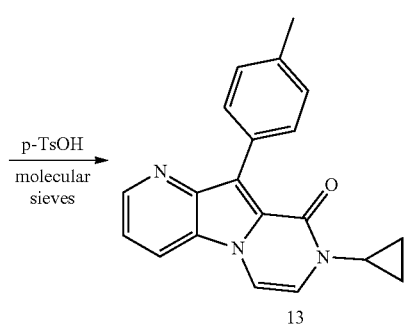

Step 1. Synthesis of ethyl 3-(4-methylphenyl)-1H-pyrrolo[3,2-b]pyridine-2-carboxylate (C49)

Toluene (10 mL) was degassed via vacuum evacuation followed by nitrogen fill. Subsequent additions of C1 (138 mg, 0.513 mmol) and (4-methylphenyl)boronic acid (140 mg, 1.03 mmol) were each followed by the same degassing procedure. An aqueous solution of cesium fluoride (1.0 M, 2.56 mL, 2.56 mmol) was introduced, followed by addition of a solution of bis[di-tert-butyl(4-dimethylaminophenyl)phosphine]dichloropalladium(II) (45.3 mg, 64 umol) in 1,2-dichloroethane, and the reaction mixture was heated to 100° C. for 3 hours. After removal of solvent in vacuo, purification via silica gel chromatography (Eluent: 30% ethyl acetate in heptane) afforded the product as a yellow solid. Yield: 137 mg, 0.489 mmol, 95%. LCMS m/z 281.2 [M+H]$^+$. $^1$H NMR (400 MHZ, CDCl$_3$) δ 9.81 (br s, 1H), 8.60 (br d, J=4.4 Hz, 1H), 7.68 (br d, J=8.4 Hz, 1H), 7.59 (br d, J=7.9 Hz, 2H), 7.23 (dd, J=8.5, 4.5 Hz, 1H), 7.21 (br d, J=7.6 Hz, 2H), 4.33 (q, J=7.1 Hz, 2H), 2.36 (s, 3H), 1.25 (t, J=7.1 Hz, 3H).

Step 2. Synthesis of ethyl 3-(4-methylphenyl)-1-(prop-2-en-1-yl)-1H-pyrrolo[3,2-b]pyridine-2-carboxylate (C50)

Powdered anhydrous potassium hydroxide (109 mg, 1.94 mmol) was treated with dimethyl sulfoxide (1.0 mL) and stirred at room temperature for 5 minutes. This was added to a solution of C49 (136 mg, 0.485 mmol) in dimethyl sulfoxide (1.0 mL), and additional dimethyl sulfoxide (0.5 mL) was used to effect complete transfer. 3-Bromoprop-1-ene (82 μL, 0.97 mmol) was then added, and the reaction mixture was stirred at room temperature for 10 minutes, whereupon it was carefully neutralized by addition of 1 N aqueous hydrochloric acid. The resulting mixture was partitioned between water and ethyl acetate; the organic layer was dried over magnesium sulfate, filtered, and concentrated in vacuo to afford the product as a yellow oil. Yield: 155 mg, 0.484 mmol, 100%. LCMS m/z 321.2 [M+H]$^+$. $^1$H NMR (400 MHZ, CDCl$_3$) δ 8.58 (br d, J=4.5 Hz, 1H), 7.71 (br d, J=8.4 Hz, 1H), 7.44 (br d, J=7.9 Hz, 2H), 7.22-7.27 (m, 3H), 5.96-6.07 (m, 1H), 5.14-5.19 (m, 3H), 5.01 (d, J=16.6 Hz, 1H), 4.22 (q, J=7.1 Hz, 2H), 2.39 (s, 3H), 1.11 (t, J=7.1 Hz, 3H).

Step 3. Synthesis of 3-(4-methylphenyl)-1-(prop-2-en-1-yl)-1H-pyrrolo[3,2-b]pyridine-2-carboxylic acid (C51)

A mixture of C50 (155 mg, 0.484 mmol), cyclopropylamine (98%, 0.346 mL, 4.83 mmol) and calcium chloride (53.7 mg, 0.484 mmol) in methanol (5 mL) was heated at 50° C. for 18 hours, then at 65° C. for 5 hours in a pressure bottle. By LCMS, the major component was not the intended amide, but the methyl ester of the starting material. The reaction mixture was cooled to room temperature and concentrated in vacuo. The residue was dissolved in ethanol (5 mL) and water (6 mL), treated with aqueous sodium hydroxide solution (12 N, 80 μL, 0.96 mmol), and heated to 70° C. for 7 hours. The reaction mixture was concentrated to dryness, then slurried in a mixture of ethanol, tetrahydrofuran and water (1:1:1, 6 mL). Lithium hydroxide (58 mg, 2.4 mmol) was added, and the reaction mixture was allowed to stir at room temperature for 18 hours. After removal of volatiles under reduced pressure, the aqueous residue was neutralized with 6 N aqueous hydrochloric acid; this was extracted twice with a 3:1 mixture of chloroform and 2-propanol, and the combined organic layers were dried over magnesium sulfate, filtered, and concentrated in vacuo to afford the product as a solid. Yield: 105 mg, 0.359 mmol, 74%. LCMS m/z 293.1 [M+H]$^+$. $^1$H NMR (400 MHZ, CD$_3$OD), characteristic peaks: δ 8.32 (dd, J=4.9, 1.2 Hz, 1H), 8.06 (dd, J=8.3, 1.1 Hz, 1H), 7.52 (br d, J=8.1 Hz, 2H), 7.32 (dd, J=8.3, 5.0 Hz, 1H), 7.16 (br d, J=7.9 Hz, 2H), 5.97-6.08 (m, 1H), 2.32 (br s, 3H).

Step 4. Synthesis of N-cyclopropyl-3-(4-methylphenyl)-1-(prop-2-en-1-yl)-1H-pyrrolo[3,2-b]pyridine-2-carboxamide (C52)

Triethylamine (0.249 mL, 1.80 mmol) and cyclopropylamine (0.124 mL, 1.80 mmol) were added to a slurry of C51 (105 mg, 0.359 mmol) in ethyl acetate (4 mL), which was then treated with 2,4,6-tripropyl-1,3,5,2,4,6-trioxatriphosphinane 2,4,6-trioxide (T3P, ~50% solution in ethyl acetate, 0.7 mL, 1 mmol). The reaction mixture was allowed to stir at room temperature for 20 minutes, whereupon it was quenched by addition of saturated aqueous sodium bicarbonate solution and extracted twice with ethyl acetate. The combined organic layers were dried over magnesium sulfate, filtered through a ½ inch layer of silica gel, and concentrated in vacuo. Silica gel chromatography (Eluent: 40% ethyl acetate in heptane) provided the product as a white solid. Yield: 53 mg, 0.16 mmol, 45%. LCMS m/z 332.2 [M+H]$^+$. $^1$H NMR (400 MHz, CDCl$_3$) δ 8.55 (br d, J=4.3 Hz, 1H), 7.71 (br d, J=8.2 Hz, 1H), 7.48 (br d, J=7.9 Hz, 2H), 7.30 (br d, J=7.8 Hz, 2H), 7.22 (dd, J=8.4, 4.5 Hz, 1H), 5.99-6.10 (m, 1H), 5.86 (br s, 1H), 5.14-5.19 (m, 3H), 5.04 (d, J=16.4 Hz, 1H), 2.69-2.77 (m, 1H), 2.42 (s, 3H), 0.69-0.76 (m, 2H), 0.26-0.32 (m, 2H).

Step 5. Synthesis of 8-cyclopropyl-7-hydroxy-10-(4-methylphenyl)-7,8-dihydropyrido[2',3':4,5]pyrrolo[1,2-a]pyrazin-9(6H)-one (C53)

Osmium tetroxide (2.5 weight percent solution in tert-butanol, 0.8 mL, 60 umol) was added to a solution of C52 (53 mg, 0.16 mmol) in acetone (5 mL) and water (5 mL), and the reaction mixture was stirred for 5 minutes. Sodium periodate (110 mg, 0.51 mmol) was added, and stirring was continued for 2 hours, whereupon aqueous sodium thiosulfate solution was added. The mixture was partitioned between dichloromethane and water; the aqueous layer was extracted with dichloromethane, and the combined organic layers were dried over magnesium sulfate, filtered, and concentrated in vacuo. The residue was passed through a plug of silica gel, eluting with dichloromethane and ethyl acetate, and the eluent was concentrated under reduced pressure to provide the product as a light peach solid, which was carried forward without additional purification. Yield: 22 mg, 66 umol, 41%. LCMS m/z 334.1 [M+H]+. 1H NMR (400 MHZ, CD3OD), characteristic peaks: δ 8.42 (br d, J=4.4 Hz, 1H), 8.03 (br d, J=8.4 Hz, 1H), 7.54 (br d, J=8.0 Hz, 2H), 7.41 (dd, J=8.5, 4.5 Hz, 1H), 7.25 (br d, J=8 Hz, 2H), 5.48-5.50 (m, 1H), 4.63 (dd, J=13.1, 1.7 Hz, 1H), 4.26 (dd, J=13, 3 Hz, 1H), 2.85-2.91 (m, 1H), 2.41 (s, 3H).

Step 6. Synthesis of 8-cyclopropyl-10-(4-methylphenyl)pyrido[2',3':4,5]pyrrolo[1,2-a]pyrazin-9(8H)-one (13)

To a solution of C53 (22 mg, 66 umol) in dichloromethane (2 mL) were added powdered molecular sieves followed by p-toluenesulfonic acid monohydrate (13.1 mg, 69.0 umol), and the reaction mixture was allowed to stir for 1 hour. It was then filtered through diatomaceous earth, rinsing with additional dichloromethane, and the combined filtrates were concentrated in vacuo. Purification was carried out via silica gel chromatography (Eluents: ethyl acetate, followed by 1:1 ethyl acetate/methanol). This material was partitioned between dichloromethane and saturated aqueous sodium bicarbonate solution; concentration of the organic layer under reduced pressure afforded the product as a fluorescent yellow solid. Yield: 16 mg, 51 umol, 77%. LCMS m/z 316.3 [M+H]+. 1H NMR (400 MHz, CDCl3) δ 8.74 (dd, J=4.5, 1.2 Hz, 1H), 7.97 (dd, J=8.5, 1.1 Hz, 1H), 7.72 (br d, J=8.0 Hz, 2H), 7.33 (dd, J=8.5, 4.5 Hz, 1H), 7.30 (br d, J=7.9 Hz, 2H), 7.22 (d, J=6.0 Hz, 1H), 6.56 (d, J=6.0 Hz, 1H), 3.17-3.24 (m, 1H), 2.40 (s, 3H), 1.05-1.11 (m, 2H), 0.85-0.91 (m, 2H).

Example 14

4-(7-Cyclopropyl-8-oxo-5,6,7,8-tetrahydro[1,3]thiazolo[4',5':4,5]pyrrolo[1,2-a]pyrazin-9-yl)-3-methylbenzonitrile (14)

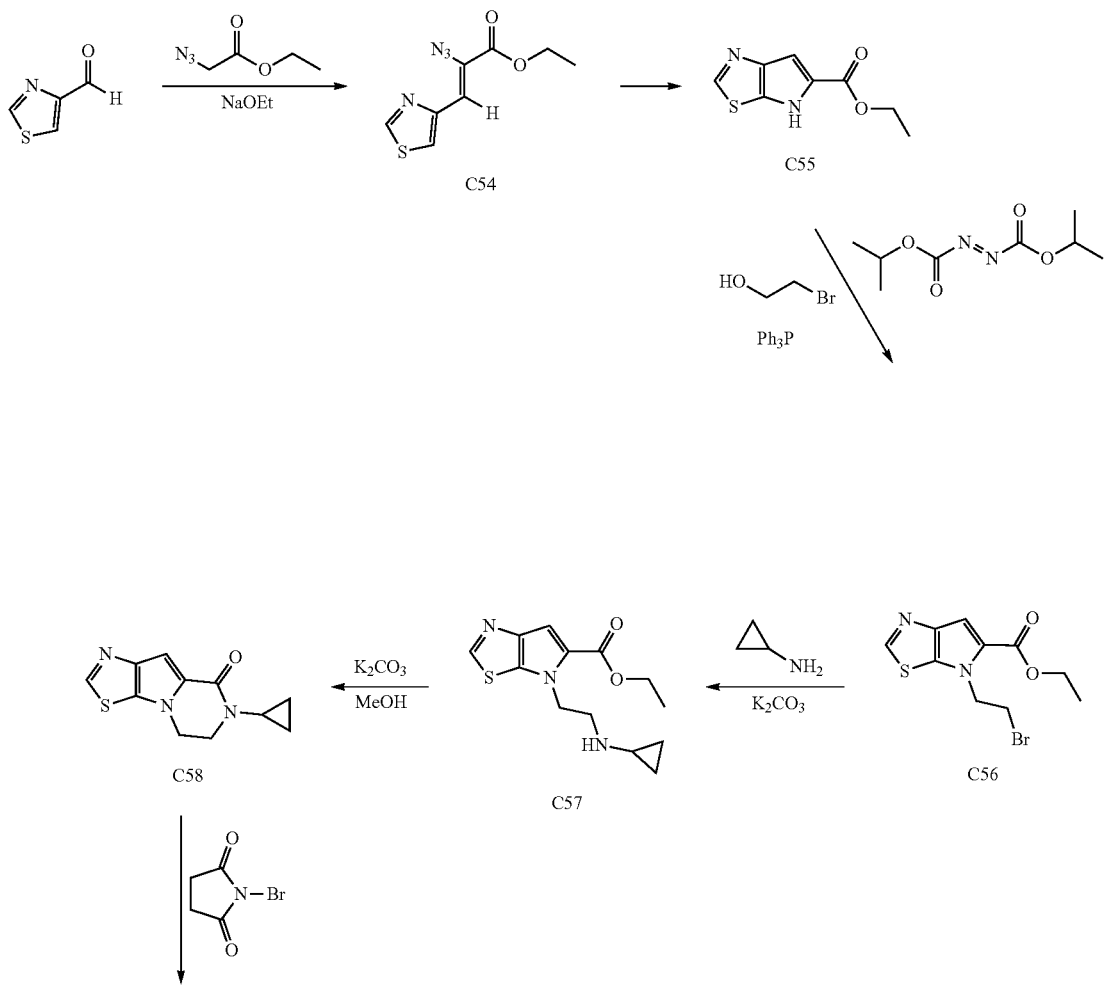

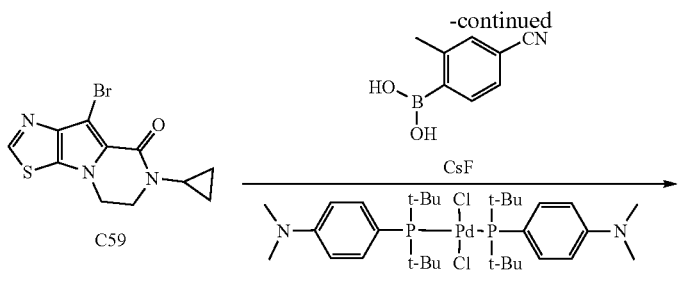
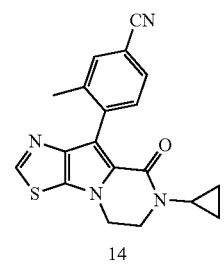

Step 1. Synthesis of ethyl 2-azido-3-(1,3-thiazol-4-yl)prop-2-enoate (C54)

To a 0° C. solution of sodium ethoxide [prepared from sodium metal (7.36 g, 320 mmol) and ethanol (120 mL)] was slowly added a solution of 1,3-thiazole-4-carbaldehyde (9.13 g, 80.7 mmol) and ethyl azidoacetate (20.64 g, 159.8 mmol) in ethanol (120 mL) over 1.5 hours. The reaction mixture was stirred for 1 additional hour at 10° C., cooled to −40° C., and treated with a solution of ammonium chloride (8.4 g, 160 mmol) in water (100 mL). The resulting mixture was poured into ice-cold water, and the precipitate was collected via filtration to afford the product as an off-white solid. Yield: 3.94 g, 17.6 mmol, 22%. $^1$H NMR (400 MHZ, CDCl$_3$) δ 8.81 (d, J=2.0 Hz, 1H), 8.24 (br d, J=2.0 Hz, 1H), 7.27 (br s, 1H), 4.38 (q, J=7.1 Hz, 2H), 1.40 (t, J=7.2 Hz, 3H).

Step 2. Synthesis of ethyl 4H-pyrrolo[3,2-d][1,3]thiazole-5-carboxylate (C55)

A solution of C54 (2.0 g, 8.9 mmol) in xylene (200 mL) was heated at reflux for 20 minutes, then concentrated in vacuo. Silica gel chromatography (Gradient: 10% to 30% ethyl acetate in petroleum ether) provided the product as a white solid. Yield: 0.83 g, 4.2 mmol, 47%. $^1$H NMR (400 MHZ, CDCl$_3$) δ 9.40 (br s, 1H), 8.56 (s, 1H), 7.34 (s, 1H), 4.40 (q, J=7.1 Hz, 2H), 1.41 (t, J=7.2 Hz, 3H).

Step 3. Synthesis of ethyl 4-(2-bromoethyl)-4H-pyrrolo[3,2-d][1,3]thiazole-5-carboxylate (C56)

Compound C55 was converted to the product using the method described for synthesis of C12 in Example 3, except that 2-bromoethanol was employed in place of tert-butyl (2R)-2-(hydroxymethyl)pyrrolidine-1-carboxylate. Chromatography in this case was carried out using a gradient of 5% to 16% ethyl acetate in petroleum ether. The product was isolated as a white solid. Yield: 7.0 g, 23 mmol, 92%. $^1$H NMR (400 MHz, CDCl$_3$) δ 8.56 (s, 1H), 7.43 (s, 1H), 4.84 (t, J=6.3 Hz, 2H), 4.35 (q, J=7.1 Hz, 2H), 3.80 (t, J=6.3 Hz, 2H), 1.41 (t, J=7.1 Hz, 3H).

Step 4. Synthesis of ethyl 4-[2-(cyclopropylamino)ethyl]-4H-pyrrolo[3,2-d][1,3]thiazole-5-carboxylate (C57)

Compound C56 was converted to the product according to the method described for synthesis of C46 in Example 12. Purification was carried out via silica gel chromatography (Gradient: 10% to 50% ethyl acetate in petroleum ether), affording the product as a colorless oil. Yield: 6.34 g, 22.7 mmol, 99%. $^1$H NMR (400 MHz, CDCl$_3$) δ 8.52 (s, 1H), 7.38 (s, 1H), 4.59 (t, J=6.3 Hz, 2H), 4.34 (q, J=7.1 Hz, 2H), 3.16 (t, J=6.3 Hz, 2H), 2.12-2.18 (m, 1H), 1.39 (t, J=7.1 Hz, 3H), 0.39-0.45 (m, 2H), 0.25-0.30 (m, 2H).

Step 5. Synthesis of 7-cyclopropyl-6,7-dihydro[1,3]thiazolo[4',5':4,5]pyrrolo[1,2-a]pyrazin-8(5H)-one (C58)

Potassium carbonate (3.13 g, 22.6 mmol) was added to a solution of C57 (6.34 g, 22.7 mmol) in methanol (200 mL), and the reaction mixture was stirred at 35° C. for 18 hours. After the mixture had been concentrated in vacuo, the residue was extracted with dichloromethane (3×300 mL). The combined organic layers were washed with saturated aqueous sodium chloride solution (300 mL), dried over sodium sulfate, filtered, and concentrated under reduced pressure. Silica gel chromatography (Gradient: 50% to 80% ethyl acetate in petroleum ether) provided the product as a yellow solid. Yield: 3.5 g, 15 mmol, 66%. LCMS m/z 233.8 [M+H]$^+$. $^1$H NMR (400 MHZ, CDCl$_3$) δ 8.52 (s, 1H), 7.38 (s, 1H), 4.16-4.22 (m, 2H), 3.79-3.84 (m, 2H), 2.78-2.84 (m, 1H), 0.92-0.99 (m, 2H), 0.72-0.78 (m, 2H).

Step 6. Synthesis of 9-bromo-7-cyclopropyl-6,7-dihydro[1,3]thiazolo[4',5':4,5]-pyrrolo[1,2-a]pyrazin-8(5H)-one (C59)

N-Bromosuccinimide (420 mg, 2.36 mmol) was added to a 0° C. solution of C58 (500 mg, 2.14 mmol) in dichloromethane (21 mL). After 20 minutes at 0° C., the reaction mixture was treated with water, and the layers were separated. The organic layer was dried over magnesium sulfate, filtered, and concentrated in vacuo to afford the product as a light tan solid. Yield: 670 mg, 2.1 mmol, 98%. LCMS m/z 312.0, 314.0 [M+H]$^+$. $^1$H NMR (400 MHZ, CDCl$_3$) δ 8.57 (s, 1H), 4.17-4.21 (m, 2H), 3.78-3.83 (m, 2H), 2.76-2.83 (m, 1H), 0.93-0.99 (m, 2H), 0.73-0.79 (m, 2H).

Step 7. Synthesis of 4-(7-cyclopropyl-8-oxo-5,6,7,8-tetrahydro[1,3]thiazolo[4',5':4,5]pyrrolo[1,2-a]pyrazin-9-yl)-3-methylbenzonitrile (14)

Compound C59 was reacted with (4-cyano-2-methylphenyl)boronic acid using the method described for synthesis of C49 in Example 13, except that the reaction was allowed to proceed for 48 hours. In this case, the silica gel chromatography was carried out with ethyl acetate as eluent; the material isolated from the chromatography was slurried in diethyl ether for 30 minutes and then collected by filtration to afford the product as a solid. Yield: 3.0 mg, 8.6 umol, 11%. LCMS m/z 349.1 [M+H]$^+$. $^1$H NMR (400 MHZ, CDCl$_3$) δ 8.54 (s, 1H), 7.57-7.59 (m, 1H), 7.49-7.54 (m, 2H), 4.25-4.29 (m, 2H), 3.84-3.90 (m, 2H), 2.72-2.78 (m, 1H), 2.31 (br s, 3H), 0.88-0.95 (m, 2H), 0.68-0.74 (m, 2H).

Example 15

10-(4-Chloro-2-fluoro-5-methoxyphenyl)-8-cyclopropyl-7,8-dihydropyrido[2',3':4,5]pyrrolo[1,2-a]pyrazin-9(6H)-one (15)

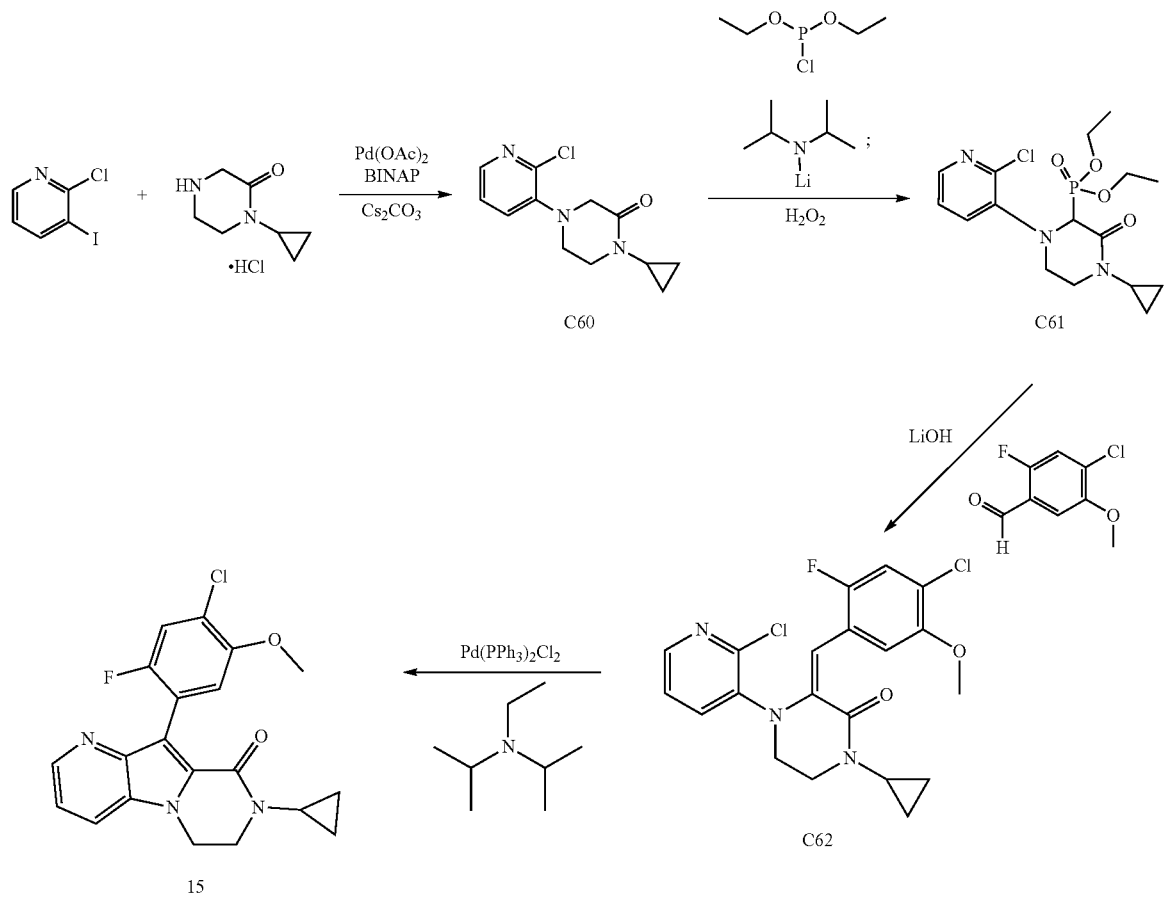

Step 1. Synthesis of 4-(2-chloropyridin-3-yl)-1-cyclopropylpiperazin-2-one (C60)

1,1'-Binaphthalene-2,2'-diylbis(diphenylphosphane) (BINAP, 2.5 g, 4.0 mmol) and palladium(II) acetate (1.0 g, 4.5 mmol) were added to a mixture of 1-cyclopropylpiperazin-2-one hydrochloride (12.6 g, 71.3 mmol), 2-chloro-3-iodopyridine (20.5 g, 85.6 mmol) and cesium carbonate (139 g, 427 mmol) in toluene (500 mL). After being degassed several times with nitrogen, the reaction mixture was stirred at room temperature for 20 minutes and then at 120° C. for 18 hours. The mixture was filtered and the filter cake was washed with ethyl acetate (2×200 mL); the combined filtrates were concentrated in vacuo and purified by chromatography on silica gel (Gradient: 50% to 100% ethyl acetate in petroleum ether) to afford the product as a brown solid. Yield: 7.3 g, 29.0 mmol, 41%. LCMS m/z 251.9 [M+H]$^+$. 1H NMR (400 MHZ, CD$_3$OD) δ 8.07 (d, J=4.6 Hz, 1H), 7.58 (d, J=7.9 Hz, 1H), 7.38 (dd, J=8.0, 4.6 Hz, 1H), 3.76 (s, 2H), 3.46-3.52 (m, 2H), 3.37-3.42 (m, 2H), 2.76-2.83 (m, 1H), 0.82-0.89 (m, 2H), 0.73-0.80 (m, 2H).

Step 2. Synthesis of diethyl [1-(2-chloropyridin-3-yl)-4-cyclopropyl-3-oxopiperazin-2-yl]phosphonate (C61)

n-Butyllithium (2.5 M in hexanes, 8.4 mL, 21 mmol) was added to a −78° C. solution of diisopropylamine (2.94 mL, 21.0 mmol) in tetrahydrofuran (40 mL). After this mixture had been stirred for 10 minutes, a solution of C60 (2.52 g, 10.0 mmol) in tetrahydrofuran (10 mL) was added dropwise, and stirring was continued at −78° C. for an additional 10 minutes. Diethyl chlorophosphite (3.16 mL, 22.0 mmol) was then added, and the reaction mixture was maintained at −78° C. for 30 minutes, whereupon it was warmed to room temperature, treated with aqueous citric acid (10% solution, 20 mL) and cooled to 0° C. Hydrogen peroxide (30% in water, 3.4 mL, 30 mmol) was added, and the reaction mixture was stirred at 0° C. for 10 minutes. Sodium sulfite (3.78 g, 30 mmol) was then added to the cold reaction mixture, and stirring was continued for 30 minutes. The mixture was extracted twice with ethyl acetate, and the combined organic layers were dried over magnesium sulfate, filtered, and concentrated in vacuo. Silica gel chromatography (Eluents: ethyl acetate, followed by 5% methanol in ethyl acetate) afforded a pale yellow oil (3.68 g), which was assigned as a mixture of the intended product and its enol phosphate by LCMS and ¹H NMR analysis. LCMS m/z 388.2 and 524.2 [M+H]⁺. ¹H NMR (400 MHz, CDCl₃), characteristic peaks: δ [8.13 (br dd, J=4.6, 1.6 Hz) and 8.06 (dd, J=4.6, 1.7 Hz), total 1H], [7.49 (dd, J=7.9, 1.8 Hz) and 7.39 (br dd, J=7.9, 1.6 Hz), total 1H], [7.21 (br dd, J=7.9, 4.6 Hz) and 7.15 (dd, J=7.9, 4.6 Hz), total 1H]. This material was combined with the products of several similar reactions using C60 (total C60: 7.81 g, 31.0 mmol) for hydrolysis of the enol phosphate: the combined products were heated at reflux in ethanol for 16 hours, then concentrated in vacuo and purified via chromatography on silica gel (Gradient: 0% to 10% methanol in ethyl acetate). The isolated material (11 g) still contained the enol phosphate, so it was dissolved in ethanol (30 mL) and heated at reflux for an additional 4 hours. After removal of solvent under reduced pressure, the residue was crystallized from heptane/ethyl acetate to afford the product as a white solid. Yield: 7.0 g, 18 mmol, 58%. LCMS m/z 388.2, 390.2 [M+H]⁺. ¹H NMR (400 MHZ, CDCl₃) δ 8.13 (dd, J=4.6, 1.7 Hz, 1H), 7.39 (dd, J=8.0, 1.7 Hz, 1H), 7.22 (dd, J=7.9, 4.6 Hz, 1H), 4.62 (dd, J=22.8, 1.5 Hz, 1H), 4.13-4.27 (m, 3H), 3.98-4.08 (m, 2H), 3.26-3.45 (m, 3H), 2.79-2.86 (m, 1H), 1.33 (br t, J=7.1 Hz, 3H), 1.13 (br t, J=7.1 Hz, 3H), 0.82-0.95 (m, 2H), 0.71-0.78 (m, 1H), 0.63-0.71 (m, 1H).

Step 3. Synthesis of 3-(4-chloro-2-fluoro-5-methoxybenzylidene)-4-(2-chloropyridin-3-yl)-1-cyclopropylpiperazin-2-one (C62)

Lithium hydroxide monohydrate (16.8 mg, 0.400 mmol) was added to a mixture of 4-chloro-2-fluoro-5-methoxybenzaldehyde (20.7 mg, 0.110 mmol) and C61 (38.8 mg, 0.100 mmol) in tetrahydrofuran (0.5 mL) and ethanol (50 µL). After the reaction mixture had stirred at room temperature for 5 hours, it was diluted with saturated aqueous sodium chloride solution and extracted with ethyl acetate. The combined organic layers were concentrated in vacuo to afford the product. Yield: 34 mg, 80 umol, 80%. LCMS m/z 422.1, 424.1, 426.0 [M+H]⁺.

Step 4. Synthesis of 10-(4-chloro-2-fluoro-5-methoxyphenyl)-8-cyclopropyl-7,8-dihydropyrido [2',3':4,5]pyrrolo[1,2-a]pyrazin-9(6H)-one (15)

A mixture of C62 (42.2 mg, 99.9 umol), dichlorobis(triphenylphosphine)palladium(II) (7.0 mg, 10 umol) and N,N-diisopropylethylamine (87 µL, 0.50 mmol) in N,N-dimethylformamide (0.5 mL) was stirred at 120° C. for 16 hours, then concentrated in vacuo. Purification via reversed phase HPLC (Column: Waters XBridge C18, 5 um; Mobile phase A: 0.03% ammonium hydroxide in water (v/v); Mobile phase B: 0.03% ammonium hydroxide in acetonitrile (v/v); Gradient: 30% to 100% B) afforded the product. Yield: 9.5 mg, 25 umol, 25%. LCMS m/z 386.2, 388.1 [M+H]⁺. ¹H NMR (600 MHZ, DMSO-d₆) δ 8.46 (dd, J=4.3, 1.2 Hz, 1H), 8.07 (dd, J=8.5, 1.0 Hz, 1H), 7.43 (d, J=8.9 Hz, 1H), 7.36 (dd, J=8.4, 4.4 Hz, 1H), 7.23 (d, J=6.4 Hz, 1H), 4.40 (br s, 2H), 3.82 (s, 3H), 3.81 (br s, 2H), 2.81-2.87 (m, 1H), 0.70-0.82 (m, 4H).

Example 16

4-(8-Cyclopropyl-9-oxo-3,4,6,7,8,9-hexahydro-2H-pyrano[2',3':4,5]pyrrolo[1,2-a]pyrazin-10-yl)-2-fluoro-5-methylbenzonitrile (16)

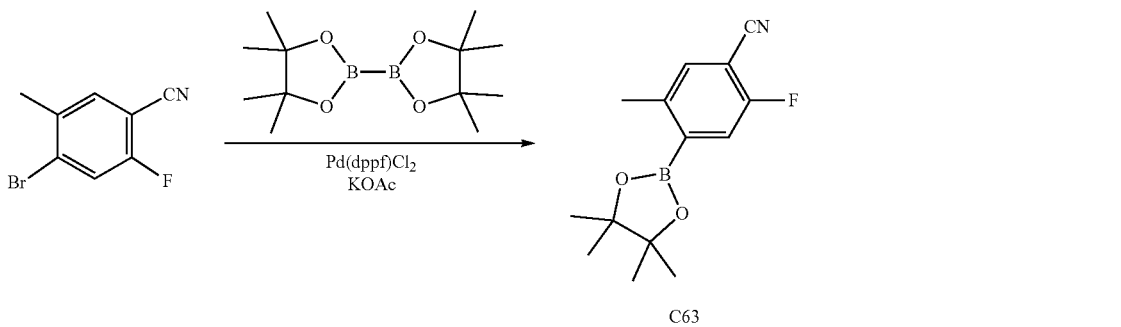

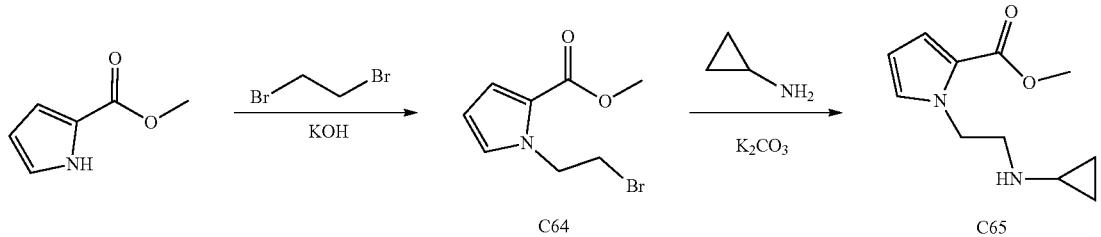

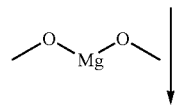

-continued
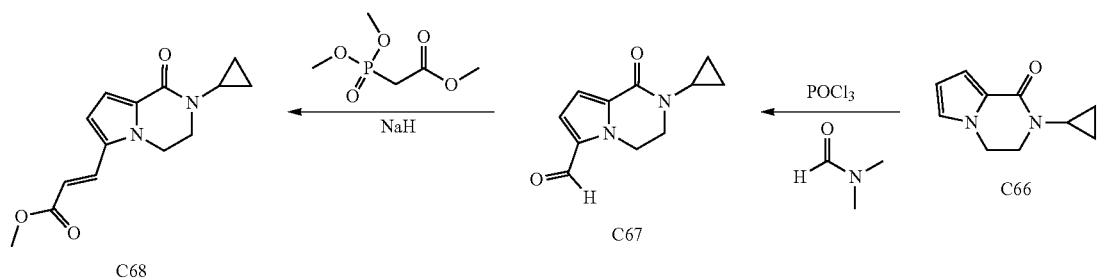
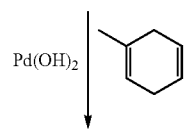
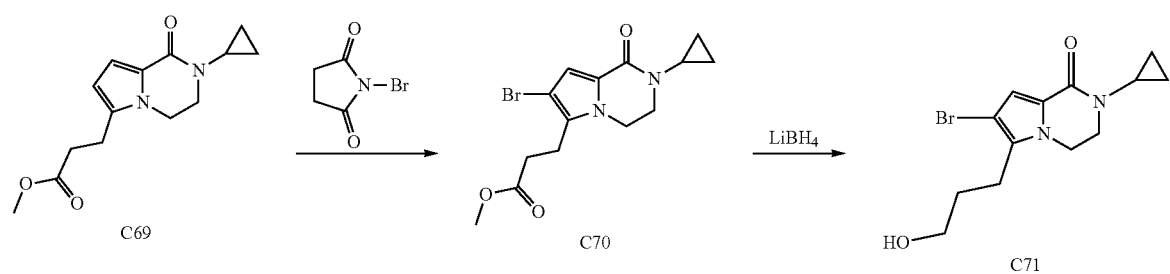

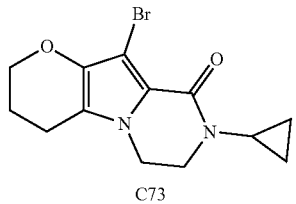
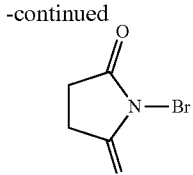
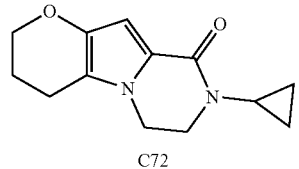

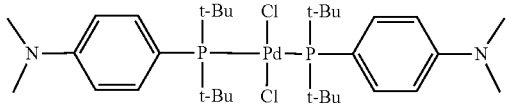

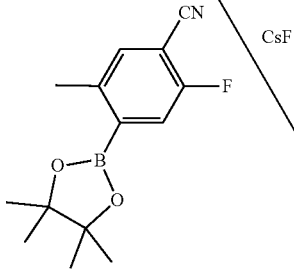

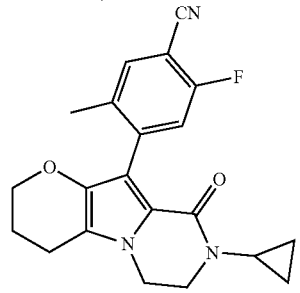

Step 1. Synthesis of 2-fluoro-5-methyl-4-(4,4,5,5-tetramethyl-1,3,2-dioxaborolan-2-yl)benzonitrile (C63)

4-Bromo-2-fluoro-5-methylbenzonitrile was converted to the product according to the method described for synthesis of C16 in Example 4a. The product was obtained as a white solid. Yield: 281 mg, 1.08 mmol, 45%. GCMS m/z 261 [M*]. 1H NMR (400 MHZ, CDCl$_3$) δ 7.56 (d, J=9.3 Hz, 1H), 7.38 (br d, J=5.9 Hz, 1H), 2.51 (br s, 3H), 1.36 (s, 12H).

Step 2. Synthesis of methyl 1-(2-bromoethyl)-1H-pyrrole-2-carboxylate (C64)

Potassium hydroxide (11.2 g, 200 mmol) was added in one portion to a solution of methyl 1H-pyrrole-2-carboxylate (5.0 g, 40 mmol) in dimethyl sulfoxide (40 mL), and the mixture was stirred for 1.25 hours, at which point approximately half of the potassium hydroxide had dissolved. The reaction mixture was cooled to 0° C. and 1,2-dibromoethane (37.5 g, 200 mmol) was added via syringe over 3-5 minutes. The cooling bath was removed, and the reaction mixture was allowed to warm to room temperature and stir for 18 hours. It was then partitioned between diethyl ether (150 mL) and water (100 mL); the organic layer was washed twice with half-saturated aqueous sodium chloride solution, washed once with saturated aqueous sodium chloride solution, dried over magnesium sulfate, filtered, and concentrated in vacuo. Silica gel chromatography (Gradient: 0% to 60% ethyl acetate in heptane) afforded the product as a colorless oil. Yield: 7.05 g, 30.4 mmol, 76%. $^1$H NMR (400 MHZ, CDCl$_3$) δ 7.00 (dd, J=4.0, 1.8 Hz, 1H), 6.93 (br dd, J=2.6, 1.8 Hz, 1H), 6.16 (dd, J=4.0, 2.6 Hz, 1H), 4.67 (t, J=6.4 Hz, 2H), 3.83 (s, 3H), 3.69 (t, J=6.4 Hz, 2H).

Step 3. Synthesis of methyl 1-[2-(cyclopropylamino)ethyl]-1H-pyrrole-2-carboxylate (C65)

Compound C64 was converted to the product using the method described for synthesis of C7 in Example 2. The product was obtained as a light yellow oil. Yield: 6.30 g, 30.2 mmol, 99%. LCMS m/z 209.2 [M+H]$^+$. $^1$H NMR (400 MHZ, CDCl$_3$) δ 6.97 (dd, J=4.0, 1.8 Hz, 1H), 6.89-6.91 (m, 1H), 6.14 (dd, J=4.0, 2.5 Hz, 1H), 4.45 (t, J=6.3 Hz, 2H), 3.82 (s, 3H), 3.07 (t, J=6.3 Hz, 2H), 2.10-2.16 (m, 1H), 0.42-0.47 (m, 2H), 0.31-0.36 (m, 2H).

Step 4. Synthesis of 2-cyclopropyl-3,4-dihydropyr-rolo[1,2-a]pyrazin-1(2H)-one (C66)

Compound C65 was converted to the product using the method described for synthesis of C8 in Example 2. The product was obtained as a white solid. Yield: 3.23 g, 18.3 mmol, 61%. LCMS m/z 177.1 [M+H]$^+$. $^1$H NMR (400 MHZ, CDCl$_3$) δ 6.93 (dd, J=3.9, 1.6 Hz, 1H), 6.70 (dd, J=2.5, 1.6 Hz, 1H), 6.21 (dd, J=3.8, 2.5 Hz, 1H), 4.06-4.11 (m, 2H), 3.66-3.70 (m, 2H), 2.72-2.78 (m, 1H), 0.87-0.93 (m, 2H), 0.68-0.73 (m, 2H).

Step 5. Synthesis of 2-cyclopropyl-1-oxo-1,2,3,4-tetrahydropyrrolo[1,2-a]pyrazine-6-carbaldehyde (C67)

Phosphorus oxychloride (1.43 mL, 15.6 mmol) was added drop-wise to a 0° C. mixture of N,N-dimethylformamide (98%, 1.23 mL, 15.5 mmol) and 1,2-dichloroethane (15 mL). After 20 minutes, a solution of C66 (2.49 g, 14.1 mmol) in 1,2-dichloroethane (10 mL) was added via syringe, and the reaction mixture was heated at reflux for 3.5 hours. Water was added to the reaction mixture, which was then adjusted to a pH of 9 with 1 M aqueous sodium hydroxide and a small amount of saturated aqueous sodium bicarbonate solution. The aqueous layer was extracted twice with dichloromethane, and the combined organic layers were dried over magnesium sulfate, filtered, and concentrated in vacuo. Silica gel chromatography (Gradient: 0% to 100% ethyl acetate in heptane) provided the product as a white solid. Yield: 1.18 g, 5.78 mmol, 41%. LCMS m/z 205.1 [M+H]$^+$. $^1$H NMR (400 MHZ, CDCl$_3$) δ 9.67 (s, 1H), 6.95 (AB quartet, upfield half is broadened, J$_{AB}$=4.2 Hz, Δ$_{VAB}$=6.4 Hz, 2H), 4.57-4.61 (m, 2H), 3.69-3.73 (m, 2H), 2.77-2.83 (m, 1H), 0.91-0.97 (m, 2H), 0.72-0.77 (m, 2H).

Step 6. Synthesis of methyl (2E)-3-(2-cyclopropyl-1-oxo-1,2,3,4-tetrahydropyrrolo-[1,2-a]pyrazin-6-yl)prop-2-enoate (C68)

Methyl (dimethoxyphosphoryl)acetate (98%, 1.05 mL, 7.14 mmol) was added drop-wise over 3-4 minutes to a 0° C. suspension of sodium hydride (60% in mineral oil, 285 mg, 7.13 mmol) in tetrahydrofuran (15 mL). Additional tetrahydrofuran (10 mL) was added to facilitate stirring, and the reaction mixture was stirred for 30 minutes, whereupon a solution of C67 (1.12 g, 5.47 mmol) in tetrahydrofuran (5 mL) was added. The reaction mixture was allowed to warm to room temperature and stir for 18 hours. After removal of solvent in vacuo, the residue was partitioned between water and dichloromethane. The aqueous layer was extracted twice with dichloromethane, and the combined organic layers were dried over magnesium sulfate, filtered, and concentrated under reduced pressure. Chromatography on silica gel (Gradient: 0% to 4% methanol in dichloromethane) provided the product as a white solid. Yield: 1.21 g, 4.65 mmol, 85%. LCMS m/z 261.2 [M+H]$^+$. $^1$H NMR (400 MHZ, CDCl$_3$) δ 7.51 (br d, J=15.7 Hz, 1H), 6.97 (dd, J=4.2, 0.6 Hz, 1H), 6.67 (d, J=4.2 Hz, 1H), 6.29 (d, J=15.7 Hz, 1H), 4.12-4.16 (m, 2H), 3.80 (s, 3H), 3.71-3.75 (m, 2H), 2.74-2.80 (m, 1H), 0.90-0.96 (m, 2H), 0.70-0.75 (m, 2H).

Step 7. Synthesis of methyl 3-(2-cyclopropyl-1-oxo-1,2,3,4-tetrahydropyrrolo[1,2-a]pyrazin-6-yl)propanoate (C69)

Compound C68 was converted to the product according to the method described for synthesis of C44 in Example 11. The product was obtained as a gray solid, a portion of which was taken into the following step without further purification.

Step 8. Synthesis of methyl 3-(7-bromo-2-cyclopropyl-1-oxo-1,2,3,4-tetrahydropyrrolo[1,2-a]pyrazin-6-yl)propanoate (C70)

Compound C69 was converted to the product using the method described for synthesis of C1 in Example 1. The product was obtained as a white solid. Yield: 618 mg, 1.81 mmol, 79%. LCMS m/z 341.0, 343.0 [M+H]$^+$. $^1$H NMR (400 MHZ, CDCl$_3$) δ 6.91 (s, 1H), 4.06-4.11 (m, 2H), 3.67 (s, 3H), 3.63-3.67 (m, 2H), 2.90 (dd, J=7.2, 7.1 Hz, 2H), 2.17-2.77 (m, 1H), 2.64 (dd, J=7.3, 7.0 Hz, 2H), 0.87-0.93 (m, 2H), 0.67-0.72 (m, 2H).

Step 9. Synthesis of 7-bromo-2-cyclopropyl-6-(3-hydroxypropyl)-3,4-dihydropyrrolo-[1,2-a]pyrazin-1(2H)-one (C71)

A solution of lithium borohydride in tetrahydrofuran (2 M, 1.12 mL, 2.24 mmol) was added to a solution of C70 (586 mg, 1.72 mmol) in tetrahydrofuran (6 mL). The reaction mixture was heated to reflux for 2 hours, stirred at room temperature for 18 hours, and then quenched with saturated aqueous sodium bicarbonate solution. The mixture was extracted three times with ethyl acetate, and the combined organic layers were dried over magnesium sulfate, filtered, and concentrated in vacuo. Silica gel chromatography (Gradient: 0% to 4% methanol in methylene chloride) afforded the product as a white solid. Yield: 429 mg, 1.37 mmol, 80%. LCMS m/z 313.1, 315.0 [M+H]$^+$. $^1$H NMR (400 MHZ, CDCl$_3$) δ 6.92 (s, 1H), 3.99-4.04 (m, 2H), 3.61-3.68 (m, 4H), 2.70-2.78 (m, 3H), 1.76-1.84 (m, 2H), 1.51 (br t, J=5 Hz, 1H), 0.87-0.93 (m, 2H), 0.67-0.72 (m, 2H).

Step 10. Synthesis of 8-cyclopropyl-3,4,7,8-tetrahydro-2H-pyrano[2',3':4,5]pyrrolo-[1,2-a]pyrazin-9(6H)-one (C72)

A solution of potassium 2-methylbutan-2-olate (~1.7 M in toluene, 0.44 mL, 0.75 mmol) was added via syringe to a mixture of C71 (79 mg, 0.25 mmol) and dichloro(1,10-phenanthroline)copper(II) (9 mg, 0.03 mmol) in tetrahydrofuran (2 mL). Argon was bubbled through the solution for 2 minutes, whereupon the reaction mixture was heated at 100° C. in a microwave reactor for 18 hours. It was then diluted with water and ethyl acetate, and the aqueous layer was extracted twice with ethyl acetate. The combined organic layers were dried over magnesium sulfate, filtered, and concentrated under reduced pressure. Silica gel chromatography (Gradient: 0% to 100% ethyl acetate in heptane) afforded the product. Yield: 17 mg, 73 umol, 29%. LCMS m/z 233.2 [M+H]$^+$. $^1$H NMR (400 MHZ, CDCl$_3$) δ 6.46 (s, 1H), 4.06-4.10 (m, 2H), 3.82-3.87 (m, 2H), 3.63-3.67 (m, 2H), 2.69-2.75 (m, 1H), 2.60 (dd, J=6.5, 6.5 Hz, 2H), 1.99-2.06 (m, 2H), 0.85-0.91 (m, 2H), 0.65-0.70 (m, 2H).

Step 11. Synthesis of 10-bromo-8-cyclopropyl-3,4,7,8-tetrahydro-2H-pyrano-[2',3': 4,5]pyrrolo[1,2-a]pyrazin-9(6H)-one (C73)

N-Bromosuccinimide (13 mg, 73 umol) was added to a 0° C. solution of C72 (17 mg, 73 umol) in dichloromethane (1 mL), and the reaction mixture was stirred for 15 minutes at 0° C. It was then washed with 0.5 M aqueous sodium hydroxide solution and concentrated in vacuo to afford the product as a yellow oil. Yield: 22 mg, 71 umol, 97%. LCMS m/z 311.1, 313.0 [M+H]$^+$. $^1$H NMR (400 MHZ, CDCl$_3$) δ 4.13-4.17 (m, 2H), 3.83-3.87 (m, 2H), 3.62-3.67 (m, 2H), 2.68-2.74 (m, 1H), 2.61 (dd, J=6.5, 6.4 Hz, 2H), 2.02-2.08 (m, 2H), 0.85-0.91 (m, 2H), 0.66-0.71 (m, 2H).

Step 12. Synthesis of 4-(8-cyclopropyl-9-oxo-3,4,6,7,8,9-hexahydro-2H-pyrano[2',3':4,5]pyrrolo[1,2-a]pyrazin-10-yl)-2-fluoro-5-methylbenzonitrile (16)

A solution of cesium fluoride (53 mg, 0.35 mmol) in water (0.40 mL) was added to a mixture of C63 (42.3 mg, 0.162 mmol) and C73 (36 mg, 0.12 mmol) in toluene (2 mL); bis[di-tert-butyl(4dimethylaminophenyl)phosphine] dichloropalladium(II) (8.5 mg, 12 umol) was then added. The reaction flask was evacuated and filled with nitrogen three times, whereupon the reaction mixture was heated for 18 hours at 80° C. Solvent was removed in vacuo, and the residue was partitioned between water and dichloromethane. The aqueous layer was extracted twice with dichloromethane, and the combined organic layers were concentrated under reduced pressure. Purification via reversed phase HPLC (Column: Waters Sunfire C18, 5 μm; Mobile phase A: 0.05% trifluoroacetic acid in water (v/v); Mobile phase B: 0.05% trifluoroacetic acid in acetonitrile (v/v); Gradient: 30% to 100% B) afforded the product. Yield: 17 mg, 46 umol, 38%. LCMS m/z 366.2 [M+H]$^+$. $^1$H NMR (600 MHz, DMSO-d$_6$) δ 7.70 (d, J=6.8 Hz, 1H), 7.19 (d, J=10.5 Hz, 1H), 3.98-4.01 (m, 2H), 3.94 (dd, J=5.8, 5.8 Hz, 2H), 3.56-3.64 (m, 2H), 2.62-2.67 (m, 3H), 2.15 (s, 3H), 1.92-1.97 (m, 2H), 0.67-0.71 (m, 2H), 0.56-0.60 (m, 2H).

Preparations

Preparation P1

10-Bromo-8-cyclopropylpyrido[2',3':4,5]pyrrolo[1,2-a]pyrazin-9(8H)-one (P1)

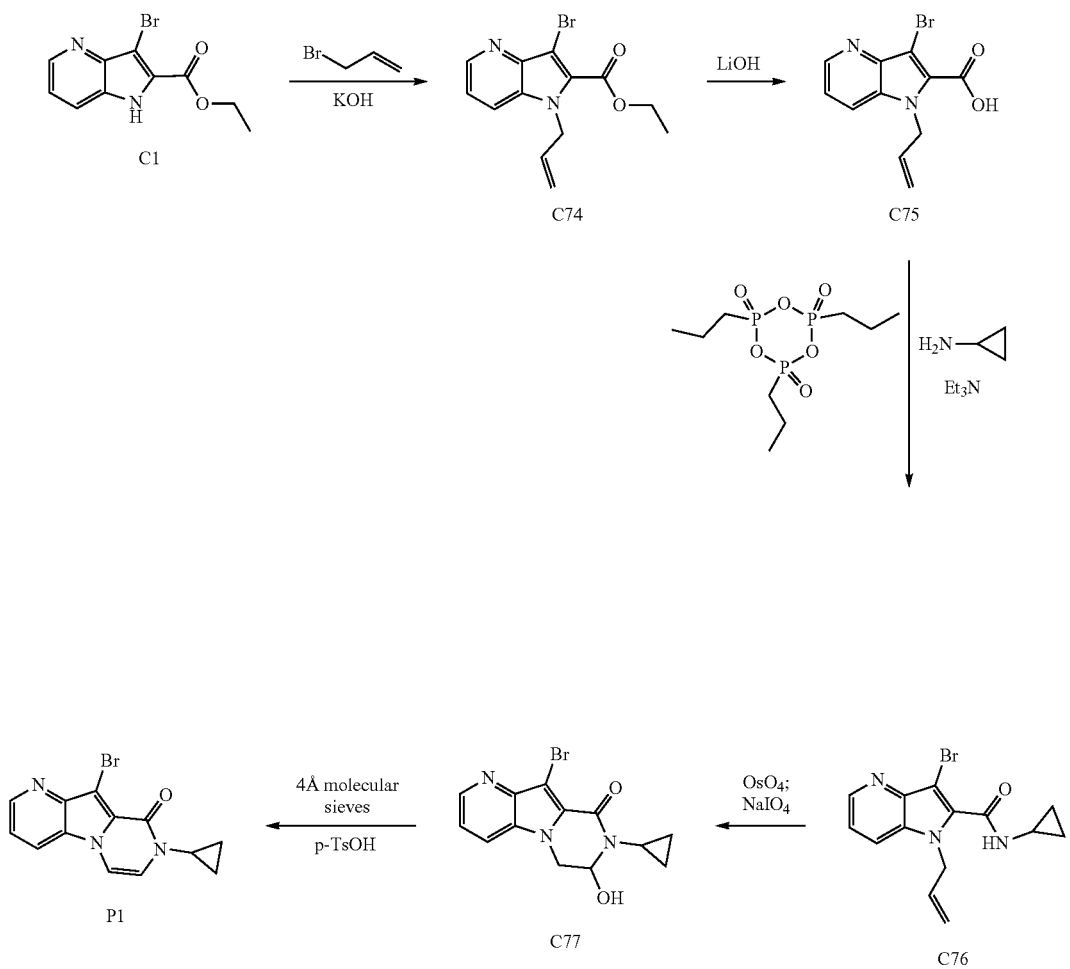

Step 1. Synthesis of ethyl 3-bromo-1-(prop-2-en-1-yl)-1H-pyrrolo[3,2-b]pyridine-2-carboxylate (C74)

Compound C1 was converted to the product using the method described for synthesis of C50 in Example 13. When the reaction was judged to be complete via LCMS analysis, water was added, and the reaction mixture was extracted three times with ethyl acetate. The combined organic layers were washed with saturated aqueous sodium chloride solution, dried over sodium sulfate, filtered, and concentrated in vacuo. Silica gel chromatography (Gradient: 3% to 15% ethyl acetate in petroleum ether) afforded the product as a white solid. Yield: 2.7 g, 8.7 mmol, 79%. LCMS m/z 308.9 [M+H]$^+$.

Step 2. Synthesis of 3-bromo-1-(prop-2-en-1-yl)-1H-pyrrolo[3,2-b]pyridine-2-carboxylic acid (C75)

Lithium hydroxide (0.42 g, 17.5 mmol) was added to a solution of C74 (2.7 g, 8.7 mmol) in a mixture of tetrahydrofuran, ethanol, and water (1:1:1 ratio, 45 mL), and the reaction mixture was stirred at room temperature for 2 hours. Removal of solvents in vacuo afforded the product as a yellow solid, which was used without additional purification. Yield: 1.7 g, 6.0 mmol, 69%.

Step 3. Synthesis of 3-bromo-N-cyclopropyl-1-(prop-2-en-1-yl)-1H-pyrrolo[3,2-b]pyridine-2-carboxamide (C76)

Compound C75 was converted to the product using the method described for synthesis of C52 in Example 13, except that the reaction was allowed to proceed for 24 hours. The product was obtained as a gray solid. Yield: 2.81 g, 8.78 mmol, 80%. $^1$H NMR (400 MHZ, CDCl$_3$) δ 8.63 (dd, J=4.5, 1.2 Hz, 1H), 7.71 (dd, J=8.4, 1.1 Hz, 1H), 7.28 (dd, J=8.4, 4.4 Hz, 1H, assumed; partially obscured by solvent peak), 6.95 (br s, 1H), 5.94-6.05 (m, 1H), 5.21 (br d, J=5.1 Hz, 2H), 5.15 (br d, J=10.4 Hz, 1H), 4.97 (br d, J=17.1 Hz, 1H), 2.92-3.00 (m, 1H), 0.91-0.98 (m, 2H), 0.70-0.76 (m, 2H).

Step 4. Synthesis of 10-bromo-8-cyclopropyl-7-hydroxy-7,8-dihydropyrido-[2',3':4,5]pyrrolo[1,2-a]pyrazin-9(6H)-one (C77)

Compound C76 was converted to the product using the method described for synthesis of C53 in Example 13. The product was obtained as a white solid. Yield: 3.4 g, 11 mmol, 69%. $^1$H NMR (400 MHZ, DMSO-d$_6$) δ 8.52 (dd, J=4.4, 1.2 Hz, 1H), 8.10 (dd, J=8.5, 1.2 Hz, 1H), 7.40 (dd, J=8.5, 4.5 Hz, 1H), 6.69 (d, J=5.5 Hz, 1H), 5.32-5.37 (m, 1H), 4.58 (dd, J=13.0, 1.4 Hz, 1H), 4.19 (dd, J=12.9, 2.5 Hz, 1H), 2.80-2.87 (m, 1H), 0.90-0.98 (m, 1H), 0.70-0.80 (m, 3H).

Step 5. Synthesis of 10-bromo-8-cyclopropylpyrido[2',3':4,5]pyrrolo[1,2-a]pyrazin-9(8H)-one (P1)

To a solution of C77 (1.0 g, 3.1 mmol) in dichloromethane (30 mL) were added p-toluenesulfonic acid monohydrate (619 mg, 3.25 mmol) and 4 Å molecular sieves (7.9 g), and the reaction mixture was stirred at room temperature. After 18 hours, it was filtered through diatomaceous earth and the filter pad was washed with dichloromethane; the combined filtrates were washed sequentially with saturated aqueous sodium bicarbonate solution and saturated aqueous sodium chloride solution, dried over sodium sulfate, filtered, and concentrated in vacuo. Silica gel chromatography (Gradient: 10% to 50% ethyl acetate in petroleum ether) afforded the product as a yellow solid. Yield: 0.56 g, 1.8 mmol, 58%. LCMS m/z 304.1 [M+H]$^+$. $^1$H NMR (400 MHZ, CDCl$_3$) δ 8.79 (br d, J=4.4 Hz, 1H), 7.95 (br d, J=8.5 Hz, 1H), 7.37 (dd, J=8.5, 4.5 Hz, 1H), 7.19 (d, J=6.2 Hz, 1H), 6.57 (d, J=6.2 Hz, 1H), 3.18-3.26 (m, 1H), 1.10-1.17 (m, 2H), 0.90-0.96 (m, 2H).

Method A

Synthesis of 8-cyclopropyl-10-(substituted phenyl)-7,8-dihydropyrido[2',3':4,5]pyrrolo[1,2-a]pyrazin-9 (6H)-ones via Suzuki reaction

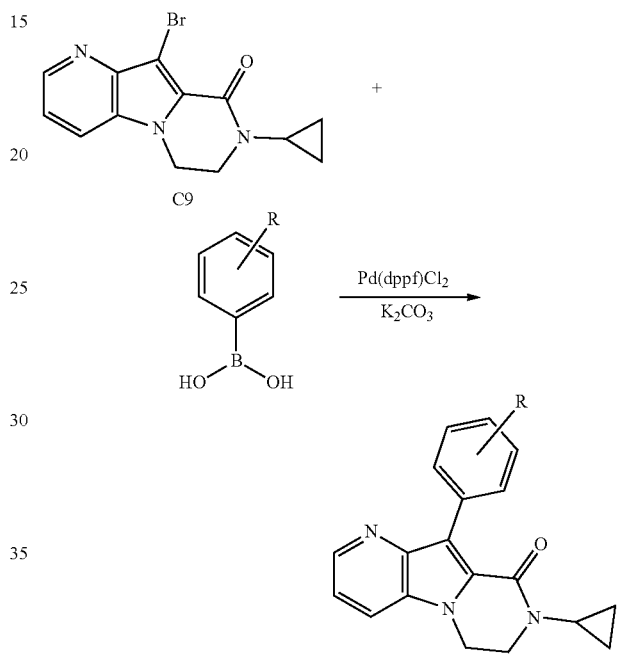

A suspension of C9 (61 mg, 0.20 mmol) in degassed 1,4-dioxane (0.8 mL) was added to the appropriate substituted phenylboronic acid (0.3 mmol) in a vial. Aqueous potassium carbonate solution (3 M, 0.2 mL, 0.6 mmol) and [1,1'-bis(diphenylphosphino)ferrocene]dichloropalladium (II), dichloromethane complex (8 mg, 0.01 mmol) were introduced, and the reaction mixture was degassed via two cycles of vacuum evacuation followed by nitrogen fill. The reaction mixture was heated with shaking at 70° C. for 20 hours, then partitioned between water (1.5 mL) and ethyl acetate (2.5 mL). The organic layer was loaded onto an SCX-2 solid phase extraction cartridge (Silicycle, 6 mL, 1 g). Extraction of the aqueous layer was carried out twice more, and the organic layers were loaded onto the same cartridge. The cartridge was eluted with methanol (5 mL), and then with a solution of triethylamine in methanol (1 M, 7.2 mL); the basic eluent was collected and concentrated in vacuo. Products were purified via reversed phase HPLC (Column: Waters XBridge C18, 5 µm; Mobile phase A: 0.03% ammonium hydroxide in water (v/v); Mobile phase B: 0.03% ammonium hydroxide in acetonitrile (v/v); Gradient: 10% to 100% B).

Using the methodology described above for Examples 1-16, Examples 17-77 were synthesized. See Table 6 and Table 7 for specific methods employed, as well as characterization data for these Examples.

TABLE 6

Method of Synthesis and Physicochemical Data for Examples 17-29.

| Example Number | Structure | Method of Synthesis: Example Number; Source of Non-commercial Starting Materials | $^1$H NMR (400 MHz, CDCl$_3$), δ (ppm); LCMS, observed ion m/z [M + H]$^+$ |
|---|---|---|---|
| 17 | 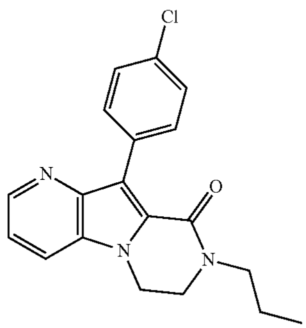 [SMILES: CCCN1CCn2c(c(-c3ccc(Cl)cc3)c3ncccc32)C1=O] | Alternate synthesis of Example 2; C10 | $^1$H NMR (400 MHz, DMSO-d$_6$), δ 8.48 (dd, J = 4.4, 1.1 Hz, 1H), 8.06 (br d, J = 8.3 Hz, 1H), 7.77 (br d, J = 8.5 Hz, 2H), 7.44 (br d, J = 8.5 Hz, 2H), 7.37 (dd, J = 8.5, 4.5 Hz, 1H), 4.40-4.45 (m, 2H), 3.84-3.90 (m, 2H), 3.44-3.50 (m, 2H), 1.56-1.64 (m, 2H), 0.89 (t, J = 7.3 Hz, 3H); 340.0 |
| 18 | 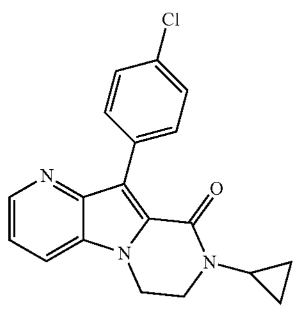 | Example 8; C29 | 8.58 (d, J = 2.4 Hz, 1H), 8.42 (d, J = 2.4 Hz, 1H), 7.79 (br d, J = 8.7 Hz, 2H), 7.45 (br d, J = 8.7 Hz, 2H), 4.47-4.51 (m, 2H), 3.88-3.93 (m, 2H), 2.85-2.91 (m, 1H), 0.96-1.02 (m, 2H), 0.77-0.82 (m, 2H); 338.9 |
| 19 | 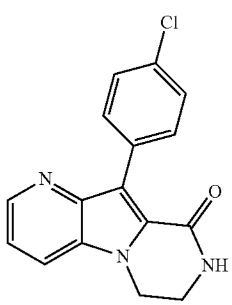 [SMILES: O=C1NCCn2c1c(-c1ccc(Cl)cc1)c1ncccc12] | C2$^1$ | 8.63 (br d, J = 4.5 Hz, 1H), 7.81 (br d, J = 8.4 Hz, 2H), 7.71 (br d, J = 8.4 Hz, 1H), 7.44 (br d, J = 8.5 Hz, 2H), 7.32 (dd, J = 8.5, 4.4 Hz, 1H), 6.30 (br s, 1H), 4.32-4.37 (m, 2H), 3.83-3.89 (m, 2H); 298.0 |
| 20 | 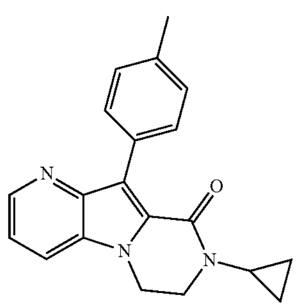 [SMILES: Cc1ccc(-c2c3n(c4cccnc24)CCN(C2CC2)C3=O)cc1] | Example 8; C9 | 8.55 (dd, J = 4.5, 1.4 Hz, 1H), 7.68 (br d, J = 8.1 Hz, 2H), 7.57 (dd, J = 8.4, 1.4 Hz, 1H), 7.26 (br d, J = 8 Hz, 2H), 7.20 (dd, J = 8.4, 4.5 Hz, 1H), 4.13-4.18 (m, 2H), 3.74-3.79 (m, 2H), 2.76-2.83 (m, 1H), 2.37 (s, 3H), 0.86-0.92 (m, 2H), 0.68-0.74 (m, 2H); 318.2 |

TABLE 6-continued

Method of Synthesis and Physicochemical Data for Examples 17-29.

| Example Number | Structure | Method of Synthesis: Example Number; Source of Non-commercial Starting Materials | $^1$H NMR (400 MHz, CDCl$_3$), δ (ppm); LCMS, observed ion m/z [M + H]$^+$ |
|---|---|---|---|
| 21 | 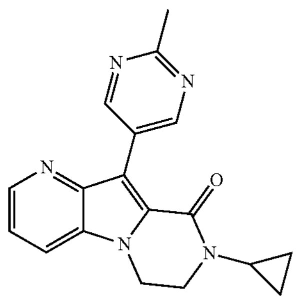 [SMILES: Cc1ncc(-c2c3n(c4cccnc24)CCN(C2CC2)C3=O)cn1] | Example 8; C9$^2$ | 9.08 (s, 2H), 8.61 (dd, J = 4.4, 1.2 Hz, 1H), 7.71 (dd, J = 8.4, 1.2 Hz, 1H), 7.33 (dd, J = 8.5, 4.5 Hz, 1H), 4.30-4.35 (m, 2H), 3.89-3.94 (m, 2H), 2.83-2.89 (m, 1H), 2.79 (s, 3H), 0.94-1.01 (m, 2H), 0.75-0.81 (m, 2H); 319.9 |
| 22 | 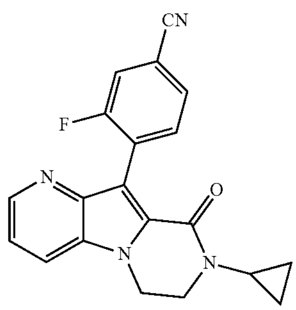 [SMILES: N#Cc1ccc(-c2c3n(c4cccnc24)CCN(C2CC2)C3=O)c(F)c1] | Example 2; C9 | 8.61 (br d, J = 4.5 Hz, 1H), 7.79 (br dd, J = 7.6, 7.3 Hz, 1H), 7.72 (br d, J = 8.4 Hz, 1H), 7.56 (dd, J = 8.0, 1.3 Hz, 1H), 7.47 (dd, J = 9.2, 1.2 Hz, 1H), 7.33 (dd, J = 8.4, 4.5 Hz, 1H), 4.22-4.44 (br m, 2H), 3.81-4.06 (br m, 2H), 2.81-2.88 (m, 1H), 0.96 (br s, 2H), 0.77 (br s, 2H); 346.9 |
| 23 | 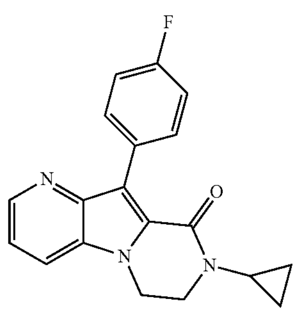 [SMILES: O=C1c2c(-c3ccc(F)cc3)c3ncccc3n2CCN1C1CC1] | Example 3; C9 | 8.60 (dd, J = 4.5, 1.5 Hz, 1H), 7.80 (br dd, J = 8.9, 5.6 Hz, 2H), 7.66 (dd, J = 8.4, 1.5 Hz, 1H), 7.28 (dd, J = 8.4, 4.4 Hz, 1H), 7.15 (br dd, J = 8.9, 8.9 Hz, 2H), 4.25-4.30 (m, 2H), 3.85-3.90 (m, 2H), 2.81-2.87 (m, 1H), 0.92-0.98 (m, 2H), 0.73-0.79 (m, 2H); 322.2 |
| 24 | 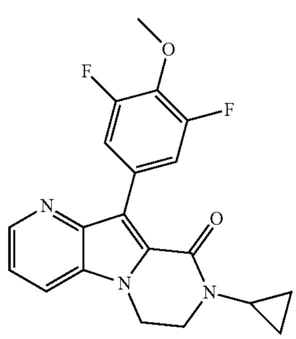 [SMILES: COc1c(F)cc(-c2c3n(c4cccnc24)CCN(C2CC2)C3=O)cc1F] | Example 8; C9$^2$ | 8.59 (d, J = 4.5 Hz, 1H), 7.66 (d, J = 8.4 Hz, 1H), 7.38-7.46 (m, 2H), 7.29 (dd, J = 8.4, 4.5 Hz, 1H), 4.25-4.30 (m, 2H), 4.02 (s, 3H), 3.85-3.90 (m, 2H), 2.82-2.89 (m, 1H), 0.93-1.00 (m, 2H), 0.73-0.80 (m, 2H); 370.1 |

TABLE 6-continued

Method of Synthesis and Physicochemical Data for Examples 17-29.

| Example Number | Structure | Method of Synthesis: Example Number; Source of Non-commercial Starting Materials | $^1$H NMR (400 MHz, CDCl$_3$), δ (ppm); LCMS, observed ion m/z [M + H]$^+$ |
| --- | --- | --- | --- |
| 25 | 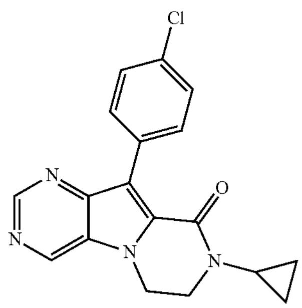 [SMILES: O=C1c2c(-c3ccc(Cl)cc3)c3ncncc3n2CCN1C1CC1] | Example 7; C26 | 9.12 (s, 1H), 8.97 (s, 1H), 7.74 (br d, J = 8.5 Hz, 2H), 7.45 (br d, J = 8.7 Hz, 2H), 4.39-4.44 (m, 2H), 3.92-3.97 (m, 2H), 2.84-2.91 (m, 1H), 0.96-1.03 (m, 2H), 0.77-0.82 (m, 2H); 339.1 |
| 26 | 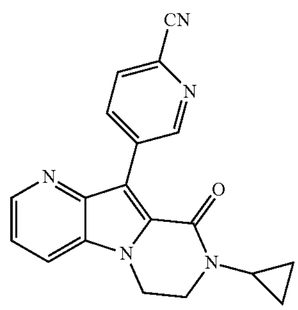 [SMILES: N#Cc1ccc(-c2c3n(c4cccnc24)CCN(C2CC2)C3=O)cn1] | Example 8; C9$^2$ | $^1$H NMR (400 MHz, DMSO-d$_6$), δ 9.13 (dd, J = 2.1, 0.8 Hz, 1H), 8.54 (dd, J = 4.4, 1.4 Hz, 1H), 8.42 (dd, J = 8.1, 2.2 Hz, 1H), 8.13 (dd, J = 8.4, 1.4 Hz, 1H), 8.09 (dd, J = 8.1, 0.9 Hz, 1H), 7.43 (dd, J = 8.5, 4.5 Hz, 1H), 4.40-4.45 (m, 2H), 3.82-3.86 (m, 2H), 2.86-2.92 (m, 1H), 0.74-0.85 (m, 4H); 330.2 |
| 27 | 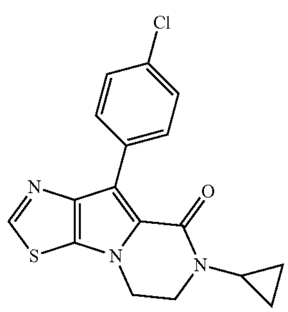 [SMILES: O=C1c2c(-c3ccc(Cl)cc3)c3ncsc3n2CCN1C1CC1] | Example 8; C57 | 8.55 (s, 1H), 7.93 (br d, J = 8 Hz, 2H), 7.39 (br d, J = 8 Hz, 2H), 4.18-4.23 (m, 2H), 3.81-3.87 (m, 2H), 2.76-2.83 (m, 1H), 0.90-0.97 (m, 2H), 0.70-0.76 (m, 2H); 344.1 |
| 28 | 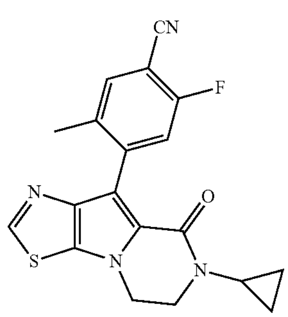 [SMILES: Cc1cc(C#N)c(F)cc1-c1c2n(c3scnc13)CCN(C1CC1)C2=O] | Example 8; C57, C63 | 8.55 (s, 1H), 7.50 (d, J = 6.4 Hz, 1H), 7.24-7.28 (m, 1H, assumed; partially obscured by solvent peak), 4.25-4.30 (m, 2H), 3.84-3.91 (m, 2H), 2.72-2.79 (m, 1H), 2.25 (s, 3H), 0.88-0.96 (m, 2H), 0.69-0.75 (m, 2H); 367.1 |

TABLE 6-continued

Method of Synthesis and Physicochemical Data for Examples 17-29.

| Example Number | Structure | Method of Synthesis: Example Number; Source of Non-commercial Starting Materials | $^1$H NMR (400 MHz, CDCl$_3$), δ (ppm); LCMS, observed ion m/z [M + H]$^+$ |
|---|---|---|---|
| 29 | 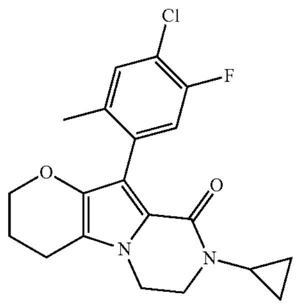 [SMILES: Cc1cc(Cl)c(F)cc1-c1c2c(n3c1C(=O)N(C1CC1)CC3)CCCO2] | Example 16; C73 | $^1$H NMR (400 MHz, DMSO-d$_6$), δ 7.36 (d, J = 7.8 Hz, 1H), 7.05 (d, J = 10.5 Hz, 1H), 3.96-4.00 (m, 2H), 3.92 (dd, J = 5.9, 5.8 Hz, 2H), 3.54-3.62 (m, 2H), 2.61-2.66 (m, 3H), 2.10 (s, 3H), 1.91-1.96 (m, 2H), 0.66-0.70 (m, 2H), 0.55-0.59 (m, 2H); 375.1, 377.1 |

[1] Compound C2 was subjected to a Mitsunobu reaction with tert-butyl (2-hydroxyethyl)carbamate to provide ethyl 1-{2-[(tert-butoxycarbonyl)amino]ethyl}-3-(4-chlorophenyl)-1H-pyrrolo[3,2-b]pyridine-2-carboxylate. Acid-mediated removal of the tert-butoxycarbonyl group afforded ethyl 1-(2-aminoethyl)-3-(4-chlorophenyl)-1H-pyrrolo[3,2-b]pyridine-2-carboxylate, which was cyclized to Example 19 using triethylamine and calcium chloride in methanol at 50 °C.

[2] In this case, the 4,4,5,5-tetramethyl-1,3,2-dioxaborolan-2-yl derivative was used, rather than the boronic acid.

TABLE 7

Method of Synthesis and Physicochemical Data for Examples 30-77.

| Example Number | Structure | Method of Synthesis: Example Number; Source of Non-commercial Starting Materials | LCMS, observed ion m/z [M + H]$^+$ |
|---|---|---|---|
| 30 | 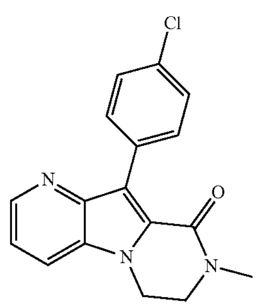 [SMILES: CN1CCn2c(c(-c3ccc(Cl)cc3)c3ncccc32)C1=O] | Alternate to Example 2; C2[1] | 311.9 |
| 31 | 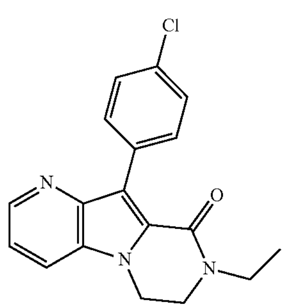 [SMILES: CCN1CCn2c(c(-c3ccc(Cl)cc3)c3ncccc32)C1=O] | Footnote 2 | 326.0, 328.0 |

TABLE 7-continued

Method of Synthesis and Physicochemical Data for Examples 30-77.

| Example Number | Structure | Method of Synthesis: Example Number; Source of Non-commercial Starting Materials | LCMS, observed ion m/z [M + H]+ |
| --- | --- | --- | --- |
| 32 | 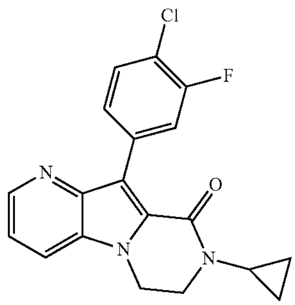 [SMILES: O=C1c2c(-c3ccc(Cl)c(F)c3)c3ncccc3n2CCN1C1CC1] | Example 3; C9 | 356.1, 358.1 |
| 33 | 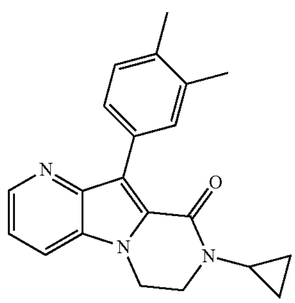 [SMILES: Cc1ccc(-c2c3n(c4cccnc24)CCN(C2CC2)C3=O)cc1C] | Method A; C9 | 332.2 |
| 34 | 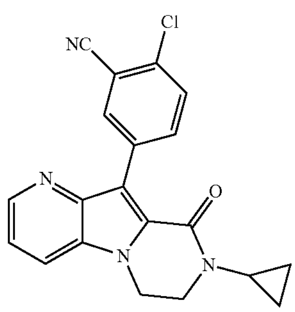 [SMILES: N#Cc1cc(-c2c3n(c4cccnc24)CCN(C2CC2)C3=O)ccc1Cl] | Method A; C9 | 363.2, 365.1 |
| 35 | 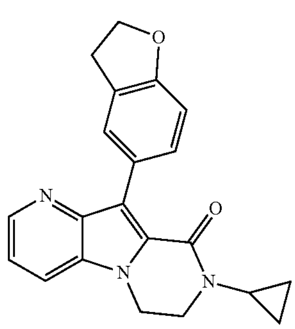 [SMILES: O=C1c2c(-c3ccc4c(c3)CCO4)c3ncccc3n2CCN1C1CC1] | Method A; C9 | 346.2 |

TABLE 7-continued

Method of Synthesis and Physicochemical Data for Examples 30-77.

| Example Number | Structure | Method of Synthesis: Example Number; Source of Non-commercial Starting Materials | LCMS, observed ion m/z [M + H]+ |
|---|---|---|---|
| 36 | 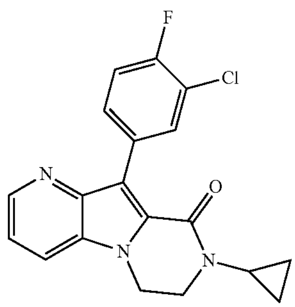 [SMILES: O=C1c2c(-c3ccc(F)c(Cl)c3)c3ncccc3n2CCN1C1CC1] | Method A; C9 | 356.1, 358.1 |
| 37 | 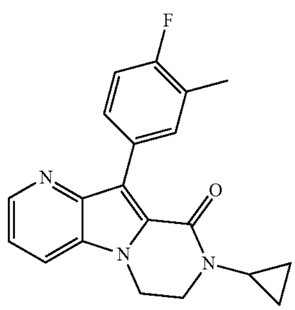 [SMILES: Cc1cc(-c2c3n(c4cccnc24)CCN(C2CC2)C3=O)ccc1F] | Method A; C9 | 336.2 |
| 38 | 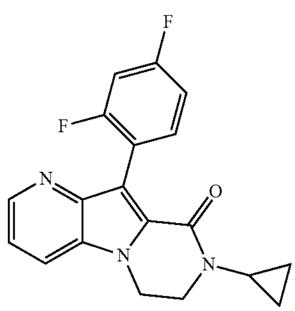 [SMILES: O=C1c2c(-c3ccc(F)cc3F)c3ncccc3n2CCN1C1CC1] | Method A; C9 | 340.2 |
| 39 | 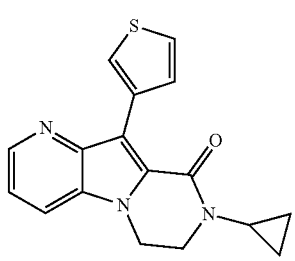 [SMILES: O=C1c2c(-c3ccsc3)c3ncccc3n2CCN1C1CC1] | Method A; C9 | 310.2 |
| 40 | 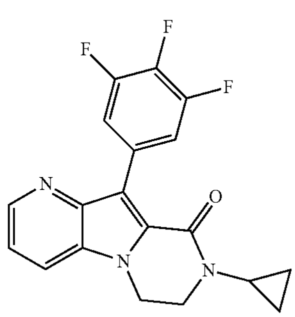 [SMILES: O=C1c2c(-c3cc(F)c(F)c(F)c3)c3ncccc3n2CCN1C1CC1] | Method A; C9 | 358.1 |

TABLE 7-continued
Method of Synthesis and Physicochemical Data for Examples 30-77.
| Example Number | Structure | Method of Synthesis: Example Number; Source of Non-commercial Starting Materials | LCMS, observed ion m/z [M + H]+ |
|---|---|---|---|
| 41 | 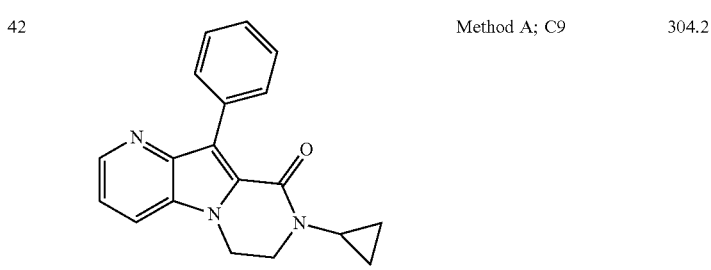 | Method A; C9 | 322.2 |
| 42 | 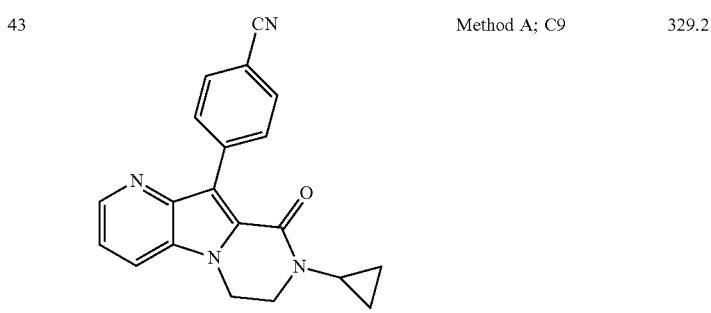 | Method A; C9 | 304.2 |
| 43 | 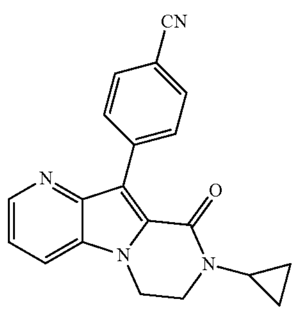 [SMILES: N#Cc1ccc(-c2c3n(c4cccnc24)CCN(C2CC2)C3=O)cc1] | Method A; C9 | 329.2 |
| 44 | 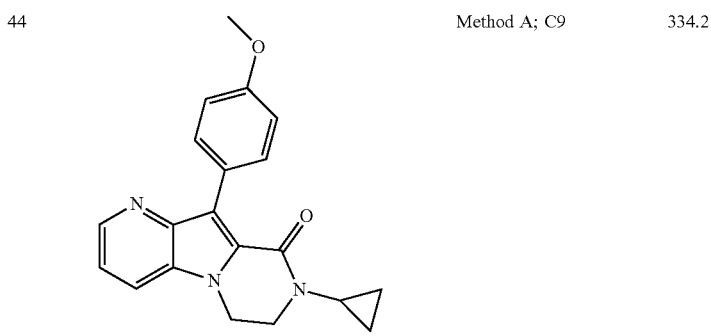 | Method A; C9 | 334.2 |

TABLE 7-continued

Method of Synthesis and Physicochemical Data for Examples 30-77.

| Example Number | Structure | Method of Synthesis: Example Number; Source of Non-commercial Starting Materials | LCMS, observed ion m/z [M + H]+ |
|---|---|---|---|
| 45 | 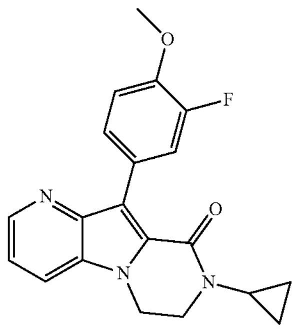 [SMILES: COc1ccc(-c2c3n(c4cccnc24)CCN(C2CC2)C3=O)cc1F] | Method A; C9 | 352.2 |
| 46 | 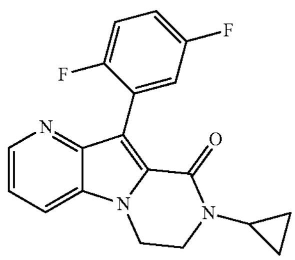 [SMILES: O=C1c2c(-c3cc(F)ccc3F)c3ncccc3n2CCN1C1CC1] | Method A; C9 | 340.2 |
| 47 | 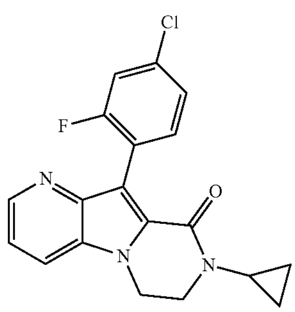 | Method A; C9 | 356.1, 358.1 |
| 48 | 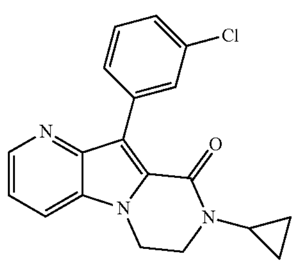 | Method A; C9 | 338.2, 340.1 |
| 49 | 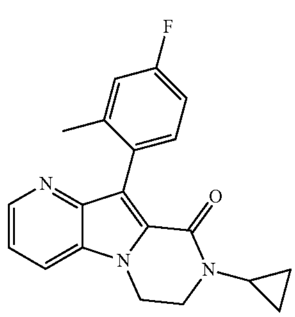 [SMILES: Cc1cc(F)ccc1-c1c2n(c3cccnc13)CCN(C1CC1)C2=O] | Method A; C9 | 336.2 |

TABLE 7-continued

Method of Synthesis and Physicochemical Data for Examples 30-77.

| Example Number | Structure | Method of Synthesis: Example Number; Source of Non-commercial Starting Materials | LCMS, observed ion m/z [M + H]+ |
|---|---|---|---|
| 50 | 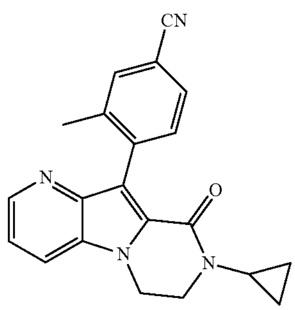 [SMILES: Cc1cc(C#N)ccc1-c1c2n(c3cccnc13)CCN(C1CC1)C2=O] | Method A; C9[3] | 343.2 |
| 51 | 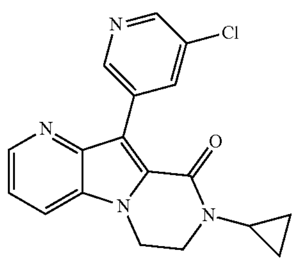 [SMILES: O=C1c2c(-c3cncc(Cl)c3)c3ncccc3n2CCN1C1CC1] | Method A; C9 | 339.1, 341.1 |
| 52 | 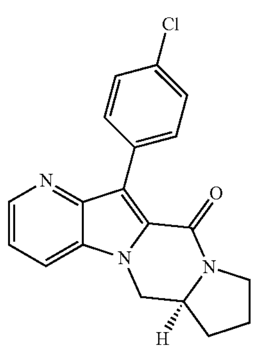 [SMILES: O=C1c2c(-c3ccc(Cl)cc3)c3ncccc3n2C[C@@H]2CCCN12] | Example 3 | 338.0, 340.0 |
| 53 | 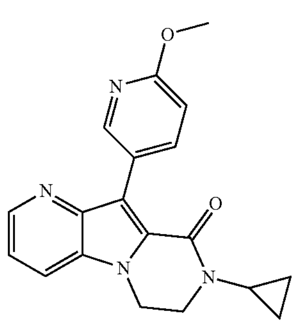 [SMILES: COc1ccc(-c2c3n(c4cccnc24)CCN(C2CC2)C3=O)cn1] | Example 3; C9 | 335.2 |

TABLE 7-continued

Method of Synthesis and Physicochemical Data for Examples 30-77.

| Example Number | Structure | Method of Synthesis: Example Number; Source of Non-commercial Starting Materials | LCMS, observed ion m/z [M + H]+ |
|---|---|---|---|
| 54 | 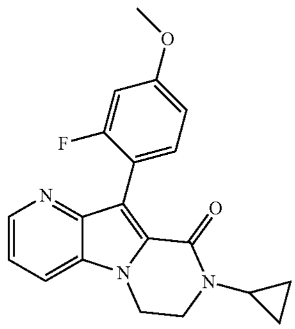 [SMILES: COc1ccc(-c2c3n(c4cccnc24)CCN(C2CC2)C3=O)c(F)c1] | Example 3; C9 | 352.1 |
| 55 | 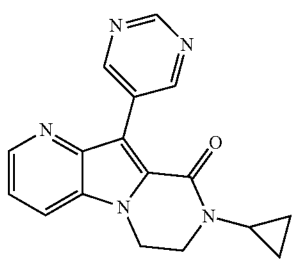 [SMILES: O=C1c2c(-c3cncnc3)c3ncccc3n2CCN1C1CC1] | Example 3; C9[3] | 306.1 |
| 56 | 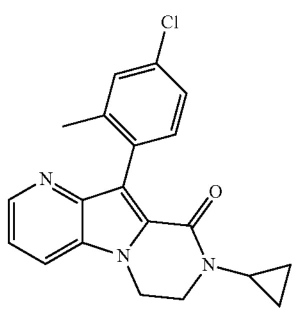 [SMILES: Cc1cc(Cl)ccc1-c1c2n(c3cccnc13)CCN(C1CC1)C2=O] | Example 3; C9 | 352.1, 354.1 |
| 57 | 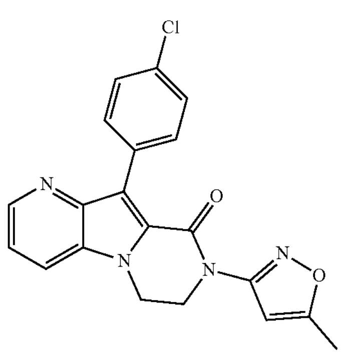 [SMILES: Cc1cc(N2CCn3c(c(-c4ccc(Cl)cc4)c4ncccc43)C2=O)no1] | Examples 5 and 6; C2[4] | 379.0, 381.0 |

TABLE 7-continued

Method of Synthesis and Physicochemical Data for Examples 30-77.

| Example Number | Structure | Method of Synthesis: Example Number; Source of Non-commercial Starting Materials | LCMS, observed ion m/z [M + H]+ |
|---|---|---|---|
| 58 | 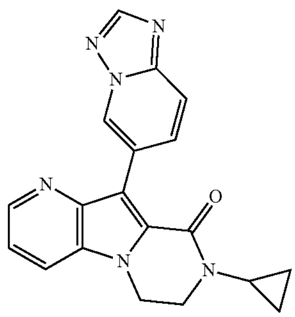 [SMILES: O=C1c2c(-c3ccc4ncnn4c3)c3ncccc3n2CCN1C1CC1] | Example 8; C9[5] | 345.1 |
| 59 | 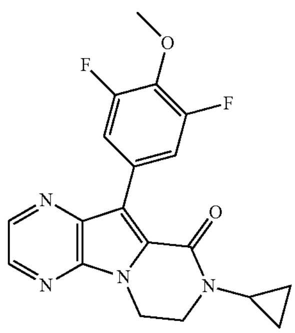 [SMILES: COc1c(F)cc(-c2c3n(c4nccnc24)CCN(C2CC2)C3=O)cc1F] | Example 7; C29[6] | 371.0 |
| 60 | 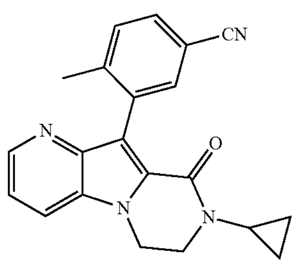 [SMILES: Cc1ccc(C#N)cc1-c1c2n(c3cccnc13)CCN(C1CC1)C2=O] | Example 8; C9[3] | 343.1 |
| 61 | 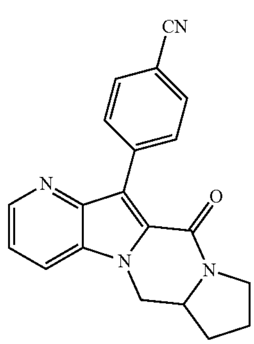 [SMILES: N#Cc1ccc(-c2c3n(c4cccnc24)CC2CCCN2C3=O)cc1] | Example 3 | 329.2 |

TABLE 7-continued

Method of Synthesis and Physicochemical Data for Examples 30-77.

| Example Number | Structure | Method of Synthesis: Example Number; Source of Non-commercial Starting Materials | LCMS, observed ion m/z [M + H]+ |
|---|---|---|---|
| 62 | 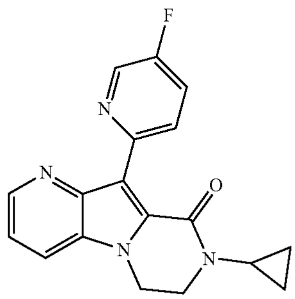 [SMILES: O=C1c2c(-c3ccc(F)cn3)c3ncccc3n2CCN1C1CC1] | Example 15; C59 | 323.1 |
| 63 | 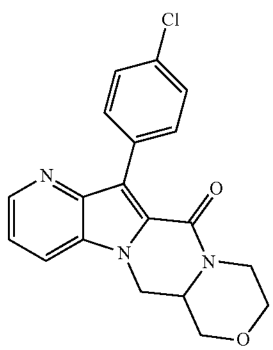 [SMILES: O=C1c2c(-c3ccc(Cl)cc3)c3ncccc3n2CC2COCCN12] | Example 3[7] | 354.2 |
| 64 | 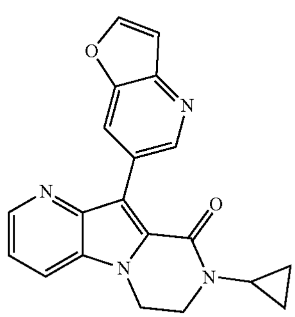 [SMILES: O=C1c2c(-c3cnc4ccoc4c3)c3ncccc3n2CCN1C1CC1] | Example 15; C59 | 345.1 |
| 65 | 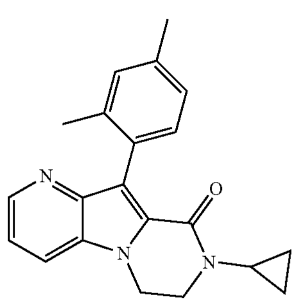 [SMILES: Cc1ccc(-c2c3n(c4cccnc24)CCN(C2CC2)C3=O)c(C)c1] | Example 8; C9 | 332.2 |

TABLE 7-continued

Method of Synthesis and Physicochemical Data for Examples 30-77.

| Example Number | Structure | Method of Synthesis: Example Number; Source of Non-commercial Starting Materials | LCMS, observed ion m/z [M + H]$^+$ |
| --- | --- | --- | --- |
| 66 | 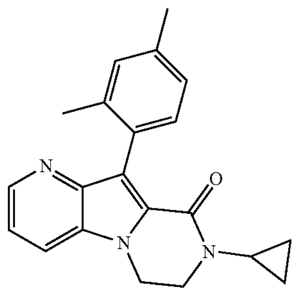 [SMILES: Cc1ccc(-c2c3n(c4cccnc24)CCN(C2CC2)C3=O)c(C)c1] | Example 13; C1 | 330.2 |
| 67 | (+/−) | Example 3 | 323.8 |
| 68 | ENT-1 | Example 67[8] | 324.1, 326.2 |
| 69 | ENT-2 | Example 67[8] | 324.1, 326.1 |

TABLE 7-continued

Method of Synthesis and Physicochemical Data for Examples 30-77.

| Example Number | Structure | Method of Synthesis: Example Number; Source of Non-commercial Starting Materials | LCMS, observed ion m/z [M + H]+ |
|---|---|---|---|
| 70 | 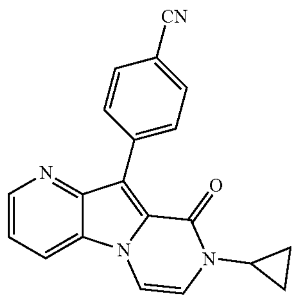 [SMILES: N#Cc1ccc(-c2c3ncccc3n3ccn(C4CC4)c(=O)c23)cc1] | Example 8; P1 | 327.1 |
| 71 | 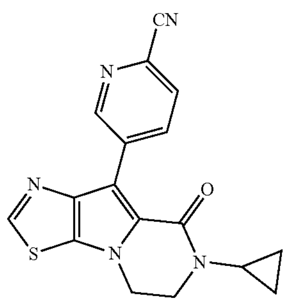 [SMILES: N#Cc1ccc(-c2c3n(c4scnc24)CCN(C2CC2)C3=O)cn1] | Example 8; C57[3] | 336.1 |
| 72 | 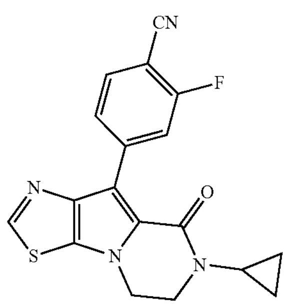 [SMILES: N#Cc1ccc(-c2c3n(c4scnc24)CCN(C2CC2)C3=O)cc1F] | Example 8; C57 | 353.3 |
| 73 | ·CF$_3$COOH | Example 8; C1[9] | 390.2, 392.1 |

TABLE 7-continued
Method of Synthesis and Physicochemical Data for Examples 30-77.
| Example Number | Structure | Method of Synthesis: Example Number; Source of Non-commercial Starting Materials | LCMS, observed ion m/z [M + H]+ |
|---|---|---|---|
| 74 | 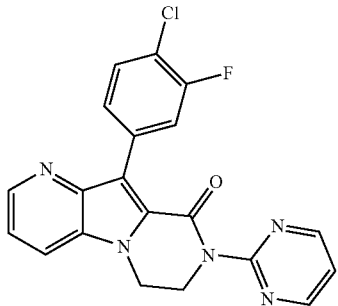 [SMILES: O=C1c2c(-c3ccc(Cl)c(F)c3)c3ncccc3n2CCN1c1ncccn1] | Example 8[10] | 394.1, 396.1 |
| 75 | 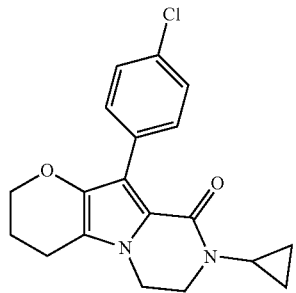 [SMILES: O=C1c2c(-c3ccc(Cl)cc3)c3c(n2CCN1C1CC1)CCCO3] | Example 16; C73 | 343.1, 345.1 |
| 76 | 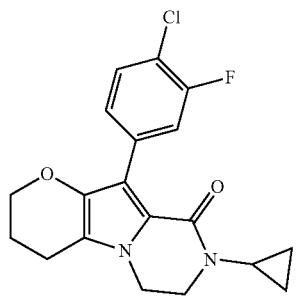 [SMILES: O=C1c2c(-c3ccc(Cl)c(F)c3)c3c(n2CCN1C1CC1)CCCO3] | Example 16; C73 | 361.2, 363.2 |

TABLE 7-continued

Method of Synthesis and Physicochemical Data for Examples 30-77.

| Example Number | Structure | Method of Synthesis: Example Number; Source of Non-commercial Starting Materials | LCMS, observed ion m/z [M + H]+ |
|---|---|---|---|
| 77 | (structure) | Example 16; C73 | 379.1, 381.1 |

[1] 3-(4-Chlorophenyl)-N-methyl-1H-pyrrolo[3,2-b]pyridine-2-carboxamide was prepared via reaction of C2 with methylamine at elevated temperature.
[2] Calcium chloride-mediated reaction (see M. W. Bundesmann et al., *Tetrahedron Lett.* 2010, 51, 3879-3882) of ethyl 1H-pyrrolo[3,2-b]pyridine-2-carboxylate with 2-(ethylamino)ethanol afforded N-ethyl-N-(2-hydroxyethyl)-1H-pyrrolo[3,2-b]pyridine-2-carboxamide, which was subjected to intramolecular Mitsunobu reaction with triphenylphosphine and diisopropyl azodicarboxylate to provide 8-ethyl-7,8-dihydropyrido[2',3':4,5]pyrrolo[1,2-a]pyrazin-9(6H)-one. This compound was reacted with 1-bromo-4-chlorobenzene in the presence of silver acetate, palladium(II) acetate, copper(II) acetate, triphenylphosphine and potassium carbonate at elevated temperature to generate Example 31.
[3] In this case, the 4,4,5,5-tetramethyl-1,3,2-dioxaborolan-2-yl derivative was used, rather than the boronic acid.
[4] In this case, intermediate ethyl 3-(4-chlorophenyl)-1-{2-[(5-methyl-1,2-oxazol-3-yl)amino]ethyl}-1H-pyrrolo[3,2-b]pyridine-2-carboxylate was prepared via Mitsunobu reaction of C2 with 2-[(5-methyl-1,2-oxazol-3-yl)amino]ethanol.
[5] The requisite 6-(4,4,5,5-tetramethyl-1,3,2-dioxaborolan-2-yl)[1,2,4]triazolo[1,5-a]pyridine was prepared from 6-bromo[1,2,4]triazolo[1,5-a]pyridine via [1,1'-bis(diphenylphosphino)ferrocene]dichloropalladium(II)-mediated reaction with 4,4,4',4',5,5,5',5'-octamethyl-2,2'-bi-1,3,2-dioxaborolane.
[6] The requisite 2-(3,5-difluoro-4-methoxyphenyl)-4,4,5,5-tetramethyl-1,3,2-dioxaborolane was prepared from 5-bromo-1,3-difluoro-2-methoxybenzene via [1,1'-bis(diphenylphosphino)ferrocene]dichloropalladium(II)-mediated reaction with 4,4,4',4',5,5,5',5'-octamethyl-2,2'-bi-1,3,2-dioxaborolane.
[7] 6a,7,9,10-Tetrahydro-6H,12H-pyrido[2",3":4',5']pyrrolo[1",2':4,5]pyrazino[2,1-c][1,4]oxazin-12-one was synthesized via O-(7-azabenzotriazol-1-yl)-N,N,N',N'-tetramethyluronium hexafluorophosphate-mediated reaction between 1H-pyrrolo[3,2-b]pyridine-2-carboxylic acid and morpholin-3-ylmethanol to provide [3-(hydroxymethyl)morpholin-4-yl](1H-pyrrolo[3,2-b]pyridin-2-yl)methanone, followed by intramolecular Mitsunobu reaction.
[8] Racemic Example 67 was separated into its component atropenantiomers via supercritical fluid chromatography (Column: Chiral Technologies, Chiralpak AS-H, 5 μm; Eluent: 3:1 carbon dioxide/2-propanol). The first-eluting atropenantiomer (ENT-1) was assigned as Example 68, and the second-eluting atropenantiomer (ENT-2) as Example 69.
[9] Compound C1 was converted to 10-bromo-6,7-dihydro-9H-pyrido[2',3':4,5]pyrrolo[2,1-c][1,4]oxazin-9-one using the chemistry described in Example 1. Subsequent lactone opening with pyrimidin-2-amine as described in Example 1 provided 3-bromo-1-(2-hydroxyethyl)-N-(pyrimidin-2-yl)-1H-pyrrolo[3,2-b]pyridine-2-carboxamide, which was cyclized using a Mitsunobu reaction to afford the requisite 10-bromo-8-(pyrimidin-2-yl)-7,8-dihydropyrido[2',3':4,5]pyrrolo[1,2-a]pyrazin-9(6H)-one.
[10] 10-Bromo-8-(pyrimidin-2-yl)-7,8-dihydropyrido[2',3':4,5]pyrrolo[1,2-a]pyrazin-9(6H)-one was prepared as described in footnote 9.

The compounds in Table 8 were prepared using methods analogous to those described for compounds 1-77, or can be prepared by methods known to those skilled in the art.

TABLE 8

Physicochemical Data for Examples 78-97.

| Example Number | Structure | LCMS, observed ion m/z [M+H]+ |
|---|---|---|
| 78 | (structure) | 340.1, 342.1 |

TABLE 8-continued
Physicochemical Data for Examples 78-97.
| Example Number | Structure | LCMS, observed ion m/z [M+H]+ |
|---|---|---|
| 79 | 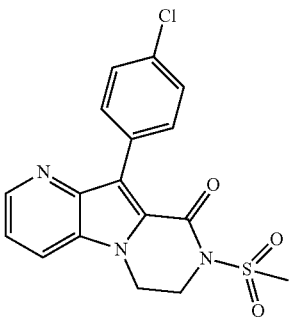 [SMILES: CS(=O)(=O)N1CCn2c(c(-c3ccc(Cl)cc3)c3ncccc32)C1=O] | 376.1, 378.1 |
| 80 | 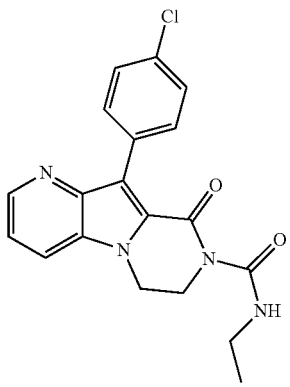 [SMILES: CCNC(=O)N1CCn2c(c(-c3ccc(Cl)cc3)c3ncccc32)C1=O] | 369.1, 371.1 |
| 81 | 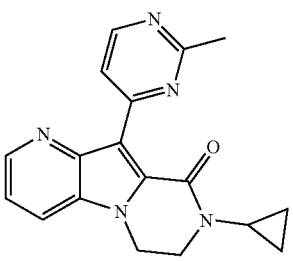 [SMILES: Cc1nccc(-c2c3n(c4cccnc24)CCN(C2CC2)C3=O)n1] | 320.1 |
| 82 | 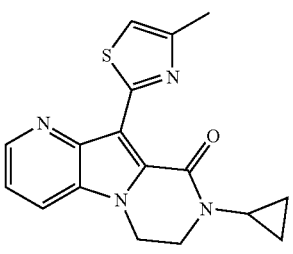 [SMILES: Cc1csc(-c2c3n(c4cccnc24)CCN(C2CC2)C3=O)n1] | 325 |
| 83 | 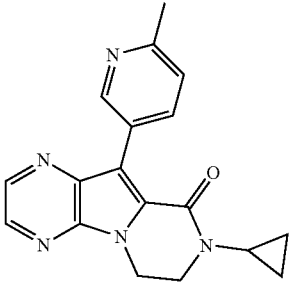 [SMILES: Cc1ccc(-c2c3n(c4nccnc24)CCN(C2CC2)C3=O)cn1] | 320.2 |

TABLE 8-continued

Physicochemical Data for Examples 78-97.

| Example Number | Structure | LCMS, observed ion m/z [M+H]+ |
|---|---|---|
| 84 | 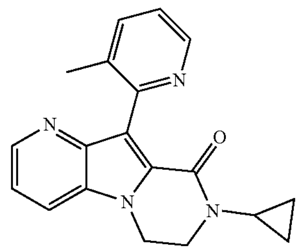 [SMILES: Cc1cccnc1-c1c2n(c3cccnc13)CCN(C1CC1)C2=O] | 319.1 |
| 85 | 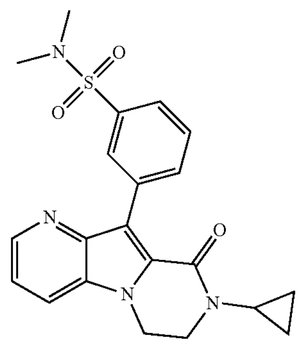 [SMILES: CN(C)S(=O)(=O)c1cccc(-c2c3n(c4cccnc24)CCN(C2CC2)C3=O)c1] | 411 |
| 86 | 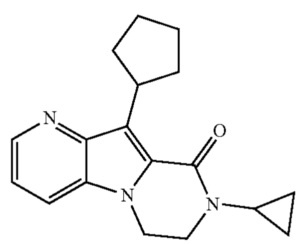 [SMILES: O=C1c2c(C3CCCC3)c3ncccc3n2CCN1C1CC1] | 296.2 |
| 87 | 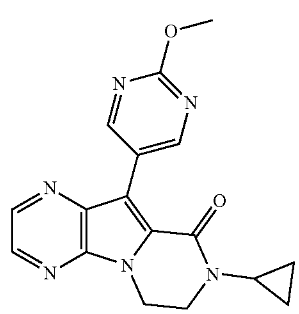 [SMILES: COc1ncc(-c2c3n(c4nccnc24)CCN(C2CC2)C3=O)cn1] | 337 |
| 88 | 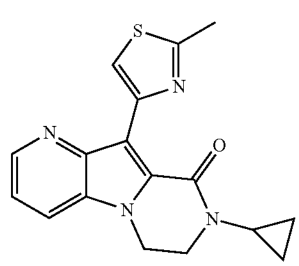 [SMILES: Cc1nc(-c2c3n(c4cccnc24)CCN(C2CC2)C3=O)cs1] | 325 |

TABLE 8-continued

Physicochemical Data for Examples 78-97.

| Example Number | Structure | LCMS, observed ion m/z [M+H]+ |
|---|---|---|
| 89 | 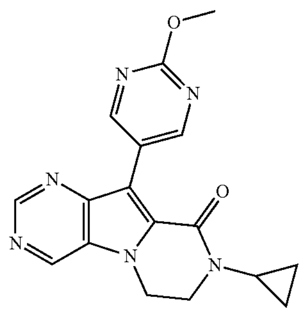 [SMILES: COc1ncc(-c2c3n(c4cncnc24)CCN(C2CC2)C3=O)cn1] | 337.2 |
| 90 | 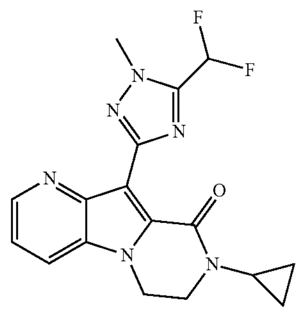 [SMILES: Cn1nc(-c2c3n(c4cccnc24)CCN(C2CC2)C3=O)nc1C(F)F] | 359.1 |
| 91 | 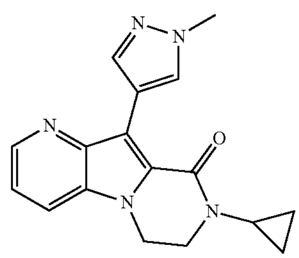 [SMILES: Cn1cc(-c2c3n(c4cccnc24)CCN(C2CC2)C3=O)cn1] | 308.3 |
| 92 | 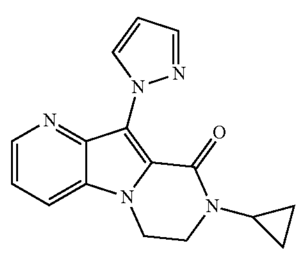 [SMILES: O=C1c2c(-n3cccn3)c3ncccc3n2CCN1C1CC1] | 294.1 |
| 93 | 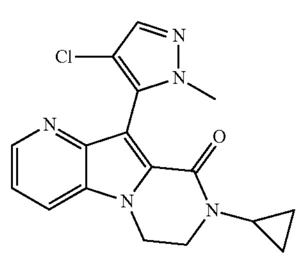 [SMILES: Cn1ncc(Cl)c1-c1c2n(c3cccnc13)CCN(C1CC1)C2=O] | 342.1, 344.0 |

TABLE 8-continued

Physicochemical Data for Examples 78-97.

| Example Number | Structure | LCMS, observed ion m/z [M+H]+ |
|---|---|---|
| 94 | 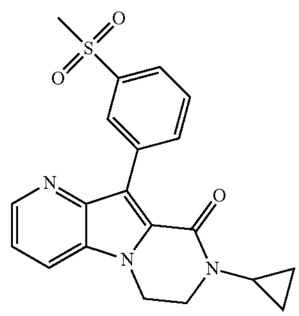 [SMILES: CS(=O)(=O)c1cccc(-c2c3n(c4cccnc24)CCN(C2CC2)C3=O)c1] | 382.1 |
| 95 | 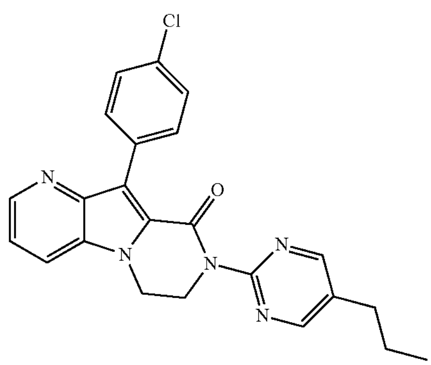 [SMILES: CCCc1cnc(N2CCn3c(c(-c4ccc(Cl)cc4)c4ncccc43)C2=O)nc1] | 418.3, 420.3 |
| 96 | 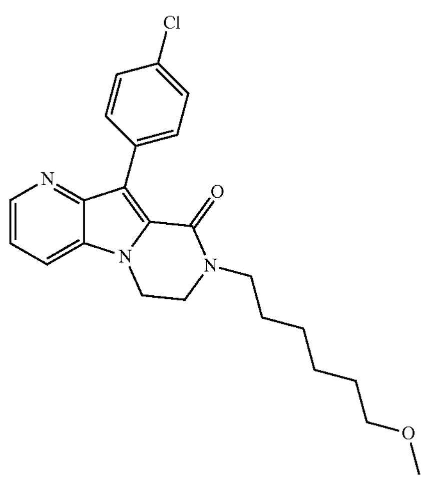 [SMILES: COCCCCCCN1CCn2c(c(-c3ccc(Cl)cc3)c3ncccc32)C1=O] | 412.1, 414.2 |
| 97 | 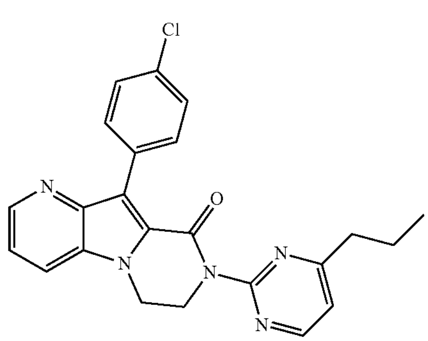 [SMILES: CCCc1ccnc(N2CCn3c(c(-c4ccc(Cl)cc4)c4ncccc43)C2=O)n1] | 418.3, 420.3 |

The PDE4A, PDE4B, PDE4C and PDE4D binding affinity for the compounds of the present invention was determined utilizing the following biological assay(s):

Biological Assays

Human PDE4A3 coding sequence (amino acids 2 to 825 from the sequence with accession number NP_001104779) was cloned into the baculovirus expression vector pFastBac (Invitrogen) engineered to include an N-terminal His6 affinity tag and a c-terminal FLAG affinity tag to aid in purification. The recombinant Bacmid was isolated and used to transfect insect cells to generate a viral stock. To generate cell paste for purification, insect cells were infected with the virus stock and cells were harvested 72 hours after infection. Insect cell paste was lysed and after centrifugation, the supernatant was batch bound to Ni-NTA agarose (GE Healthcare) and eluted with 250 mM imidazole. This eluate was diluted with FLAG buffer (50 mM Tris HCL PH 7.5, 100 mM NaCl, 5% Glycerol, 1 mM TCEP with protease inhibitors) and batch bound to ant-FLAG M2 agarose (Sigma) overnight at 4° C. The agarose was packed into a column, washed with buffer and eluted with buffer containing elute using 250 ug/ml Flag-peptide. Fractions were analyzed using SDS-PAGE Coomassie blue staining and pooled based on purity. Pooled fractions were chromatographed on a S200 120 ml column (GE Healthcare) in 50 mM Tris HCL PH 7.5, 150 mM NaCl, 10% Glycerol, 2 mM TCEP with protease inhibitors. PDE4A3 fractions were analyzed by SDS-PAGE Coomassie blue staining, pooled based on purity, dialyzed against 50 mM Tris HCL pH 7.5, 100 mM NaCl, 20% Glycerol, 2 mM TCEP, frozen and stored at −80° C.

Human PDE4B1 coding sequence (amino acids 122 to 736 from the sequence with accession number Q07343) with the mutations resulting in the amino acid substitutions S134E, S654A, S659A, and S661A was cloned into the baculovirus expression vector pFastBac (Invitrogen) engineered to include a N-terminal His6 affinity tag to aid in purification followed by a thrombin cleavage site. The recombinant Bacmid was isolated and used to transfect insect cells to generate a viral stock. To generate cell paste for purification, insect cells were infected with the virus stock and cells were harvested 72 hours after infection as described in Seeger, T. F. et al., Brain Research 985 (2003) 113-126. Insect cell paste was lysed and after centrifugation, the supernatant was chromatographed on Ni-NTA agarose (Qiagen) as described in Seeger, T. F. et al., Brain Research 985 (2003) 113-126. Ni-NTA agarose eluting fractions containing PDE4 were pooled, diluted with Q buffer A (20 mM Tris HCl PH 8, 5% glycerol, 1 mM TCEP) to reduce NaCl to ~100 mM and loaded on a Source 15Q (GE Healthcare) column. After washing with Q buffer A/10% buffer B to baseline, PDE4D was eluted with a gradient from 10% to 60% of Buffer B (20 mM Tris HCl pH 8, 1 M NaCl, 5% glycerol, 1 mM TCEP). PDE4D fractions were analyzed by SDS-PAGE Coomassie blue staining, pooled based on purity, frozen and stored at −80° C.

Human PDE4C1 coding sequence (amino acids 2 to 712 from the sequence with accession number NP_000914.2) was cloned into the baculovirus expression vector pFastBac (Invitrogen) engineered to include an N-terminal His6 affinity tag and a c-terminal FLAG affinity tag to aid in purification. The recombinant Bacmid was isolated and used to transfect insect cells to generate a viral stock. To generate cell paste for purification, insect cells were infected with the virus stock and cells were harvested 72 hours after infection. Insect cell paste was lysed and after centrifugation, the supernatant was batch bound to Ni-NTA agarose (GE Healthcare) and eluted with 250 mM imidazole. This eluate was diluted with FLAG buffer (50 mM Tris HCL pH 7.5, 100 mM NaCl, 5% Glycerol, 1 mM TCEP with protease inhibitors) and batch bound to ant-FLAG M2 agarose (Sigma) overnight at 4° C. The agarose was packed into a column, washed with buffer and eluted with buffer containing elute using 250 ug/ml Flag-peptide. Fractions were analyzed using SDS-PAGE Coomassie blue staining and pooled based on purity. Pooled fractions were chromatographed on a S200 120 ml column (GE Healthcare) in 50 mM Tris HCL pH 7.5, 150 mM NaCl, 10% Glycerol, 2 mM TCEP with protease inhibitors. PDE4C1 fractions were analyzed by SDS-PAGE Coomassie blue staining, pooled based on purity, dialyzed against 50 mM Tris HCL pH 7.5, 100 mM NaCl, 20% Glycerol, 2 mM TCEP, frozen and stored at −80° C.

A portion of the human PDE4D3 coding sequence (amino acids 50 to 672 from the sequence with accession number Q08499-2) was cloned into the baculovirus expression vector pFastBac (Invitrogen) engineered to include a C-terminal His6 affinity tag to aid in purification as described in Seeger, T. F. et al., Brain Research 985 (2003) 113-126. The recombinant Bacmid was isolated and used to transfect insect cells to generate a viral stock. To generate cell paste for purification, insect cells were infected and cells were harvested 72 hours after infection. Insect cell paste was lysed and after centrifugation, the supernatant was chromatographed on Ni-NTA agarose (Qiagen) as described in Seeger, T. F. et al., Brain Research 985 (2003) 113-126. Ni-NTA agarose eluting fractions containing PDE4 were pooled, diluted with Q Buffer A (50 mM Tris HCl pH 8, 4% glycerol, 100 mM NaCl, 1 mM TCEP, Protease inhibitors EDTA-free (Roche)) to reduce NaCl to ~200 mM, and loaded on a Q Sepharose (GE Healthcare) column. After washing with Q buffer A to baseline, PDE4D was eluted with a gradient from 10% to 60% of Buffer B (50 mM Tris HCl PH 8, 1 M NaCl, 4% glycerol, 1 mM TCEP). PDE4D fractions were analyzed by SDS-PAGE Coomassie blue staining, pooled based on purity, frozen and stored at −80° C.

The PDE4A3, PDE4B1, PDE4C1 and PDE4D3 assays use the Scintillation Proximity Assay (SPA) technology to measure the inhibition of human recombinant PDE4A1, PDE4B3, PDE4C1, and PDE4D3 enzyme activity by compounds in vitro. The PDE4A1, PDE4B3, PDE4C1, and PDE4D3 assays are run in parallel using identical parameters, except for the concentration of enzyme (80 pM PDE4A3, 40 pM PDE4B3, 40 pM PDE4C1 and 10 pM PDE4D). The assays are performed in a 384-well format with 50 uL assay buffer (50 mM TRIS pH7.5; 1.3 mM MgCl2; 0.01% Brij) containing enough PDE4A3, PDE4B1, PDE4C1, and PDE4D to convert ~20% of substrate (1 μM cAMP consisting of 20 nM 3H-cAMP+980 uM cold CAMP) and a range of inhibitors. Reactions are incubated for 30 min at 25° C. The addition of 20 uL of 8 mg/ml yttrium silicate SPA beads (Perkin Elmer) stops the reaction. The plates are sealed (TopSeal, Perkin Elmer) and the beads are allowed to settle for 8 hrs, after which they are read on the Trilux Microbeta overnight.

TABLE 9

Biological Data for Examples 1-77.

| Example Number | Human PDE4A FL; IC$_{50}$ (nM)$^a$ | Human PDE4B FL; IC$_{50}$ (nM)$^a$ | Human PDE4C FL; IC$_{50}$ (nM)$^a$ | Human PDE4D FL; IC$_{50}$ (nM)$^a$ | IUPAC Name |
|---|---|---|---|---|---|
| 1 | 18.8$^b$ | 16.1$^b$ | 182$^b$ | 1230$^b$ | 10-(4-Chlorophenyl)-8-(pyrimidin-2-yl)-7,8-dihydropyrido[2',3':4,5]pyrrolo[1,2-a]pyrazin-9(6H)-one |
| 2 | <0.99 | <0.42 | 4 | 75.3 | 10-(4-Chlorophenyl)-8-cyclopropyl-7,8-dihydropyrido[2',3':4,5]pyrrolo[1,2-a]pyrazin-9(6H)-one |
| 3 | ND | 1.38 | ND | 150 | (6aR)-12-(4-Chlorophenyl)-6a,7,8,9-tetrahydro-6H,11H-pyrido[2',3':4,5]pyrrolo[1,2-a]pyrrolo[1,2-d]pyrazin-11-one, trifluoroacetate salt |
| 4 | 4.66 | <0.81$^b$ | 17.0 | 36.3$^b$ | 4-(8-Cyclopropyl-9-oxo-6,7,8,9-tetrahydropyrido[2',3':4,5]pyrrolo[1,2-a]pyrazin-10-yl)-2-fluorobenzonitrile |
| 5 | ND | 5.87 | ND | 476 | 10-(4-Chlorophenyl)-8-(1H-1,2,4-triazol-3-yl)-7,8-dihydropyrido-[2',3':4,5]pyrrolo[1,2-a]pyrazin-9(6H)-one |
| 6 | ND | 8.32 | ND | 2670 | 10-(4-Chlorophenyl)-8-(1H-1,2,4-triazol-3-yl)pyrido[2',3':4,5]pyrrolo[1,2-a]pyrazin-9(8H)-one |
| 7 | 14.3 | 2.53 | 71.4 | 159 | 10-(4-Chloro-3-fluorophenyl)-8-cyclopropyl-7,8-dihydropyrazino[1',2':1,5]pyrrolo[3,2-d]pyrimidin-9(6H)-one |
| 8 | 1.19 | <1.27 | 13.9 | 88.5 | 10-(4-Chloro-3-fluorophenyl)-8-cyclopropyl-7,8-dihydropyrrolo[1,2-a:4,5-b']dipyrazin-9(6H)-one |
| 9 | 129 | 298$^b$ | 127 | 8190$^b$ | 5-(4-Chlorophenyl)-7-cyclopropyl-8,9-dihydropyrido[3',2':4,5]pyrrolo[1,2-a]pyrazin-6(7H)-one |
| 10 | 15.5 | 12.2$^b$ | 28.2 | 768$^b$ | (7R)-10-(4-Chlorophenyl)-8-cyclopropyl-7-methyl-7,8-dihydropyrido[2',3':4,5]pyrrolo[1,2-a]pyrazin-9(6H)-one |
| 11 | <0.3 | <0.52$^b$ | <0.57 | 28.7$^b$ | (7S)-10-(4-Chlorophenyl)-8-cyclopropyl-7-methyl-7,8-dihydropyrido[2',3':4,5]pyrrolo[1,2-a]pyrazin-9(6H)-one |
| 12 | 12.0 | 19.2$^b$ | 23.5 | 3090$^b$ | 10-(4-Chlorophenyl)-2-cyclopropyl-3,4-dihydropyrazino[1,2-a]indol-1(2H)-one |
| 13 | 1.86 | 2.70 | 6.59 | 182$^b$ | 8-Cyclopropyl-10-(4-methylphenyl)pyrido[2',3':4,5]pyrrolo[1,2-a]pyrazin-9(8H)-one |
| 14 | 18.5 | 19.3 | 79.0 | 2090 | 4-(7-Cyclopropyl-8-oxo-5,6,7,8-tetrahydro[1,3]thiazolo[4',5':4,5]pyrrolo[1,2-a]pyrazin-9-yl)-3-methylbenzonitrile |
| 15 | ND | 6.87 | ND | 442 | 10-(4-Chloro-2-fluoro-5-methoxyphenyl)-8-cyclopropyl-7,8-dihydropyrido[2',3':4,5]pyrrolo[1,2-a]pyrazin-9(6H)-one |
| 16 | 1.57 | 1.78 | 15.2 | 45.5 | 4-(8-Cyclopropyl-9-oxo-3,4,6,7,8,9-hexahydro-2H-pyrano[2',3':4,5]pyrrolo[1,2-a]pyrazin-10-yl)-2-fluoro-5-methylbenzonitrile |
| 17 | ND | 1.00 | ND | 81.0 | 10-(4-Chlorophenyl)-8-propyl-7,8-dihydropyrido[2',3':4,5]pyrrolo[1,2-a]pyrazin-9(6H)-one |
| 18 | 4.12 | 10.2 | 24.4 | 345 | 10-(4-Chlorophenyl)-8-cyclopropyl-7,8-dihydropyrrolo[1,2-a:4,5-b']dipyrazin-9(6H)-one |
| 19 | ND | 18.5 | ND | 1600 | 10-(4-Chlorophenyl)-7,8-dihydropyrido[2',3':4,5]pyrrolo[1,2-a]pyrazin-9(6H)-one |

TABLE 9-continued

Biological Data for Examples 1-77.

| Example Number | Human PDE4A FL; IC$_{50}$ (nM)[a] | Human PDE4B FL; IC$_{50}$ (nM)[a] | Human PDE4C FL; IC$_{50}$ (nM)[a] | Human PDE4D FL; IC$_{50}$ (nM)[a] | IUPAC Name |
| --- | --- | --- | --- | --- | --- |
| 20 | 2.52 | 4.88 | 11.5 | 465 | 8-Cyclopropyl-10-(4-methylphenyl)-7,8-dihydropyrido[2',3':4,5]pyrrolo[1,2-a]pyrazin-9(6H)-one |
| 21 | 8.60 | 75.9 | 132 | 4340 | 8-Cyclopropyl-10-(2-methylpyrimidin-5-yl)-7,8-dihydropyrido[2',3':4,5]pyrrolo[1,2-a]pyrazin-9(6H)-one |
| 22 | 7.47 | 11.3[b] | 20.2 | 872[b] | 4-(8-Cyclopropyl-9-oxo-6,7,8,9-tetrahydropyrido[2',3':4,5]pyrrolo[1,2-a]pyrazin-10-yl)-3-fluorobenzonitrile |
| 23 | 13.0[c] | 3.13 | 82.0[c] | 321 | 8-Cyclopropyl-10-(4-fluorophenyl)-7,8-dihydropyrido[2',3':4,5]pyrrolo[1,2-a]pyrazin-9(6H)-one |
| 24 | 4.48 | 2.94[b] | 24.5 | 125[b] | 8-Cyclopropyl-10-(3,5-difluoro-4-methoxyphenyl)-7,8-dihydropyrido[2',3':4,5]pyrrolo[1,2-a]pyrazin-9(6H)-one |
| 25 | 25.0[c] | 48.2 | 100[c] | 1780 | 10-(4-Chlorophenyl)-8-cyclopropyl-7,8-dihydropyrazino[1',2':1,5]pyrrolo[3,2-d]pyrimidin-9(6H)-one |
| 26 | 8.15 | 2.98[b] | 14.8 | 138[b] | 5-(8-Cyclopropyl-9-oxo-6,7,8,9-tetrahydropyrido[2',3':4,5]pyrrolo[1,2-a]pyrazin-10-yl)pyridine-2-carbonitrile |
| 27 | 2.28 | 3.04[b] | 9.03 | 434[b] | 9-(4-Chlorophenyl)-7-cyclopropyl-6,7-dihydro[1,3]thiazolo[4',5':4,5]pyrrolo[1,2-a]pyrazin-8(5H)-one |
| 28 | 3.92 | 2.14 | 21.0 | 85.7 | 4-(7-Cyclopropyl-8-oxo-5,6,7,8-tetrahydro[1,3]thiazolo[4',5':4,5]pyrrolo[1,2-a]pyrazin-9-yl)-2-fluoro-5-methylbenzonitrile |
| 29 | 1.00 | 1.00 | 2.45 | 12.7 | 10-(4-Chloro-5-fluoro-2-methylphenyl)-8-cyclopropyl-3,4,7,8-tetrahydro-2H-pyrano[2',3':4,5]pyrrolo[1,2-a]pyrazin-9(6H)-one |
| 30 | ND | 27.9 | ND | 803 | 10-(4-Chlorophenyl)-8-methyl-7,8-dihydropyrido[2',3':4,5]pyrrolo[1,2-a]pyrazin-9(6H)-one |
| 31 | ND | 2.43 | ND | 87.9 | 10-(4-Chlorophenyl)-8-ethyl-7,8-dihydropyrido[2',3':4,5]pyrrolo[1,2-a]pyrazin-9(6H)-one |
| 32 | <0.45 | <0.70 | 1.44 | 9.07 | 10-(4-Chloro-3-fluorophenyl)-8-cyclopropyl-7,8-dihydropyrido[2',3':4,5]pyrrolo[1,2-a]pyrazin-9(6H)-one |
| 33 | 4.93 | 6.09 | 11.2 | 497 | 8-Cyclopropyl-10-(3,4-dimethylphenyl)-7,8-dihydropyrido[2',3':4,5]pyrrolo[1,2-a]pyrazin-9(6H)-one |
| 34 | 0.98 | <0.64 | 2.88 | 23.3 | 2-Chloro-5-(8-cyclopropyl-9-oxo-6,7,8,9-tetrahydropyrido[2',3':4,5]pyrrolo[1,2-a]pyrazin-10-yl)benzonitrile |
| 35 | 2.08 | 4.15 | 5.52 | 141 | 8-Cyclopropyl-10-(2,3-dihydro-1-benzofuran-5-yl)-7,8-dihydropyrido[2',3':4,5]pyrrolo[1,2-a]pyrazin-9(6H)-one |
| 36 | <0.67 | <1.10 | 3.48 | 28.1 | 10-(3-Chloro-4-fluorophenyl)-8-cyclopropyl-7,8-dihydropyrido[2',3':4,5]pyrrolo[1,2-a]pyrazin-9(6H)-one |
| 37 | 2.52 | 3.76 | 3.30 | 98.7 | 8-Cyclopropyl-10-(4-fluoro-3-methylphenyl)-7,8-dihydropyrido[2',3':4,5]pyrrolo[1,2-a]pyrazin-9(6H)-one |
| 38 | 5.59 | 10.9 | 21.0 | 569 | 8-Cyclopropyl-10-(2,4-difluorophenyl)-7,8-dihydropyrido[2',3':4,5]pyrrolo[1,2-a]pyrazin-9(6H)-one |

TABLE 9-continued

Biological Data for Examples 1-77.

| Example Number | Human PDE4A FL; IC$_{50}$ (nM)$^a$ | Human PDE4B FL; IC$_{50}$ (nM)$^a$ | Human PDE4C FL; IC$_{50}$ (nM)$^a$ | Human PDE4D FL; IC$_{50}$ (nM)$^a$ | IUPAC Name |
|---|---|---|---|---|---|
| 39 | ND | 78.7 | ND | 1720 | 8-Cyclopropyl-10-(thiophen-3-yl)-7,8-dihydropyrido[2',3':4,5]pyrrolo[1,2-a]pyrazin-9(6H)-one |
| 40 | <0.41 | <0.67 | 4.36 | 17.2 | 8-Cyclopropyl-10-(3,4,5-trifluorophenyl)-7,8-dihydropyrido[2',3':4,5]pyrrolo[1,2-a]pyrazin-9(6H)-one |
| 41 | 1.26 | 2.38 | 9.22 | 130 | 8-Cyclopropyl-10-(3-fluorophenyl)-7,8-dihydropyrido[2',3':4,5]pyrrolo[1,2-a]pyrazin-9(6H)-one |
| 42 | 12.2 | 23.3 | 54.1 | 1050 | 8-Cyclopropyl-10-phenyl-7,8-dihydropyrido[2',3':4,5]pyrrolo[1,2-a]pyrazin-9(6H)-one |
| 43 | ND | 26.5 | ND | 1470 | 4-(8-Cyclopropyl-9-oxo-6,7,8,9-tetrahydropyrido[2',3':4,5]pyrrolo[1,2-a]pyrazin-10-yl)benzonitrile |
| 44 | 33.0$^c$ | 6.37 | 86.0$^c$ | 212 | 8-Cyclopropyl-10-(4-methoxyphenyl)-7,8-dihydropyrido[2',3':4,5]pyrrolo[1,2-a]pyrazin-9(6H)-one |
| 45 | 1.59 | 5.81 | 7.88 | 281 | 8-Cyclopropyl-10-(3-fluoro-4-methoxyphenyl)-7,8-dihydropyrido[2',3':4,5]pyrrolo[1,2-a]pyrazin-9(6H)-one |
| 46 | 2.29 | 4.04 | 6.98 | 203 | 8-Cyclopropyl-10-(2,5-difluorophenyl)-7,8-dihydropyrido[2',3':4,5]pyrrolo[1,2-a]pyrazin-9(6H)-one |
| 47 | 2.00 | 1.14 | 2.88 | 142 | 10-(4-Chloro-2-fluorophenyl)-8-cyclopropyl-7,8-dihydropyrido[2',3':4,5]pyrrolo[1,2-a]pyrazin-9(6H)-one |
| 48 | 1.00 | <0.72 | 3.16 | 19.8 | 10-(3-Chlorophenyl)-8-cyclopropyl-7,8-dihydropyrido[2',3':4,5]pyrrolo[1,2-a]pyrazin-9(6H)-one |
| 49 | 2.71 | 5.79 | 9.39 | 395 | 8-Cyclopropyl-10-(4-fluoro-2-methylphenyl)-7,8-dihydropyrido[2',3':4,5]pyrrolo[1,2-a]pyrazin-9(6H)-one |
| 50 | 2.99 | 6.90 | 9.62 | 356$^b$ | 4-(8-Cyclopropyl-9-oxo-6,7,8,9-tetrahydropyrido[2',3':4,5]pyrrolo[1,2-a]pyrazin-10-yl)-3-methylbenzonitrile |
| 51 | 86.7 | 26.1 | 694 | 2010 | 10-(5-Chloropyridin-3-yl)-8-cyclopropyl-7,8-dihydropyrido[2',3':4,5]pyrrolo[1,2-a]pyrazin-9(6H)-one |
| 52 | ND | 12.4 | ND | 1110 | (6aS)-12-(4-Chlorophenyl)-6a,7,8,9-tetrahydro-6H,11H-pyrido[2',3':4,5]pyrrolo[1,2-a]pyrrolo[1,2-d]pyrazin-11-one |
| 53 | ND | 6.54 | ND | 426 | 8-Cyclopropyl-10-(6-methoxypyridin-3-yl)-7,8-dihydropyrido[2',3':4,5]pyrrolo[1,2-a]pyrazin-9(6H)-one |
| 54 | 21.2 | 54.6 | 35.8 | 3770 | 8-Cyclopropyl-10-(2-fluoro-4-methoxyphenyl)-7,8-dihydropyrido[2',3':4,5]pyrrolo[1,2-a]pyrazin-9(6H)-one |
| 55 | 222 | 111$^b$ | 500 | 3700$^b$ | 8-Cyclopropyl-10-(pyrimidin-5-yl)-7,8-dihydropyrido[2',3':4,5]pyrrolo[1,2-a]pyrazin-9(6H)-one |
| 56 | ND | 5.52 | ND | 253 | 10-(4-Chloro-2-methylphenyl)-8-cyclopropyl-7,8-dihydropyrido[2',3':4,5]pyrrolo[1,2-a]pyrazin-9(6H)-one |
| 57 | 3.49 | 3.81$^b$ | 10.8 | 38.3$^b$ | 10-(4-Chlorophenyl)-8-(5-methyl-1,2-oxazol-3-yl)-7,8-dihydropyrido[2',3':4,5]pyrrolo[1,2-a]pyrazin-9(6H)-one |

TABLE 9-continued

Biological Data for Examples 1-77.

| Example Number | Human PDE4A FL; IC$_{50}$ (nM)$^a$ | Human PDE4B FL; IC$_{50}$ (nM)$^a$ | Human PDE4C FL; IC$_{50}$ (nM)$^a$ | Human PDE4D FL; IC$_{50}$ (nM)$^a$ | IUPAC Name |
|---|---|---|---|---|---|
| 58 | 12.6 | 24.0 | 62.6 | 624$^b$ | 8-Cyclopropyl-10-([1,2,4]triazolo[1,5-a]pyridin-6-yl)-7,8-dihydropyrido[2',3':4,5]pyrrolo[1,2-a]pyrazin-9(6H)-one |
| 59 | 12.6 | 9.73 | 87.7 | 290 | 8-Cyclopropyl-10-(3,5-difluoro-4-methoxyphenyl)-7,8-dihydropyrrolo[1,2-a:4,5-b']dipyrazin-9(6H)-one |
| 60 | 11.8 | 11.2 | 99.0 | 397 | 3-(8-Cyclopropyl-9-oxo-6,7,8,9-tetrahydropyrido[2',3':4,5]pyrrolo[1,2-a]pyrazin-10-yl)-4-methylbenzonitrile |
| 61 | 35.1 | 39.0$^b$ | 60.3 | 1640$^b$ | 4-(11-Oxo-6a,7,8,9-tetrahydro-6H,11H-pyrido[2',3':4,5]pyrrolo[1,2-a]pyrrolo[1,2-d]pyrazin-12-yl)benzonitrile |
| 62 | ND | 332 | ND | >30000 | 8-Cyclopropyl-10-(5-fluoropyridin-2-yl)-7,8-dihydropyrido[2',3':4,5]pyrrolo[1,2-a]pyrazin-9(6H)-one |
| 63 | 219 | 32.1 | 731 | 1350 | 13-(4-Chlorophenyl)-6a,7,9,10-tetrahydro-6H,12H-pyrido[2'',3'':4',5']pyrrolo[1',2':4,5]pyrazino[2,1-c][1,4]oxazin-12-one |
| 64 | 3.56 | 11.5 | 37.5 | 458 | 8-Cyclopropyl-10-(furo[3,2-b]pyridin-6-yl)-7,8-dihydropyrido[2',3':4,5]pyrrolo[1,2-a]pyrazin-9(6H)-one |
| 65 | 5.65 | 6.70 | 13.8 | 481 | 8-Cyclopropyl-10-(2,4-dimethylphenyl)-7,8-dihydropyrido[2',3':4,5]pyrrolo[1,2-a]pyrazin-9(6H)-one |
| 66 | 5.42 | 6.87 | 16.7 | 460 | 8-Cyclopropyl-10-(2,4-dimethyl-phenyl)pyrido[2',3':4,5]pyrrolo[1,2-a]pyrazin-9(8H)-one |
| 67 | ND | 4.93 | ND | 862 | 11-(4-Chlorophenyl)-6,6a,7,8-tetrahydro-10H-azeto[1,2-a]pyrido[2',3':4,5]pyrrolo[1,2-d]pyrazin-10-one |
| 68 | 26.0$^c$ | 18.5 | 26.0$^c$ | 538 | 11-(4-Chlorophenyl)-6,6a,7,8-tetrahydro-10H-azeto[1,2-a]pyrido[2',3':4,5]pyrrolo[1,2-d]pyrazin-10-one, ENT-1 |
| 69 | 8.87 | 16.3$^b$ | 24.3 | 689$^b$ | 11-(4-Chlorophenyl)-6,6a,7,8-tetrahydro-10H-azeto[1,2-a]pyrido[2',3':4,5]pyrrolo[1,2-d]pyrazin-10-one, ENT-2 |
| 70 | 2.80 | 2.67 | 8.55 | 108 | 4-(8-Cyclopropyl-9-oxo-8,9-dihydropyrido[2',3':4,5]pyrrolo[1,2-a]pyrazin-10-yl)benzonitrile |
| 71 | 27.6 | 43.5 | 52.5 | 1070 | 5-(7-Cyclopropyl-8-oxo-5,6,7,8-tetrahydro[1,3]thiazolo[4',5':4,5]pyrrolo[1,2-a]pyrazin-9-yl)pyridine-2-carbonitrile |
| 72 | 3.53 | 4.36 | 15.1 | 90.4 | 4-(7-Cyclopropyl-8-oxo-5,6,7,8-tetrahydro[1,3]thiazolo[4',5':4,5]pyrrolo[1,2-a]pyrazin-9-yl)-2-fluorobenzonitrile |
| 73 | 7.66 | 25.2 | 122 | 700 | 10-(4-Chloro-2-methylphenyl)-8-(pyrimidin-2-yl)-7,8-dihydropyrido[2',3':4,5]pyrrolo[1,2-a]pyrazin-9(6H)-one, trifluoroacetate salt |
| 74 | 19.0$^c$ | 27.0$^c$ | 52.0$^c$ | 660$^c$ | 10-(4-Chloro-3-fluorophenyl)-8-(pyrimidin-2-yl)-7,8-dihydropyrido[2',3':4,5]pyrrolo[1,2-a]pyrazin-9(6H)-one |
| 75 | 1.26 | 3.99 | 11.7 | 286 | 10-(4-Chlorophenyl)-8-cyclopropyl-3,4,7,8-tetrahydro-2H-pyrano[2',3':4,5]pyrrolo[1,2-a]pyrazin-9(6H)-one |

TABLE 9-continued

Biological Data for Examples 1-77.

| Example Number | Human PDE4A FL; IC$_{50}$ (nM)[a] | Human PDE4B FL; IC$_{50}$ (nM)[a] | Human PDE4C FL; IC$_{50}$ (nM)[a] | Human PDE4D FL; IC$_{50}$ (nM)[a] | IUPAC Name |
|---|---|---|---|---|---|
| 76 | <0.31 | <0.55 | 2.00 | 21.6 | 10-(4-Chloro-3-fluorophenyl)-8-cyclopropyl-3,4,7,8-tetrahydro-2H-pyrano[2',3':4,5]pyrrolo[1,2-a]pyrazin-9(6H)-one |
| 77 | 1.00 | 0.84 | 5.94 | 56.2 | 10-(4-Chloro-2,5-difluorophenyl)-8-cyclopropyl-3,4,7,8-tetrahydro-2H-pyrano[2',3':4,5]pyrrolo[1,2-a]pyrazin-9(6H)-one |

[a]Values represent the geometric mean of 2-9 determinations, unless otherwise indicated.
[b]Value represents the geometric mean of ≥10 determinations.
[c]Value represents a single determination.
ND. Value was not determined.

Biological data for the compounds of Examples 78-97 are found in Table 10 below:

TABLE 10

| Example Number | Human PDE4A FL; IC$_{50}$ (nM)[a] | Human PDE4B FL; IC$_{50}$ (nM)[a] | Human PDE4C FL; IC$_{50}$ (nM)[a] | Human PDE4D FL; IC$_{50}$ (nM)[a] | IUPAC Name |
|---|---|---|---|---|---|
| 78 | ND | 59.5 | ND | 30.6 | 8-Acetyl-10-(4-chlorophenyl)-7,8-dihydropyrido[2',3':4,5]pyrrolo[1,2-a]pyrazin-9(6H)-one |
| 79 | 104 | 212 | 173 | 120 | 10-(4-Chlorophenyl)-8-(methylsulfonyl)-7,8-dihydropyrido[2',3':4,5]pyrrolo[1,2-a]pyrazin-9(6H)-one |
| 80 | 44.0 | 66.2 | 106 | 42.8 | 10-(4-Chlorophenyl)-N-ethyl-9-oxo-6,7-dihydropyrido[2',3':4,5]pyrrolo[1,2-a]pyrazine-8(9H)-carboxamide |
| 81 | >30000[b] | >30000 | 29688[b] | >30000 | 8-Cyclopropyl-10-(2-methylpyrimidin-4-yl)-7,8-dihydropyrido [2',3':4,5] pyrrolo[1,2-a]pyrazin-9(6H)-one |
| 82 | 11100[b] | 18500 | 4820[b] | >30000 | 8-Cyclopropyl-10-(4-methylthiazol-2-yl)-7,8-dihydropyrido[2',3':4,5]pyrrolo[1,2-a]pyrazin-9(6H)-one |
| 83 | ND | 15400 | ND | >29700 | 8-Cyclopropyl-10-(6-methylpyridin-3-yl)-7,8-dihydropyrrolo[1,2-a:4,5-b']dipyrazin-9(6H)-one |
| 84 | 15500[b] | >25800 | >30000[b] | >30000 | 8-Cyclopropyl-10-(3-methylpyridin-2-yl)-7,8-dihydropyrido[2',3':4,5]pyrrolo[1,2-a]pyrazin-9(6H)-one |
| 85 | 254[b] | 437 | 4960[b] | 724 | 3-(8-Cyclopropyl-9-oxo-6,7,8,9-tetrahydropyrido[2',3':4,5]pyrrolo[1,2-a]pyrazin-10-yl)-N,N-dimethylbenzenesulfonamide |
| 86 | 2.52 | 2.63 | 18.1 | 29 | 10-Cyclopentyl-8-cyclopropyl-7,8-dihydropyrido[2',3':4,5]pyrrolo[1,2-a]pyrazin-9(6H)-one |
| 87 | ND | 2640 | ND | >28700 | 8-Cyclopropyl-10-(2-methoxypyrimidin-5-yl)-7,8-dihydropyrrolo[1,2-a:4,5-b']dipyrazin-9(6H)-one |
| 88 | 8080[b] | 11000 | 8420[b] | 16100 | 8-Cyclopropyl-10-(2-methylthiazol-4-yl)-7,8-dihydropyrido[2',3':4,5]pyrrolo[1,2-a]pyrazin-9(6H)-one |
| 89 | ND | 2960 | ND | >30000 | 8-Cyclopropyl-10-(2-methoxypyrimidin-5-yl)-7,8-dihydropyrazino[1',2':1,5]pyrrolo[3,2-d]pyrimidin-9(6H)-one |

TABLE 10-continued

| Example Number | Human PDE4A FL; IC$_{50}$ (nM)$^a$ | Human PDE4B FL; IC$_{50}$ (nM)$^a$ | Human PDE4C FL; IC$_{50}$ (nM)$^a$ | Human PDE4D FL; IC$_{50}$ (nM)$^a$ | IUPAC Name |
|---|---|---|---|---|---|
| 90 | >30000$^b$ | >30000 | ND | >30000 | 8-Cyclopropyl-10-(5-(difluoromethyl)-1-methyl-1H-1,2,4-triazol-3-yl)-7,8-dihydropyrido[2',3':4,5]pyrrolo[1,2-a]pyrazin-9(6H)-one |
| 91 | 889 | 2760 | 2360 | 4450 | 8-Cyclopropyl-10-(1-methyl-1H-pyrazol-4-yl)-7,8-dihydropyrido[2',3':4,5]pyrrolo[1,2-a]pyrazin-9(6H)-one |
| 92 | ND | 15300 | ND | >29900 | 8-Cyclopropyl-10-(1H-pyrazol-1-yl)-7,8-dihydropyrido[2',3':4,5]pyrrolo[1,2-a]pyrazin-9(6H)-one |
| 93 | 24000$^b$ | >24700 | 6970$^b$ | >30000 | 10-(4-Chloro-1-methyl-1H-pyrazol-5-yl)-8-cyclopropyl-7,8-dihydropyrido[2',3':4,5]pyrrolo[1,2-a]pyrazin-9(6H)-one |
| 94 | 720$^b$ | 467 | 1050$^b$ | 858 | 8-Cyclopropyl-10-(3-(methylsulfonyl)phenyl)-7,8-dihydropyrido[2',3':4,5]pyrrolo[1,2-a]pyrazin-9(6H)-one |
| 95 | 345 | 1890 | 649 | 1920 | 10-(4-Chlorophenyl)-8-(5-propylpyrimidin-2-yl)-7,8-dihydropyrido[2',3':4,5]pyrrolo[1,2-a]pyrazin-9(6H)-one |
| 96 | 87.5 | 98.4 | 52.8 | 137 | 10-(4-Chlorophenyl)-8-(6-methoxyhexyl)-7,8-dihydropyrido[2',3':4,5]pyrrolo[1,2-a]pyrazin-9(6H)-one |
| 97 | 287 | 1040 | 526 | 1130 | 10-(4-Chlorophenyl)-8-(4-propylpyrimidin-2-yl)-7,8-dihydropyrido[2',3':4,5]pyrrolo[1,2-a]pyrazin-9(6H)-one |

$^a$Values represent the geometric mean of 2-9 determinations, unless otherwise indicated.
$^b$Value represents a single determination.
ND. Value not determined.

What is claimed:

1. A method of treating a condition selected from the group consisting of: schizophrenia, depression, anxiety, Alzheimer's disease, and multiple sclerosis, in a patient in need thereof, comprising administering to the patient a therapeutically effective amount of a compound of Formula I:

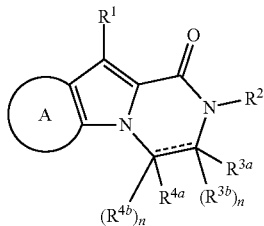

Formula I or a pharmaceutically acceptable salt thereof, wherein:
Ring A is a fused (5- to 6-membered)nitrogen-containing heteroaryl ring selected from the group consisting of pyridinyl, pyrimidinyl, pyrazinyl, and thiazolyl, each of which is optionally substituted with one $R^8$,
$R^1$ is selected from the group consisting of $(C_3-C_8)$cycloalkyl, (4 to 10-membered)-heterocycloalkyl, phenyl, naphthyl and (5-, 6-, 9-, or 10-membered) heteroaryl, and the $(C_3-C_8)$cycloalkyl, (4- to 10-membered)heterocycloalkyl, phenyl, naphthyl and (5-, 6-, 9- or 10-membered)heteroaryl moieties are optionally substituted with one to six $R^9$;
$R^2$ is selected from the group consisting of $(C_1-C_6)$alkyl, $(C_1-C_{15})$alkyl-OR$^5$, —C(=O)—R$^5$, —(SO$_2$)R$^5$, $(C_3-C_8)$cycloalkyl, and (5- to 6-membered)heteroaryl, and the (5- to 6-membered)heteroaryl is optionally substituted with one $(C_1-C_6)$alkyl;
$R^{3a}$ is selected from the group consisting of hydrogen and $(C_1-C_6)$alkyl; or
$R^2$ and $R^{3a}$ taken together with the nitrogen and carbon atoms to which they are attached form a (4- to 6-membered)heterocycloalkyl ring;
when present, $R^{3b}$ is hydrogen;
$R^{4a}$ is hydrogen;
when present, $R^{4b}$ is hydrogen;
$R^5$ and $R^6$ at each occurrence are each independently selected from the group consisting of hydrogen and $(C_1-C_6)$alkyl;
$R^7$ is $(C_1-C_6)$alkyl;
when present, $R^8$ is fluoro;
when present, $R^9$ at each occurrence is independently selected from the group consisting of halogen, cyano, hydroxy, —SF$_5$, nitro, $(C_1-C_6)$alkyl, $(C_2-C_6)$alkenyl, $(C_2-C_6)$alkynyl, $(C_1-C_6)$alkylthio, $(C_1-C_6)$alkoxy, —N(R$^5$)(R$^6$), —N(R$^5$)(C(O)R$^6$), —C(=O), —C(=O)—R$^5$, —C(=O)—OR$^5$, —(SO$_2$)R$^7$, and —S(=O)$_2$N(R$^5$)(R$^6$), wherein the alkyl, alkenyl, alkynyl, alkylthio and alkoxy are each optionally substituted with one to three substituents selected from the group consisting of halogen, cyano, hydroxy, —SF$_5$, (C$_1$-C$_6$)alkylthio, nitro, —C(=O)—R$^5$ and —N(R$^5$)(R$^6$);

---- is absent (forming a single bond) or a bond (forming a double bond); and n is an integer selected from 0 or 1, provided when ------ is present to form a double bond then n is 0, and when ------ is absent to form a single bond n is 1.

2. The method of claim 1, wherein the condition is schizophrenia.

3. The method of claim 1, wherein the condition is depression.

4. The method of claim 1, wherein the condition is anxiety.

5. The method of claim 1, wherein the condition is Alzheimer's disease.

6. The method of claim 1, wherein the condition is multiple sclerosis.

7. The method of claim 1, wherein the therapeutically effective amount is 0.01, 0.05, 0.1, 0.5, 1.0, 2.5, 5.0, 10.0, 15.0, 25.0, 50.0, 75.0, 100, 125, 150, 175, 200, 250, or 500 mg of the compound of Formula (I).

8. The method of claim 1, further comprising administering to the patient one or more additional pharmaceutically active agent(s).

9. The method of claim 8, wherein the one or more additional pharmaceutically active agent(s) is selected from the group consisting of: acetylcholinesterase inhibitors, amyloid-β0 or fragments thereof, antibodies to amyloid-ß, amyloid-lowering or -inhibiting agents, alpha-adrenergic receptor agonists, beta-adrenergic receptor blocking agents, anticholinergics, anticonvulsants, antipsychotics, calcium channel blockers, catechol O-methyltransferase inhibitors, central nervous system stimulants, corticosteroids, dopamine receptor agonists, dopamine receptor antagonists, dopamine reuptake inhibitors, gamma-amino-butyric acid receptor agonists, histamine 3 antagonists, immunomodulators, immunosuppressants, interferons, levodopa, N-methyl-D-aspartate receptor antagonists, monoamine oxidase inhibitors, muscarinic receptor agonists, neuroprotective drugs, nicotinic receptor agonists, norepinephrine reuptake inhibitors, phosphodiesterase inhibitors, quinolones, γ-secretase inhibitors and modulators, serotonin 1A (5-HT$_{1A}$) receptor antagonists, serotonin 2C (5-HT$_{2C}$) receptor agonists, serotonin 4 (5-HT$_4$) receptor agonists, serotonin 6 (5-HT$_6$) receptor antagonists, serotonin reuptake inhibitors, trophic factors, glycine transporter-1 inhibitors, AMPA-type glutamate receptor modulators, and janus kinase inhibitors.

10. The method of claim 8, wherein the one or more additional pharmaceutically active agent(s) is selected from the group consisting of: anticonvulsants, antipsychotics, dopamine receptor agonists, dopamine receptor antagonists, dopamine reuptake inhibitors, gamma-amino-butyric acid receptor agonists, norepinephrine reuptake inhibitors, serotonin 1A (5-HT$_{1A}$) receptor antagonists, serotonin 2C (5-HT$_{2C}$) receptor agonists, serotonin 4 (5-HT$_4$) receptor agonists, serotonin 6 (5-HT$_6$) receptor antagonists, and serotonin reuptake inhibitors.

\* \* \* \* \*

UNITED STATES PATENT AND TRADEMARK OFFICE
CERTIFICATE OF CORRECTION

PATENT NO. : 12,049,465 B2
APPLICATION NO. : 17/886807
DATED : July 30, 2024
INVENTOR(S) : Thomas Allen Chappie et al.

Page 1 of 1

It is certified that error appears in the above-identified patent and that said Letters Patent is hereby corrected as shown below:

In the Claims

In Claim 1, Column 187, Line 63: delete "$R^8$," and insert --$R^8$;--.

In Claim 9, Column 189, Line 29: delete "amyloid-β0" and insert --amyloid-β--.

Signed and Sealed this
Seventeenth Day of September, 2024

Katherine Kelly Vidal
*Director of the United States Patent and Trademark Office*